US008569511B2

(12) United States Patent
Bearss et al.

(10) Patent No.: US 8,569,511 B2
(45) Date of Patent: Oct. 29, 2013

(54) SUBSTITUTED 3-(1H-BENZO[D]IMIDAZOL-2-YL)-1H-INDAZOLE ANALOGS AS INHIBITORS OF THE PDK1 KINASE

(75) Inventors: David J. Bearss, Alpine, UT (US); Hariprasad Vankayalapati, Draper, UT (US); Venkataswamy Sorna, Salt Lake City, UT (US); Steven L. Warner, Sandy, UT (US); Sunil Sharma, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 13/436,905

(22) Filed: Mar. 31, 2012

(65) Prior Publication Data

US 2012/0277229 A1    Nov. 1, 2012

Related U.S. Application Data

(60) Provisional application No. 61/471,024, filed on Apr. 1, 2011.

(51) Int. Cl.
| | |
|---|---|
| *A61K 31/5377* | (2006.01) |
| *A61K 31/454* | (2006.01) |
| *A61K 31/4184* | (2006.01) |
| *C07D 401/14* | (2006.01) |
| *C07D 403/04* | (2006.01) |
| *C07D 413/14* | (2006.01) |

(52) U.S. Cl.
USPC ............... 548/305.1; 514/234.5; 514/322; 514/394; 544/139; 546/199

(58) Field of Classification Search
USPC ...................................... 548/305.1
See application file for complete search history.

(56) References Cited

U.S. PATENT DOCUMENTS

| | | | |
|---|---|---|---|
| 2002/0161022 A1 | 10/2002 | Reich et al. | |
| 2004/0048868 A1 | 3/2004 | Edwards et al. | |
| 2006/0079564 A1* | 4/2006 | Jansen et al. | 514/394 |
| 2011/0034441 A1 | 2/2011 | Hood et al. | |

FOREIGN PATENT DOCUMENTS

| | | |
|---|---|---|
| WO | 00/78761 A1 | 12/2000 |
| WO | 01/02369 A2 | 1/2001 |
| WO | WO-01/53268 A2 * | 7/2001 |
| WO | 03/004488 A1 | 1/2003 |
| WO | 03/035065 A1 | 5/2003 |
| WO | 2009/147187 A1 | 12/2009 |
| WO | 2012/135799 A1 | 10/2012 |

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
Golub et al., Science, vol. 286, Oct. 15, 1999, pp. 531-537.*
Angiolini et al., "Structure-based optimization of potent PDK1 inhibitors," Bioorganic & Medicinal Chemistry Letters, 1-5, 2010.
Foloppe et al., "Identification of a buried pocket for potent and selective inhibition of Chk1: Prediction and verification," Bioorganic & Medicinal Chemistry, 14:1792-1804, 2006.
Howard et al., "Fragment-Based Discovery of the Pyrazol-4-yl Urea (AT9283), a Multitargeted Kinase inhibitor with Potent Aurora Kinase Activity," Journal of Medicinal Chemistry, 52(2):379-388, 2009.
Islam et al., "Indolinone based phosphoinositide-dependent kinase-1 (PDK1) inhbitors. Part 1: Design, synthesis and biological activity," Bioorganic & Medicinal Chemistry Letters, 17:3814-3818, 2007.
Islam et al., "Indolinone based phosphoinositide-dependent kinase-1 (PDK1) inihibitors. Part 2: Optimization of BX-517," 17:3819-3825, 2007.
McBride et al., "Design and structure-activity relationship of 3-benzimidazol-2-yl-1*H*-indazoles as inhibitors of receptor tyrosine kinases," Bioorganic & Medicinal Chemistry Letters, 16:3595-3599, 2006.
Medina et al., "Aminoindazole PDK1 Inhibitors: A Case Study in Fragment-Based Drug Discovery," American Chemical Society, 1-4, 2010.
Medina et al., "Structure-Based Design of Potent and Selective 3-Phosphoinositide-Dependent Kinase-1 (PDK1) Inhibitors," Journal of Medicinal Chemistry, 1-25, 2010.
Peifer et al., "Small-Molecule Inhibitors of PDK1," ChemMedChem, 3:1810-1838, 2008.
Velankar et al., "Synthesis and biological evaluation of novel (4 or 5-Aryl)pyrazolyl-indoles as inhibitors of interleukin-2 inducible T-cell kinase (ITK)," Bioorganic & Medicinal Chemistry, 1-37, 2010.
Carnero, "The PKB/AKT Pathway in Cancer," Current Pharmaceutical Design, 16(1):34-44, 2010.
Cully et al., "Beyond PTEN mutations: the PI3K pathway as an integrator of multiple inputs during tumorigenesis," Nature Reviews, 6:184-192, 2006.
Flynn et al , "Inhibition of PDK-1 activity causes a reduction in cell proliferation and survival," Current Biology, 10:1439-1442, 2000.
Parsons et al., "Mutations in a signalling pathway," Nature, 436:792, 2005.
Stephens et al., "Protein Kinase B Kinases That Mediate Phosphatidylinositol 3,4,5-Trisphospahte-Dependent Activation of Protein Kinase B," Science, 279:710-714, 1998.
Vanhaesebroeck et al., "Synthesis and Function of 3-phosphorylated Inositol Lipids," Annual Review Biochemistry, 70:535-602, 2001.
International Search Report for corresponding PCT Application No. PCT/US2012/031767, dated Jun. 28, 2012.
Written Opinion for corresponding PCT Application No. PCT/US2012/031767, dated Jun. 28, 2012.

* cited by examiner

*Primary Examiner* — Laura L. Stockton
(74) *Attorney, Agent, or Firm* — Seed IP Law Group PLLC

(57) ABSTRACT

In one aspect, the invention relates to substituted 3-(1H-benzo[d]imidazol-2-yl)-1H-indazole analogs, derivatives thereof, and related compounds, which are useful as inhibitors of the PDK1 kinase; synthetic methods for making the compounds; pharmaceutical compositions comprising the compounds; and methods of using the compounds and compositions for treating disorders associated with dysfunction of the PDK1 kinase. This abstract is intended as a scanning tool for purposes of searching in the particular art and is not intended to be limiting of the present invention.

17 Claims, 14 Drawing Sheets

7A

7B

9A

9B

10A

10B

10C

SUBSTITUTED 3-(1H-BENZO[D]IMIDAZOL-2-YL)-1H-INDAZOLE ANALOGS AS INHIBITORS OF THE PDK1 KINASE

CROSS-REFERENCE TO RELATED APPLICATIONS

This application claims the benefit of U.S. Provisional Application No. 61/471,024, filed on Apr. 1, 2011, which is incorporated herein by reference in its entirety.

BACKGROUND

Protein kinases play an important role in a large percentage of the biochemical processes that regulate the functions of cells that are critical in tumor developments including; cell proliferation, genomic repair, apoptosis, migration and invasion. These proteins serve, in many cases, as molecular "switches" regulating the activity of target proteins through the process of phosphorylation. In normal cell physiology, the coordination of multiple kinases is a tightly regulated process allowing the cell to function in a manner in which it was designed. Protein kinases and phosphatases play a prominent role in the tumorigenic process. Normal cell physiology is dependent on the appropriate balance between kinase and phosphatase activity to keep important signaling pathways within tolerated levels. Mutations in the genes that encode these proteins often leads to aberrant signaling that lays the foundation for changes in cellular function. Alterations in numerous protein kinase pathways ultimately lead to deregulation of cellular function that affect pathways that are hallmarks of the tumor phenotype.

One kinase pathway that plays a prominent role in tumor development and progression is the phosphoinositol 3 Kinase (PI3K)/Akt pathway. This pathway typifies the multi-component regulatory mechanisms that regulate normal cell function but lead to malignant phenotypes when proteins are genetically modified and aberrantly regulated. Many of the proteins in this pathway are genetically altered and aberrantly activated conferring tumorigenic properties in cultured cells and in human tumors (e.g. see A. Carnero, Curr Pharm Des, 2010, 16:34). Multiple kinases in this pathway have been the subject of pharmacological intervention. One kinase in this pathway, the phosphoinositide-dependent kinase1 (PDK1), is a critical activator of multiple proteins involved in pro-survival and oncogenic activity. As such, it provides drug development groups an attractive target for new cancer therapies.

Activation of PI3K by engagement of cell surface receptor tyrosine kinases by insulin and growth factors generates phosphatidyl-inositol,3,4,5 triphosphate PIP3 (2). PDK1 and Akt are recruited to the cell membrane and subsequently activated in response to increases in PIP3 generated by the activity of PI3K. The recruitment of PDK1 and Akt to the cell membrane is mediated through interactions of homologous pleckstrin homology domains. Localization of these proteins to the plasma membrane allows PDK1 to activate AKT by phosphorylation at residue threonine-308 (e.g. see L. Stephens et al., Science 1998, 279:710). Activated PDK1 phosphorylates Akt as part of an important signaling pathway that ultimately regulates the signaling of multiple biological processes. As a transducer of the PI3K signal and as a regulator of numerous kinases involved in promoting cancer growth, proliferation and survival, PDK1 distinguishes itself as an attractive target for drug development.

It has also been observed that about 50% of common human tumor types possess mutations in genes that regulate PIP3 production, and these mutations impart these cancer cells with abnormally high levels of this second messenger (Vanhaesebroeck, B., et al. Ann. Rev. Biochem., 70:535-602 (2001)). A common mutation affecting PIP3 production is in PTEN, the lipid phosphatase that breaks down PIP3. The finding that mice expressing half the normal amount of PTEN are protected from developing a wide range of tumors by reducing PDK1 expression levels supports this idea. The potential of PDK1 inhibitors as anti-cancer compounds has also been suggested by transfection of a PTEN negative human cancer cell line (U87MG) with antisense oligonucleotides directed against PDK1. The resulting decrease in PDK1 protein levels led to a reduction in cellular proliferation and survival (Flynn, P., et al., Curr. Biol., 10: 1439-1442 (2000)). The PDK1/Akt pathway is activated in many cancer via mutations in other proteins such as Receptor Tyrosine Kinases (RTKs), Ras, or PI-3 kinase (Cully et al., Nature Reviews Cancer 6:184-192 (2006)). Mutations in PDK1 itself have been found to be associated with a variety of cancer types. For example, the identification of PDK1 mutations (PDK1 T35414, PDK1 D527E) in human colorectal cancers suggests that inhibitors of this kinase may have therapeutic value by directly inhibiting either wild-type or mutant forms of this protein. See, Parsons et al., Nature 436, 792 (11 Aug. 2005).

In summary, PDK1 is a central activator of several signaling pathways that are frequently altered in human cancers making it an attractive target for therapeutic intervention. Consequently, there is a great need in the art for effective inhibitors of PDK1.

SUMMARY

In accordance with the purpose(s) of the invention, as embodied and broadly described herein, the invention, in one aspect, relates to compounds useful as inhibitors of the PI3K/Akt pathway, compounds useful as inhibitors of PDK1, methods of making same, pharmaceutical compositions comprising same, and methods of treating disorders of uncontrolled cellular proliferation using same.

Disclosed are compounds having a structure represented by a formula:

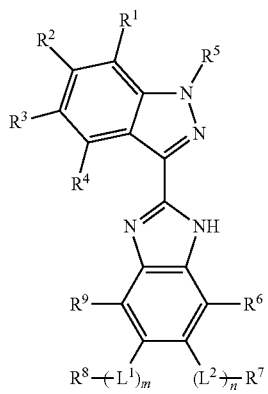

wherein $L^1$ is C=O or $(CH_2)_p$, wherein p is an integer from 1 to 3, wherein m is 0 or 1; wherein $L^2$ is C=O or $(CH_2)_q$, wherein q is an integer from 1 to 3, wherein n is 0 or 1; wherein $R^1$ is selected from hydrogen, halogen, cyano, and C1-C6 alkyl; wherein $R^2$ is selected from hydrogen, halogen, cyano, and C1-C6 alkyl; wherein $R^3$ is selected from hydrogen, $Ar^1$, NHC=$OR^{11}$, and NHC=$ONHR^{11}$; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino; wherein $R^{10}$ is selected from hydrogen and C1-C6 alkyl; wherein $R^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, C3-C6 heterocycloalkyl, and $Ar^1$; wherein $R^4$ is selected from hydrogen, $Ar^1$, $NHR^{11}$, and $NHC=ONR^{11}$, provided only one of $R^3$ and $R^4$ is not hydrogen; wherein $R^5$ is selected from hydrogen and C1-C6 alkyl; wherein $R^6$ is selected from hydrogen, halogen, and C1-C6 alkyl; wherein $R^7$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl) piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; wherein R8 is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; and wherein $R^9$ is selected from hydrogen, halogen, and C1-C6 alkyl; or a pharmaceutically acceptable salt, hydrate, solvate, or polymorph thereof.

Also disclosed are pharmaceutical compositions comprising a therapeutically effective amount of a disclosed compound and a pharmaceutically acceptable carrier.

Also disclosed are synthetic methods comprising the steps of: (a) providing a first compound having a structure represented by a formula:

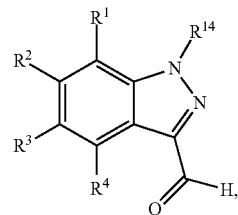

wherein $R^1$ is selected from hydrogen, halogen, cyano, and C1-C6 alkyl; wherein $R^2$ is selected from hydrogen, halogen, cyano, and C1-C6 alkyl; wherein one of $R^3$ and $R^4$ is selected from halogen or nitro, and the other is hydrogen; wherein $R^{14}$ is a protecting group; and (b) reacting the first compound with a second compound having a structure represented by the formula:

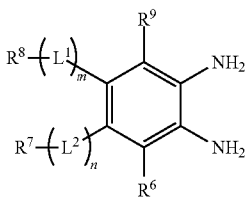

wherein $L^1$ is $C=O$ or $(CH_2)_p$, wherein p is an integer from 1 to 3, wherein m is 0 or 1; wherein $L^2$ is $C=O$ or $(CH_2)_q$, wherein q is an integer from 1 to 3, wherein n is 0 or 1; wherein $R^6$ is selected from hydrogen, halogen, and C1-C6 alkyl; wherein $R^7$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; wherein $R^8$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; and wherein $R^9$ is selected from hydrogen, halogen, and C1-C6 alkyl.

Disclosed are methods for the treatment of a disorder of uncontrolled cellular proliferation disorder in a mammal, the method comprising the step of administering to the mammal an effective amount of least one compound having a structure represented by a formula:

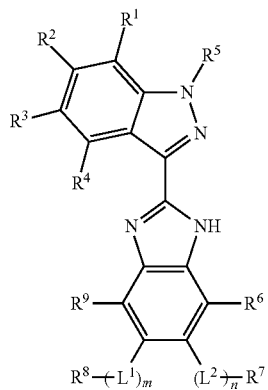

wherein $L^1$ is C=O or $(CH_2)_p$, wherein p is an integer from 1 to 3, wherein m is 0 or 1; wherein $L^2$ is C=O or $(CH_2)_q$, wherein q is an integer from 1 to 3, wherein n is 0 or 1; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino; wherein $R^{10}$ is selected from hydrogen and C1-C6 alkyl; wherein $R^1$ is selected from hydrogen, halogen, cyano, and C1-C6 alkyl; wherein $R^2$ is selected from hydrogen, halogen, cyano, and C1-C6 alkyl; wherein $R^3$ is selected from hydrogen, $Ar^1$, NHC=$OR^{11}$, and NHC=$ONHR^{11}$; wherein $R^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, C3-C6 heterocycloalkyl, and $Ar^1$; wherein $R^4$ is selected from hydrogen, $Ar^1$, $NHR^{11}$, and NHC=$ONR^{11}$, provided only one of $R^3$ and $R^4$ is not hydrogen; wherein $R^5$ is selected from hydrogen and C1-C6 alkyl; wherein $R^6$ is selected from hydrogen, halogen, and C1-C6 alkyl; wherein $R^7$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; wherein R8 is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; and wherein $R^9$ is selected from hydrogen, halogen, and C1-C6 alkyl; or a pharmaceutically acceptable salt, hydrate, solvate, or polymorph thereof.

Also disclosed are methods for decreasing kinase activity in a mammal, the method comprising the step of administering to the mammal a therapeutically effective amount of at least one compound having a structure represented by a formula:

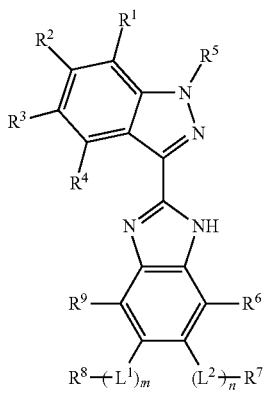

wherein $L^1$ is C=O or $(CH_2)_p$, wherein p is an integer from 1 to 3, wherein m is 0 or 1; wherein $L^2$ is C=O or $(CH_2)_q$, wherein q is an integer from 1 to 3, wherein n is 0 or 1; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino; wherein $R^{10}$ is selected from hydrogen and C1-C6 alkyl; wherein $R^1$ is selected from hydrogen, halogen, cyano, and C1-C6 alkyl; wherein $R^2$ is selected from hydrogen, halogen, cyano, and C1-C6 alkyl; wherein $R^3$ is selected from hydrogen, $Ar^1$, NHC=$OR^{11}$, and NHC=$ONHR^{11}$; wherein $R^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, C3-C6 heterocycloalkyl, and $Ar^1$; wherein $R^4$ is selected from hydrogen, $Ar^1$, $NHR^{11}$, and NHC=$ONR^{11}$, provided only one of $R^3$ and $R^4$ is not hydrogen; wherein $R^5$ is selected from hydrogen and C1-C6 alkyl; wherein $R^6$ is selected from hydrogen, halogen, and C1-C6 alkyl; wherein $R^7$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; wherein R8 is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; and wherein $R^9$ is selected from hydrogen, halogen, and C1-C6 alkyl; or a pharmaceutically acceptable salt, hydrate, solvate, or polymorph thereof.

Also disclosed are methods for decreasing kinase activity in at least one cell, the method comprising the step of contacting the at least one cell with an effective amount of least one compound having a structure represented by a formula:

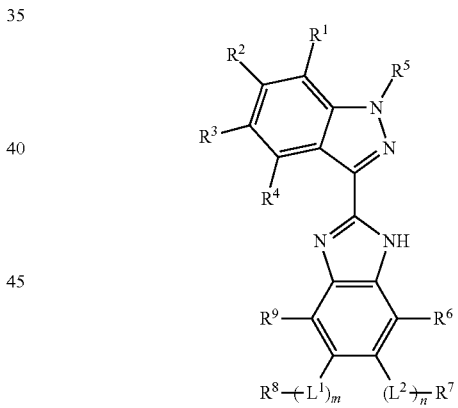

wherein $L^1$ is C=O or $(CH_2)_p$, wherein p is an integer from 1 to 3, wherein m is 0 or 1; wherein $L^2$ is C=O or $(CH_2)_q$, wherein q is an integer from 1 to 3, wherein n is 0 or 1; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino; wherein $R^{10}$ is selected from hydrogen and C1-C6 alkyl; wherein $R^1$ is selected from hydrogen, halogen, cyano, and C1-C6 alkyl; wherein $R^2$ is selected from hydrogen, halogen, cyano, and C1-C6 alkyl; wherein $R^3$ is selected from hydrogen, $Ar^1$, NHC=$OR^{11}$, and NHC=$ONHR^{11}$; wherein $R^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, C3-C6 heterocycloalkyl, and $Ar^1$; wherein $R^4$ is selected from hydrogen, $Ar^1$, $NHR^{11}$, and NHC=$ONR^{11}$, provided only one of $R^3$ and $R^4$ is not hydrogen; wherein $R^5$ is selected from hydrogen and C1-C6 alkyl; wherein $R^6$ is selected from hydrogen, halogen, and C1-C6 alkyl; wherein $R^7$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; wherein $R^8$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; and wherein $R^9$ is selected from hydrogen, halogen, and C1-C6 alkyl; or a pharmaceutically acceptable salt, hydrate, solvate, or polymorph thereof.

Also disclosed are uses of a compound for decreasing kinase activity, the compound having a structure represented by a formula:

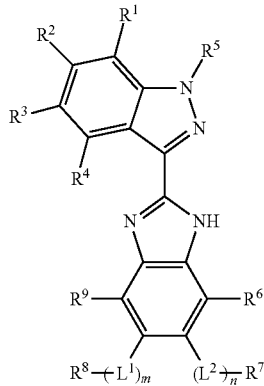

wherein $L^1$ is C=O or $(CH_2)_p$, wherein p is an integer from 1 to 3, wherein m is 0 or 1; wherein $L^2$ is C=O or $(CH_2)_q$, wherein q is an integer from 1 to 3, wherein n is 0 or 1; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino; wherein $R^{10}$ is selected from hydrogen and C1-C6 alkyl; wherein $R^1$ is selected from hydrogen, halogen, cyano, and C1-C6 alkyl; wherein $R^2$ is selected from hydrogen, halogen, cyano, and C1-C6 alkyl; wherein $R^3$ is selected from hydrogen, $Ar^1$, NHC=$OR^{11}$, and NHC=$ONHR^{11}$; wherein $R^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, C3-C6 heterocycloalkyl, and $Ar^1$; wherein $R^4$ is selected from hydrogen, $Ar^1$, $NHR^{11}$, and NHC=$ONR^{11}$, provided only one of $R^3$ and $R^4$ is not hydrogen; wherein $R^5$ is selected from hydrogen and C1-C6 alkyl; wherein $R^6$ is selected from hydrogen, halogen, and C1-C6 alkyl; wherein $R^7$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; wherein $R^8$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; and wherein $R^9$ is selected from hydrogen, halogen, and C1-C6 alkyl; or a pharmaceutically acceptable salt, hydrate, solvate, or polymorph thereof.

Also disclosed are pharmaceutical compositions comprising a pharmaceutically acceptable carrier and an effective amount of a compound represented by a formula:

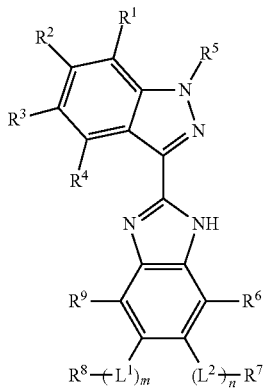

wherein $L^1$ is C=O or $(CH_2)_p$, wherein p is an integer from 1 to 3, wherein m is 0 or 1; wherein $L^2$ is C=O or $(CH_2)_q$, wherein q is an integer from 1 to 3, wherein n is 0 or 1; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino; wherein $R^{10}$ is selected from hydrogen and C1-C6 alkyl; wherein $R^1$ is selected from hydrogen, halogen, cyano, and C1-C6 alkyl; wherein $R^2$ is selected from hydrogen, halogen, cyano, and C1-C6 alkyl; wherein $R^3$ is selected from hydrogen, $Ar^1$, NHC=$OR^{11}$, and NHC=$ONHR^{11}$; wherein $R^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, C3-C6 heterocycloalkyl, and $Ar^1$; wherein $R^4$ is selected from hydrogen, $Ar^1$, $NHR^{11}$, and NHC=$ONR^{11}$, provided only one of $R^3$ and $R^4$ is not hydrogen; wherein $R^5$ is selected from hydrogen and C1-C6 alkyl; wherein $R^6$ is selected from hydrogen, halogen, and C1-C6 alkyl; wherein $R^7$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; wherein $R^8$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; and wherein $R^9$ is selected from hydrogen, halogen, and C1-C6 alkyl; or a pharmaceutically acceptable salt, hydrate, solvate, or polymorph thereof.

Also disclosed are kits comprising at least one compound having a structure represented by a formula:

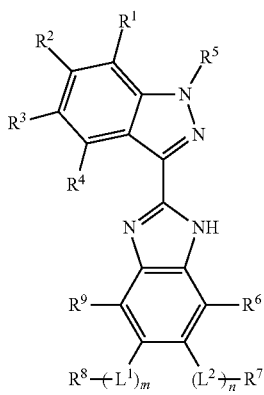

wherein $L^1$ is C=O or $(CH_2)_p$, wherein p is an integer from 1 to 3, wherein m is 0 or 1; wherein $L^2$ is C=O or $(CH_2)_q$, wherein q is an integer from 1 to 3, wherein n is 0 or 1; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino; wherein $R^{10}$ is selected from hydrogen and C1-C6 alkyl; wherein $R^1$ is selected from hydrogen, halogen, cyano, and C1-C6 alkyl; wherein $R^2$ is selected from hydrogen, halogen, cyano, and C1-C6 alkyl; wherein $R^3$ is selected from hydrogen, $Ar^1$, NHC=$OR^{11}$, and NHC=$ONHR^{11}$; wherein $R^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, C3-C6 heterocycloalkyl, and $Ar^1$; wherein $R^4$ is selected from hydrogen, $Ar^1$, $NHR^{11}$, and NHC=$ONR^{11}$, provided only one of $R^3$ and $R^4$ is not hydrogen; wherein $R^5$ is selected from hydrogen and C1-C6 alkyl; wherein $R^6$ is selected from hydrogen, halogen, and C1-C6 alkyl; wherein $R^7$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrrolidinyl, oxazolidinyl, imidazolidinyl, pyrazolidinyl, thiomorpholinyl 1,1-dioxide; and 1-(alkylsulfonyl)piperazinyl; wherein $R^8$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrrolidinyl, oxazolidinyl, imidazolidinyl, pyrazolidinyl, thiomorpholinyl 1,1-dioxide; and 1-(alkylsulfonyl)piperazinyl; and wherein $R^9$ is selected from hydrogen, halogen, and C1-C6 alkyl; or a pharmaceutically acceptable salt, hydrate, solvate, or polymorph thereof, and one or more of: (a) at least one agent known to increase kinase activity; (b) at least one agent known to decrease kinase activity; (c) at least one agent known to treat a disorder of uncontrolled cellular proliferation; or (d) instructions for treating a disorder associated with uncontrolled cellular proliferation.

Also disclosed are methods for manufacturing a medicament comprising combining at least one disclosed compound or at least one disclosed product with a pharmaceutically acceptable carrier or diluent.

Also disclosed are uses of a disclosed compound or a disclosed product in the manufacture of a medicament for the treatment of a disorder associated with a kinase dysfunction in a mammal.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
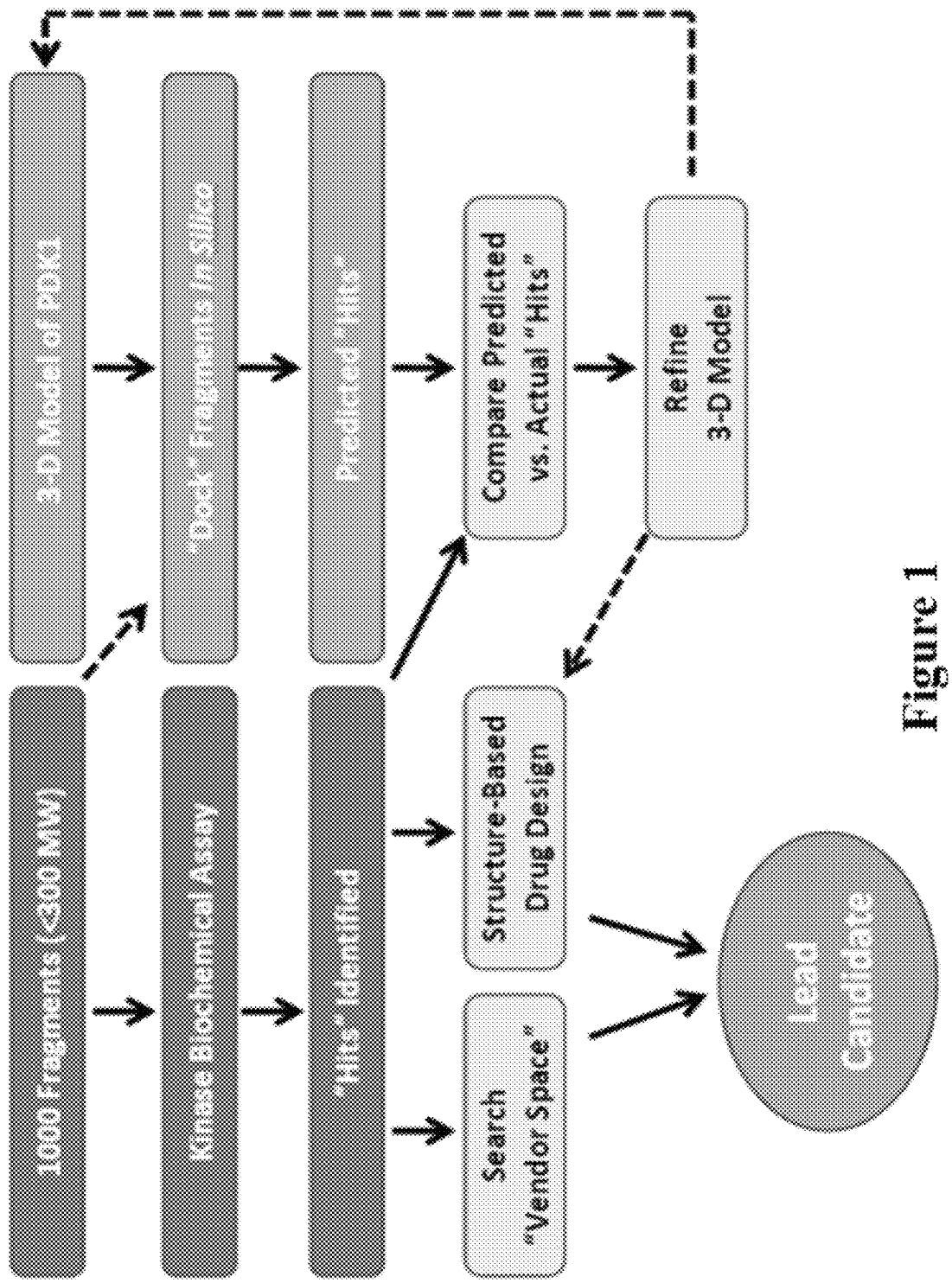
FIG. 1 shows a representative approach to fragment-based identification of PDK1 inhibitors.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "PDK1" or "3-phosphoinositide-dependent protein kinase 1" can be used interchangeably and refers to a protein kinase encoded by the PDK1 gene (alternatively referred to as the PDPK1 gene), which has a gene map locus of 16p13.3. The term is inclusive of splice isoforms of this gene, of which at least three variants have been described. The variant commonly referred to as Isoform 1 is often taken as the canonical sequence, whereas Isoform 2 omits amino acids 1-50 of Isoform 1 and Isoform 2 omits amino acids 238-263 of isoform. The IUBMB Enzyme Nomenclature classification of PDK1 is EC 2.7.11.1. The term PDK1 is inclusive of and can be used interchangeably with the terms (and hence protein kinases) referred to by those skilled in the art 3-phosphoinositide dependent protein kinase-1; 3-phosphoinositide-dependent protein kinase 1; hPDK1; MGC20087; MGC35290; PDK1; PDPK1; PkB kinase like gene 1; PkB-like 1 protein kinase; OTTHUMP00000174525, and PRO0461

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of a disorder of uncontrolled cellular proliferation associated with a protein kinase dysfunction prior to the administering step. In some aspects of the disclosed method, the subject has been diagnosed with a need for inhibition of a protein kinase prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder of uncontrolled cellular proliferation" means having been subjected to a physical examination by a person of skill, for example, a physician, and found to have a condition that can be diagnosed or treated by a compound or composition that can inhibit a protein kinase. As a further example, "diagnosed with a need for inhibition of a protein kinase" refers to having been subjected to a physical examination by a person of skill, for example, a physician, and found to have a condition characterized by a protein kinase dysfunction. Such a diagnosis can be in reference to a disorder, such as a disorder of uncontrolled cellular proliferation, cancer and the like, as discussed herein. For example, the term "diagnosed with a need for inhibition of protein kinase activity" refers to having been subjected to a physical examination by a person of skill, for example, a physician, and found to have a condition that can be diagnosed or treated by inhibition of protein kinase activity. For example, "diagnosed with a need for treatment of one or more disorders of uncontrolled cellular proliferation associated with a protein kinase dysfunction" means having been subjected to a physical examination by a person of skill, for example, a physician, and found to have one or more disorders of uncontrolled cellular proliferation associated with a protein kinase dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to a dysfunction of protein kinase activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target protein kinase, or other biological entity together in such a manner that the compound can affect the activity of the target (e.g., spliceosome, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14 th edition), the Physicians' Desk Reference (64 th edition), and The Pharmacological Basis of Therapeutics (12 th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "$EC_{50}$," is intended to refer to the concentration of a substance (e.g., a compound or a drug) that is required for 50% agonism or activation of a biological process, or component of a process, including a protein, subunit, organelle, ribonucleoprotein, etc. In one aspect, an $EC_{50}$ can refer to the concentration of a substance that is required for 50% agonism or activation in vivo, as further defined elsewhere herein. In a further aspect, $EC_{50}$ refers to the concentration of agonist or activator that provokes a response halfway between the baseline and maximum response.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. For example, an $IC_{50}$ can refer to the concentration of a substance that is required for 50% inhibition in vivo or the inhibition is measured in vitro, as further defined elsewhere herein. Alternatively, $IC_{50}$ refers to the half maximal (50%) inhibitory concentration (IC) of a substance. The inhibition can be measured in a cell-line such as AN3-CA, RL95-2 or HEC-1A cells. In a yet further aspect, the inhibition is measured in a cell-line, e.g. HEK-293 or HeLa, transfected with a mutant or wild-type mammalian protein kinase, e.g. PDK1.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

For example, a "C1-C3 alkyl" group can be selected from methyl, ethyl, n-propyl, i-propyl, and cyclopropyl, or from a subset thereof. In certain aspects, the "C1-C3 alkyl" group can be optionally further substituted. As a further example, a "C1-C4 alkyl" group can be selected from methyl, ethyl, n-propyl, i-propyl, cyclopropyl, n-butyl, i-butyl, s-butyl, t-butyl, and cyclobutyl, or from a subset thereof. In certain aspects, the "C1-C4 alkyl" group can be optionally further substituted. As a further example, a "C1-C6 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, and cyclohexane, or from a subset thereof. In certain aspects, the "C1-C6 alkyl" group can be optionally further substituted. As a further example, a "C1-C8 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, cyclohexane, heptane, cycloheptane, octane, and cyclooctane, or from a subset thereof. In certain aspects, the "C1-C8 alkyl" group can be optionally further substituted. As a further example, a "C1-C12 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, cyclohexane, heptane, cycloheptane, octane, cyclooctane, nonane, cyclononane, decane, cyclodecane, undecane, cycloundecane, dodecane, and cyclododecane, or from a subset thereof. In certain aspects, the "C1-C12 alkyl" group can be optionally further substituted.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The cycloalkyl group can be substituted or unsubstituted. The cycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The cycloalkenyl group can be substituted or unsubstituted. The cycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The cycloalkynyl group can be substituted or unsubstituted. The cycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the it clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula -$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formulas —NH(-alkyl) and —N(-alkyl)$_2$, and where alkyl is as described herein. The alkyl group can be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like, up to and including a C1-C24 alkyl. Representative examples include, but are not limited to, methylamino group, ethylamino group, propylamino group, isopropylamino group, butylamino group, isobutylamino group, (sec-butyl) amino group, (tert-butyl)amino group, pentylamino group, isopentylamino group, (tert-pentyl)amino group, hexylamino group, N-ethyl-N-methylamino group, N-methyl-N-propylamino group, and N-ethyl-N-propylamino group. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group, and the like.

The term "monoalkylamino" as used herein is represented by the formula —NH(-alkyl), where alkyl is as described herein. The alkyl group can be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like, up to and including a C1-C24 alkyl. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$, where alkyl is as described herein. The alkyl group can be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like, up to and including a C1-C24 alkyl. It is understood that each alkyl group can be independently varied, e.g. as in the representative compounds such as N-ethyl-N-methylamino group, N-methyl-N-propylamino group, and N-ethyl-N-propylamino group. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group, and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O) C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1$O$A^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted, and the heteroaryl group can be monocyclic, bicyclic or multicyclic aromatic ring. The heteroaryl group can be substituted with one or more groups including, but not limited to, alkyl, cycloalkyl, alkoxy, amino, ether, halide, hydroxy, nitro, silyl, sulfo-oxo, or thiol as described herein. It is understood that a heteroaryl group may be bound either through a heteroatom in the ring, where chemically possible, or one of carbons comprising the heteroaryl ring.

A variety of heteroaryl groups are known in the art and include, without limitation, oxygen-containing rings, nitrogen-containing rings, sulfur-containing rings, mixed heteroatom-containing rings, fused heteroatom containing rings, and combinations thereof. Non-limiting examples of heteroaryl rings include furyl, pyrrolyl, pyrazolyl, imidazolyl, triazolyl, pyridyl, pyridazinyl, pyrimidinyl, pyrazinyl, azepinyl, triazinyl, thienyl, oxazolyl, thiazolyl, oxadiazolyl, oxatriazolyl, oxepinyl, thiepinyl, diazepinyl, benzofuranyl, thionapthene, indolyl, benzazolyl, pyranopyrrolyl, isoindazolyl, indoxazinyl, benzoxazolyl, quinolinyl, isoquinolinyl, benzodiazonyl, naphthyridinyl, benzothienyl, pyridopyridinyl, acridinyl, carbazolyl and purinyl rings.

The term "monocyclic heteroaryl," as used herein, refers to a monocyclic ring system which is aromatic and in which at least one of the ring atoms is a heteroatom. Monocyclic heteroaryl groups include, but are not limited, to the following exemplary groups: pyridine, pyrimidine, furan, thiophene, pyrrole, isoxazole, isothiazole, pyrazole, oxazole, thiazole, imidazole, oxadiazole, including, 1,2,3-oxadiazole, 1,2,5-oxadiazole and 1,3,4-thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3, 4-tetrazole and 1,2,4,5-tetrazole, pyridazine, pyrazine, triazine, including 1,2,4-triazine and 1,3,5-triazine, tetrazine, including 1,2,4,5-tetrazine, and the like. Monocyclic heteroaryl groups are numbered according to standard chemical nomenclature.

The term "bicyclic heteroaryl," as used herein, refers to a ring system comprising a bicyclic ring system in which at least one of the two rings is aromatic and at least one of the two rings contains a heteroatom. Bicyclic heteroaryl encompasses ring systems wherein an aromatic ring is fused with another aromatic ring, or wherein an aromatic ring is fused with a non-aromatic ring. Bicyclic heteroaryl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Examples of bicyclic heteroaryl groups include without limitation indolyl, isoindolyl, indolyl, indolinyl, indolizinyl, quinolinyl, isoquinolinyl, benzofuryl, bexothiophenyl, indazolyl, benzimidazolyl, benzothiazinyl, benzothiazolyl, purinyl, quinolizyl, quinolyl, isoquinolyl, cinnolinyl, phthalazinyl, quinazolizinyl, quinoxalyl, naphthyridinyl, and pteridyl. Bicyclic heteroaryls are numbered according to standard chemical nomenclature.

The term "heterocycloalkyl" as used herein refers to an aliphatic, partially unsaturated or fully saturated, 3- to 14-membered ring system, including single rings of 3 to 8 atoms and bi- and tricyclic ring systems where at least one of the carbon atoms of the ring is replaced with a heteroatom such as, but not limited to, nitrogen, oxygen, sulfur, or phosphorus. A heterocycloalkyl can include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited, to the following exemplary groups: pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. The term heterocycloalkyl group can also be a C2 heterocycloalkyl, C2-C3 heterocycloalkyl, C2-C4 heterocycloalkyl, C2-C5 heterocycloalkyl, C2-C6 heterocycloalkyl, C2-C7 heterocycloalkyl, C2-C8 heterocycloalkyl, C2-C9 heterocycloalkyl, C2-C10 heterocycloalkyl, C2-C11 heterocycloalkyl, and the like up to and including a C2-C14 heterocycloalkyl. For example, a C2 heterocycloalkyl comprises a group which has two carbon atoms and at least one heteroatom, including, but not limited to, aziridinyl, diazetidinyl, oxiranyl, thiiranyl, and the like. Alternatively, for example, a C5 heterocycloalkyl comprises a group which has five carbon atoms and at least one heteroatom, including, but not limited to, piperidinyl, tetrahydropyranyl, tetrahydrothiopyranyl, diazepanyl, and the like. It is understood that a heterocycloalkyl group may be bound either through a heteroatom in the ring, where chemically possible, or one of carbons comprising the heterocycloalkyl ring. The heterocycloalkyl group can be substituted or unsubstituted. The heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "hydroxyl" or "hydroxyl," as used herein can be used interchangeably and refers to a group represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido," as used herein can be used interchangeably and refers to a group represented by the formula —$N_3$.

The term "nitro" as used herein is represented by the formula —$NO_2$.

The term "nitrile" or "cyano," as used herein can be used interchangeably and refers to a group represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$—CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O) NR$^O$)$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$SR—, —(CH$_2$)$_{0-4}$SC(O)R$^\circ$; —(CH$_2$)$_{0-4}$C(O)NR$^\circ$$_2$; —C(S)NR$^\circ$$_2$; —C(S)SR$^\circ$; SC(S)SR$^\circ$, —(CH$_2$)$_{0-4}$OC(O)NR$^\circ$$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; S(O)$_2$NR$^\circ$$_2$; —(CH$_2$)$_{0-4}$S(O) R$^\circ$; —N(R$^\circ$)S(O)$_2$NR$^\circ$$_2$; —N(R$^\circ$)S(O)$_2$R$^\circ$; —N(OR$^\circ$)R$^\circ$; —C(NH)NR$^\circ$$_2$; —P(O)$_2$R$^\circ$; —P(O)R$^\circ$$_2$; —OP(O)R$^\circ$$_2$; —OP(O)(OR$^\circ$)$_2$; SiR$^\circ$$_3$; —(C$_{1-4}$ straight or branched) alkylene) O—N(R$^\circ$)$_2$; or —(C$_{1-4}$ straight or branched)alkylene)C(O)O—N(R$^\circ$)$_2$, wherein each R$^\circ$may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$(or the ring formed by taking two independent occurrences of R$^\circ$together with their intervening atoms), are independently halogen, —(CH$_2$)$_{0-2}$ R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$ C(O)R$^\bullet$, —(CH$_2$)$_{0-2}$C(O)OH, —(CH$_2$)$_{0-2}$C(O) OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$ NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R$^*$$_2$))$_{2-3}$O—, or —S(C(R$^*$$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O) R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R†)S(O)₂R†; wherein each R† is independently hydrogen, C₁₋₆ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH₂, —NHR•, —NR•₂, or —NO₂, wherein each R• is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides—including chloro, bromo, and iodo- and pseudohalides (sulfonate esters)—including triflate, mesylate, tosylate, and brosylate. It is also contemplated that a hydroxyl moiety can be converted into a leaving group via Mitsunobu reaction.

The term "protecting group" means a group which protects one or more functional groups of a compound giving rise to a protected derivative of the specified compound. Functional groups which may be protected include, by way of example, amino groups, hydroxyl groups, and the like. Protecting groups are well-known to those skilled in the art and are described, for example, in T. W. Greene and G. M. Wuts, Protecting Groups in Organic Synthesis, Third Edition, Wiley, New York, 1999, and references cited therein.

The term "amino-protecting group" means a protecting group suitable for preventing undesired reactions at an amino group, include, but are not limited to, tert-butoxycarbonyl (BOC), trityl (Tr), benzyloxycarbonyl (Cbz), 9-fluorenylmethoxycarbonyl (FMOC), formyl, trimethylsilyl (TMS), tert-butyldimethylsilyl (TBS), benzyl, p-methoxybenzyl, p-fluorobenzyl, p-chlorobenzyl, p-bromobenzyl, diphenylmethyl naphtylmethyl, and the like.

The term "hydroxyl-protecting group" means a protecting group suitable for preventing undesirable reactions at a hydroxyl group. Representative hydroxyl-protecting groups include, but are not limited to, silyl groups including tri(1-6C)-alkylsilyl groups, such as trimethylsilyl (TMS), triethylsilyl (TES), tert-butyldimethylsilyl (TBS), and the like; esters (acyl groups) including (1-6C)-alkanoyl groups, such as formyl, acetyl, and the like; arylmethyl groups, such as benzyl (Bn), p-methoxybenzyl (PMB), 9-fluorenylmethyl (Fm), diphenylmethyl (benzhydryl, DPM), and the like.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

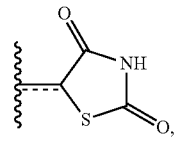

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound. For example, a compound prefixed with (−) or l meaning that the compound is levorotatory or a compound prefixed with (+) or d is dextrorotatory. For a given chemical structure, these compounds, called stereoisomers, are identical except that they are non-superimposable minor images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

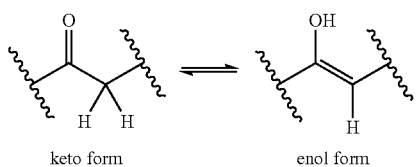

keto form        enol form

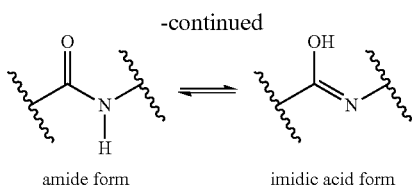

amide form  imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

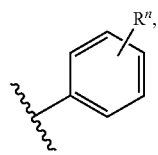

which is understood to be equivalent to a formula:

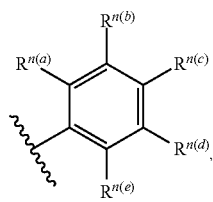

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful as inhibitors of the PI3K/Akt pathway. In a further aspect, the compounds are useful as inhibitors of protein kinase. In a still further aspect, the protein kinase is 3-phosphoinositide-dependent protein kinase 1, aurora kinase A, c-abl oncogene 1 kinase (T315I form), fms-related tyrosine kinase 3, fibroblast growth factor receptor 1, interleukin-1 receptor-associated kinase 4, Janus kinase 1, Janus kinase 2, Janus kinase 3, mitogen-activated protein kinase kinase kinase kinase 4 (MAP4K4), ret proto-oncogene, spleen tyrosine kinase, tyrosine-protein kinase Fyn, vascular endothelial growth factor receptor 2, or vascular endothelial growth factor receptor 3. In a yet further aspect, protein kinase is 3-phosphoinositide-dependent protein kinase 1. More specifically, in one aspect, the present invention relates to compounds that inhibit 3-phosphoinositide-dependent protein kinase 1 activity ("PDK1").

In one aspect, the compounds of the invention are useful in the treatment of disorders of uncontrolled cellular proliferations. In a further aspect, the disorder of uncontrolled cellular proliferation is a cancer or a tumor. In a still further aspect, the disorder of uncontrolled cellular proliferation is associated with a dysfunction in the PI3K/Akt pathway and other diseases in which a PDK1 dysfunction is involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a compound having a structure represented by a formula:

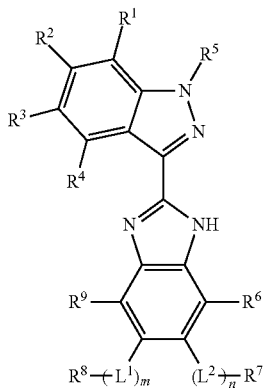

wherein $L^1$ is C=O or $(CH_2)_p$, wherein p is an integer from 1 to 3, wherein m is 0 or 1; wherein $L^2$ is C=O or $(CH_2)_q$, wherein q is an integer from 1 to 3, wherein n is 0 or 1; wherein $R^1$ is selected from hydrogen, halogen, cyano, and C1-C6 alkyl; wherein $R^2$ is selected from hydrogen, halogen, cyano, and C1-C6 alkyl; wherein $R^3$ is selected from hydrogen, $Ar^1$, NHC=$OR^{11}$, and NHC=$ONHR^{11}$; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino; wherein $R^{10}$ is selected from hydrogen and C1-C6 alkyl; wherein $R^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, C3-C6 heterocycloalkyl, and $Ar^1$; wherein $R^4$ is selected from hydrogen, $Ar^1$, $NHR^{11}$, and NHC=$ONR^{11}$, provided only one of $R^3$ and $R^4$ is not hydrogen; wherein $R^5$ is selected from hydrogen and C1-C6 alkyl; wherein $R^6$ is selected from hydrogen, halogen, and C1-C6 alkyl; wherein $R^7$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl) piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; wherein $R^8$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; and wherein $R^9$ is selected from hydrogen, halogen, and C1-C6 alkyl; or a pharmaceutically acceptable salt, hydrate, solvate, or polymorph thereof.

In a further aspect, the compound has a structure represented by a formula:

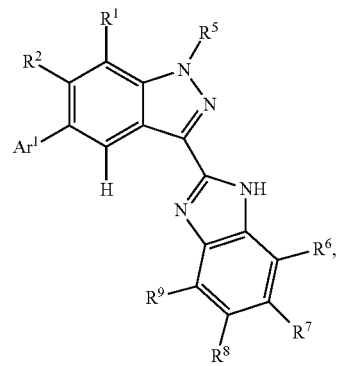

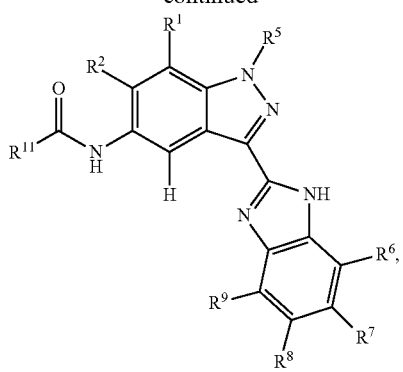
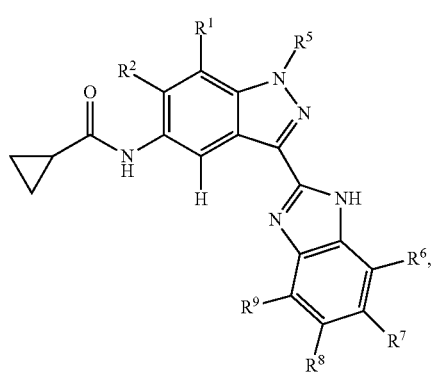
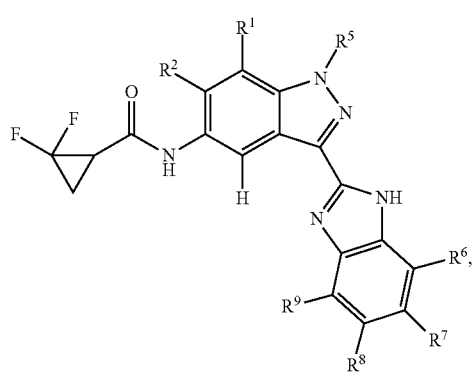
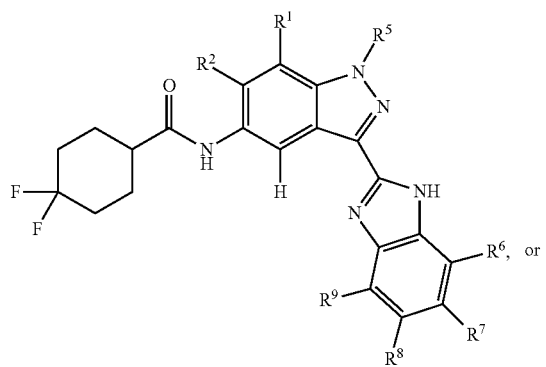
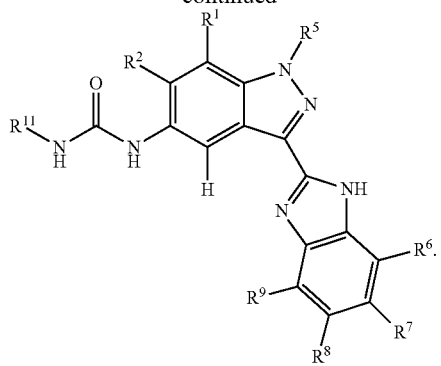
In a further aspect, the compound has a structure represented by a formula:
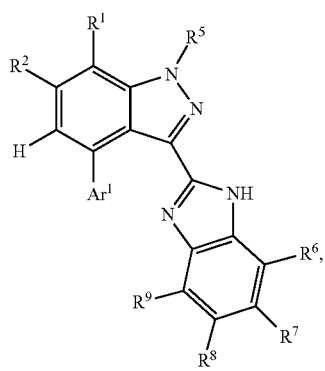
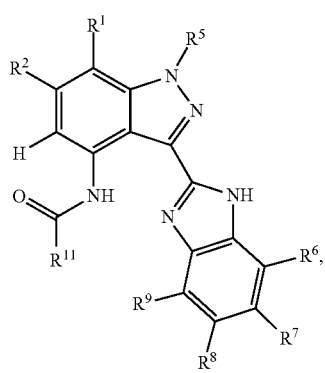
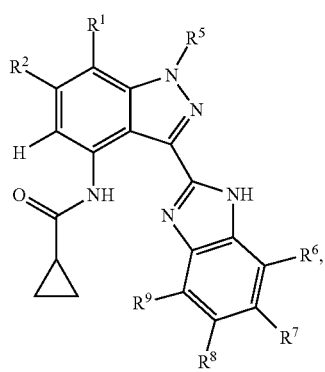

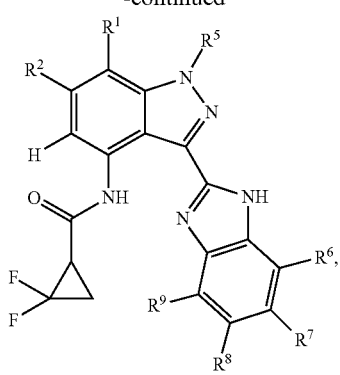
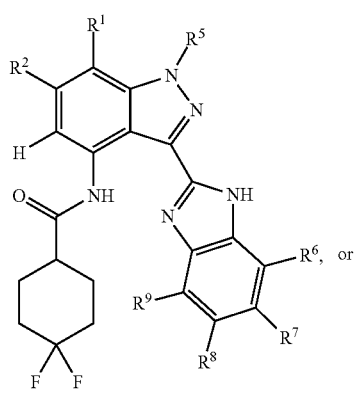
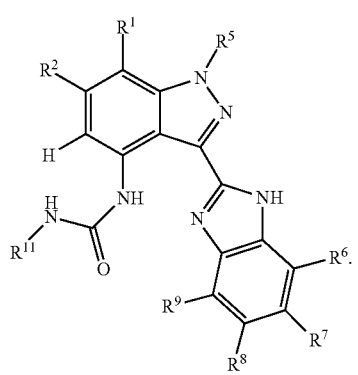
In a further aspect, the compound has a structure represented by a formula:
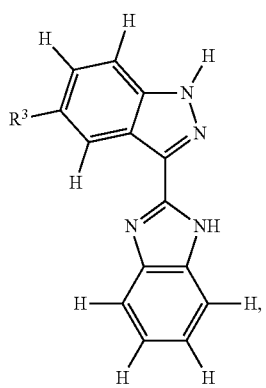
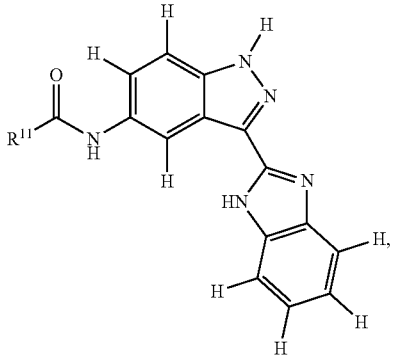
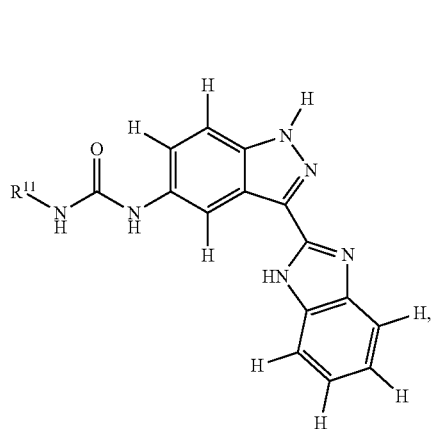
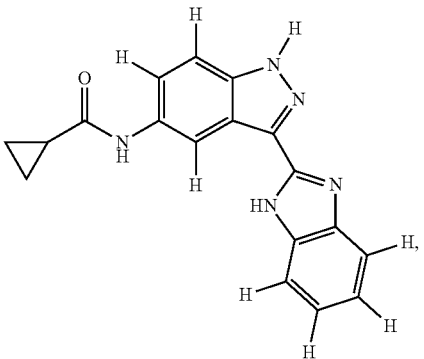
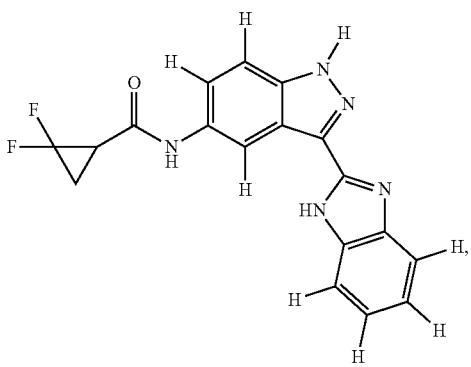

-continued
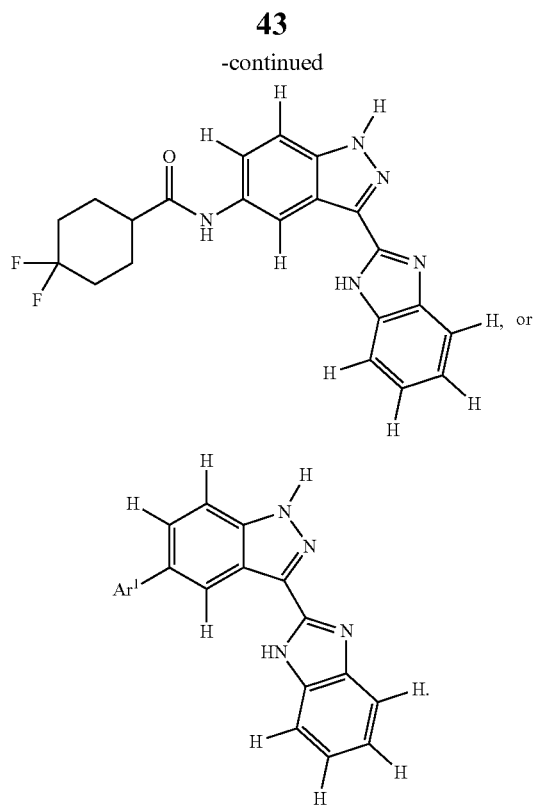
In a further aspect, the compound has a structure represented by a formula:
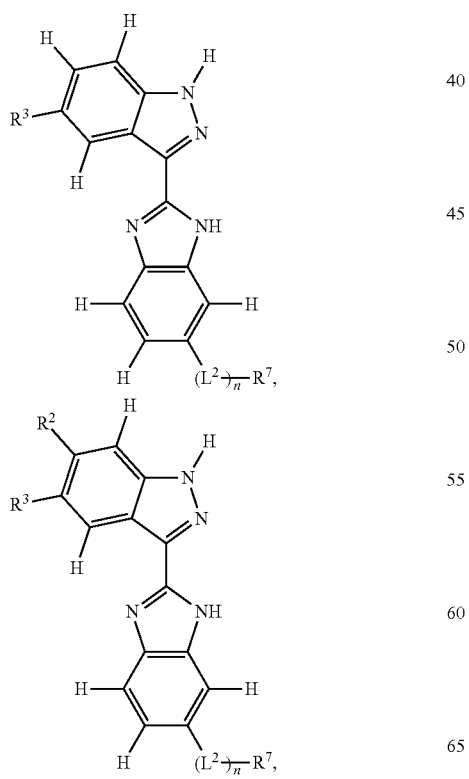
-continued
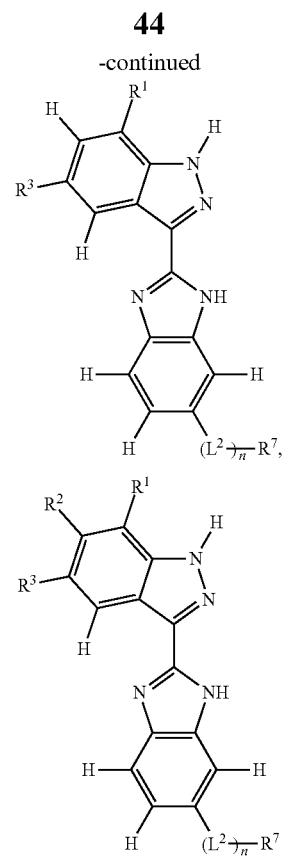
In a further aspect, the compound has a structure represented by a formula:
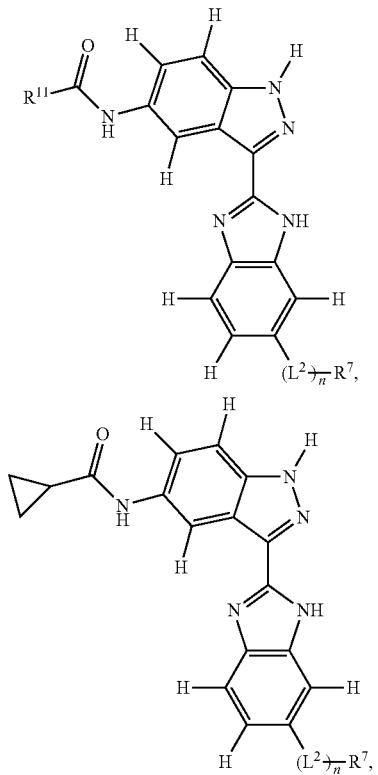

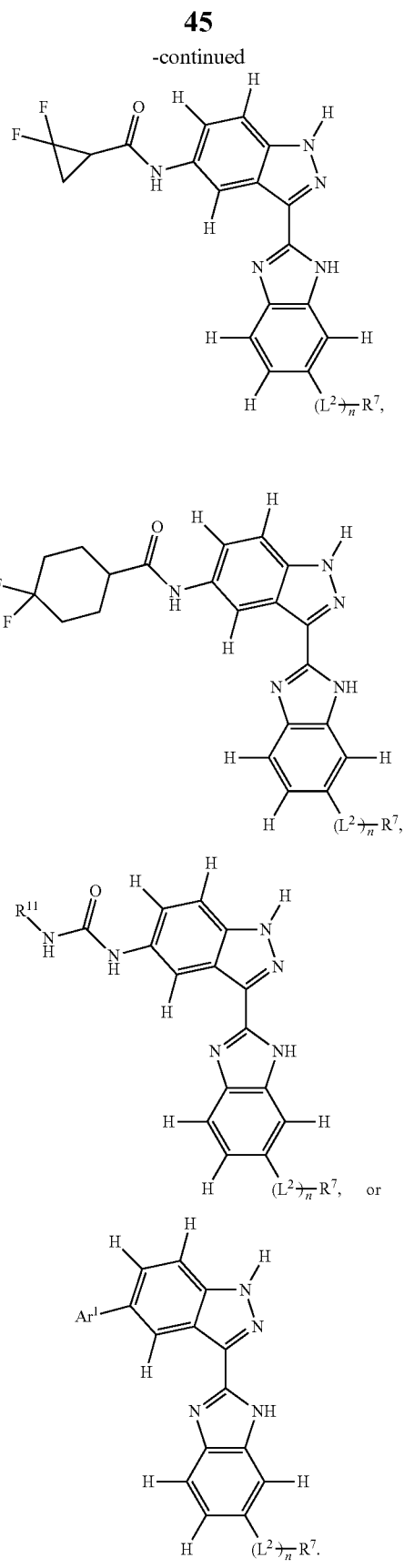
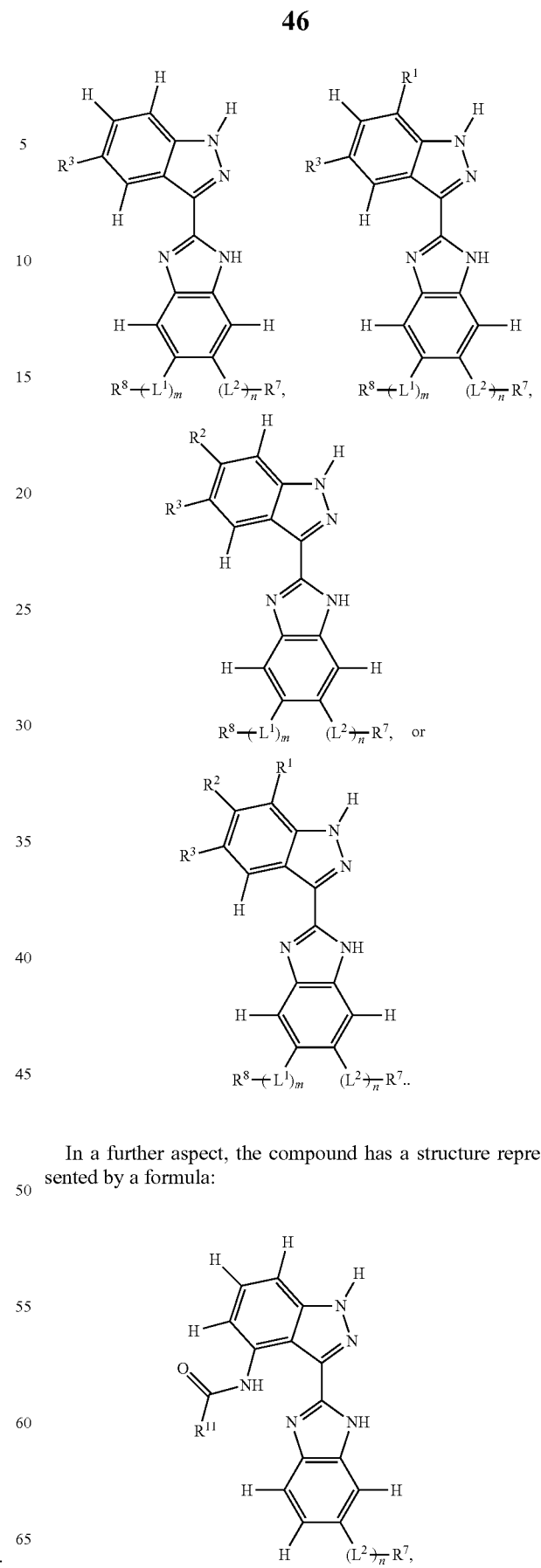
In a further aspect, the compound has a structure represented by a formula:
In a further aspect, the compound has a structure represented by a formula:

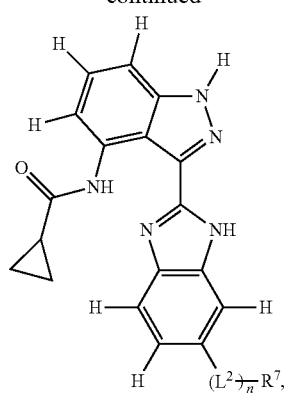
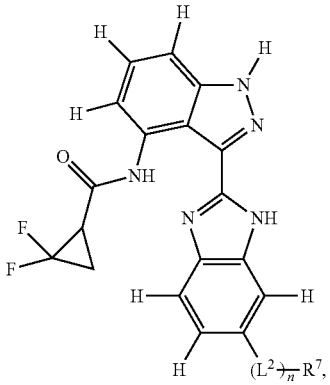
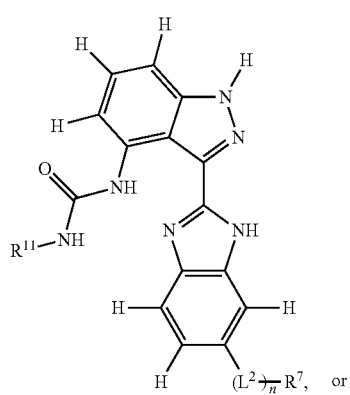
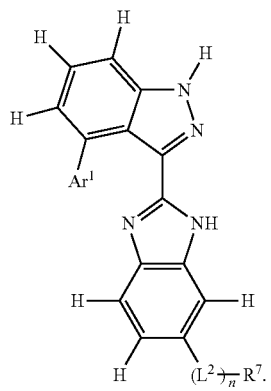
In a further aspect, the compound has a structure represented by a formula:
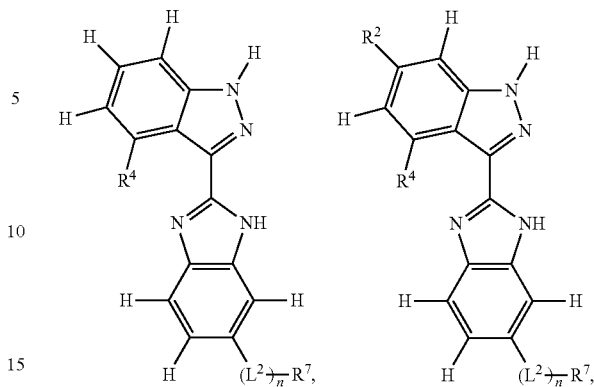
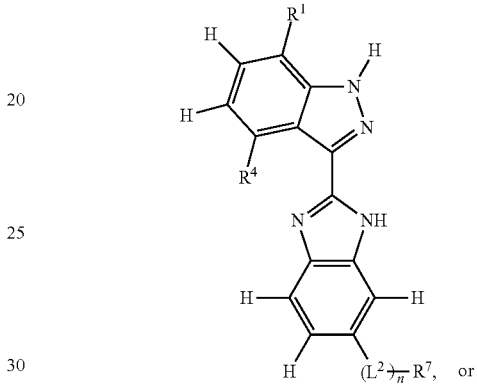
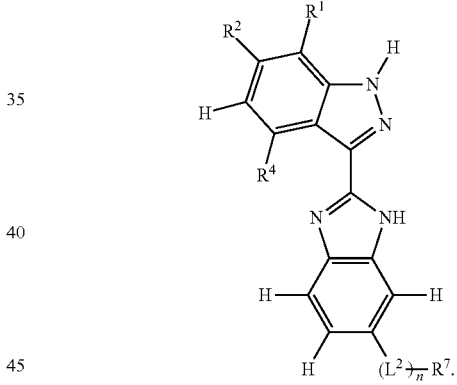
In a further aspect, the compound has a structure represented by a formula:
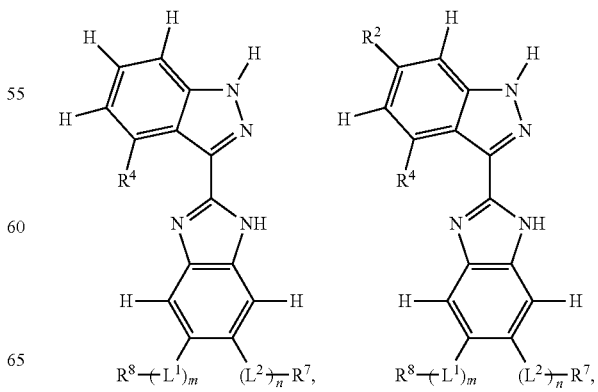

-continued
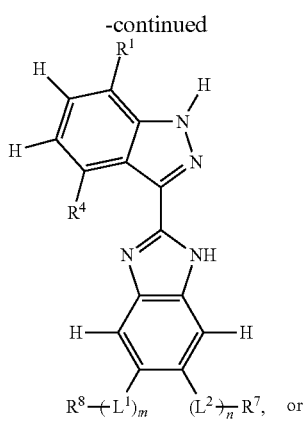
, or
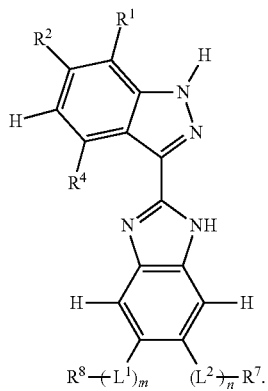
.
In a further aspect, the compound has a structure represented by a formula:
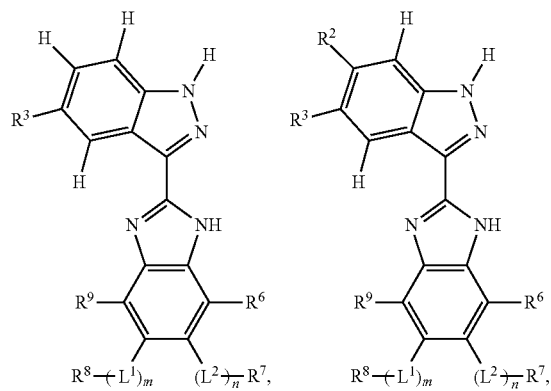
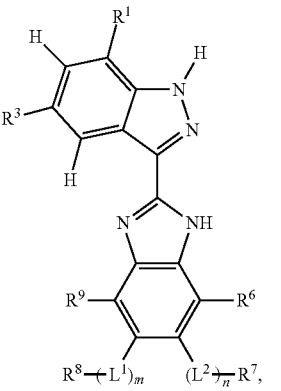
, or
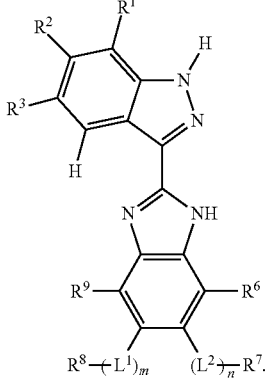
.
In a further aspect, the compound has a structure represented by a formula:
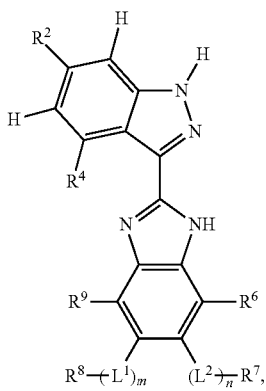
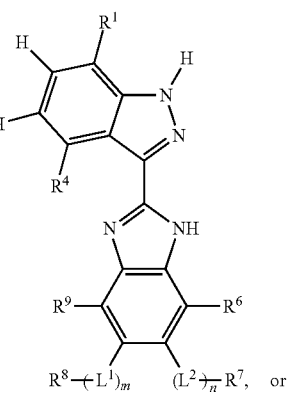
, or -continued
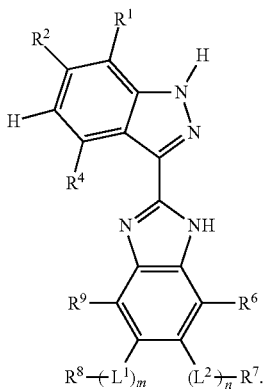
In a further aspect, the compound has a structure represented by a formula:
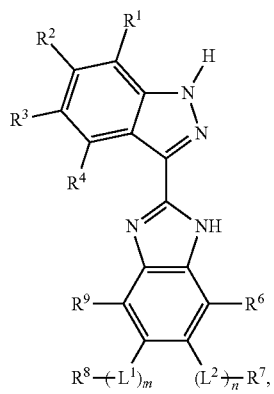
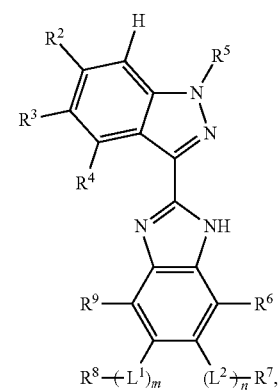
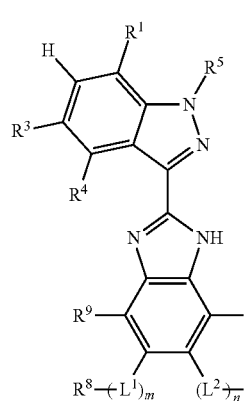
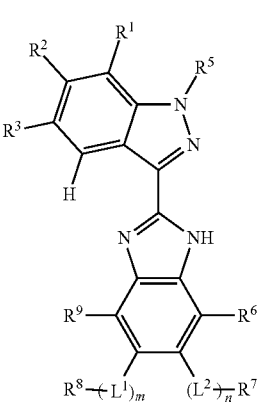 or
-continued
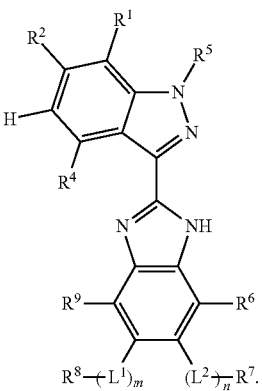
In a further aspect, the compound has a structure represented by a formula:
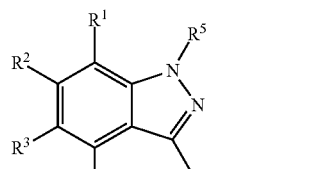
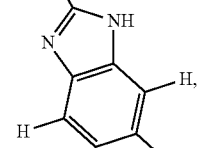
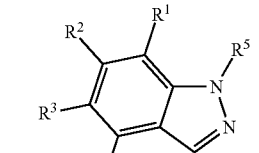
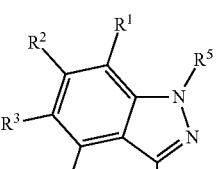, or
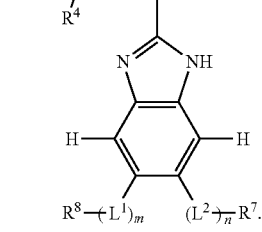

In a further aspect, the compound has a structure represented by a formula:

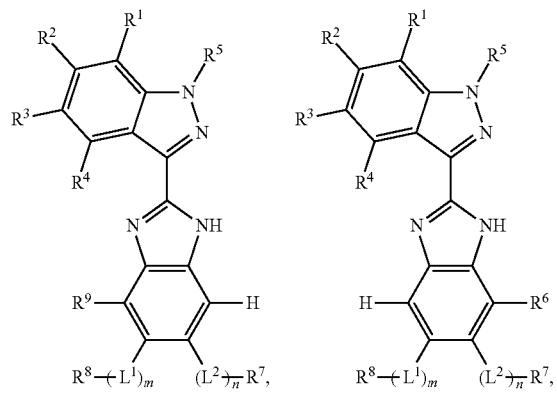

In a further aspect, the compound has a structure represented by a formula:

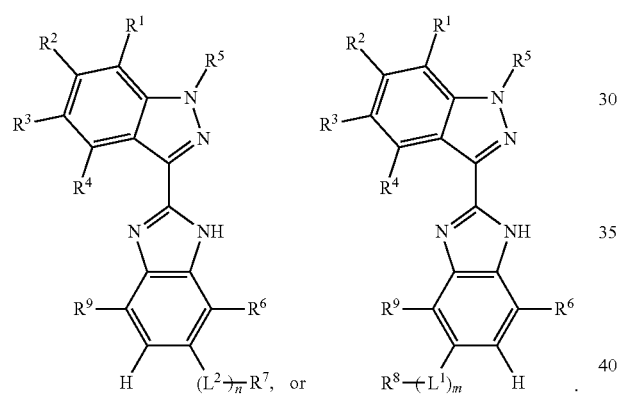

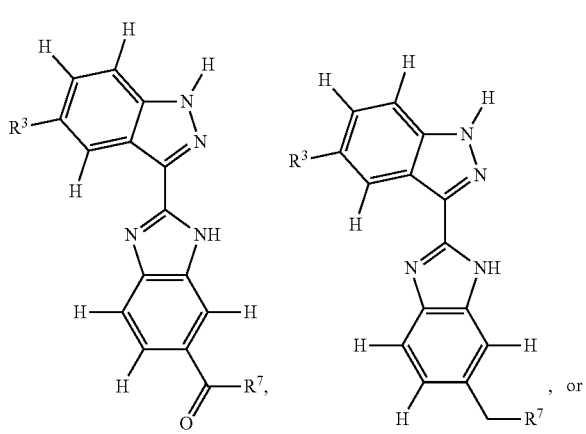

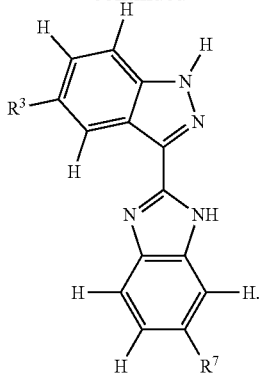

In a further aspect, the compound has a structure represented by a formula:

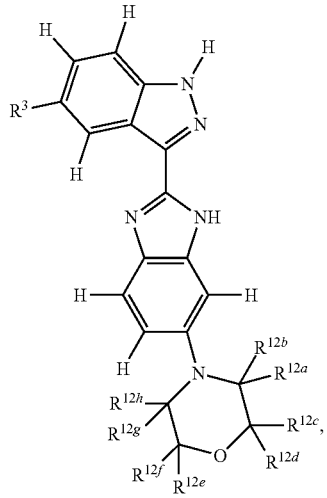

wherein 0-2 of $R^{12a}$, $R^{12b}$, $R^{12c}$, $R^{12d}$, $R^{12e}$, $R^{12f}$, $R^{12g}$, and $R^{12h}$ has a substituent independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl) piperazinyl provided that if two of $R^{12a}$, $R^{12b}$, $R^{12c}$, $R^{12d}$, $R^{12e}$, $R^{12f}$, $R^{12g}$, and $R^{12h}$ have substituents, then they must be geminally substituted and each of $R^{12a}$, $R^{12b}$, $R^{12c}$, $R^{12d}$, $R^{12e}$, $R^{12f}$, $R^{12g}$, and $R^{12h}$ that does not have a substituent is hydrogen.

In a further aspect, the compound has a structure represented by a formula:

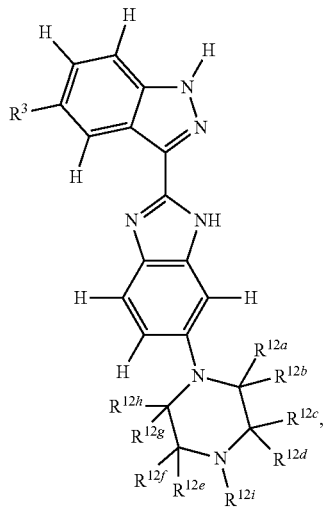

wherein each of $R^{12a}$, $R^{12b}$, $R^{12c}$, $R^{12d}$, $R^{12e}$, $R^{12f}$, $R^{12g}$, and $R^{12h}$ is independently selected from hydrogen, halogen, cyano, C1-C6 alkyl, C1-C6 alkoxy, C1-C6 haloalkyl, C1-C6 polyhaloalkyl, and wherein $R^{12i}$ is selected from hydrogen, halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl, provided that no more than two of $R^{12a}$, $R^{12b}$, $R^{12c}$, $R^{12d}$, $R^{12e}$, $R^{12f}$, $R^{12g}$, $R^{12h}$, and $R^{12i}$ are not hydrogen.

In a further aspect, the compound has a structure represented by a formula:

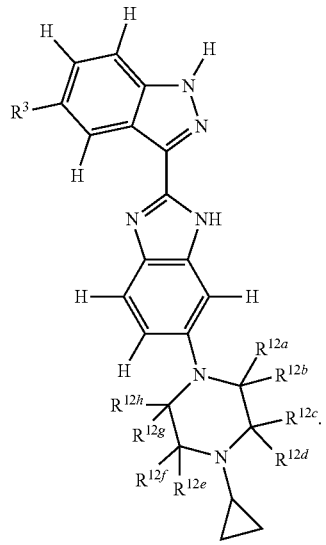

In a further aspect, the compound has a structure represented by a formula:

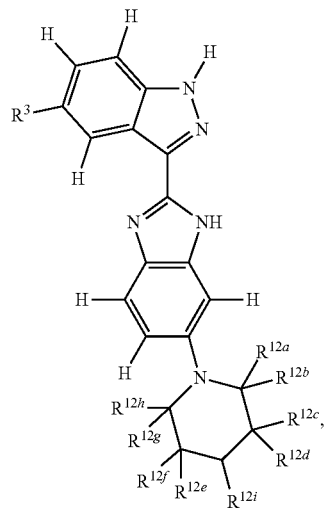

wherein each of $R^{12a}$, $R^{12b}$, $R^{12c}$, $R^{12d}$, $R^{12e}$, $R^{12f}$, $R^{12g}$, and $R^{12h}$ is independently selected from hydrogen, halogen, cyano, C1-C6 alkyl, C1-C6 alkoxy, C1-C6 haloalkyl, C1-C6 polyhaloalkyl, and wherein $R^{12i}$ is selected from hydrogen, halogen, cyano, C1-C6 alkyl, C3-C6 cycloalkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl, provided that no more than two of $R^{12a}$, $R^{12b}$, $R^{12c}$, $R^{12d}$, $R^{12e}$, $R^{12f}$, $R^{12g}$, $R^{12h}$, and $R^{12i}$ are not hydrogen.

In a further aspect, the compound has a structure represented by a formula:

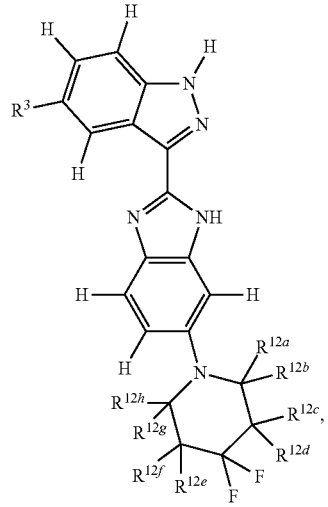

-continued

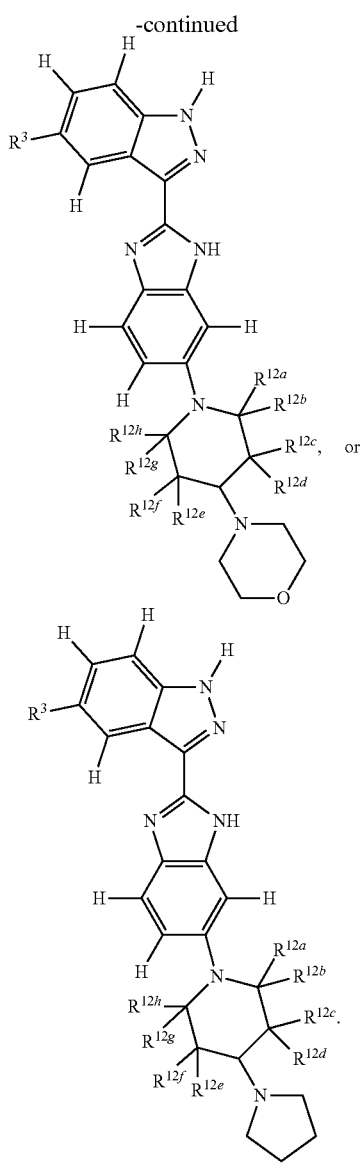

In a further aspect, the compound has a structure represented by a formula:

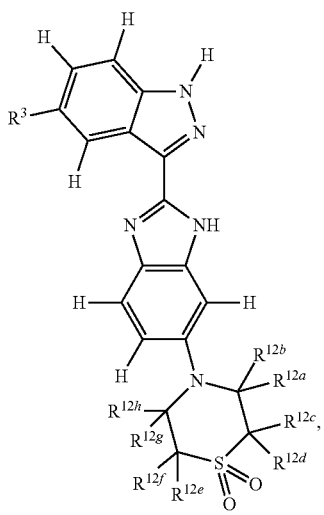

wherein 0-2 of $R^{12a}$, $R^{12b}$, $R^{12c}$, $R^{12d}$, $R^{12e}$, $R^{12f}$, $R^{12g}$, and $R^{12h}$ has a substituent independently selected from halogen, cyano, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl, provided that no more than two of $R^{12a}$, $R^{12b}$, $R^{12c}$, $R^{12d}$, $R^{12e}$, $R^{12f}$, $R^{12g}$, $R^{12h}$, and $R^{12i}$ are not hydrogen.

In a further aspect, the compound has a structure represented by a formula:

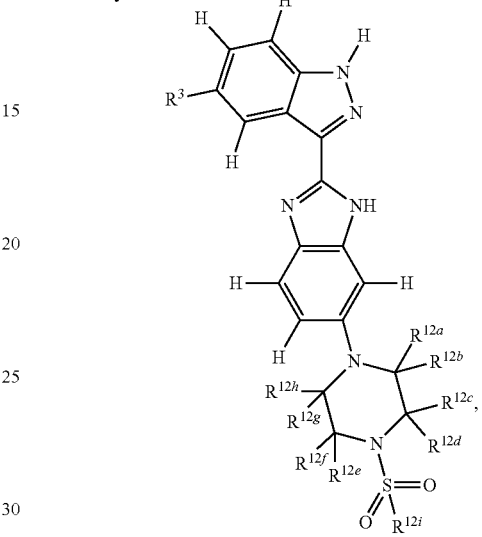

wherein each of $R^{12a}$, $R^{12b}$, $R^{12c}$, $R^{12d}$, $R^{12e}$, $R^{12f}$, $R^{12g}$, and $R^{12h}$ is independently selected from hydrogen, halogen, cyano, C1-C6 alkyl, C1-C6 alkoxy, C1-C6 haloalkyl, C1-C6 polyhaloalkyl, and wherein $R^{12i}$ is selected from hydrogen, C1-C6 alkyl, C1-C6 alkoxy, C1-C6 haloalkyl, C1-C6 polyhaloalkyl, C3-C6 cycloalkyl and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl, provided that no more than two of $R^{12a}$, $R^{12b}$, $R^{12c}$, $R^{12d}$, $R^{12e}$, $R^{12f}$, $R^{12g}$, $R^{12h}$ and $R^{12i}$ are not hydrogen.

In a further aspect, the compound has a structure represented by a formula:

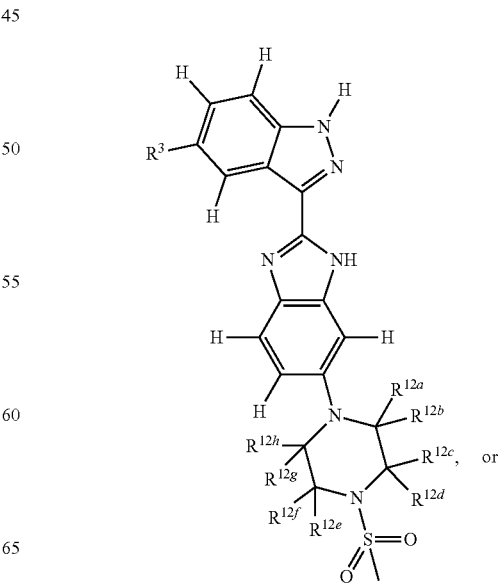

-continued

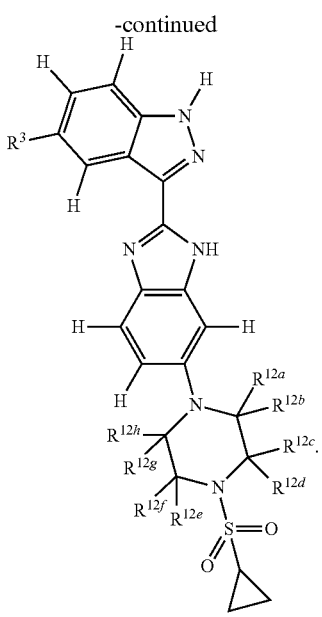

In a further aspect, the compound has a structure represented by a formula:

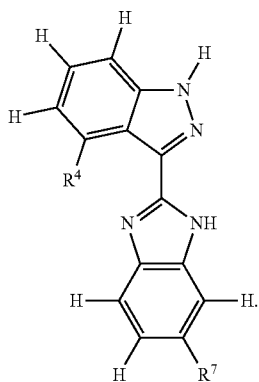

In a further aspect, the compound has a structure represented by a formula:

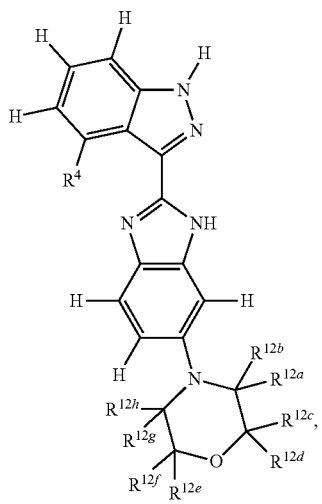

wherein 0-2 of $R^{12a}$, $R^{12b}$, $R^{12c}$, $R^{12d}$, $R^{12e}$, $R^{12f}$, $R^{12g}$, and $R^{12h}$ has a substituent independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl provided that if two of $R^{12a}$, $R^{12b}$, $R^{12c}$, $R^{12d}$, $R^{12e}$, $R^{12f}$, $R^{12g}$, and $R^{12h}$ have substituents, then they must be geminally substituted and each of $R^{12a}$, $R^{12b}$, $R^{12c}$, $R^{12d}$, $R^{12e}$, $R^{12f}$, $R^{12g}$, and $R^{12h}$ that does not have a substituent is hydrogen.

In a further aspect, the compound has a structure represented by a formula:

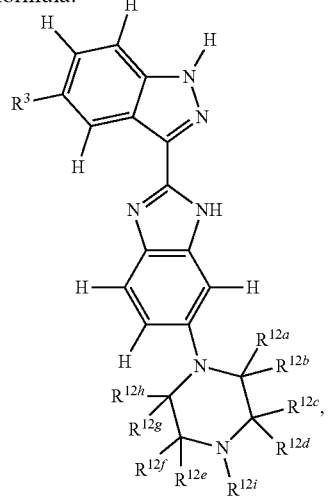

wherein each of $R^{12a}$, $R^{12b}$, $R^{12c}$, $R^{12d}$, $R^{12e}$, $R^{12f}$, $R^{12g}$, and $R^{12h}$ is independently selected from hydrogen, halogen, cyano, C1-C6 alkyl, C1-C6 alkoxy, C1-C6 haloalkyl, C1-C6 polyhaloalkyl, and wherein $R^{12i}$ is selected from hydrogen, halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl, provided that no more than two of $R^{12a}$, $R^{12b}$, $R^{12c}$, $R^{12d}$, $R^{12e}$, $R^{12f}$, $R^{12g}$, $R^{12h}$, and $R^{12i}$ are not hydrogen.

In a further aspect, the compound has a structure represented by a formula:

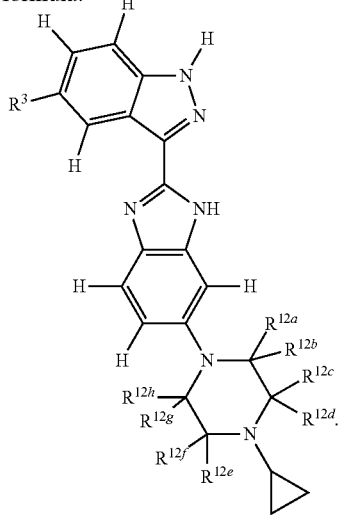

In a further aspect, the compound has a structure represented by a formula:

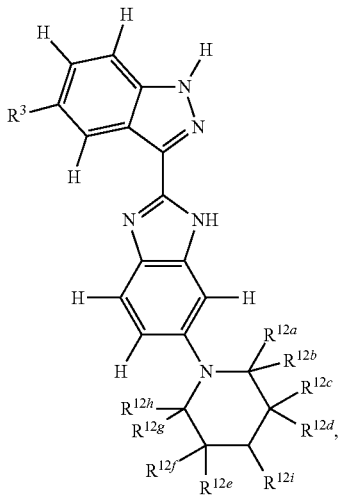

wherein each of $R^{12a}$, $R^{12b}$, $R^{12c}$, $R^{12d}$, $R^{12e}$, $R^{12f}$, $R^{12g}$, and $R^{12h}$ is independently selected from hydrogen, halogen, cyano, C1-C6 alkyl, C1-C6 alkoxy, C1-C6 haloalkyl, C1-C6 polyhaloalkyl, and wherein $R^{12i}$ is selected from hydrogen, halogen, cyano, C1-C6 alkyl, C3-C6 cycloalkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl, provided that no more than two of $R^{12a}$, $R^{12b}$, $R^{12c}$, $R^{12d}$, $R^{12e}$, $R^{12f}$, $R^{12g}$, $R^{12h}$, and $R^{12i}$ are not hydrogen.

In a further aspect, the compound has a structure represented by a formula:

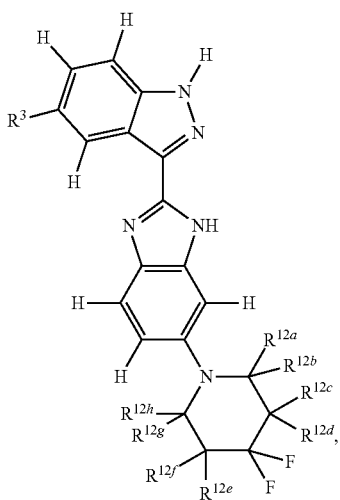

In a further aspect, the compound has a structure represented by a formula:

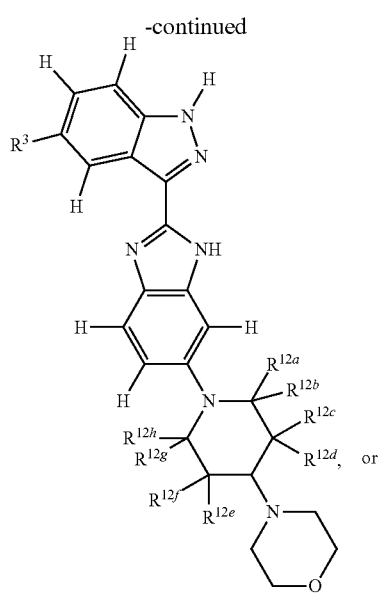

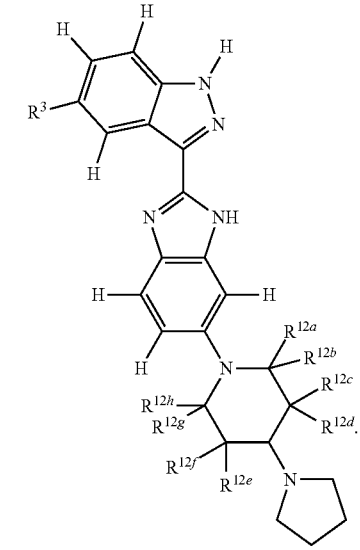

In a further aspect, the compound has a structure represented by a formula:

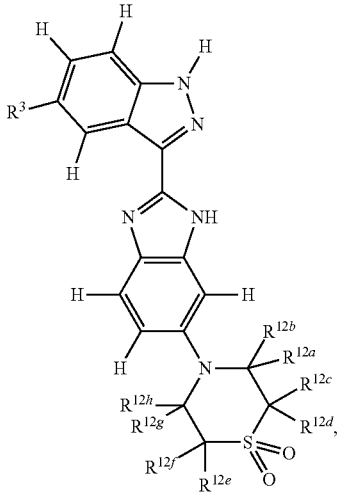

wherein 0-2 of $R^{12a}$, $R^{12b}$, $R^{12c}$, $R^{12d}$, $R^{12e}$, $R^{12f}$, $R^{12g}$, and $R^{12h}$ has a substituent independently selected from halogen, cyano, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl, provided that no more than two of $R^{12a}$, $R^{12b}$, $R^{12c}$, $R^{12d}$, $R^{12e}$, $R^{12f}$, $R^{12g}$, $R^{12h}$, and $R^{12i}$ are not hydrogen.

In a further aspect, the compound has a structure represented by a formula:

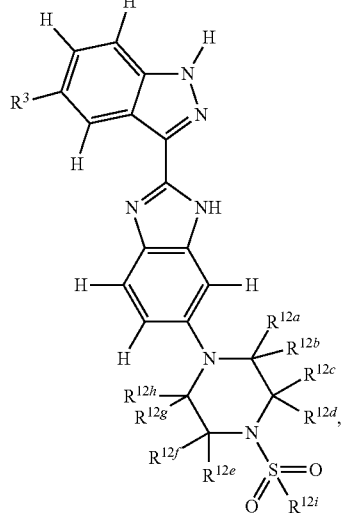

wherein each of $R^{12a}$, $R^{12b}$, $R^{12c}$, $R^{12d}$, $R^{12e}$, $R^{12f}$, $R^{12g}$, and $R^{12h}$ is independently selected from hydrogen, halogen, cyano, C1-C6 alkyl, C1-C6 alkoxy, C1-C6 haloalkyl, C1-C6 polyhaloalkyl, and wherein $R^{12i}$ is selected from hydrogen, C1-C6 alkyl, C1-C6 alkoxy, C1-C6 haloalkyl, C1-C6 polyhaloalkyl, C3-C6 cycloalkyl and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl, provided that no more than two of $R^{12a}$, $R^{12b}$, $R^{12c}$, $R^{12d}$, $R^{12e}$, $R^{12f}$, $R^{12g}$, $R^{12h}$ and $R^{12i}$ are not hydrogen.

In a further aspect, the compound has a structure represented by a formula:

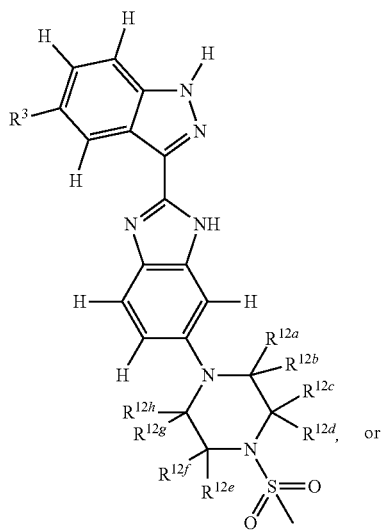

or

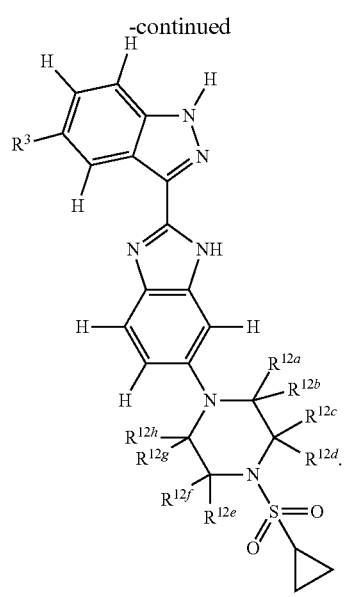

a. AR¹ Groups

In one aspect, $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino.

In a further aspect, $Ar^1$ is unsubstituted. In a still further aspect, $Ar^1$ has 1, 2 or 3 substituents.

In a further aspect, $Ar^1$ is phenyl. In a still further aspect, $Ar^1$ is phenyl substituted with 1-3 substituents independently selected from cyano, C1-C6 alkyl, C1-C6 haloalkyoxy, C1-C6 haloalkyl, C1-C6 polyhaloalkyl, C1-C6 cyanoalkyl, $SO_2R^{10}$, C1-C3 alkyl, C1-C3 alkylamine, and C1-C3 dialkylamino. In a yet further aspect, $Ar^1$ is phenyl substituted with 0-3 substituents independently selected from cyano, C1-C6 haloalkyoxy, C1-C6 haloalkyl, C1-C6 polyhaloalkyl, C1-C6 cyanoalkyl, and $SO_2R^{10}$. In an even further aspect, $Ar^1$ is phenyl monosubstituted with a substituent selected from cyano, C1-C6 haloalkyoxy, C1-C6 haloalkyl, C1-C6 polyhaloalkyl, C1-C6 cyanoalkyl, and $SO_2R^{10}$.

In a further aspect, $Ar^1$ is heteroaryl. In a still further aspect, $Ar^1$ is pyridinyl, pyridazinyl, pyrimidinyl, or pyrazinyl. In a yet further aspect, $Ar^1$ is pyridinyl, pyridazinyl, pyrimidinyl, or pyrazinyl substituted with 0-3 substituents independently selected from halo, cyano, C1-C6 alkyl, C1-C6 haloalkyoxy, C1-C6 haloalkyl, C1-C6 polyhaloalkyl, C1-C6 cyanoalkyl, $SO_2R^{10}$, C1-C3 alkyl, C1-C3 alkylamine, and C1-C3 dialkylamino. In an even further aspect, $Ar^1$ is heteroaryl substituted with 0-3 substituents independently selected from halo, cyano, C1-C6 alkyl, C1-C6 haloalkyoxy, C1-C6 haloalkyl, C1-C6 polyhaloalkyl, C1-C6 cyanoalkyl, $SO_2R^{10}$. In a still further aspect, $Ar^1$ is heteroaryl substituted with 0-3 substituents independently selected from halo, cyano, C1-C6 haloalkyoxy, C1-C6 haloalkyl, C1-C6 polyhaloalkyl, C1-C6 cyanoalkyl, and $SO_2R^{10}$. In a yet further aspect, $Ar^1$ is heteroaryl monosubstituted with a substituent selected from halo, cyano, C1-C6 haloalkyoxy, C1-C6 haloalkyl, C1-C6 polyhaloalkyl, C1-C6 cyanoalkyl, and $SO_2R^{10}$.

b. $L^1$ Groups

In one aspect, $L^1$ is C=O or $(CH_2)_p$, wherein p is an integer from 1 to 3, wherein m is 0 or 1. In a further aspect, $L^1$ is C=O. In a still further aspect, $L^1$ is $CH_2$ and p is 1.

In a further aspect, m is 0 and n is 1. In a yet further aspect, both m and n are 0. In still further aspect, m is 0.

C. $L^2$ Groups

In one aspect, $L^2$ is C=O or $(CH_2)_q$, wherein q is an integer from 1 to 3, wherein n is 0 or 1. In a further aspect, $L^2$ is C=O. In a still further aspect, $L^2$ is $CH_2$ and q is 1. In a yet further aspect, n is 0.

d. $R^1$ Groups

In one aspect, $R^1$ is selected from hydrogen, halogen, cyano, and C1-C6 alkyl.

In a further aspect, $R^1$ is selected from hydrogen, halogen, and cyano. In a still further aspect, $R^1$ is selected from hydrogen and C1-C6 alkyl. In a yet further aspect, $R^1$ is selected from halogen, cyano and C1-C6 alkyl. In an even further aspect, $R^1$ is C1-C6 alkyl In a further aspect, $R^1$ is selected from hydrogen and halogen. In a still further aspect, the halogen is fluoro or chloro. In a yet further aspect, the halogen is fluoro.

In a further aspect, $R^1$ is hydrogen. In a still further aspect, $R^1$ and $R^2$ are hydrogen. In a yet further aspect, $R^1$ and $R^3$ are hydrogen. In an even further aspect, $R^1$ and $R^4$ are hydrogen. In a still further aspect, $R^1$ and $R^5$ are hydrogen.

In a further aspect, $R^1$, $R^2$, and $R^3$ are hydrogen. In an even further aspect, $R^1$, $R^2$, and $R^4$ are hydrogen. In a still further aspect, $R^1$, $R^2$, and $R^5$ are hydrogen. In a yet further aspect, $R^1$, $R^4$ and $R^5$ are hydrogen. In an even further aspect, $R^1$, $R^2$, $R^4$ and $R^5$ are hydrogen. In a yet further aspect, $R^1$, $R^2$, $R^4$, $R^5$ and $R^6$ are hydrogen.

In a further aspect, $R^1$, $R^2$, $R^4$, $R^5$, $R^6$ and $R^8$ are hydrogen. In an even further aspect, $R^1$, $R^2$, $R^4$, $R^5$, $R^6$, $R^8$ and $R^9$ are hydrogen. In a still further aspect, $R^1$, $R^4$, $R^5$, $R^6$, $R^8$ and $R^9$ are hydrogen. In a yet further aspect, $R^1$, $R^2$, $R^5$, $R^6$, $R^8$ and $R^9$ are hydrogen. In an even further aspect, $R^1$, $R^2$, $R^4$, $R^6$, $R^8R$ and $R^9$ are hydrogen. In a still further aspect, $R^1$, $R^2$, $R^4$, $R^5$, $R^8$ and $R^9$ are hydrogen. In a yet further aspect, $R^1$, $R^2$, $R^4$, $R^5$, $R^6$ and $R^9$ are hydrogen. In an even further aspect, $R^1$, $R^2$, $R^4$, $R^5$, $R^6$ and $R^8$ are hydrogen.

In a further aspect, $R^1$, $R^2$, $R^3$ and $R^5$ are hydrogen. In a still further aspect, $R^1$, $R^2$, $R^3$, $R^5$ and $R^6$ are hydrogen. In an even further aspect, $R^1$, $R^2$, $R^3$, $R^5$, $R^6$ and $R^8$ are hydrogen. In a yet further aspect, $^1$, $R^2$, $R^3$, $R^5$, $R^6$, $R^8$ and $R^9$ are hydrogen. In a still further aspect, $R^1$, $R^3$, $R^5$, $R^6$, $R^8$ and $R^9$ are hydrogen. In a yet further aspect, $R^1$, $R^2$, $R^5$, $R^6$, $R^8$ and $R^9$ are hydrogen. In an even further aspect, $R^1$, $R^2$, $R^3$, $R^6$, $R^8$ and $R^9$ are hydrogen. In a still further aspect, $R^1$, $R^2$, $R^3$, $R^5$, $R^8$ and $R^9$ are hydrogen. In a yet further aspect, $R^1$, $R^2$, $R^3$, $R^5$, $R^6$ and $R^9$ are hydrogen. In an even further aspect, $R^1$, $R^2$, $R^3$, $R^5$, $R^6$ and $R^8$ are hydrogen.

In a further aspect, $R^1$, $R^2$, $R^3$, and $R^6$ are hydrogen. In a still further aspect, $R^1$, $R^2$, $R^3$, $R^6$ and $R^8$ are hydrogen. In a yet further aspect, $R^1$, $R^2$, $R^3$, $R^6$, $R^8$ and $R^9$ are hydrogen. In an even further aspect, $R^1$, $R^3$, $R^6$, $R^8$ and $R^9$ are hydrogen. In a yet further aspect, $R^1$, $R^2$, $R^6$, $R^8$ and $R^9$ are hydrogen. In a still further aspect, $R^1$, $R^2$, $R^3$, $R^8$ and $R^9$ are hydrogen. In a yet further aspect, $R^1$, $R^2$, $R^3$, $R^6$ and $R^9$ are hydrogen. In an even further aspect, $R^1$, $R^2$, $R^3$, $R^6$ and $R^8$ are hydrogen.

e. $R^2$ Groups

In one aspect, $R^2$ is selected from hydrogen, halogen, cyano, and C1-C6 alkyl. In a further aspect, $R^2$ is hydrogen. In a still further aspect, halogen is fluoro or chloro. In an even further aspect, halogen is chloro. In a yet further aspect, halogen is fluoro.

In a further aspect, $R^2$ and $R^3$ are hydrogen. In a still further aspect, each of $R^2$ and $R^4$ are hydrogen. In a yet further aspect, $R^2$ and $R^5$ are hydrogen. In an even further aspect, $R^2$, $R^3$ and $R^5$ are hydrogen. In a still further aspect, $R^2$, $R^4$ and $R^5$ are hydrogen.

In a further aspect, $R^2$ is selected from hydrogen, halogen, and cyano. In a still further aspect, $R^2$ is selected from hydrogen and C1-C6 alkyl. In a yet further aspect, $R^2$ is selected from halogen, cyano and C1-C6 alkyl. In an even further aspect, $R^2$ is C1-C6 alkyl. In a yet further aspect, $R^2$ is selected from hydrogen and halogen.

f. $R^3$ Groups

In one aspect, $R^3$ is selected from hydrogen, $Ar^1$, NHC=$OR^{11}$, and NHC=$ONHR^{11}$. In a further aspect, $R^3$ is hydrogen. In a still further aspect, $R^3$ and $R^5$ are hydrogen.

In a further aspect, $R^3$ is selected from NHC=$OR^{11}$ and NHC=$ONHR^{11}$. In a still further aspect, $R^3$ is $Ar^1$. In a yet further aspect, $R^3$ is NHC=$OR^{11}$. In an even further aspect, $R^3$ is NHC=$ONHR^{11}$.

g. $R^4$ Groups

In one aspect, $R^4$ is selected from hydrogen, $Ar^1$, $NHR^{11}$, and NHC=$ONR^{11}$, provided only one of $R^3$ and $R^4$ is not hydrogen. In a further aspect, $R^4$ is hydrogen. In a yet further aspect, $R^4$ and $R^5$ are hydrogen.

In a further aspect, $R^4$ is selected from NHC=$OR^{11}$ and NHC=$ONHR^{11}$. In a yet further aspect, $R^4$ is $Ar^1$. In a still further aspect, $R^4$ is NHC=$OR^{11}$. In a yet further aspect, $R^4$ is NHC=$ONHR^{11}$.

h. $R^5$ Groups

In one aspect, $R^5$ is selected from hydrogen and C1-C6 alkyl. In a further aspect, $R^5$ is hydrogen. In a still further aspect, $R^5$ is selected from C1-C6 alkyl. In a yet further aspect, $R^5$ is selected from hydrogen, methyl, and ethyl.

1. $R^6$ Groups

In one aspect, $R^6$ is selected from hydrogen, halogen, and C1-C6 alkyl. In a further aspect, $R^6$ is halogen. In a still further aspect, halogen is fluoro or chloro. In a yet further aspect, halogen is fluoro. In an even further aspect, halogen is chloro.

In a further aspect, $R^6$ is hydrogen. In a still further aspect, $R^6$ and $R^9$ are hydrogen. In a yet further aspect, $R^6$ and $R^7$ are hydrogen. In an even further aspect, $R^6$ and $R^8$ are hydrogen. In a still further aspect, $R^6$, $R^7$ and $R^9$ are hydrogen. In a yet further aspect, $R^6$, $R^8$ and $R^9$ are hydrogen.

In a further aspect, $R^6$ is selected from hydrogen and halogen. In a still further aspect, $R^6$ is selected form hydrogen, halogen, methyl, ethyl and propyl. In a yet further aspect, $R^6$ is selected form hydrogen and C1-C6 alkyl.

j. $R^7$ Groups

In one aspect, $R^7$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl;

wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrrollidinyl, oxazolidinyl, imidazolidinyl, pyrazolidinyl, thiomorpholinyl 1,1-dioxide; and 1-(alkylsulfonyl)piperazinyl.

In a further aspect, $R^7$ is halogen. In a still further aspect, halogen is fluoro. In a yet further aspect, halogen is chloro. In an even further aspect, halogen is fluoro or chloro.

In a further aspect, $R^7$ is hydrogen. In a still further aspect, one of $R^7$ and $R^8$ is hydrogen. In a yet further aspect, $R^7$ and $R^9$ are hydrogen.

In a further aspect, $R^7$ is selected from hydrogen, halogen, cyano, and C1-C6 alkyl. In a still further aspect, $R^7$ is selected from hydrogen, halogen, and cyano. In a yet further aspect, $R^7$ is selected from hydrogen, halogen, cyano, methyl, ethyl, and propyl. In an even further aspect, $R^7$ is selected from hydrogen, halogen, cyano, and C3-C6 heterocycloalkyl. In a yet further aspect, $R^7$ is selected from halogen, cyano, C1-C6 alkyl, and C3-C6 heterocycloalkyl. In a still further aspect, $R^7$ is selected from halogen, cyano, and C1-C6 alkyl. In an even further aspect, $R^7$ is selected from halogen, cyano, and C3-C6 heterocycloalkyl.

In a further aspect, the heterocycloalkyl is unsubstituted. In a still further aspect, the heterocycloalkyl is monosubstituted. In a yet further aspect, the heterocycloalkyl is disubstituted. In an even further aspect, the heterocycloalkyl is selected from unsubstituted, monosubstituted and disubstituted aziridinyl. In a still further aspect, the heterocycloalkyl is selected from unsubstituted, monosubstituted, and geminally disubstituted morpholinyl. In a yet further aspect, the heterocycloalkyl is selected from unsubstituted, monosubstituted and disubstituted piperidinyl. In an even further aspect, the heterocycloalkyl is selected from unsubstituted, monosubstituted and disubstituted piperazinyl. In a yet further aspect, the heterocycloalkyl is selected from unsubstituted, monosubstituted and disubstituted thiomorpholinyl 1,1-dioxide. In a still further aspect, the heterocycloalkyl is selected from unsubstituted, monosubstituted and disubstituted 1-(C1-C6 alkylsulfonyl)piperazinyl.

In a further aspect, one of substituents of the C3-C6 heterocycloalkyl, when present, is independently selected from an optionally substituted aziridinyl, piperazinyl, morpholinyl, pyrrollidinyl, oxazolidinyl, imidazolidinyl, pyrazolidinyl, thiomorpholinyl 1,1-dioxide; and 1-(C1-C6 alkylsulfonyl) piperazinyl. In a still further aspect, the substituent is an optionally substituted aziridinyl. In yet further aspect, the substituent is an optionally substituted piperazinyl. In an even further aspect, the substituent is an optionally substituted morpholinyl. In a still further aspect, the substituent is an optionally substituted pyrrollidinyl. In a yet further aspect, the substituent is an optionally substituted thiomorpholinyl 1,1-dioxide. In an even further aspect, the substituent is an optionally substituted 1-(C1-C6 alkylsulfonyl)piperazinyl.

In a further aspect, the substituents of the C3-C6 heterocycloalkyl, when present, are independently selected from halogen, cyano, C3-C6 cycloalkyl, C1-C6 alkyl, C1-C6 alkoxy, C1-C6 haloalkyl, and C1-C6 polyhaloalkyl.

k. $R^8$ Groups

In one aspect, $R^8$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrrollidinyl, oxazolidinyl, imidazolidinyl, pyrazolidinyl, thiomorpholinyl 1,1-dioxide; and 1-(alkylsulfonyl)piperazinyl.

In a further aspect, $R^8$ is halogen. In a still further aspect, halogen is fluoro. In a yet further aspect, halogen is chloro. In an even further aspect, halogen is fluoro or chloro.

In a further aspect, $R^8$ is hydrogen. In a still further aspect, $R^8$ and $R^9$ are hydrogen. In a yet further aspect, $R^8$ is selected from hydrogen, halogen, cyano, and C1-C6 alkyl. In an even further aspect, $R^8$ is selected from hydrogen, halogen, and cyano. In a yet further aspect, $R^8$ is selected from hydrogen, halogen, cyano, methyl, ethyl, and propyl. In a still further aspect, $R^8$ is selected from hydrogen, halogen, cyano, and C3-C6 heterocycloalkyl. In an even further aspect, $R^8$ is selected from halogen, cyano, C1-C6 alkyl, and C3-C6 heterocycloalkyl. In a still further aspect, $R^8$ is selected from halogen, cyano, and C1-C6 alkyl. In a yet further aspect, $R^8$ is selected from halogen, cyano, and C3-C6 heterocycloalkyl.

In a further aspect, the heterocycloalkyl is unsubstituted. In a still further aspect, the heterocycloalkyl is monosubstituted. In a yet further aspect, the heterocycloalkyl is disubstituted. In an even further aspect, the heterocycloalkyl is selected from unsubstituted, monosubstituted and disubstituted aziridinyl. In a still further aspect, the heterocycloalkyl is selected from unsubstituted, monosubstituted, and geminally disubstituted morpholinyl. In a yet further aspect, the heterocycloalkyl is selected from unsubstituted, monosubstituted and disubstituted piperidinyl. In an even further aspect, the heterocycloalkyl is selected from unsubstituted, monosubstituted and disubstituted piperazinyl. In a yet further aspect, the heterocycloalkyl is selected from unsubstituted, monosubstituted and disubstituted thiomorpholinyl 1,1-dioxide. In a still further aspect, the heterocycloalkyl is selected from unsubstituted, monosubstituted and disubstituted 1-(C1-C6 alkylsulfonyl)piperazinyl.

In a further aspect, one of substituents of the C3-C6 heterocycloalkyl, when present, is independently selected from an optionally substituted aziridinyl, piperazinyl, morpholinyl, pyrrollidinyl, oxazolidinyl, imidazolidinyl, pyrazolidinyl, thiomorpholinyl 1,1-dioxide; and 1-(C1-C6 alkylsulfonyl) piperazinyl. In a still further aspect, the substituent is an optionally substituted aziridinyl. In yet further aspect, the substituent is an optionally substituted piperazinyl. In an even further aspect, the substituent is an optionally substituted morpholinyl. In a still further aspect, the substituent is an optionally substituted pyrrollidinyl. In a yet further aspect, the substituent is an optionally substituted thiomorpholinyl 1,1-dioxide. In an even further aspect, the substituent is an optionally substituted 1-(C1-C6 alkylsulfonyl)piperazinyl.

In a further aspect, the substituents of the C3-C6 heterocycloalkyl, when present, are independently selected from halogen, cyano, C3-C6 cycloalkyl, C1-C6 alkyl, C1-C6 alkoxy, C1-C6 haloalkyl, and C1-C6 polyhaloalkyl.

l. $R^9$ Groups

In one aspect, $R^9$ is selected from hydrogen, halogen, and C1-C6 alkyl. In a further aspect, $R^9$ is hydrogen. In a still further aspect, $R^9$ is selected from hydrogen and halogen. In a yet further aspect, $R^9$ is selected from hydrogen, halogen, and cyano.

In a further aspect, $R^9$ is halogen. In a still further aspect, halogen is fluoro or chloro. In a yet further aspect, halogen is fluoro. In an even further aspect, halogen is chloro.

In a further aspect, $R^9$ is selected from hydrogen and C1-C6 alkyl. In a still further aspect, $R^9$ is C1-C6 alkyl. In an even further aspect, $R^9$ is selected from halogen, cyano and C1-C6 alkyl. In a still further aspect, $R^9$ is selected from methyl, ethyl and propyl. In a yet further aspect, $R^9$ is methyl.

m. $R^{10}$ Groups

In one aspect, $R^{10}$ is selected from hydrogen and C1-C6 alkyl. In a further aspect, $R^{10}$ is selected from methyl, ethyl and propyl. In a still further aspect, $R^{10}$ is methyl. In a yet further aspect, $R^{10}$ is selected from hydrogen, methyl, ethyl or propyl. In an even further aspect, $R^{10}$ is selected from hydrogen and methyl.

n. $R^{11}$ Groups

In one aspect, $R^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, C3-C6 heterocycloalkyl, and $Ar^1$.

In a further aspect, $R^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, and C3-C6 heterocycloalkyl. In an even further aspect, $R^{11}$ is selected from optionally substituted C3-C6 cycloalkyl, C3-C6 halocycloalkyl, and C3-C6 polyhalocycloalkyl. In a still further aspect, $R^{11}$ is selected from optionally substituted C3-C6 cycloalkyl and C3-C6 polyhalocycloalkyl. In a yet further aspect, $R^{11}$ is C3-C6 polyhalocycloalkyl.

In a further aspect, $R^{11}$ is $Ar^1$. In a yet further aspect, $R^{11}$ is selected from optionally substituted C3-C6 cycloalkyl, C3-C6 halocycloalkyl, C3-C6 polyhalocycloalkyl, C3-C6 heterocycloalkyl, and $Ar^1$.

In a further aspect, $R^{11}$ is selected from cyclopropyl, 2,2-dihalocyclopropyl, 2,3-dihalocyclopropyl, 2-halocyclopropyl, 4,4-dihalocyclohexyl, 4,3-dihalocyclohexyl, and 4-haloocyclohexyl.

O. $R^{12}$ Groups

In one aspect, each $R^{12a}, R^{12b}, R^{12c}, R^{12d}, R^{12e}, R^{12f}, R^{12g}$, and $R^{12h}$, when present, is independently selected from hydrogen, halogen, cyano, C1-C6 alkyl, C1-C6 alkoxy, C1-C6 haloalkyl, C1-C6 polyhaloalkyl, and wherein $R^{12i}$, when present, is selected from hydrogen, halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl) piperazinyl, provided that no more than two of $R^{12a}, R^{12b}, R^{12c}, R^{12d}, R^{12e}, R^{12f}, R^{12g}, R^{12h}$ and $R^{12i}$ are not hydrogen.

2. Example Compounds

In one aspect, a compound can be present as:

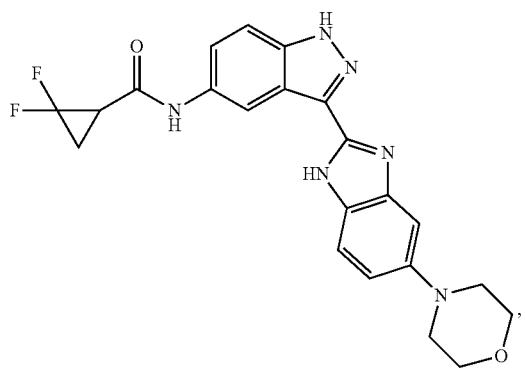

,

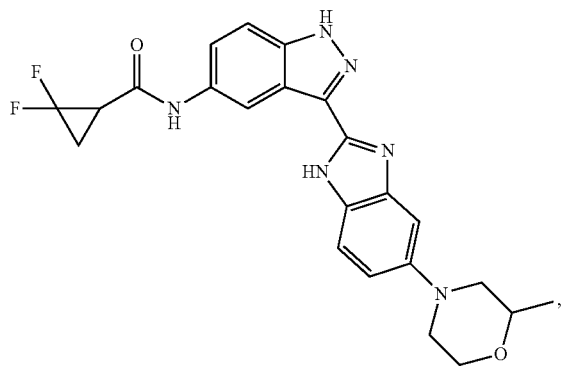

,

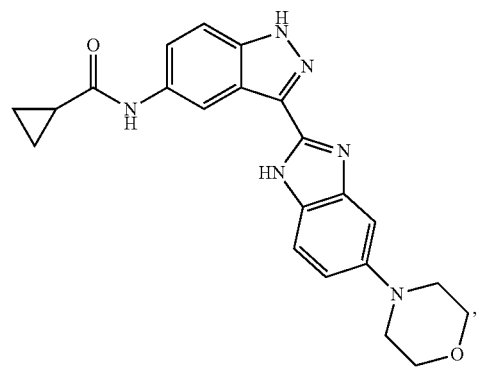

,

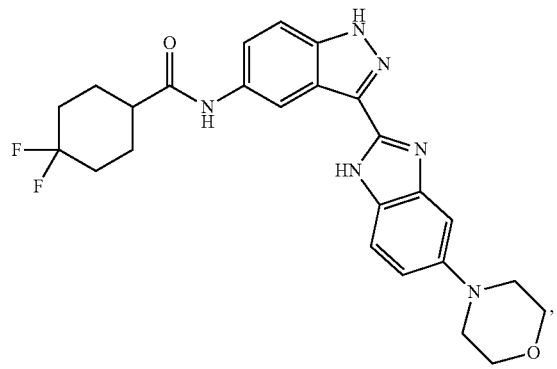

,

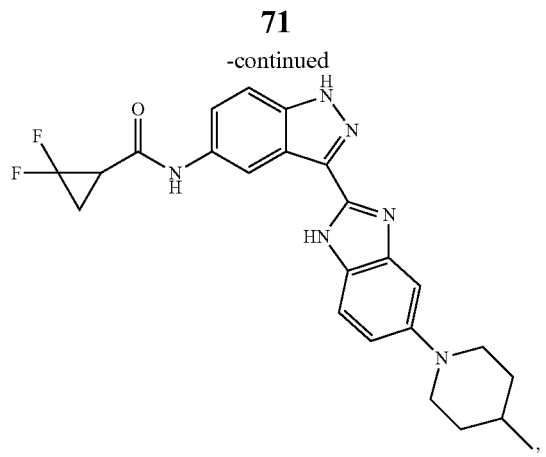
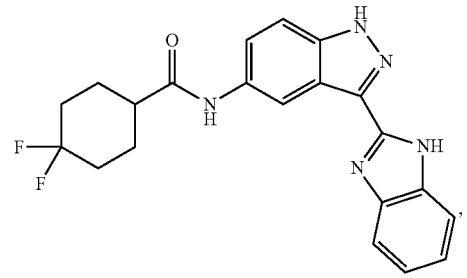
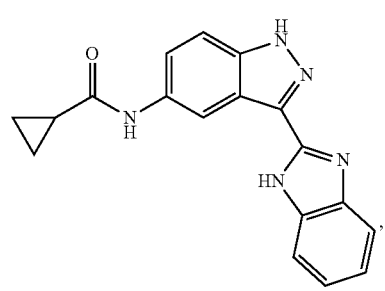
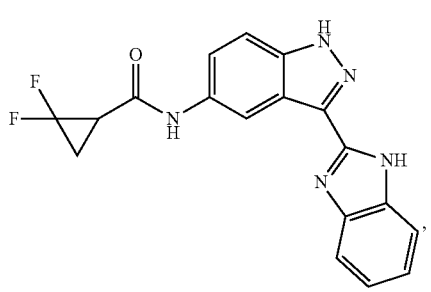
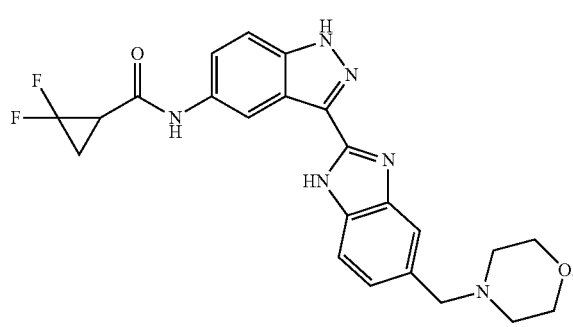
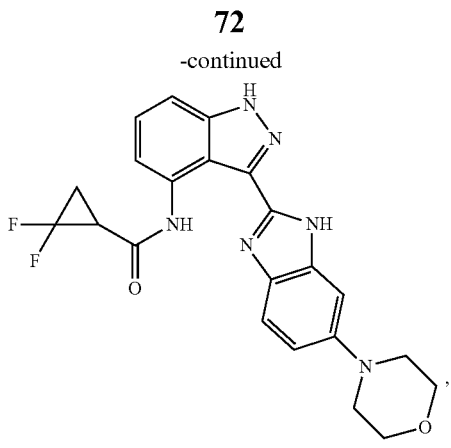
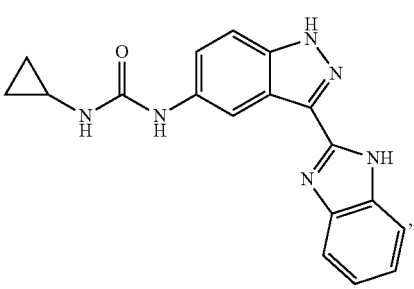
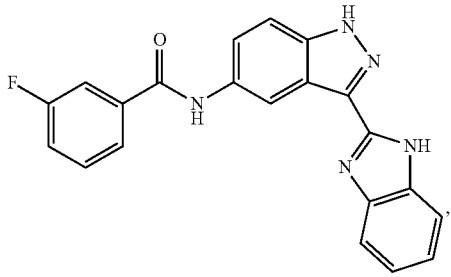
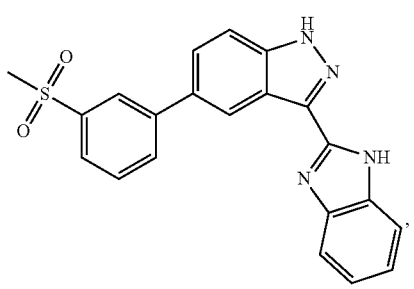
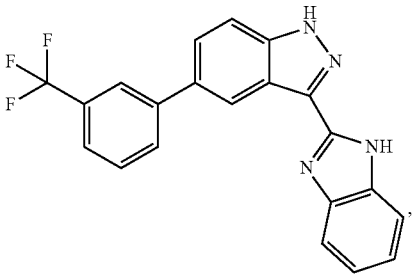

-continued
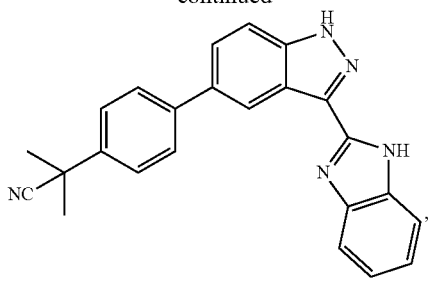
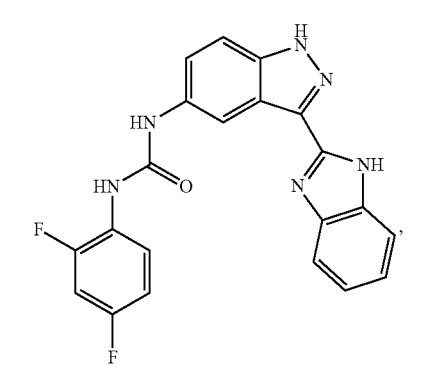
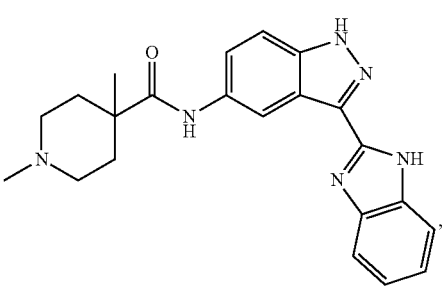
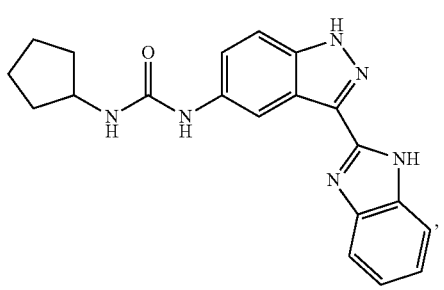
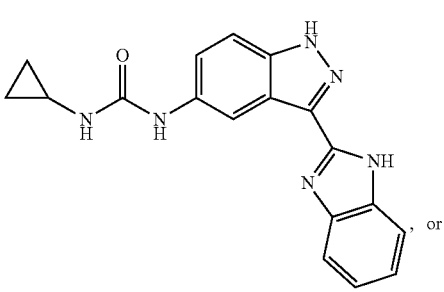
, or
-continued
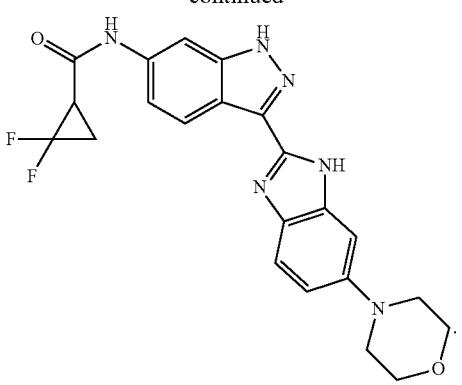
In one aspect, a compound can be present as:
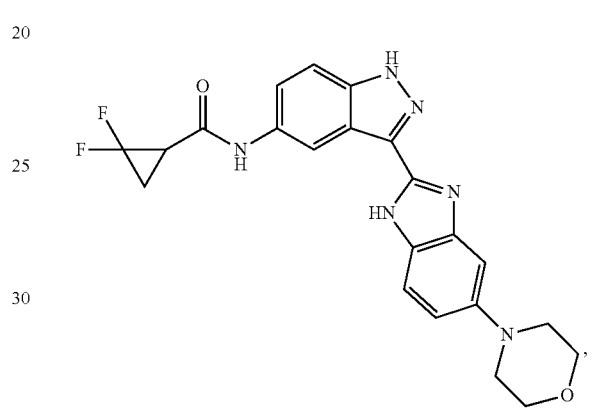
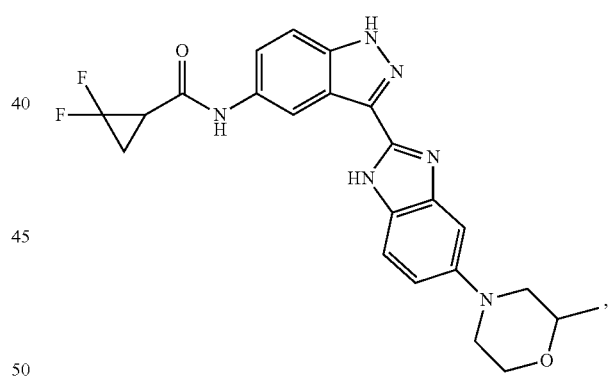
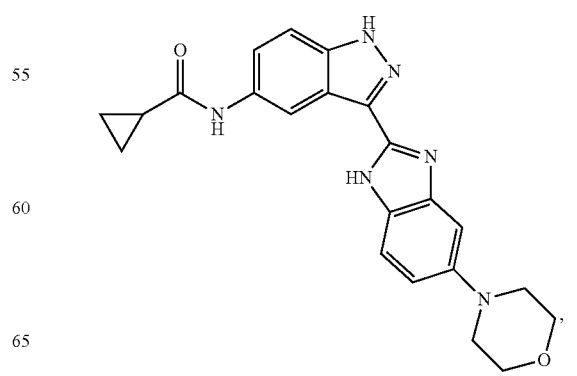
, 75
-continued
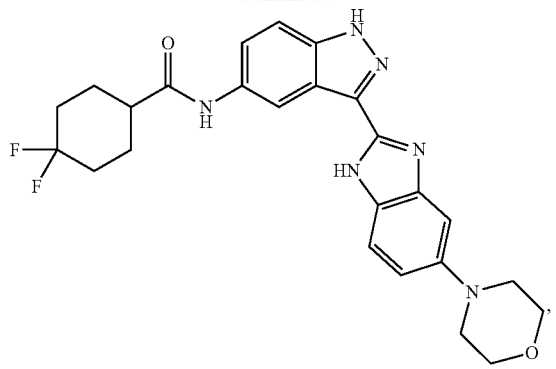
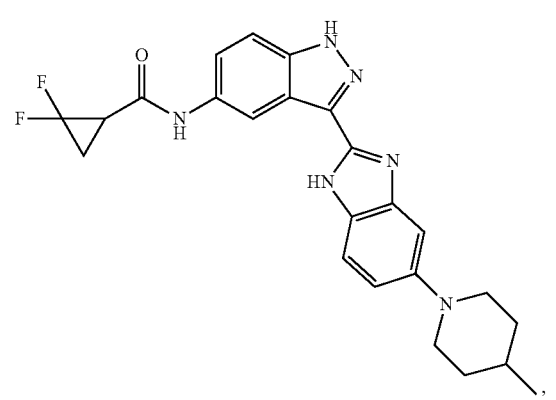
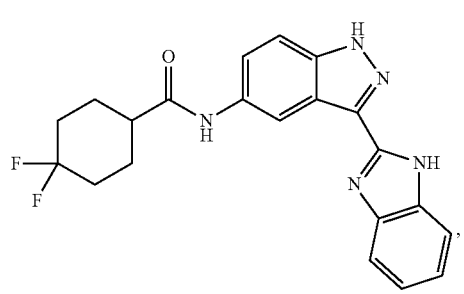
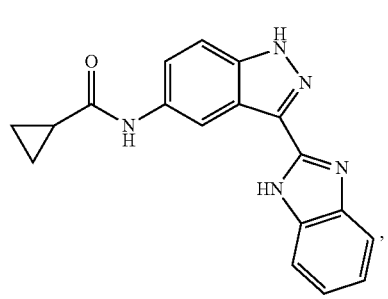
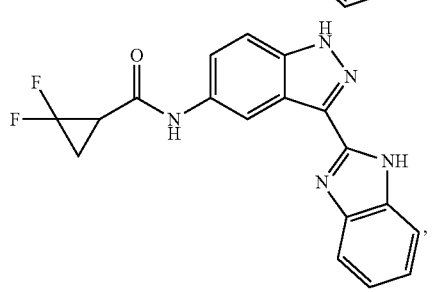
76
-continued
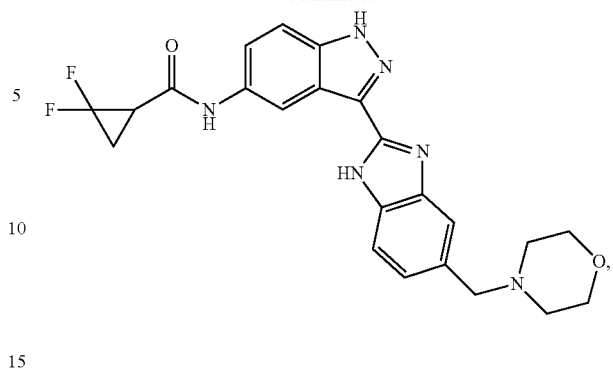
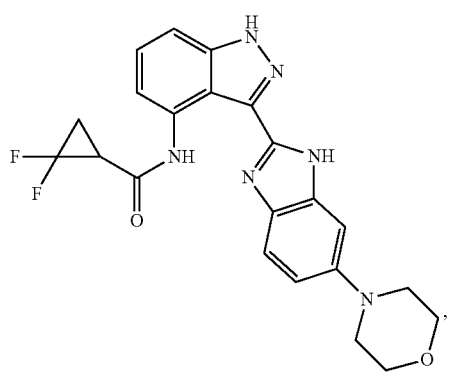
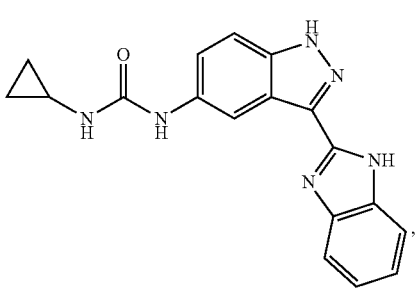
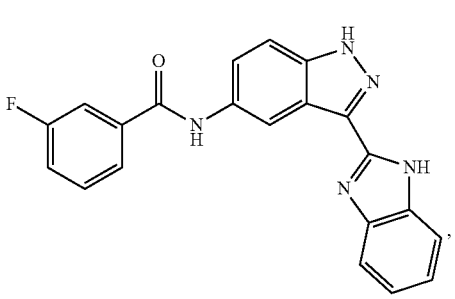
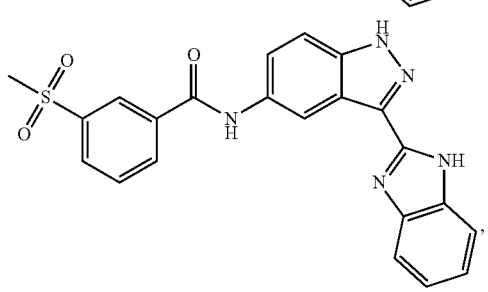

In one aspect, a compound can be present as:

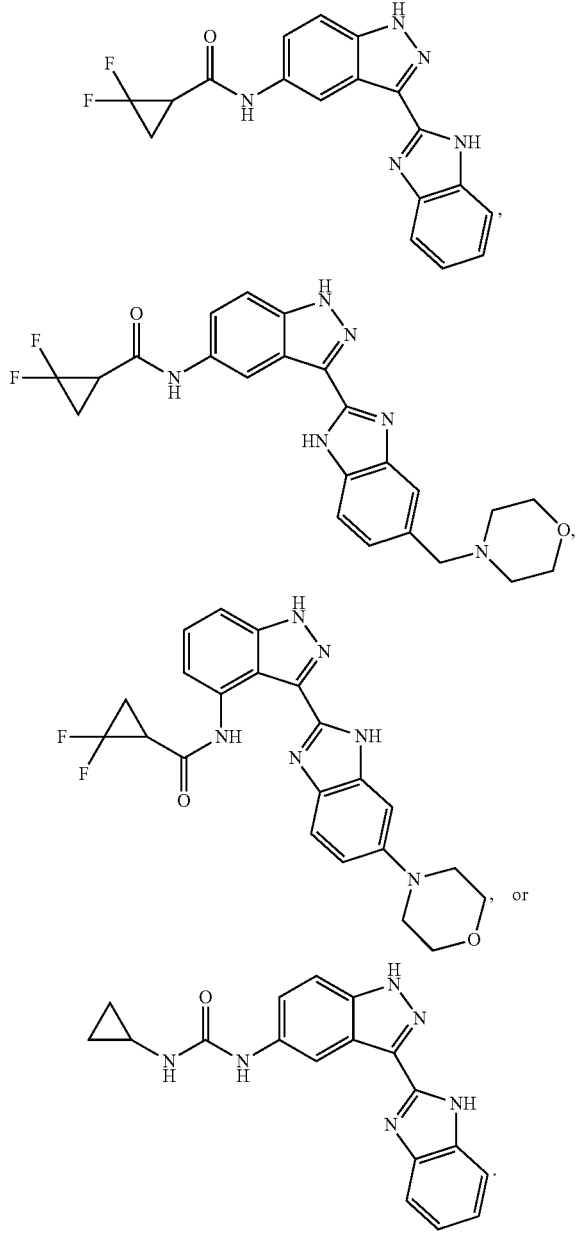
In one aspect, a compound can be present as:
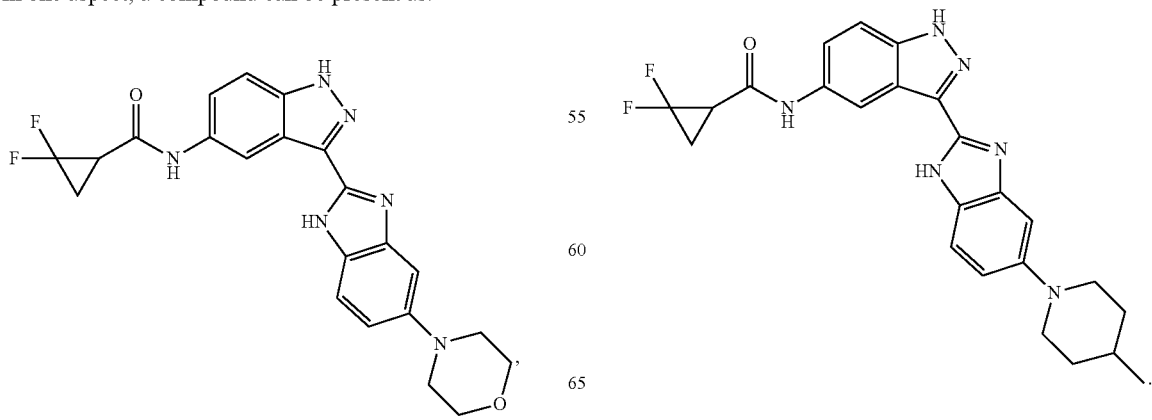

In one aspect, a compound can be present as:
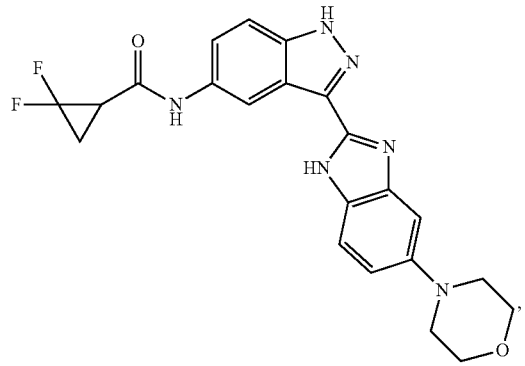
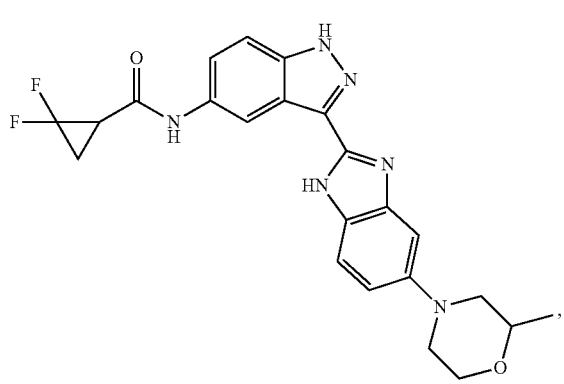
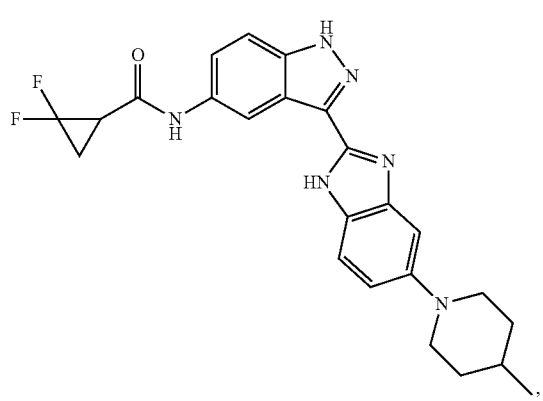 [SMILES: CC1CCN(c2ccc3[nH]c(-c4n[nH]c5ccc(NC(=O)C6CC6(F)F)cc45)nc3c2)CC1]
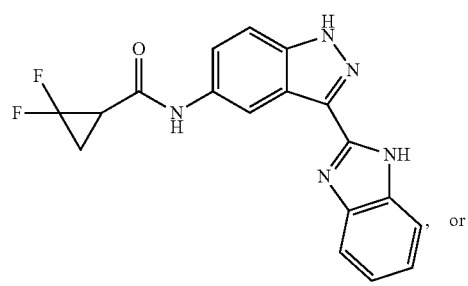, or
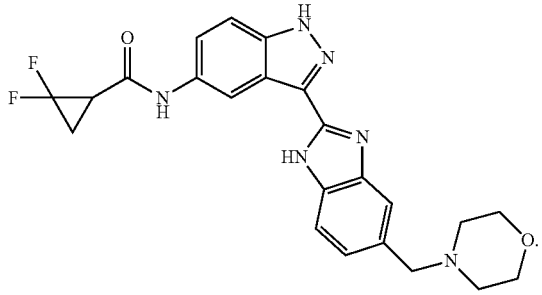 [SMILES: O=C(Nc1ccc2[nH]nc(-c3nc4cc(CN5CCOCC5)ccc4[nH]3)c2c1)C1CC1(F)F]
In one aspect, a compound can be present as:
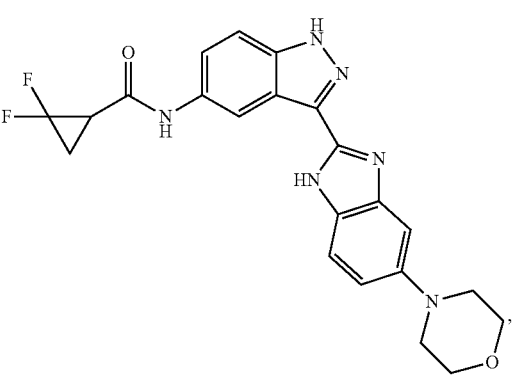
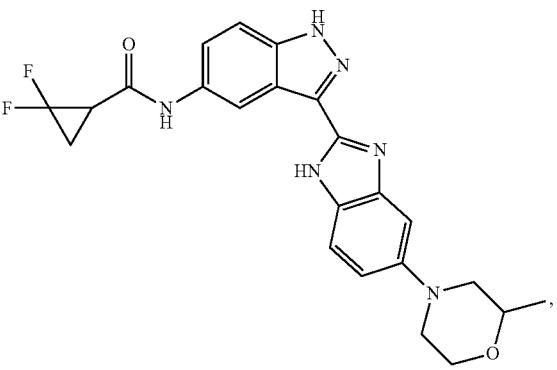
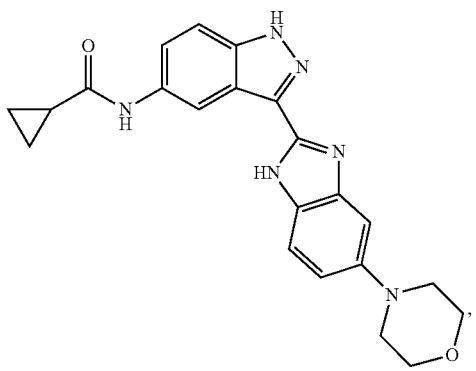

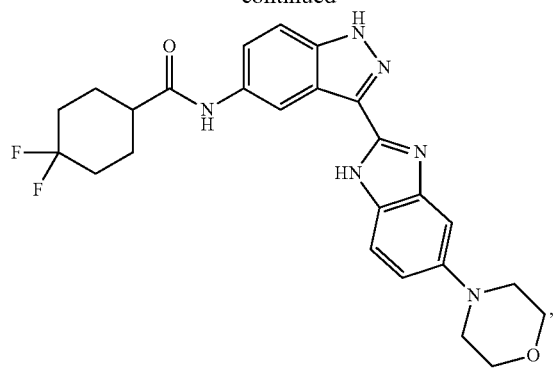
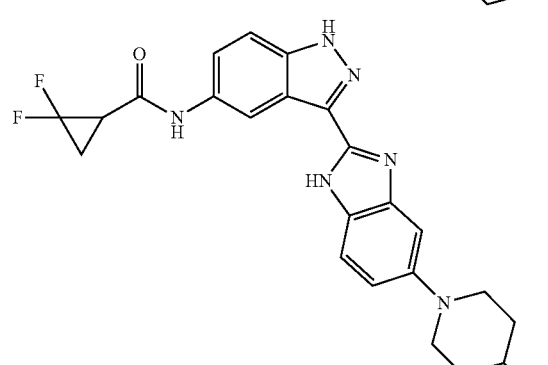
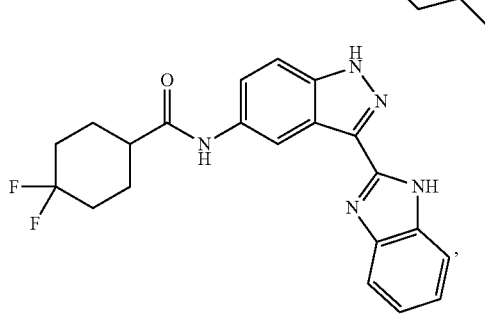
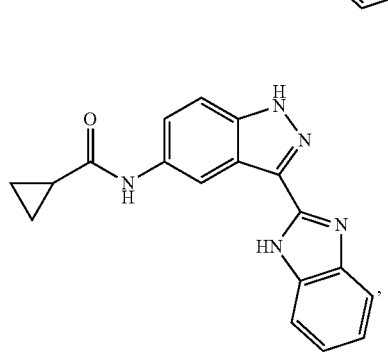
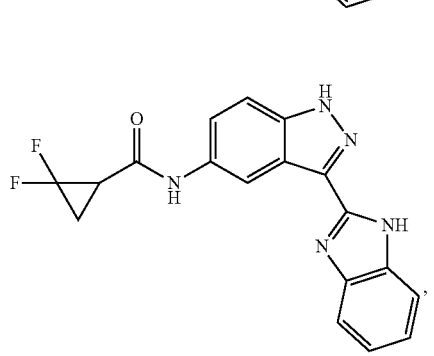
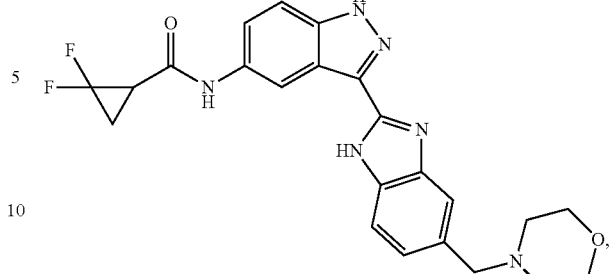
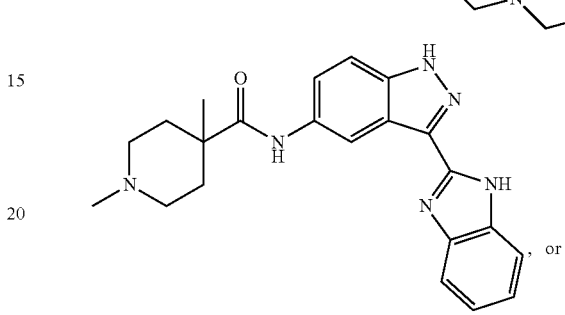
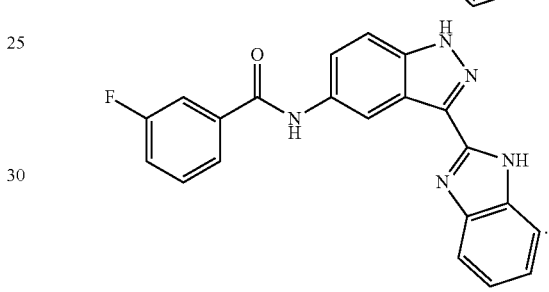
In one aspect, a compound can be present as:
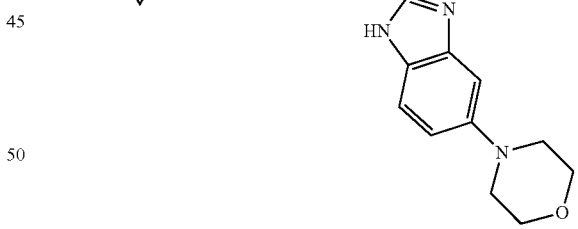
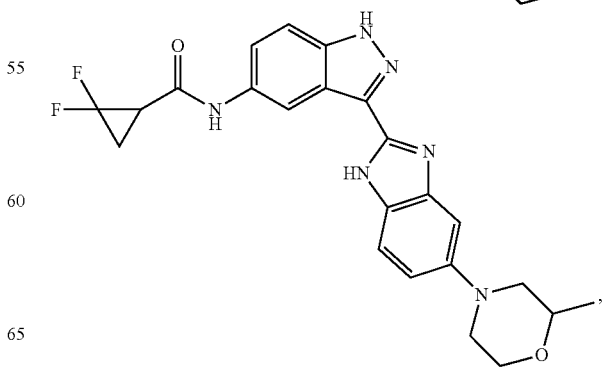

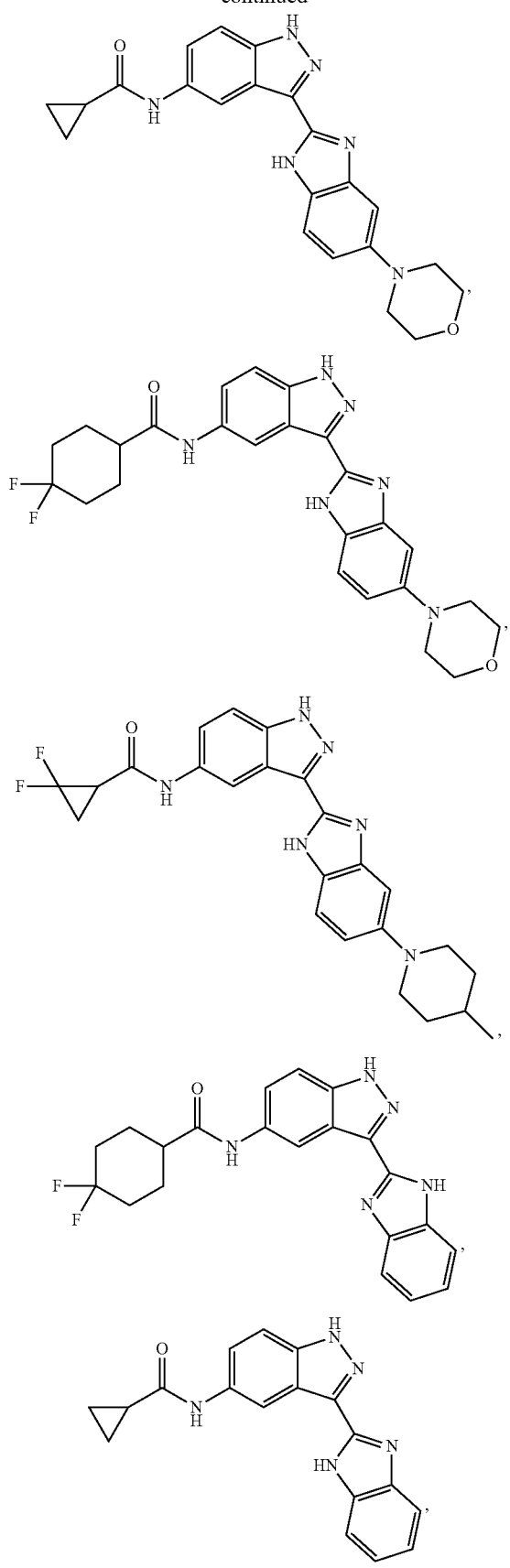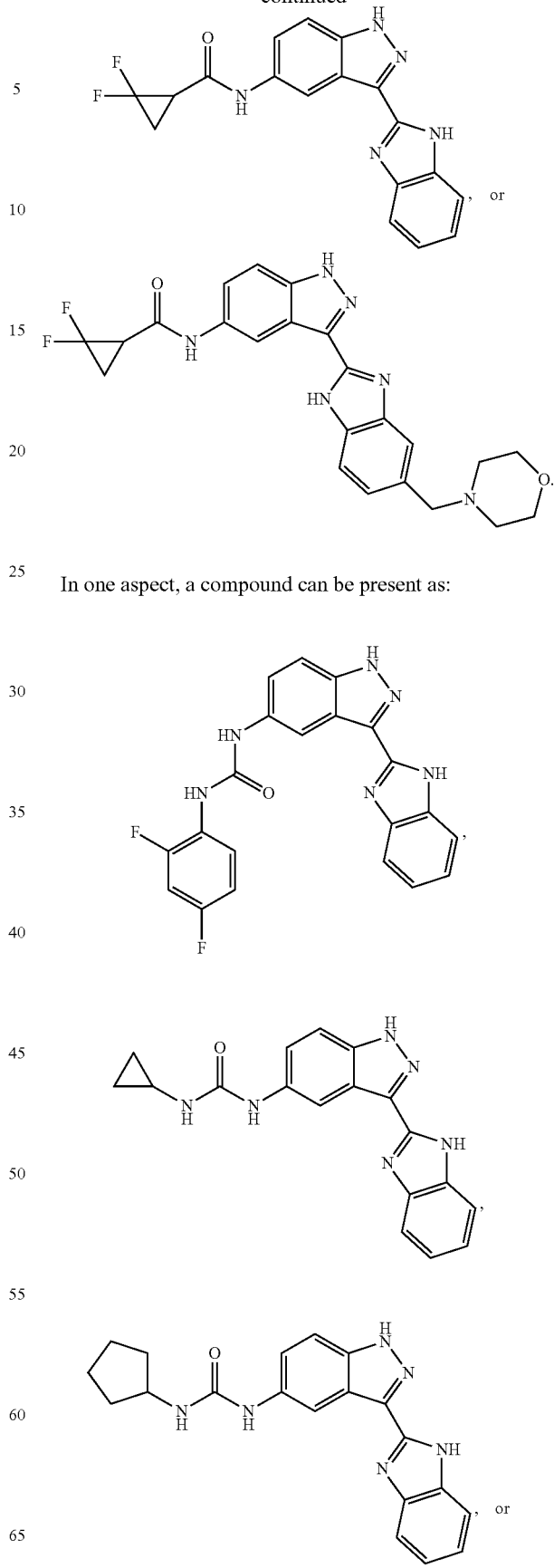
In one aspect, a compound can be present as:

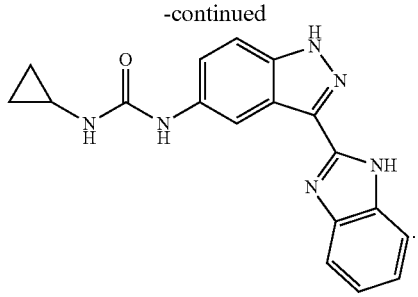

In one aspect, a compound can be present as:

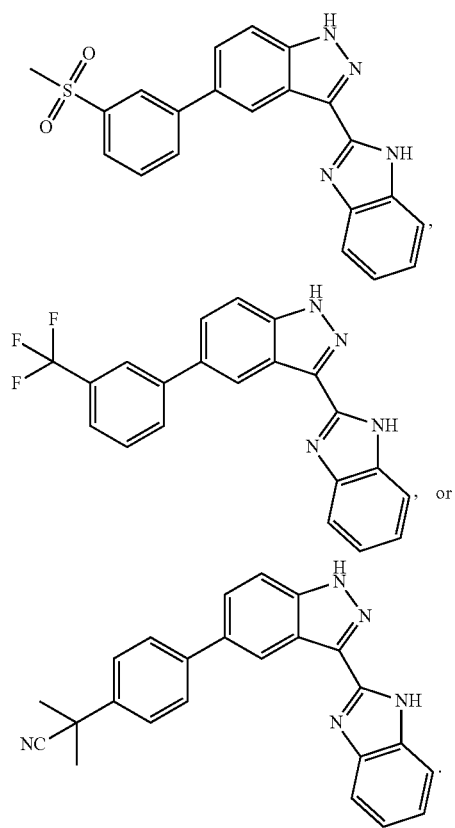

In one aspect, a compound can be present as:

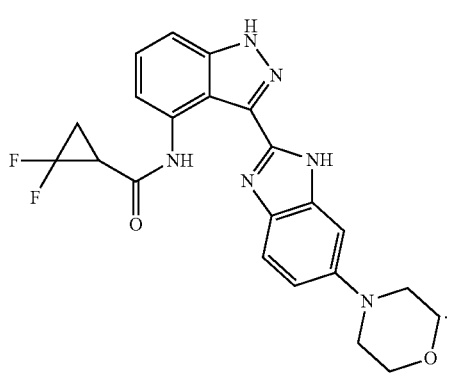 [SMILES: O=C(Nc1cccc2[nH]nc(-c3nc4ccc(N5CCOCC5)cc4[nH]3)c12)C1CC1(F)F]

In a further aspect, the compound exhibits inhibition of the PI3K/Akt pathway. In a still further aspect, the compound exhibits inhibition of cell viability. In a yet further aspect, the compound exhibits inhibition of phosphorylation of Akt in a cell.

In a further aspect, the compound exhibits inhibition of a protein kinase. In a still further aspect, the compound exhibits inhibition of a protein kinase selected from 3-phosphoinositide-dependent protein kinase 1, aurora kinase A, c-ab1 oncogene 1 kinase (T315I form), fms-related tyrosine kinase 3, fibroblast growth factor receptor 1, interleukin-1 receptor-associated kinase 4, Janus kinase 1, Janus kinase 2, Janus kinase 3, mitogen-activated protein kinase kinase kinase kinase 4 (MAP4K4), ret proto-oncogene, spleen tyrosine kinase, tyrosine-protein kinase Fyn, vascular endothelial growth factor receptor 2, and vascular endothelial growth factor receptor 3. In a yet further aspect, the compound exhibits inhibition of 3-phosphoinositide-dependent protein kinase 1 ("PDK1").

In a further aspect, the disclosed compounds exhibit inhibition with an $IC_{50}$ of less than about $1.0\times10^{-4}$ M. In a still further aspect, the disclosed compounds exhibit inhibition with an $IC_{50}$ of less than about $1.0\times10^{-5}$ M. In a yet further aspect, the disclosed compounds exhibit inhibition with an $IC_{50}$ of less than about $1.0\times10^{-6}$ M. In an even further aspect, the compounds exhibit inhibition with an $IC_{50}$ of less than about $1.0\times10^{-7}$ M. In a still further aspect, the compounds exhibit inhibition with an $IC_{50}$ of less than about $1.0\times10^{-8}$ M. In a yet further aspect, the compounds exhibit inhibition with an $IC_{50}$ of less than about $1.0\times10^{-9}$ M.

It is contemplated that one or more compounds can optionally be omitted from the disclosed invention.

3. Inhibition of Protein Kinase Activity

Generally, the disclosed compounds exhibit inhibition of the PI3K/Akt pathway. In a further aspect, the inhibition of this pathway is via inhibition of a protein kinase. In a further aspect, the compound exhibits inhibition of a protein kinase. In a still further aspect, the compound exhibits inhibition of a protein kinase selected from 3-phosphoinositide-dependent protein kinase 1, aurora kinase A, c-ab1 oncogene 1 kinase (T315I form), fms-related tyrosine kinase 3, fibroblast growth factor receptor 1, interleukin-1 receptor-associated kinase 4, Janus kinase 1, Janus kinase 2, Janus kinase 3, mitogen-activated protein kinase kinase kinase kinase 4 (MAP4K4), ret proto-oncogene, spleen tyrosine kinase, tyrosine-protein kinase Fyn, vascular endothelial growth factor receptor 2, and vascular endothelial growth factor receptor 3. In a further aspect, a disclosed compound can exhibit inhibition of one of these kineases with an $IC_{50}$ of less than about 10 µM, of less than about 1 µM, of less than about 500 nM, of less than about 100 nM, or of less than about 10 nM.

In one aspect, the disclosed compounds exhibit inhibition of 3-phosphoinositide-dependent protein kinase 1 ("PDK1"). For example, a disclosed compound can exhibit inhibition of PDK1 with an $IC_{50}$ of less than about 10 µM, of less than about 1 µM, of less than about 500 nM, of less than about 100 nM, or of less than about 10 nM.

In a further aspect, the inhibition is determined in an in vitro assay that measures catalytic activity of the protein kinase, e.g. disappearance of ATP substrate, using methods known in the art. In a yet further aspect, the assay uses a recombinant protein kinase. In a still further aspect, the recombinant protein kinase is PDK1. In some instances, it can be useful for the recombinant protein kinase to tagged with an affinity tag. An example of a useful affinity tags is the His6 tag. For example, a disclosed compound can exhibit inhibition of the catalytic activity of the protein kinase with an $IC_{50}$ of less than about 10 µM, of less than about 1 µM, of less than about 500 nM, of less than about 100 nM, or of less than about 10 nM.

In a further aspect, the in vitro assay measures inhibition by a disclosed compound of binding of an ATP competitive inhibitor to the active site of the protein kinase. In a still further aspect, a disclosed compound can exhibit inhibition of binding at the ATP binding site of the protein kinase with an $IC_{50}$ of less than about 10 µM, of less than about 1 µM, of less than about 500 nM, of less than about 100 nM, or of less than about 10 nM. An example of such an assay is LanthaScreen™ Eu Kinase Binding Assay (Invitrogen Corporation, Carlsbad, Calif.) which is based on the binding and displacement of the Alexa Fluor® 647-labeled, ATP-competitive kinase inhibitor scaffold (kinase tracer) to the kinase of interest. Binding of the tracer to the kinase is detected using a europium-labeled anti-tag antibody, which binds to the kinase of interest. Simultaneous binding of both the tracer and antibody to the kinase results in a high degree of FRET (fluorescence resonance energy transfer) from the europium (Eu) donor fluorophore to the Alexa Fluor® 647 acceptor fluorophore on the kinase tracer. Binding of an inhibitor to the kinase competes for binding with the tracer, resulting in a loss of FRET. This type of assay allows detection of multiple modes of interaction with the target kinase at the ATP binding site, including "Type II" inhibitors, which bind to both the ATP site and a second site often referred to as the "allosteric" site, compounds which bind to either active or non-activated forms of a target kinase, and compounds with slow binding kinetics.

C. Inhibition Of The Pi3K/Akt Pathway

The utility of the compounds in accordance with the present invention as inhibitors of the PI3K/Akt signaling pathway, in particular by inhibition of PDK1 activity, can be demonstrated by methodology known in the art. For example, inhibition of specific steps in the signaling pathway can be determined. In one aspect, the compounds of the present invention inhibit the phosphorylation of Akt. In a further aspect, phosphorylation of Akt at Thr308 can be determined as a measure of inhibition of the signaling pathway. For example, a compound can exhibit inhibition of Akt phosphorylation with an $IC_{50}$ of less than about 10 µM, of less than about 1 µM, of less than about 500 nM, of less than about 100 nM, or of less than about 10 nM. In a further aspect, the inhibition is of phosphorylation at Thr308 of Akt.

In one aspect, the disclosed compounds exhibit inhibition of cell viability. For example, cells with a mutation in the PTEN gene and/or PI3K activating mutations are suitable for determining inhibitory activity of the PI3K/Akt pathway. In a further aspect, inhibition is determined using a cell-line selected from AN3-CA, RL95-2, and HEC-1A cells. In a still further aspect, the cell-line is selected from AN3-CA, RL95-2, SK-OV-3, NCCIT, HCT-116, AGS, BT549, RKO, Hec-1A, 786-O, HCT-15, U87-MG, PC-3, MCF-7, H1975, HT-29, T47D, BT-20, and LNCap cells. For example, a compound can exhibit inhibition of cell viability in one of these cell-lines with an $IC_{50}$ of less than about 10 µM, of less than about 1 µM, of less than about 500 nM, of less than about 100 nM, or of less than about 10 nM. Methods to measure cell viability are known in the art and described herein.

In a further aspect, a disclosed compound exhibits inhibition in a cell that has a mutation in the PTEN gene. In a yet further aspect, the mutation is selected from one or more of the mutations described in Table I.

In a further aspect, a disclosed compound exhibits inhibition in a cell that has a mutation in associated with activation of PI3K. In a still further aspect, the mutation is selected from one or more of the mutations described in Table II.

In vivo efficacy for disclosed compounds can be measured in a number of preclinical models where known, clinically useful therapeutics display similar positive responses. For example, disclosed compounds can assess in tumor xenograft models in laboratory animals at doses ranging from 1 to 100 mg/kg administered orally, by intravenous injection, subcutaneous injection, or intraperitoneal injection. Although, nude mice are most frequently used in the tumor xenograft model, other laboratory animals may used as needed for convenience or the goals of the study. In the tumor xenograft model, the tumor volume at various points post-implantation of the tumor and/or mortality can be used as efficacy endpoints in the study. Suitable cell-lines for establishing tumor xenografts include the following: AN3-CA, RL95-2, and HEC-1A cells. In a still further aspect, the cell-line is selected from AN3-CA, RL95-2, SK-OV-3, NCCIT, HCT-116, AGS, BT549, RKO, Hec-1A, 786-0, HCT-15, U87-MG, PC-3, MCF-7, H1975, HT-29, T47D, BT-20, and LNCap cells.

TABLE I

| Mutation | Wild-Type Allele | Mutant Allele 1 | Mutant Allele 2 |
|---|---|---|---|
| K267fs*9 | A | | |
| K267fs*9 | A | DEL | |
| K267fs*9 | A | DEL | |
| K6fs*4 | AA | DEL | |
| K6fs*4 | AA | DEL | |
| K6fs*4 | AA | DEL | |
| N323fs*2 | DEL | DEL | |
| N323fs*2 | DEL | A | |
| N323fs*2 | DEL | A | |
| N323fs*21 | A | A | |
| N323fs*21 | A | DEL | |
| N323fs*21 | A | DEL | |
| P248fs*5 | DEL | DEL | |
| P248fs*5 | DEL | A | |
| P248fs*5 | DEL | A | |
| R130Q | G | A | |
| R130Q | G | A | NONE |
| R130Q | G | A | NONE |
| R130fs*4 | G | A | NONE |
| R130fs*4 | G | NONE | DEL |
| R130fs*4 | G | NONE | DEL |
| R130G | C | NONE | DEL |
| R130G | C | G | NONE |
| R130G | C | G | NONE |
| R130* | C | NONE | T |
| R130* | C | NONE | T |
| R130* | C | NONE | T |
| R173C | C | T | |
| R173C | C | T | |
| R173C | C | T | |
| R173H | G | A | |

TABLE I-continued

| Mutation | Wild-Type Allele | Mutant Allele 1 | Mutant Allele 2 |
|---|---|---|---|
| R173H | G | A | |
| R173H | G | A | |
| R233* | C | T | |
| R233* | C | T | |
| R233* | C | T | |
| R335* | C | T | |
| R335* | C | T | |
| R335* | C | T | |
| V317fs*3 | | TACT | DEL |
| V317fs*3 | | TACT | DEL |
| V317fs*3 | | TACT | DEL |

TABLE II

| PIK3CA | PIK3R1 | H-RAS | K-RAS | N-RAS |
|---|---|---|---|---|
| R38H | R574T | G12V/D | G12C | G12V/A/D |
| R88Q | A634P | G13C/R/S | G12R | G12C/R/S |
| N345K | | Q61H/H | G12S | G13V/A/D |
| C420R | | Q61L/R/P | G12V | G13C/R/S |
| P539K | | Q61K | G12D | A18T |
| E542K | | | G12A | Q61L/R/P |
| E545E | | | G12F | Q61H |
| Q546K | | | G13V/D | Q61E/K |
| H701P | | | A59T | |
| C901F | | | Q61E/K | |
| M1043I | | | Q61L/R/P | |
| H1047R/L | | | Q61H | |
| H1047Y | | | | |

D. Fragment-Based Identification Of Pdk1 Inhibitors

A fragment-based design strategy was used in identifying potential pharmacophores useful as PDK1 inhibitors. A collection of 1100 low molecular weight (<250 MW) fragments were screened against the PDK1 kinase. The screen identified 9 fragments with moderate inhibitory activity against PDK1 ($IC_{50}$ values from 45-82 mM). The present invention focuses on those scaffolds based off of a 5-Br,4-I-1H-indazol-3-amine scaffold. The selection of those scaffold as a starting point for the compounds of the present invention was based on initial activity and in keeping with the "rule of 3" for fragment-based drug design. Subsequent molecular docking studies using a crystal structure of PDK1 allowed for the structural rationalization of how these fragments bound in the ATP-binding pocket (hydrogen bonding to S160/A162 hinge residues) and provided insight for further optimization. Concurrently, scaffold-hopping searches at 2-site points for hydrophobic and solvent pocket fragments. With the addition of one fused heterocyclic ring, the potency increased to 8.8 and 10.9 µM. The systematic fragment based workflow led to the preparation of target molecules in 4 steps beginning with the condensation, cyclization, and reduction and finally installing the hydrophobic binding site fragments under normal amide coupling. Subsequent SAR and follow-up screening led to the compounds of the present invention which are potent PDK1 inhibitors with $IC_{50}$ values in the range of about 10 nM, about 50 nM, about 100 nM, about 500 nM, and about 1000 nM. Additional productive interactions sites with PDK1 were introduced to further improve both biochemical and cellular activities in panel of cancer cells. In one aspect, the compounds of the present invention demonstrated enhanced activity in PTEN-deficient cell lines compared to PTEN-wild type lines. In one aspect, the compounds of the present invention demonstrated inhibition of the activation of AKT and other downstream signaling molecules. In a still further aspect, the compounds of the present invention demonstrated high ligand efficiency with promising solubility and permeability parameters.

In a further aspect, the fragment-based workflow approach and discovery of the compounds of the present invention are outlined in FIG. 1. Briefly, 1,000 compounds from a fragment library were screened in a luminescence-based ATP-depletion assay at a concentration of 100 mM. Simultaneously, the fragments in the library (plus additional fragments) were virtually docked into the ATP-binding pocket of our PDK1 3-D model. Active fragments from the biochemical assay were compared to top-rated fragments from the virtual screen and this comparison was used to further refine the 3-D model used for structure-based design. Starting with a small fragment with mid-mM activity we used structure-based design and computational docking to optimize it to a lead candidate with nM activity.

Figure 2:
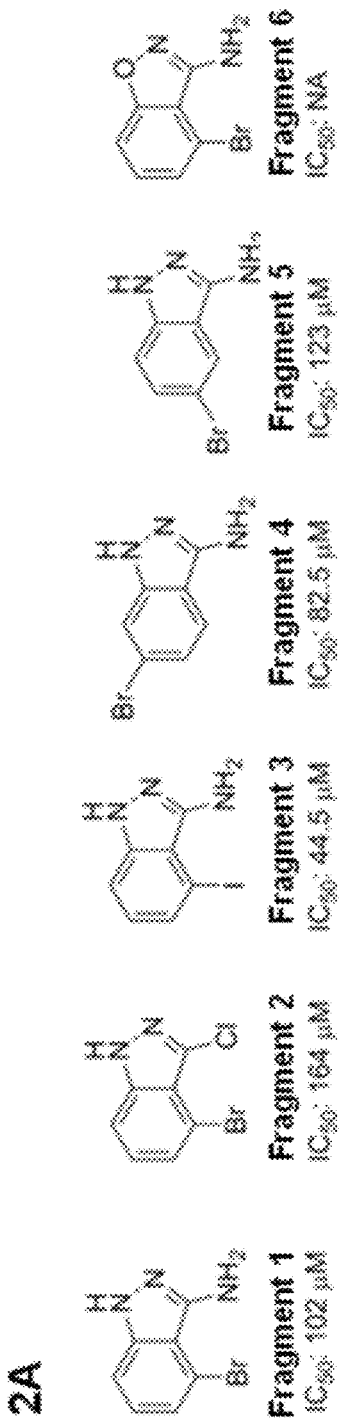
FIG. 2 shows representative fragments identified in a PDK1 screen (FIG. 2A); representative computer-based docking of Fragment 3 (left panel) and Fragment 4 (right panel) to PDK1 (FIG. 2B); and representative computer-based docking of a representative compound, 2,2-difluoro-N-(3-(5-morpholino-1H-benzo[d]imidazol-2-yl)-1H-indazol-5-yl)cyclopropanecarboxamide, to PDK1 (FIG. 2C).
Figure 2:
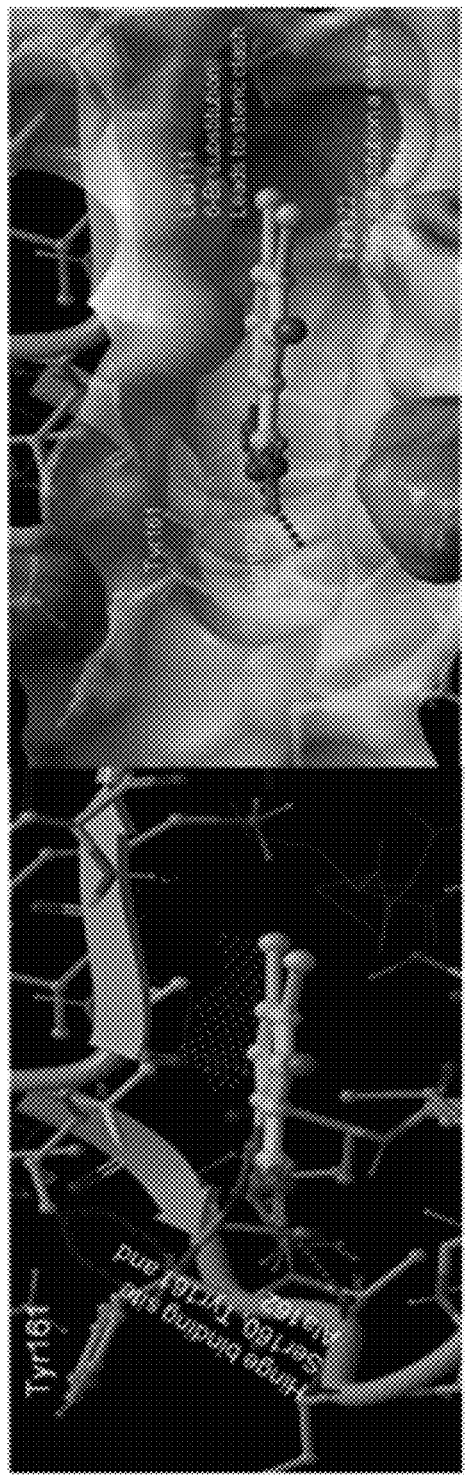
Figure 2:
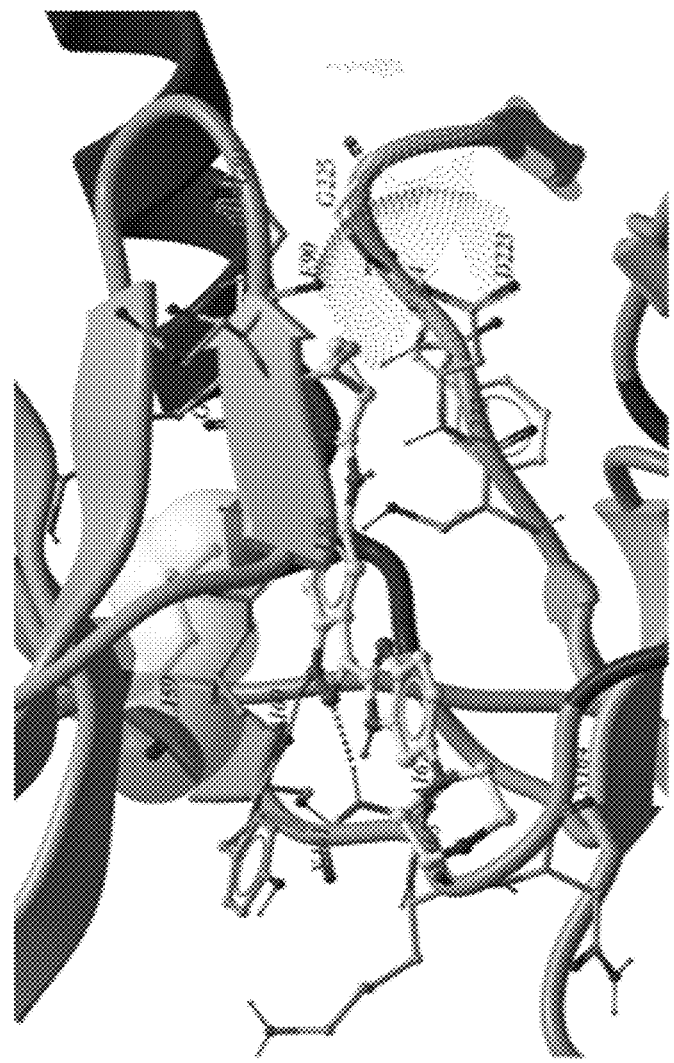

Six of the most potent fragments from the biochemical kinase assay are depicted with their $IC_{50}$ values are shown in FIG. 2A. Fragment 3 was the most potent fragment, and Fragments 4 and 5 also provide promising starting points. From docking studies (see FIG. 2B), the 4-position iodo group on Fragment 3 was not oriented correctly to expand the fragment into the hydrophobic pocket of the ATP-binding region. Whereas, the 5th and 6th position bromo groups on Fragments 4 and 5 were positioned correctly to expand the fragment. Moreover, without wishing to be bound by a particular theory, ICM and GOLD fragment docking results provide a binding mode rationale for the less potent activities of Fragments 1 and 5 compared to the corresponding more potent activity of Fragment 3. For example, the 6th position Br atom in Fragment 5 can be involved in a steric clash with Leu111 located in the hydrophobic site of PDK1. In the case of Fragment 1, the 5-Br atom is positioned towards Thr122 of PDK1, whereas the indazole interaction with Tyr122 is retained, yet with weak binding energy compared to Fragment 4. In one aspect, the approach to identification of active PDK1 inhibitors using the fragment-based approach described herein is shown in FIG. 3.

Figure 3:
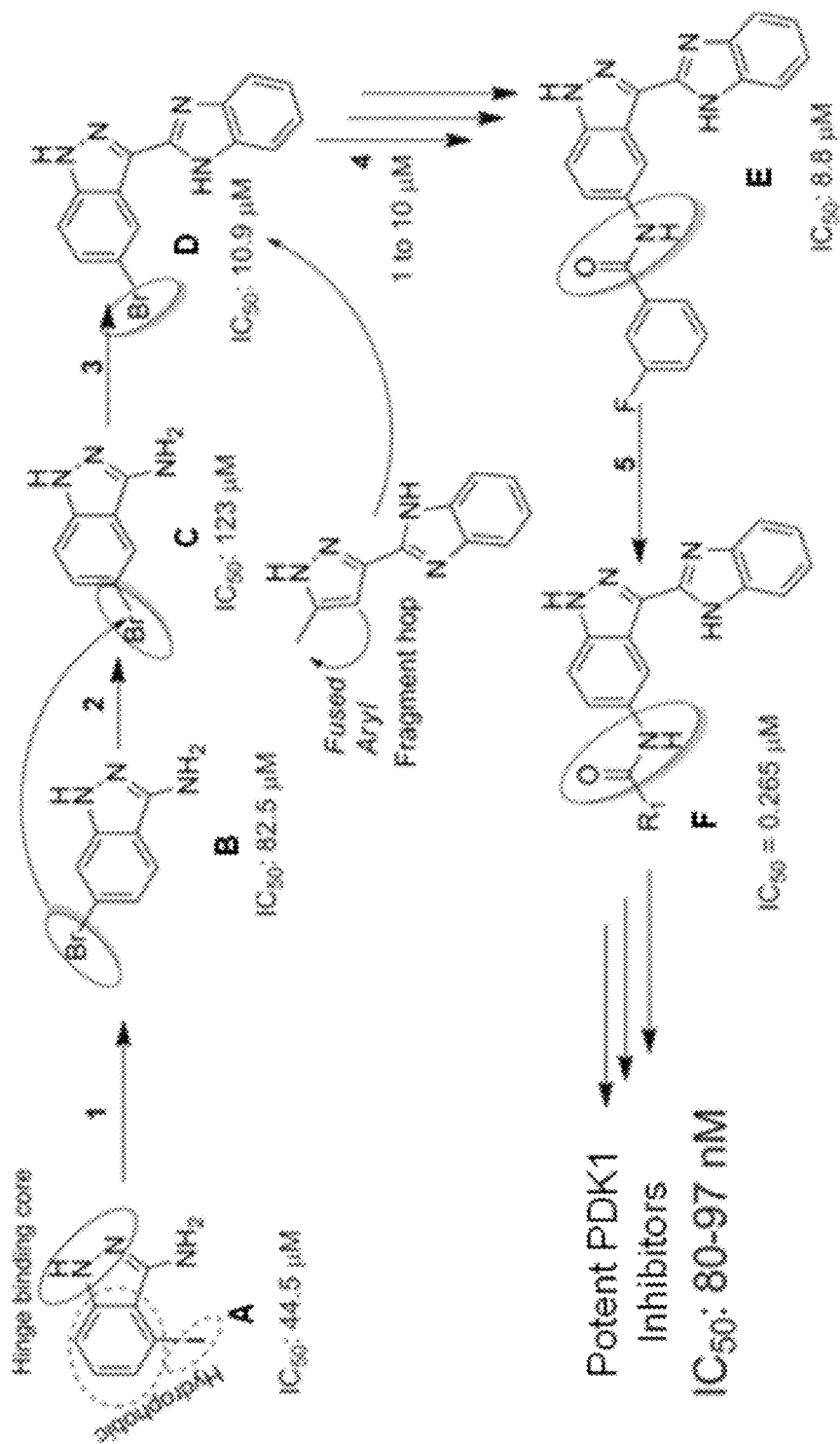
FIG. 3 shows a representative cycles of optimization using a fragment-based approach to identification of PDK1 inhibitors.

In one aspect, potent inhibitors PDK1 are based on the initial scaffold identified from our fragment screen (e.g. see FIG. 3). In another aspect, additional fragments from the fragment-based screen can be utilized to identify PDK1 inhibitors. For example, a second fragment, identified from virtual screening can be combined with Compound C (see FIG. 3) to generate Compound D. This compound was further optimized by replacing the 5-bromo group with arylamides to generate compounds such as Compound F. In a still further aspect, potent PDK1 inhibitors are generated by attaching cycloalkyls with acceptor/donor atoms to the benzimidazole group that extend into solvent exposed regions.

In various further aspects, the predicted binding mode of the disclosed compounds was assessed by ICM docking and molecular dynamic simulations of the active PDK1 kinase domain in complex with the disclosed compound, 2,2-difluoro-N-(3-(5-morpholino-1H-benzo[d]imidazol-2-yl)-1H-indazol-5-yl)cyclopropanecarboxamide, as shown in FIG. 2C. Without wishing to be bound by a particular theory, the docking studies suggest that the 1H-indazoles moiety of the disclosed compounds and its nitrogen atom can be involved in an interaction with the hinge region of the kinase through a hydrogen bond with the backbone of Ser160. In addition, without wishing to be bound by a particular theory, a second hydrogen bond can form between the backbone nitrogen atom of Tyr161 and the second nitrogen atom in the indazole scaffold of compound 32, where as the benzo[d]imidazol ring system makes π-π stacking interactions with the aromatic side chain of Tyr161. Without wishing to be bound by a particular theory, the fused aryl ring of the 1H-indazole can be involved in a non-bonded interaction with side chains of the gatekeeper residue, Leu159 and favorable hydrophobic contacts are also established between the aromatic ring of 1H-indazole and the side chain of Leu88 and the backbone atoms of Gly89. In addition, without wishing to be bound by a particular theory, the amide carbonyl functional group can be positioned within hydrogen-bonding distance of Lys 111.

E. Methods Of Making The Compounds

In one aspect, the invention relates to methods of making compounds useful as inhibitors of protein kinase, which can be useful in the treatment of disorders of uncontrolled cellular proliferation. In a further aspect, the protein kinase is PDK1.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, in addition to other standard manipulations known in the literature or to one skilled in the art. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

Thus, in one aspect, the invention relates to a method of making a compound comprising the steps of: (a) providing a first compound having a structure represented by a formula:

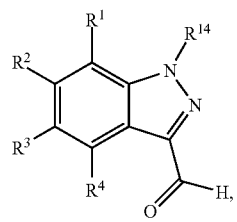

wherein $R^1$ is selected from hydrogen, halogen, cyano, and C1-C6 alkyl; wherein $R^2$ is selected from hydrogen, halogen, cyano, and C1-C6 alkyl; wherein one of $R^3$ and $R^4$ is selected from halogen or nitro, and the other is hydrogen; wherein $R^{14}$ is a protecting group; and (b) reacting the first compound with a second compound having a structure represented by the formula:

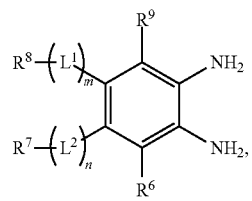

wherein $L^1$ is C=O or $(CH_2)_p$, wherein p is an integer from 1 to 3, wherein m is 0 or 1; wherein $L^2$ is C=O or $(CH_2)_q$, wherein q is an integer from 1 to 3, wherein n is 0 or 1; wherein $R^6$ is selected from hydrogen, halogen, and C1-C6 alkyl; wherein $R^7$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; wherein $R^8$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; and wherein $R^9$ is selected from hydrogen, halogen, and C1-C6 alkyl.

In a further aspect, the compound formed has a structure represented by the formula:

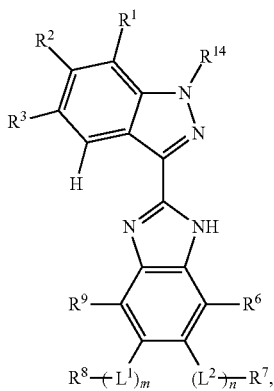

wherein R³ is selected from halogen or nitro.

In a further aspect, the compound formed has a structure represented by the formula:

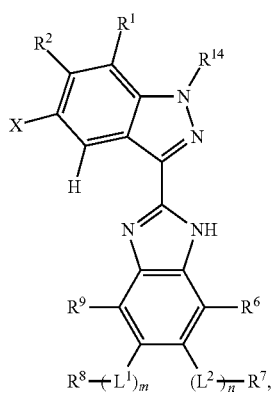

wherein X is halogen.

In a further aspect, the compound formed has a structure represented by the formula:

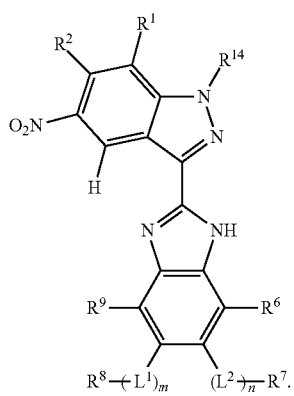

In a further aspect, the compound formed has a structure represented by the formula:

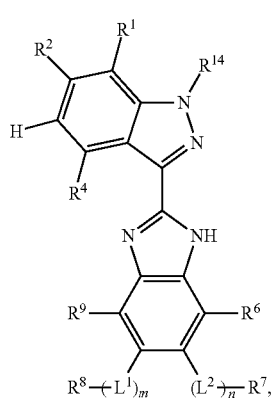

wherein R⁴ is selected from halogen or nitro.

In a further aspect, the compound formed has a structure represented by the formula:

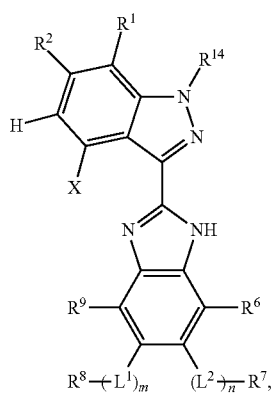

wherein X is halogen.

In a further aspect, the compound formed has a structure represented by the formula:

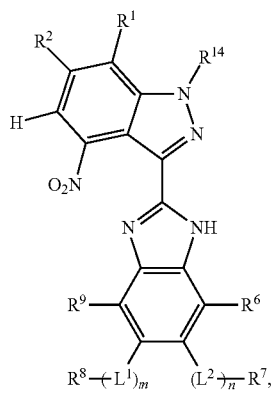

In a further aspect, the compound provided has a structure represented by the formula:

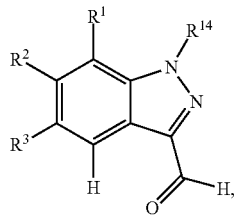

wherein $R^3$ is selected from halogen or nitro. In a still further aspect, the compound provided has a structure represented by the formula:

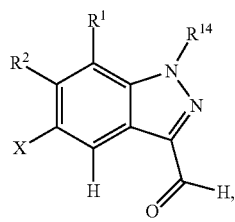

wherein X is a halogen. In a still further aspect, X is selected from chloro, bromo and iodo. In a yet further aspect, X is bromo. In a yet further aspect, the compound provided has a structure represented by the formula:

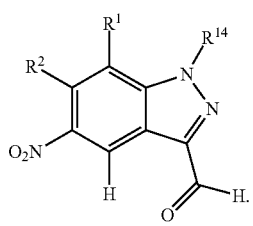

In a further aspect, the compound provided has a structure represented by the formula:

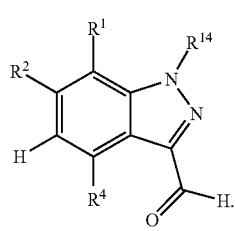

In a still further aspect, the compound provided has a structure represented by the formula:

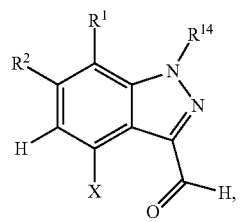

wherein X is halogen. In a still further aspect, X is selected from chloro, bromo and iodo. In a yet further aspect, X is bromo. In a yet further aspect, the compound provided has a structure represented by the formula:

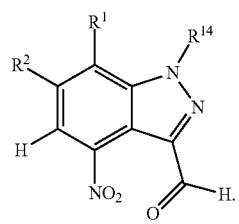

In a further aspect, $R^{14}$ is selected from tert-butyloxycarbonyl, p-methoxybenzyl carbonyl, tetrahydropyranyl, carbobenzyloxy, 9-fluorenylmethyloxycarbonyl, p-methoxybenzyl, and 3,4-dimethoxybenzyl. In a still further aspect, $R^{14}$ is tetrahydropyranyl.

In a further aspect, $R^3$ or $R^4$ is nitro, and the method further comprises the step of reducing the nitro group to yield an amine. In a still further aspect, the compound formed from reduction of the nitro group at $R^3$ has a structure represented by the formula:

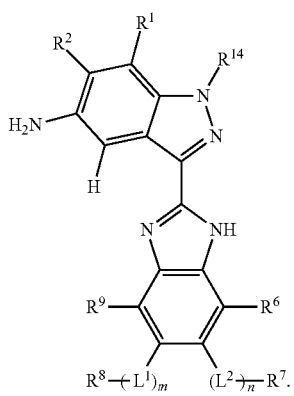

In a yet further aspect, the compound formed from reduction of the nitro group at R⁴ has a structure represented by the formula:

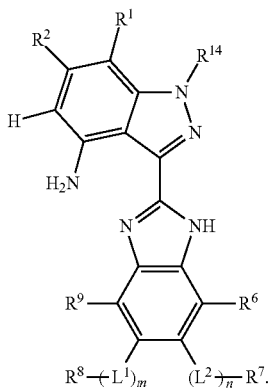

In a further aspect, the method further comprises the step of reacting the amine formed in the above reaction with $R^{11}$(C=O)$R^{13}$, wherein $R^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, C3-C6 heterocycloalkyl; and wherein $R^{13}$ is hydrogen, halogen, O(C=O)$R^{11}$, or O$R^{14}$, wherein $R^{14}$ is selected from C1-C6 alkyl. In a still further aspect, the compound formed from reacting the amine with $R^{11}$(C=O)$R^{13}$ has a structure represented by the formula:

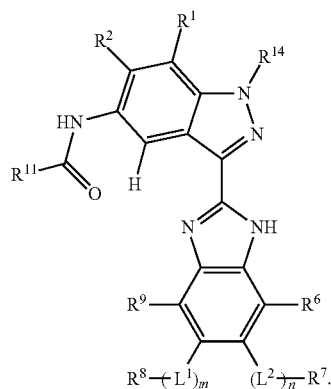

In a yet further aspect, the compound formed from reacting the amine with $R^{11}$(C=O)$R^{13}$ has a structure represented by the formula:

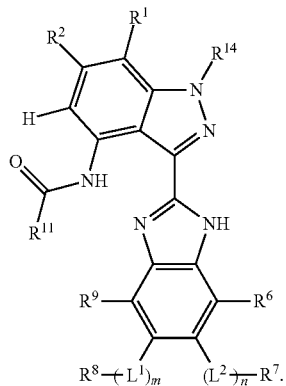

In a further aspect, the method further comprises the step of reacting the amine formed in the above reaction $R^{11}$N=C=O, wherein $R^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, C3-C6 heterocycloalkyl. In a still further aspect, the compound formed from reacting the amine with $R^{11}$N=C=O has a structure represented by the formula:

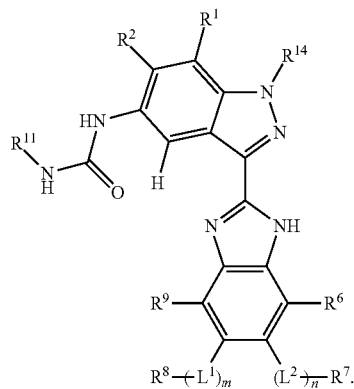

In a yet further aspect, the compound formed from reacting the amine with $R^{11}$N=C=O has a structure represented by the formula:

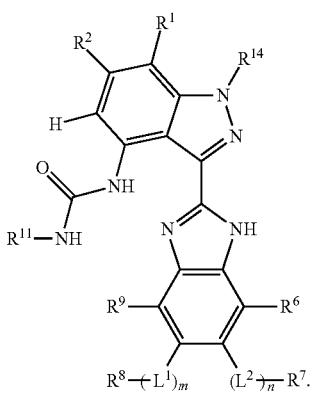

In a further aspect, wherein R³ or R⁴ is halogen, and the method further comprises the step of coupling the compound formed with the boronic acid or boronate ester derivative of Ar¹, wherein Ar¹ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, SO₂R¹⁰, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, SO₂R¹⁰, C1-C3 alkyl, C1-C3 alkylamine, and C1-C3 dialkylamino; and wherein R¹⁰ is selected from hydrogen and C1-C6 alkyl. In a still further aspect, the compound formed has a structure represented by the formula:

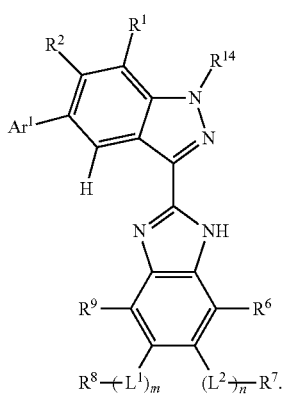

In a yet further aspect, the compound formed has a structure represented by the formula:

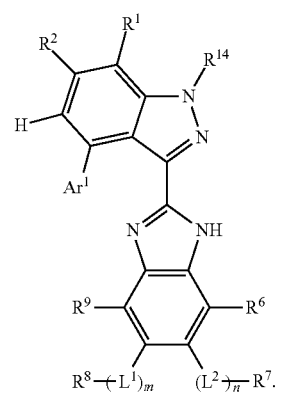

In an even further aspect, coupling is performed in the presence of a palladium catalyst and an organic ligand. In a still further aspect, the palladium catalyst is Pd(OAc)₂ and the organic ligand comprises PPh₃.

In a further aspect, the method further comprises the step of deprotection. In a still further aspect, deprotection comprises hydrolysis of R¹⁴ in the presence of an acid. In a yet further aspect, R¹⁴ is tetrahydro-2H-pyranyl. In an even further aspect, the acid used for deprotection is trifluoroacetic acid.

In a further aspect, the deprotection product is represented by the structure:

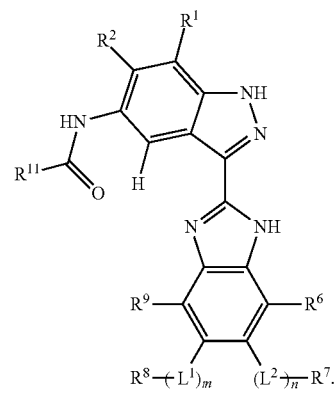

In a further aspect, the deprotection product is represented by the structure:

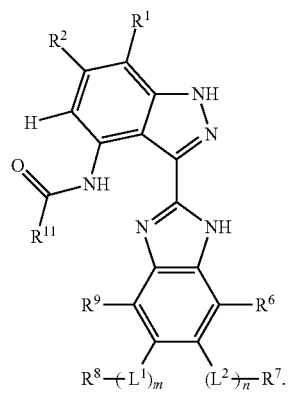

In a further aspect, the deprotection product is represented by the structure:

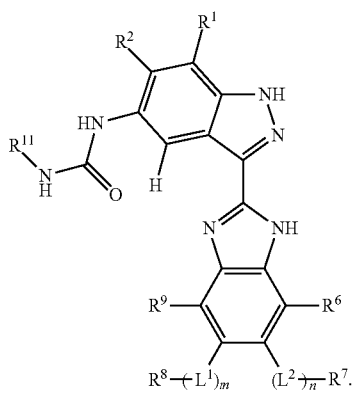

In a further aspect, the deprotection product is represented by the structure:

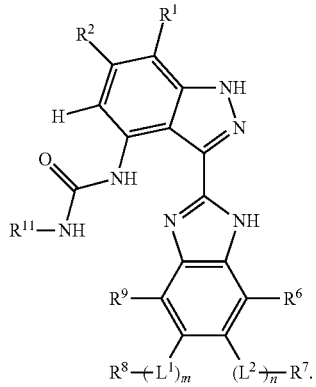

In a further aspect, the deprotection product is represented by the structure:

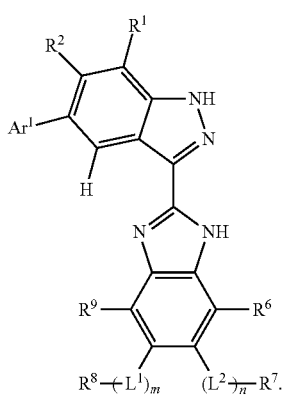

In a further aspect, the deprotection product is represented by the structure:

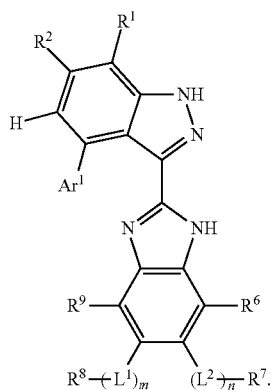

1. Route I

In one aspect, substituted 3-(1H-benzo[d]imidazol-2-yl)-1H-indazole analogs can be prepared as shown below.

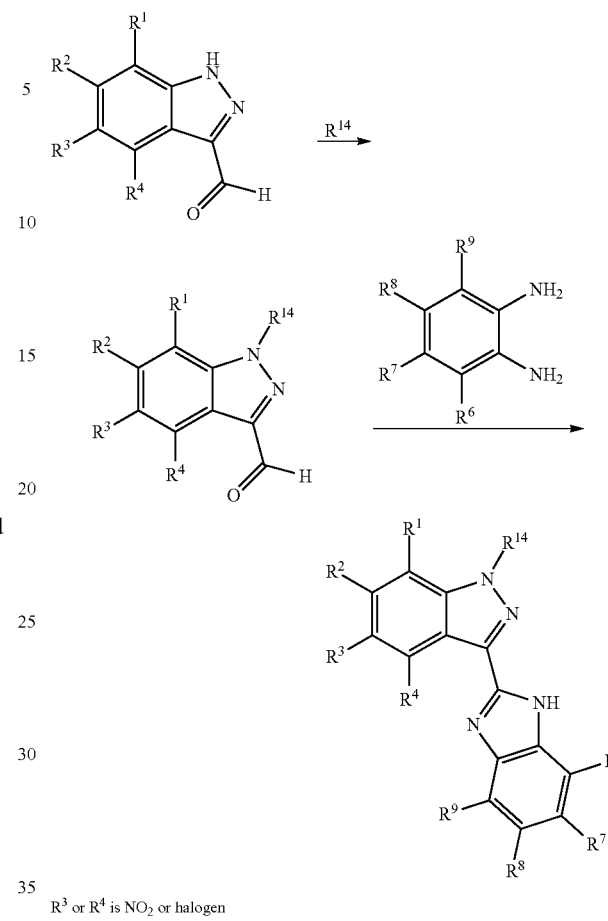

$R^3$ or $R^4$ is $NO_2$ or halogen

Compounds are represented in generic form, with substituents as noted in compound descriptions elsewhere herein. More specific examples are set forth below.

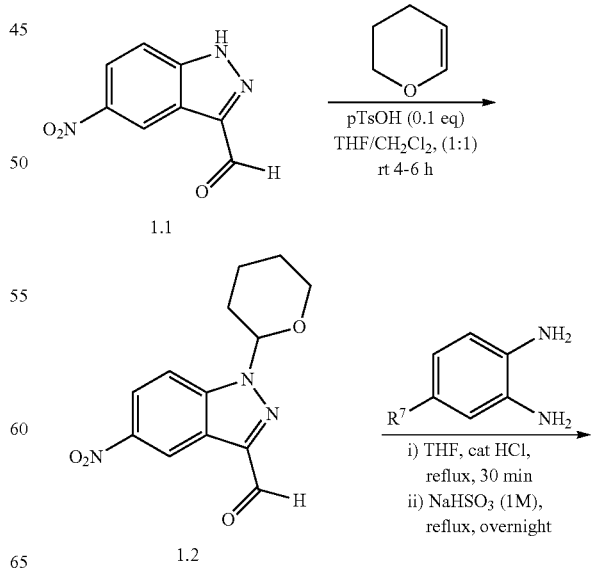

-continued

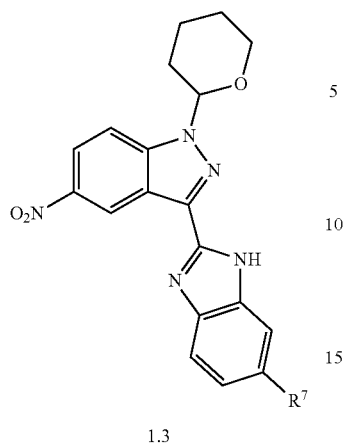

1.3

-continued

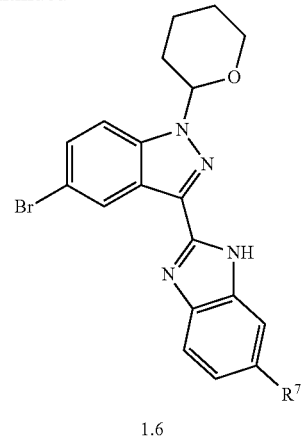

1.6

In one aspect, Route I begins with a substituted 5-nitro-1H-indazole-3-carbaldehyde such as a compound of type 1.1 shown above. To a solution of the carbaldehyde and 3,4-dihydro-2H-pyran in solvent is added p-toluenesulfonic acid and the reaction is carried out at a suitable temperature for a time sufficient to insure completion of the reaction to provide the protected compound of type 1.2. In another aspect, in addition to p-toluenesulfonic acid, other acid catalysts that can be used include, but are not limited to pyridinium trifluoromethane sulfonate or pyridinium p-toluenesulfonate. The compound of type 1.2 and a suitable diamine compound are dissolved in dry solvent, to which a catalytic amount of acid is added. A suitable solvent is dry THF, although one skilled in the art may choose other solvents as are convenient and suitable to the specific reaction. A suitable acid to catalyze the reaction is HCl, although other mineral acids may be used in catalytic quantities as well, e.g. $KHSO_4$. In some circumstances, an alternative to use of a catalytic amount of a mineral acid is use of p-toluenesulfonic acid The solution is then heated at a gentle reflux for about 30-120 min, after which sodium bisulfite is added and reflux of the solution is continued for 8-16 hr to provide a compound of type 1.3.

In one aspect, Route I alternatively begins with a substituted 5-bromo-1H-indazole-3-carbaldehyde such as a compound of type 1.4 shown above. To a solution of the carbaldehyde and 3,4-dihydro-2H-pyran in solvent is added p-toluenesulfonic acid and the reaction is carried out at a suitable temperature for a time sufficient to insure completion of the reaction to provide the protected compound of type 1.5. As described above, in other aspects, alternate acid catalysts may be used in lieu of p-toluenesulfonic acid. Similar to the reaction described above, a compound of type 1.6 and a suitable diamine compound are dissolved in dry solvent, to which a catalytic amount of acid is added. A suitable solvent is dry THF, although one skilled in the art may choose other solvents as are convenient and suitable to the specific reaction. A suitable acid to catalyze the reaction is HCl, although other mineral acids may be used as well. As described above, the solution is then heated at a gentle reflux for about 30-120 min, after which sodium bisulfite is added and reflux of the solution is continued for 8-16 hr to provide a compound of type 1.6.

2. Route II

In one aspect, substituted benzene-1,2-diamine analogs can be prepared as shown below.

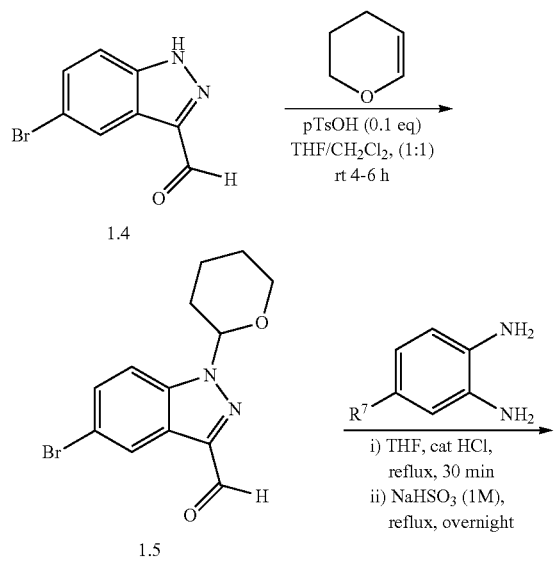

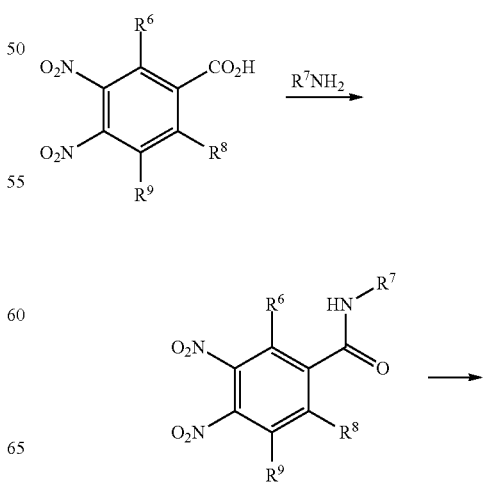

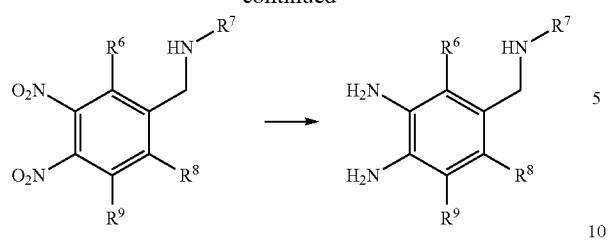

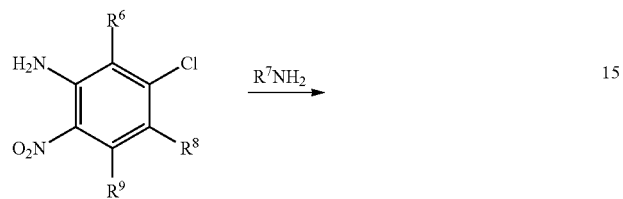

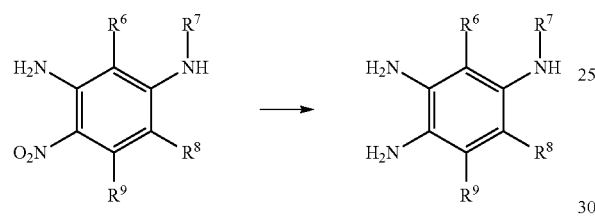

Compounds are represented in generic form, with substituents as noted in compound descriptions elsewhere herein. More specific examples are set forth below.

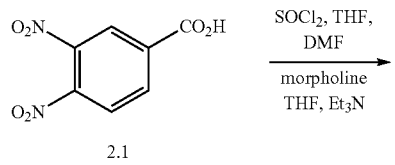

2.1

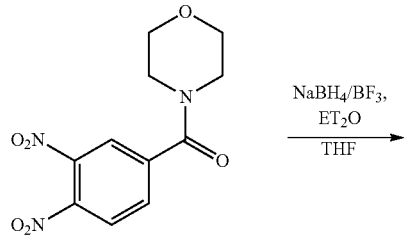

2.2

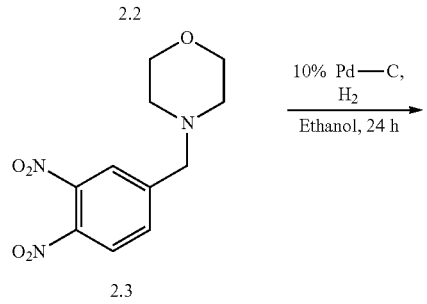

2.3

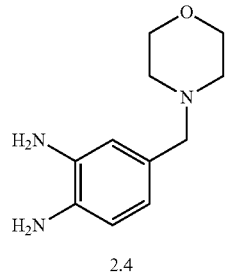

2.4

In one aspect, Route II begins with a substituted 3,4-dinitrobenzoic acid of compound type 2.1. A solution of the compound is prepared in a suitable solvent, e.g. THF, to which a small amount of DMF is added. To this solution, a suitable activating agent is added, e.g. thionyl chloride, is added and the reaction mixture is heated at reflux for a suitable time to ensure completion of the reaction to activate the carboxylic acid of compound type 2.1. The carboxylic acid may be activated by other means such as esterification, generation of a suitable acid anhydride, or use of carbodiimide based coupling chemistry. To the reaction mixture is then added a suitable base, such as triethylamine, and the reaction stirred while maintaining an the reaction mixture temperature is maintained at about 0° C. The reaction is stirred for about 30-120 min, and then a suitable compound is added, e.g. morpholine, and the reaction maintained at ambient temperature, e.g. about 20-30° C., for about 8-16 hr to provide a compound of type 2.2. The carbonyl of compound type 2.2 is reduced in the presence of, boron trifluoride etherate and sodium borohydride. The reaction is carried out for a suitable period of time at a suitable temperature to ensure completion of the reaction, e.g. about 1-6 hr at about 15-30° C. Alternatively, the carbonyl can be reduced using zinc borohydride or sodium borohydride in the presence or trifluoroacetic acid or acetic acid. The nitro moieties of compound type 2.2 are hydrogenated with hydrogen gas in the presence of palladium catalyst, e.g. 10% Pd/C, at a temperature and for a period of time sufficient to complete the reaction. For example the reaction can be carried out at a temperature of about 15-30° C. under atmospheric pressure for a period of about 18-36 hr.

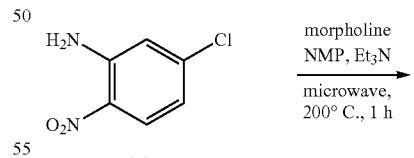

2.5

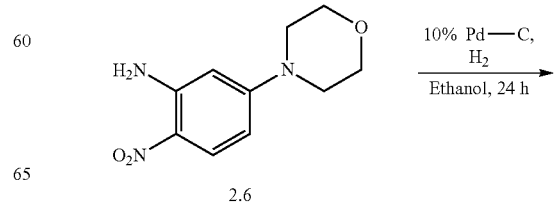

2.6

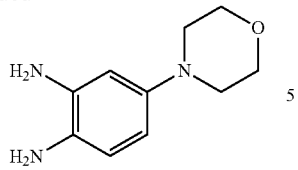

2.7

In one aspect, Route II alternatively begins with a substituted halonitroaniline, e.g. 5-chloro-2-nitroaniline in solution in a suitable solvent, e.g. NMP. To the solution is added a suitable compound to be couple to the halonitroaniline, e.g. a nitrogen containing heterocycle such as morpholine as shown above, and a suitable acid scavenger such as triethylamine. The reaction is heated at a suitable temperature for a time sufficient to complete the reaction. For example, the reaction can be carried out using microwave irradiation, e.g. about 80-200° C. for about 30-240 min. The nitro moiety is hydrogenated under reaction conditions similar to that described above.

3. Route III

In one aspect, substituted 3-(1H-benzo[d]imidazol-2-yl)-1H-indazole analogs can be prepared as shown below.

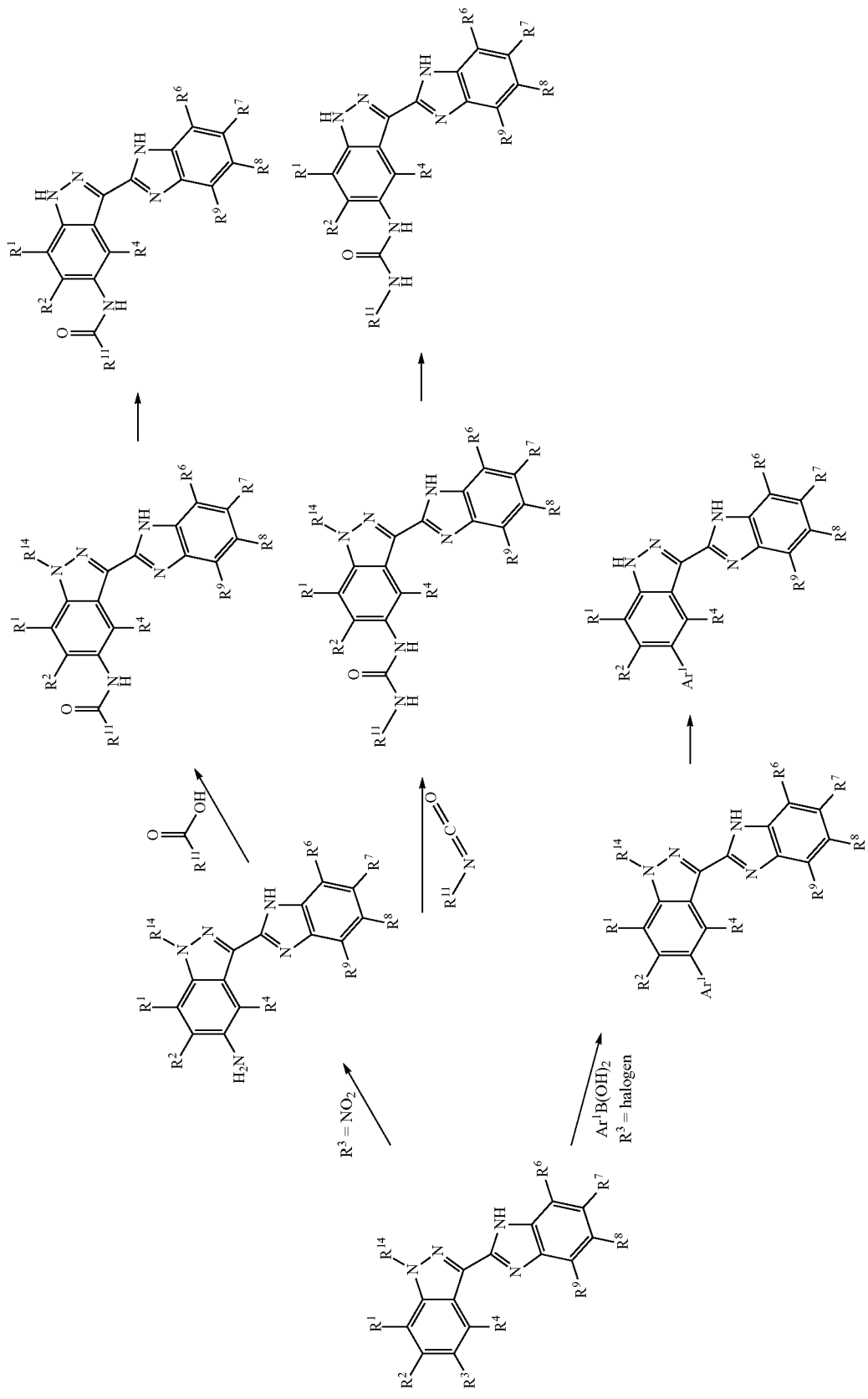

Compounds are represented in generic form, with substituents as noted in compound descriptions elsewhere herein. More specific examples are set forth below.

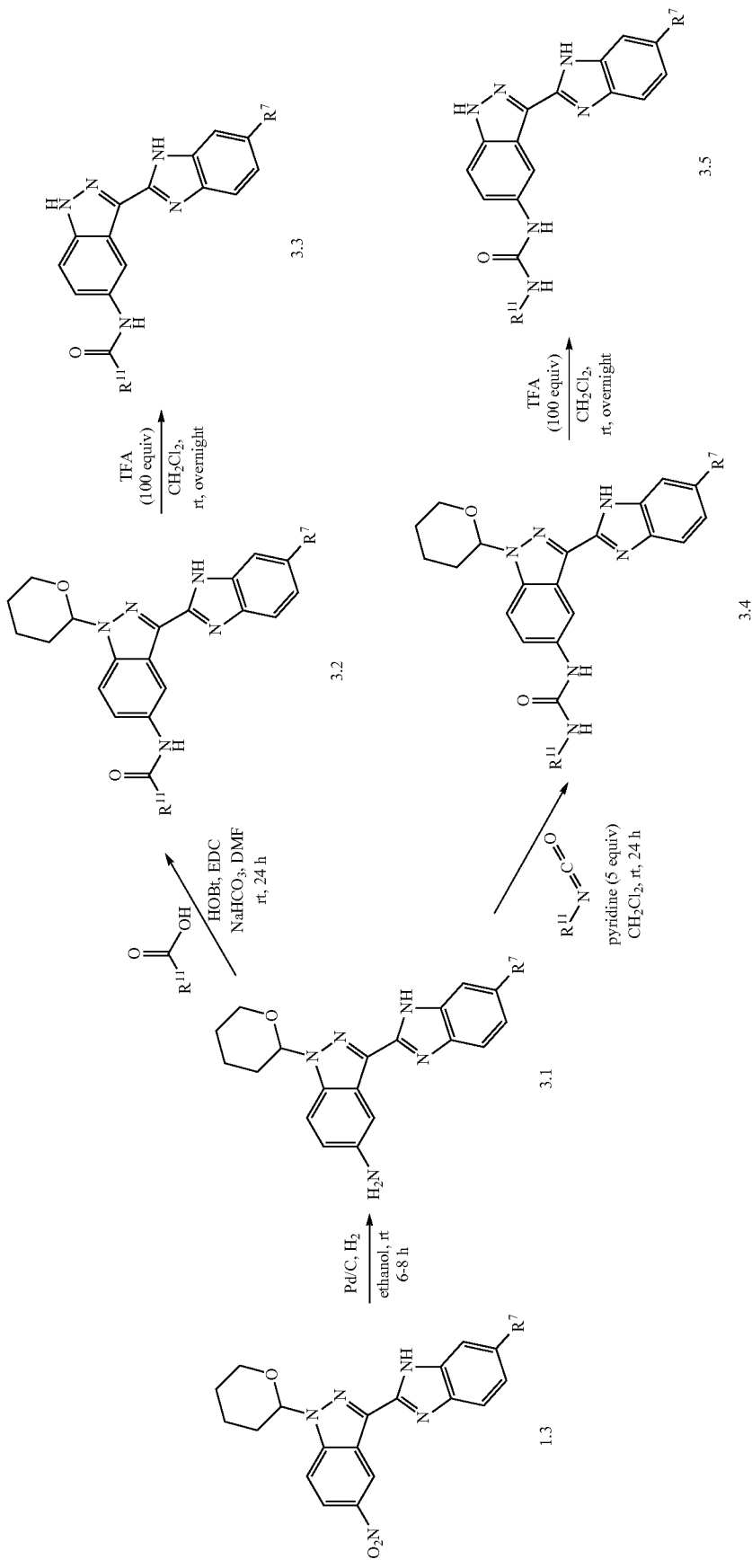

In one aspect, Route III begins with a compound of type 1.3, e.g. a substituted 3-(1H-benzo[d]imidazol-2-yl)-5-nitro-1-(tetrahydro-2H-pyran-2-yl)-1H-indazole prepared as described above in Route I. The nitro moiety is hydrogenated in the initial reaction. Briefly, to a solution of compound 10% Pd/C in a suitable solvent, e.g. ethanol, is added a compound of type 1.3. Hydrogen gas is introduced at a suitable pressure, e.g. about 60 psi, and the reaction carried out overnight at about 15-30° C. to provide a compound of type 3.1. This compound can be used to produce either a compound of type 3.3 or 3.5.

For example, reaction of compound type 3.1 with a suitable isocyanate in a suitable solvent and in the presence of a compound such as pyridine with reaction at a suitable temperature and for a time sufficient to ensure complete reaction provides a compound of type 3.4. Suitable solvents for reaction include dichloromethane, although other solvents can be used as required for the specific reaction as determined by one skilled in the art. The reaction can be carried out at about 15-30° C. for a period of 8-36 hr as is convenient or required to achieve completion of the reaction. Deprotection can be accomplished reaction of compound type 3.6 with a suitable acid, e.g. trifluoroacetic acid, in a suitable solvent, e.g. dichloromethane, for a period of time and at a temperature to ensure completion of the reaction, e.g. about 15-30° C. for a period of 8-36 hr. Deprotection provides a compound of type 3.5. Alternatively, deprotection can be carried out using Amberlyst-15 with water, or p-toluenesulfonic acid in the presence of an alcohol, or an aqueous acid.

Alternatively, a compound of type 3.3 can begin by reaction of compound type 3.1 with a suitable carboxylic acid or derivative thereof, e.g. the acyl halide, ester or acid anhydride analog thereof, in a suitable solvent, e.g. DMF, in the presence of a suitable carobodiimide, e.g. 1-Ethyl-3-(3-dimethylaminopropyl)carbodiimide, under slightly basic conditions, e.g. addition of sodium bicarbonate, and a suitable additive such as 1-Hydroxybenzotriazole (HOBt), to provide a product of compound type 3.3. Other carbodiimides may be utilized as required such as dicyclohexylcarbodiimide or N,N'-diisopropylcarbodiimide, as determined by one skilled in the art to appropriate for the specific reaction. Alternatives to HOBt may be used, e.g. 1-hydroxy-7-aza-benzotriazole (HOAt). The reaction is carried out for a time and at a temperature sufficient to ensure completion, e.g. about 15-30° C. for a period of 8-36 hr. Deprotection of compound 3.3 proceeds as described above.

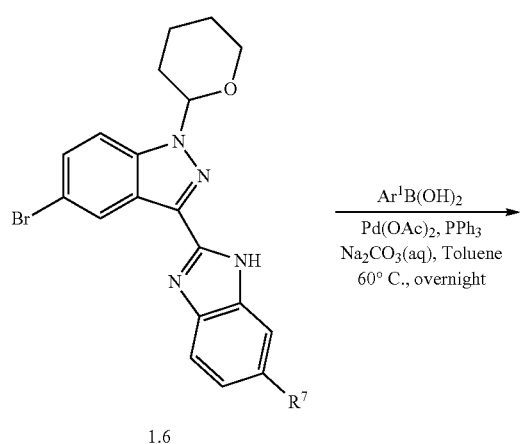

1.6

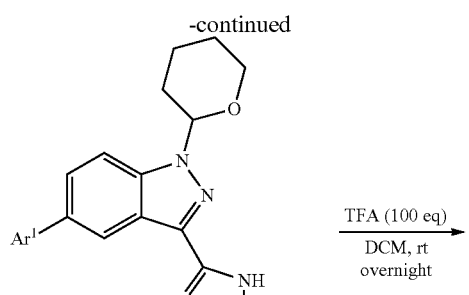

3.6

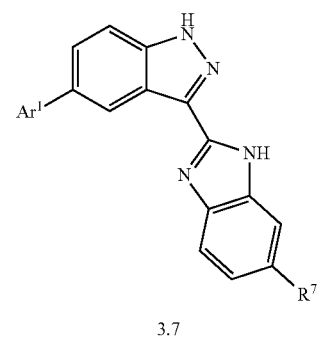

3.7

In one aspect, Route III alternatively begins with a compound of type 1.6., e.g. a substituted 3-(1H-benzo[d]imidazol-2-yl)-5-bromo-1-(tetrahydro-2H-pyran-2-yl)-1H-indazole prepared as described above in Route I. The compound, along with a suitable aryl boronic acid (or aryl boronate ester analog) and triphenylphosphine are dissolved in a mixture comprising a suitable solvent, base, and palladium catalyst. For example, a suitable palladium catalyst can be palladium (II) acetate and a suitable base can be sodium carbonate. Other palladium catalysts-ligands suitable for this Suzuki-type coupling reaction are known to one skilled in the art. Suitable solvents include toluene and THF, although other solvents may be preferred depending upon the variables of the reaction. The reaction is carried out at a temperature for a suitable period of time to ensure completion of the reaction, e.g. about 30-90° C. for a period of about 8-36 hr. Alternatively, the reaction is heated at reflux. The reaction provides a compound of type 3.6 Deprotection of compound type 3.6 to provide compound 3.7 is carried out under similar reaction conditions to those described above.

In various aspects the invention relates to methods of making a compound comprising the steps as shown in more specific examples as set forth below.

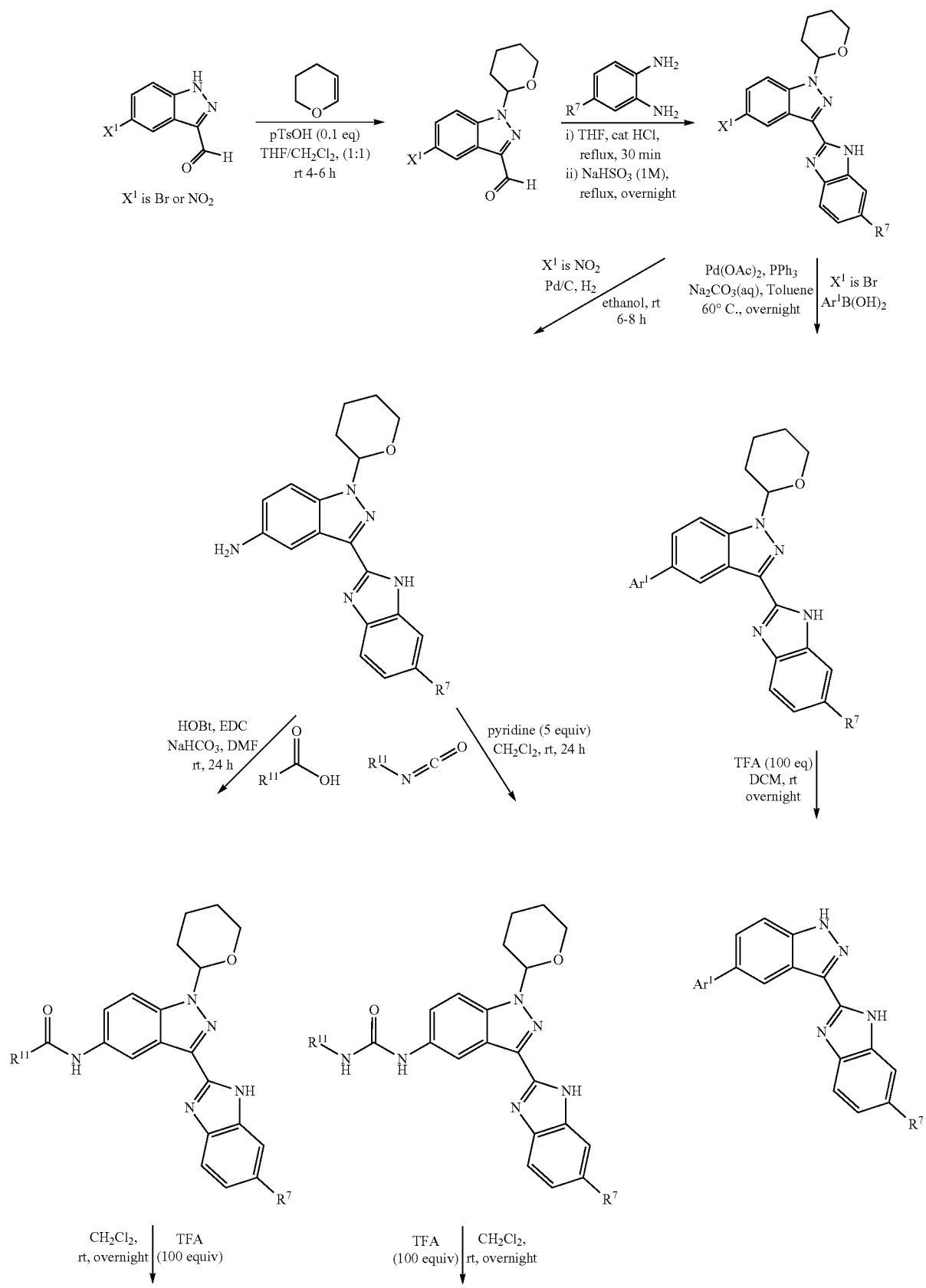

121

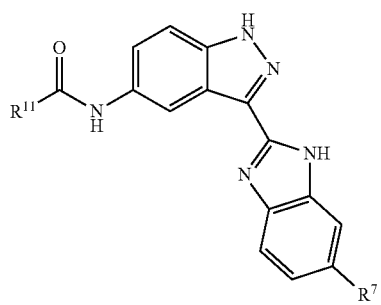

122

-continued

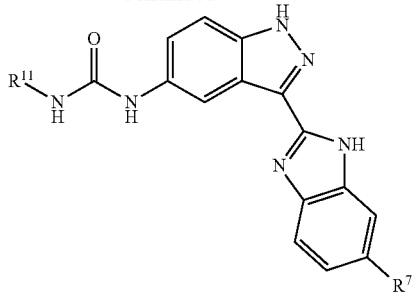

For example, in the specific examples given above, when the reagent is:

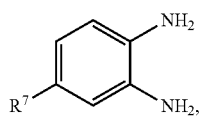

the R⁷ group can be one of the following:

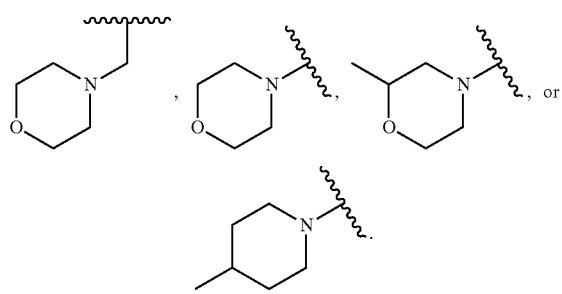

In the specific examples above, when the reagent is Ar¹B(OH)₂, the Ar¹ group can be one of the following:

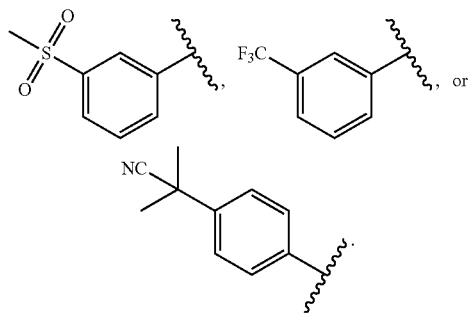

In the reaction step comprising use of the reagent:

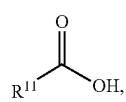

the $R^{11}$ can be one of the following:

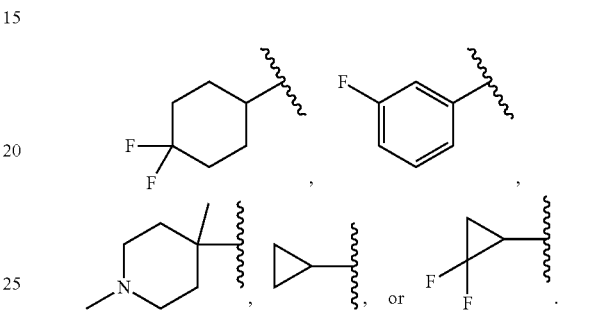

Alternatively, in the reaction step comprising use of the reagent:

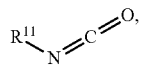

the $R^{11}$ can be one of the following:

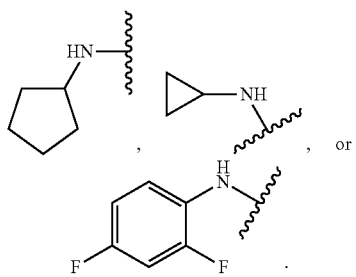

In a further aspect, the compound produced exhibits inhibition of the PI3K/Akt pathway. In a still further aspect, the compound produced exhibits inhibition of cell viability.

In a further aspect, the compound produced exhibits inhibition of a protein kinase. In a still further aspect, the compound produced exhibits inhibition of a protein kinase selected from 3-phosphoinositide-dependent protein kinase 1, aurora kinase A, c-abl oncogene 1 kinase (T315I form), fms-related tyrosine kinase 3, fibroblast growth factor receptor 1, interleukin-1 receptor-associated kinase 4, Janus kinase 1, Janus kinase 2, Janus kinase 3, mitogen-activated protein kinase kinase kinase kinase 4 (MAP4K4), ret proto-oncogene, spleen tyrosine kinase, tyrosine-protein kinase Fyn, vascular endothelial growth factor receptor 2, and vascular endothelial growth factor receptor 3. In a yet further aspect, the compound exhibits inhibition of 3-phosphoinositide-dependent protein kinase 1 ("PDK1").

In a further aspect, the compound produced exhibits inhibition with an $IC_{50}$ of less than about $1.0 \times 10^{-4}$ M. In a still further aspect, the compound produced exhibits inhibition with an $IC_{50}$ of less than about $1.0 \times 10^{-5}$ M. In a yet further aspect, the compound produced exhibits inhibition with an $IC_{50}$ of less than about $1.0 \times 10^{-6}$ M. In an even further aspect, the compound produced exhibits inhibition with an $IC_{50}$ of less than about $1.0 \times 10^{-7}$ M. In a still further aspect, the compound produced exhibits inhibition with an $IC_{50}$ of less than about $1.0 \times 10^{-8}$ M. In a yet further aspect, the compound produced exhibits inhibition with an $IC_{50}$ of less than about $1.0 \times 10^{-9}$ M.

It is contemplated that each disclosed methods can further comprise additional steps, manipulations, and/or components. It is also contemplated that any one or more step, manipulation, and/or component can be optionally omitted from the invention. It is understood that a disclosed methods can be used to provide the disclosed compounds. It is also understood that the products of the disclosed methods can be employed in the disclosed methods of using.

Tables III and IV below lists specific compounds as well as experimentally determined PDK1 kinase activity determined in the activity and/or binding assay as described below in the examples. It should be noted that the compound numbers in Table IV correspond to the numbers and respective structures given in Table III. The compounds in the tables below were synthesized with methods identical or analogous to those shown herein. The requisite starting materials were commercially available, described in the literature, or readily synthesized by one skilled in the art of organic synthesis.

TABLE III

| No. | Structure | PDK1 Kinase assays ($IC_{50}$, μM) | |
|---|---|---|---|
| | | Activity Assay * | Binding Assay ** |
| 1 | 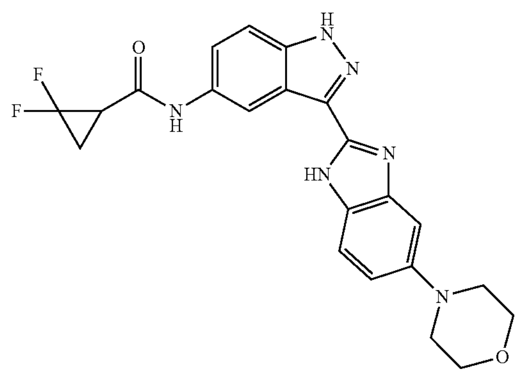 [SMILES: O=C(Nc1ccc2[nH]nc(-c3nc4cc(N5CCOCC5)ccc4[nH]3)c2c1)C1CC1(F)F] | 0.143 | 0.080 |
| 2 | 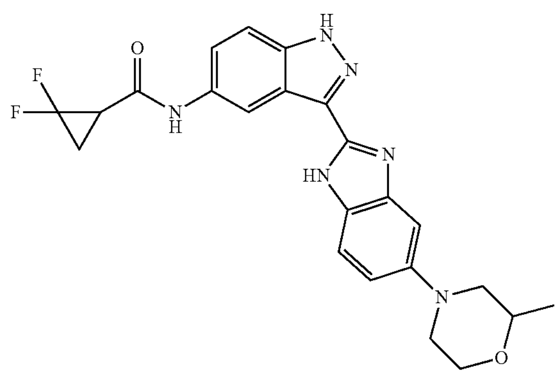 [SMILES: CC1CN(c2ccc3[nH]c(-c4n[nH]c5ccc(NC(=O)C6CC6(F)F)cc45)nc3c2)CCO1] | 0.159 | 0.094 |
| 3 | 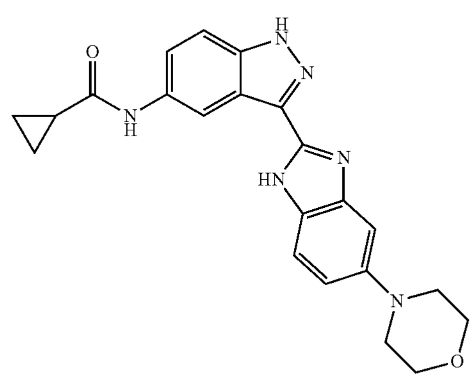 [SMILES: O=C(Nc1ccc2[nH]nc(-c3nc4cc(N5CCOCC5)ccc4[nH]3)c2c1)C1CC1] | 0.283 | 0.229 |

TABLE III-continued

| No. | Structure | PDK1 Kinase assays (IC$_{50}$, μM) Activity Assay * | Binding Assay ** |
|---|---|---|---|
| 4 | 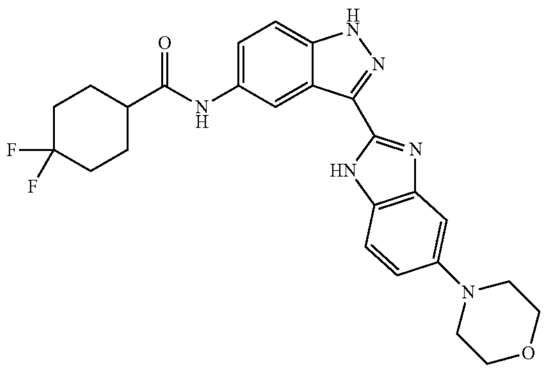 [SMILES: O=C(Nc1ccc2[nH]nc(-c3nc4cc(N5CCOCC5)ccc4[nH]3)c2c1)C1CCC(F)(F)CC1] | 0.304 | 0.265 |
| 5 | 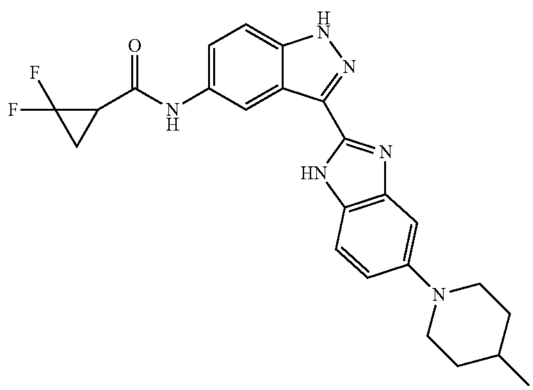 [SMILES: CC1CCN(c2ccc3[nH]c(-c4n[nH]c5ccc(NC(=O)C6CC6(F)F)cc45)nc3c2)CC1] | 0.780 | Not Tested |
| 6 | 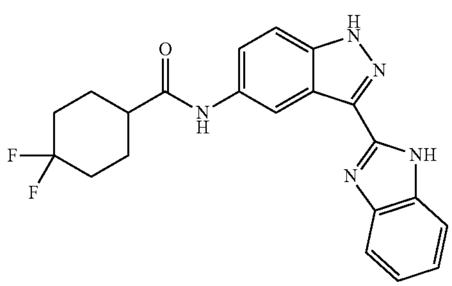 [SMILES: O=C(Nc1ccc2[nH]nc(-c3nc4ccccc4[nH]3)c2c1)C1CCC(F)(F)CC1] | 1.50 | 0.410 |
| 7 | 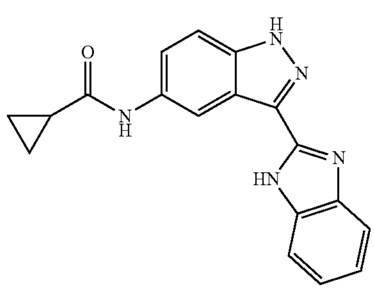 [SMILES: O=C(Nc1ccc2[nH]nc(-c3nc4ccccc4[nH]3)c2c1)C1CC1] | 1.74 | 1.23 |

TABLE III-continued

| No. | Structure | PDK1 Kinase assays (IC$_{50}$, μM) | |
|---|---|---|---|
| | | Activity Assay * | Binding Assay ** |
| 8 | 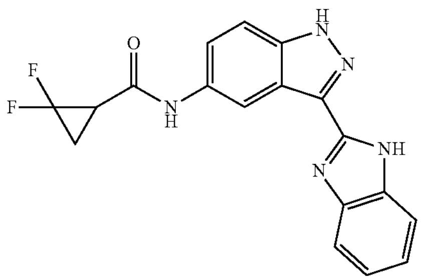 [SMILES: O=C(Nc1ccc2[nH]nc(-c3nc4ccccc4[nH]3)c2c1)C1CC1(F)F] | 1.94 | 0.280 |
| 9 | 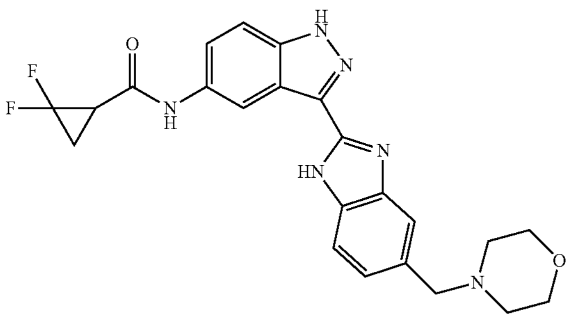 [SMILES: O=C(Nc1ccc2[nH]nc(-c3nc4cc(CN5CCOCC5)ccc4[nH]3)c2c1)C1CC1(F)F] | 3.75 | 1.22 |
| 10 | 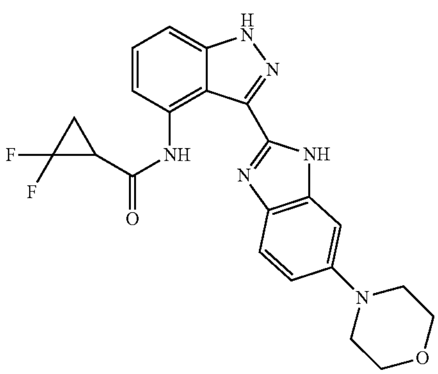 [SMILES: O=C(Nc1cccc2[nH]nc(-c3nc4ccc(N5CCOCC5)cc4[nH]3)c12)C1CC1(F)F] | 4.40 | 0.385 |
| 11 | 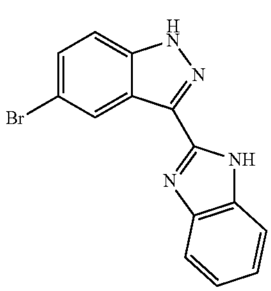 [SMILES: Brc1ccc2[nH]nc(-c3nc4ccccc4[nH]3)c2c1] | 10.9 | |

TABLE III-continued

| No. | Structure | PDK1 Kinase assays (IC$_{50}$, μM) | |
|---|---|---|---|
| | | Activity Assay * | Binding Assay ** |
| 12 | 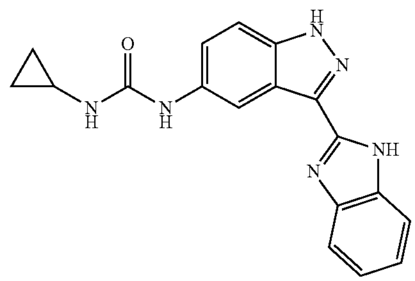 [SMILES: O=C(Nc1ccc2[nH]nc(-c3nc4ccccc4[nH]3)c2c1)NC1CC1] | 11.6 | 0.920 |
| 13 | 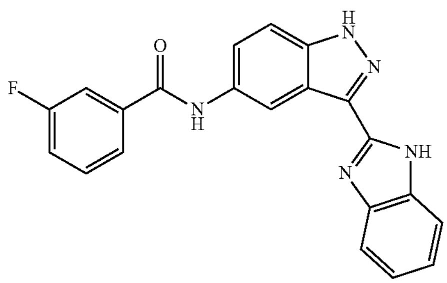 [SMILES: O=C(Nc1ccc2[nH]nc(-c3nc4ccccc4[nH]3)c2c1)c1cccc(F)c1] | 21.1 | 8.79 |
| 14 | 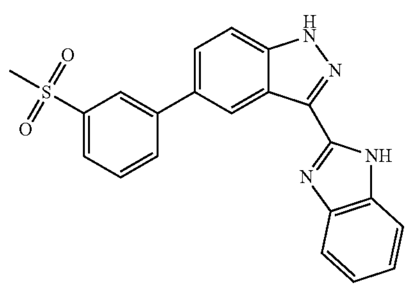 [SMILES: CS(=O)(=O)c1cccc(-c2ccc3[nH]nc(-c4nc5ccccc5[nH]4)c3c2)c1] | 23.7 | 15.3 |
| 15 | 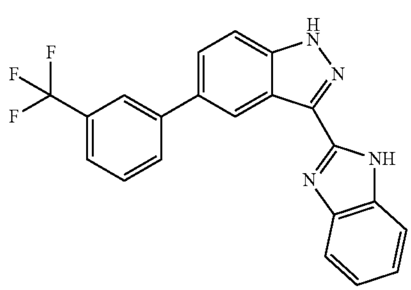 [SMILES: FC(F)(F)c1cccc(-c2ccc3[nH]nc(-c4nc5ccccc5[nH]4)c3c2)c1] | 55.7 | 30.3 |
| 16 | 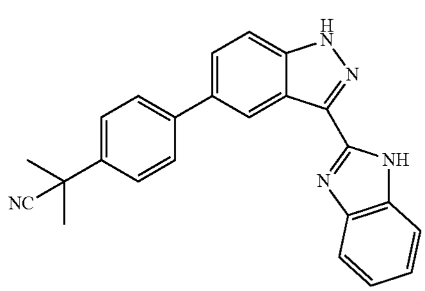 [SMILES: CC(C)(C#N)c1ccc(-c2ccc3[nH]nc(-c4nc5ccccc5[nH]4)c3c2)cc1] | 58.5 | 5.17 |

TABLE III-continued

| No. | Structure | PDK1 Kinase assays (IC$_{50}$, μM) | |
|---|---|---|---|
| | | Activity Assay * | Binding Assay ** |
| 17 | 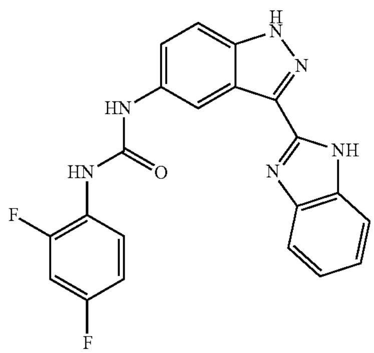 [SMILES: O=C(Nc1ccc2[nH]nc(-c3nc4ccccc4[nH]3)c2c1)Nc1ccc(F)cc1F] | >100 | >100 |
| 18 | 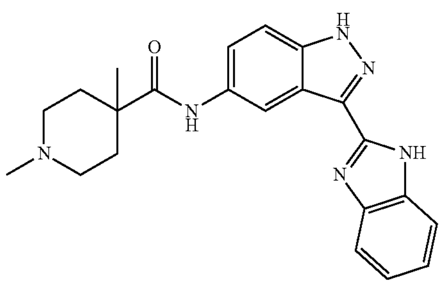 [SMILES: CN1CCC(C)(C(=O)Nc2ccc3[nH]nc(-c4nc5ccccc5[nH]4)c3c2)CC1] | >100 | 12.4 |
| 19 | 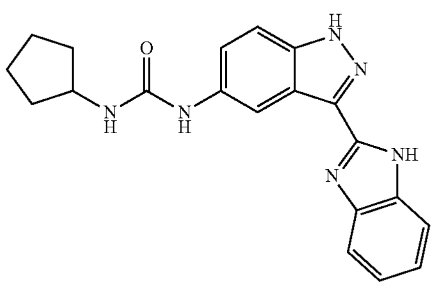 [SMILES: O=C(Nc1ccc2[nH]nc(-c3nc4ccccc4[nH]3)c2c1)NC1CCCC1] | >100 | 53.9 |
| 20 | 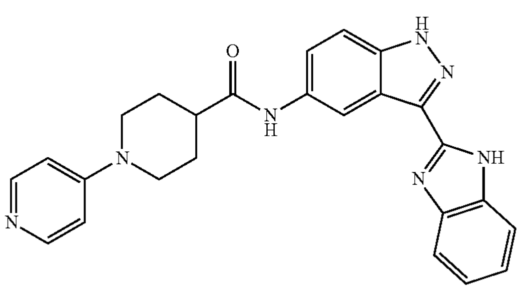 [SMILES: O=C(Nc1ccc2[nH]nc(-c3nc4ccccc4[nH]3)c2c1)C1CCN(c2ccncc2)CC1] | >100 | >100 |

TABLE III-continued

| No. | Structure | PDK1 Kinase assays (IC$_{50}$, µM) | |
| --- | --- | --- | --- |
| | | Activity Assay * | Binding Assay ** |
| 21 | [structure: N-(1H-indazol-6-yl)-2,2-difluorocyclopropanecarboxamide linked to benzimidazole with morpholine substituent] | >100 | >100 |

* PDK1 activity determined used the PDK1 ATP Depletion Assay as described in the Examples below using the PDKtide substrate (Millipore Corporation, Billerica, Massachussetts).
** PDK1 binding activity determined in the the Time Resolved-FRET Lanthascreen Kinase Binding Assay (Invitrogen Corporation, Carlsbad, California) as described in the Examples below.

TABLE IV

| No. | PDK1 Kinase assays * (IC$_{50}$, µM) |
| --- | --- |
| 1 | 0.080 |
| 2 | 0.094 |
| 3 | 0.23 |
| 4 | 0.265 |
| 5 | 0.780 |
| 6 | 0.41 |
| 7 | 1.23 |
| 8 | 0.28 |
| 9 | 1.22 |
| 10 | 0.385 |
| 11 | n.d. |
| 12 | 0.92 |
| 13 | 8.8 |
| 14 | 15.3 |
| 15 | 30.3 |
| 16 | 5.2 |
| 17 | n.d. |
| 18 | 12.39 |
| 19 | 53.9 |
| 20 | n.d. |
| 21 | n.d. |

* PDK1 activity determined in a fluorometric assay performed by Life Technologies as described in the Examples below; "n.d." indicates that the IC$_{50}$ was not determined for the indicated compound.

F. Pharmaceutical Compositions

In one aspect, the invention relates to pharmaceutical compositions comprising a pharmaceutically acceptable carrier and an effective amount of a compound represented by a formula:

[structure: substituted indazole-benzimidazole core with substituents $R^1$–$R^9$, $L^1$, $L^2$]

wherein $L^1$ is C=O or $(CH_2)_p$, wherein p is an integer from 1 to 3, wherein m is 0 or 1; wherein $L^2$ is C=O or $(CH_2)_q$, wherein q is an integer from 1 to 3, wherein n is 0 or 1; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino; wherein $R^{10}$ is selected from hydrogen and C1-C6 alkyl; wherein $R^1$ is selected from hydrogen, halogen, cyano, and C1-C6 alkyl; wherein $R^2$ is selected from hydrogen, halogen, cyano, and C1-C6 alkyl; wherein $R^3$ is selected from hydrogen, $Ar^1$, NHC=O$R^{11}$, and NHC=ONH$R^{11}$; wherein $R^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, C3-C6 heterocycloalkyl, and $Ar^1$; wherein $R^4$ is selected from hydrogen, $Ar^1$, NH$R^{11}$, and NHC=ON$R^{11}$, provided only one of $R^3$ and $R^4$ is not hydrogen; wherein $R^5$ is selected from hydrogen and C1-C6 alkyl;

wherein R⁶ is selected from hydrogen, halogen, and C1-C6 alkyl; wherein R⁷ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; wherein R⁸ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; and wherein R⁹ is selected from hydrogen, halogen, and C1-C6 alkyl; or a pharmaceutically acceptable salt, hydrate, solvate, or polymorph thereof.

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier. In a still further aspect, the effective amount is a therapeutically effective amount. In a yet still further aspect, the effective amount is a prophylactically effective amount.

In a further aspect, the pharmaceutical composition exhibits inhibition of the PI3K/Akt pathway. In a still further aspect, the inhibition of PI3K/Akt pathway is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the pharmaceutical composition exhibits inhibition of the phosphorylation of Akt. In a still further aspect, the inhibition of Akt phosphorylation is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the pharmaceutical composition exhibits inhibition of a protein kinase. In a still further aspect, the protein kinase that is inhibited is selected from 3-phosphoinositide-dependent protein kinase 1, aurora kinase A, c-abl oncogene 1 kinase (T315I form), fms-related tyrosine kinase 3, fibroblast growth factor receptor 1, interleukin-1 receptor-associated kinase 4, Janus kinase 1, Janus kinase 2, Janus kinase 3, mitogen-activated protein kinase kinase kinase kinase 4 (MAP4K4), ret proto-oncogene, spleen tyrosine kinase, tyrosine-protein kinase Fyn, vascular endothelial growth factor receptor 2, and vascular endothelial growth factor receptor 3. In a still further aspect, the protein kinase that is inhibited is 3-phosphoinositide-dependent protein kinase 1.

In a still further aspect, the protein kinase is inhibited with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the pharmaceutical composition exhibits inhibition of cell viability. In a still further aspect, inhibition of cell viability is determined in a cell line selected from AN3-CA, LNCaP, RL95-2, KG-1, MV4-11, BT-20, RKO, MCF7, BT549, U87-MG, PC3, and Kasumi cells. In a yet further aspect, the inhibition of cell viability is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the pharmaceutical composition is administered to a mammal. In a yet further aspect, the mammal is a human. In a still further aspect, the pharmaceutical composition is administered following identification of a mammal in need of treatment of a disorder of uncontrolled cellular proliferation. In a still further aspect, the mammal has been diagnosed with a need for treatment of a disorder of uncontrolled cellular proliferation prior to the administering step.

In a further aspect, the pharmaceutical composition is administered to treat a disorder of uncontrolled cellular proliferation. In a yet further aspect, the pharmaceutical composition is administered to treat a disorder of uncontrolled cellular proliferation associated with a protein kinase dysfunction. In a still further aspect, the disorder of uncontrolled cellular proliferation is a cancer. In a yet further aspect, the cancer is a leukemia. In an even further aspect, the cancer is a lymphoma. In a yet further aspect, the cancer is a solid tumor. In a still further aspect, the cancer is selected from cancers of the brain, genitourinary tract, gastrointestinal tract, colon, rectum, breast, kidney, lymphatic system, stomach, lung, pancreas, and skin. In an even further aspect, the cancer is selected from cancers of the prostate cancer, glioblastoma multiforme, endometrial cancer, breast cancer, and colon cancer.

In a further aspect, the cancer is a cancer of the brain. In a still further aspect, the cancer is selected from acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor cell.

In a further aspect, the cancer is a cancer associated with a loss of PTEN function. For example, the loss of PTEN function can result from a genetic mutation in the PTEN gene. In a further aspect, the genetic mutation in the PTEN gene is selected from K267fs*9, K267fs*9, K267fs*9, K6fs*4, K6fs*4, K6fs*4, N323fs*2, N323fs*2, N323fs*2, N323fs*21, N323fs*21, N323fs*21, P248fs*5, P248fs*5, P248fs*5, R130Q, R130Q, R130Q, R130fs*4, R130fs*4, R130fs*4, R130G, R130G, R130G, R130*, R130*, R130*, R173c, R173c, R173c, R173H, R173H, R173H, R233*, R233*, R233*, R335*, R335*, R335*, V317fs*3, V317fs*3, and V317fs*3.

In a further aspect, the cancer is a cancer associated with PI3K activation. In a further aspect, the PI3K activation is associated with a genetic mutation in a gene. In an even further aspect, the genetic mutation is in a gene selected from PIK3CA, PIKR1, H-RAS, K-RAS, and N-RAS. In a still further aspect, the genetic mutation is a PIK3CA mutation selected from R38H, R88Q, N345K, C420R, P359R, E542K, E545K, Q546K, H701P, C901F, M1043I, H1047R/L, and H1047Y. In a yet further aspect, the genetic mutation is a PIK3R1 mutation selected from R574T and A634P. In an even further aspect, the genetic mutation is a H-RAS mutation selected from G12V/D, G13R/C/S, Q61H/H, G61L/R/P, and QQ61K. In a still further aspect, the genetic mutation is a K-RAS mutation selected from G12C, G12R, G12S, G12V, G12D, G12A, G12F, G13V/D, A59T, Q61E/K, Q61L/R/P, and Q61H. In a yet further aspect, the genetic mutation is a N-RAS mutation selected from G12V/A/D, G12C/R/S, G13V/A/D, G13C/R/S, A18T, Q61L/R/P, Q61H, and Q61E/K.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require inhibition of protein kinase activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament inhibiting protein kinase activity (e.g., treatment of one more types of cancer) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

G. Methods of Using the Compounds and Compositions

Figure 4:
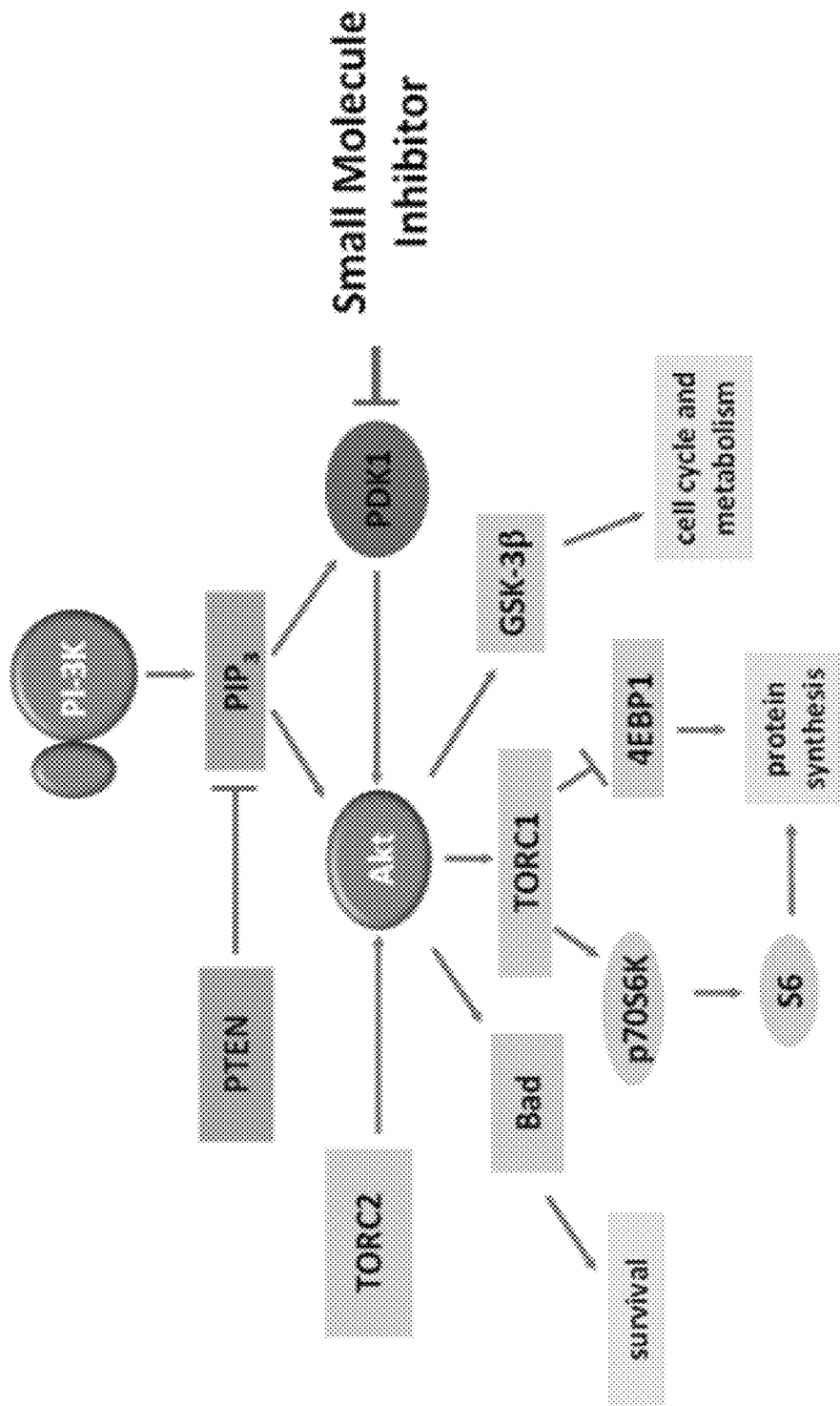
FIG. 4 shows aspects of the PI3K/Akt signaling pathway.

PDK1 is a critical activator of multiple proteins involved in pro-survival and oncogenic activity. Activation of PI3K by engagement of cell surface receptor tyrosine kinases by insulin and growth factors generates phosphatidyl-inositol,3,4,5 triphosphate PIP3 (M. Whitman, et al., Nature 1998, 332: 644). PDK1 and Akt are recruited to the cell membrane and subsequently activated in response to increases in PIP3 generated by the activity of PI3K. The recruitment of PDK1 and AKT to the cell membrane is mediated through interactions of homologous pleckstrin homology domains. Localization of these proteins to the plasma membrane allows PDK1 to activate AKT by phosphorylation at residue threonine-308 (L. Stephens et al., Science 1998, 279:710). Activated PDK1 phosphorylates Akt as part of an important signaling pathway that ultimately regulates the signaling of multiple biological processes. The PDK1 kinase domain has a minimum of three ligand-binding sites: the ATP biding pocket, the peptide substrate-binding site and a groove in the N-terminal lob that binds the C-terminal hydrophobic motif of its kinase substrates (R. M. Biondi et al., EMBO J. 2002, 21:4219). In addition to Akt, PDK1 phosphorylates the conserved activation loop residue of many members of other protein kinase families in different cell types including S6K, SGK, and PKC (A. Mora, et al., Semin Cell Dev Biol 2004, 15:161). In one aspect, the signaling pathway involving PDK1 is as described in FIG. 4.

Unchecked signaling through the PI3K pathways has disastrous consequences for the cell and the organism, including the development of cancer. The tumor suppressor phosphatase and tensin homologue deleted on chromosome 10 (PTEN) is the major negative regulator of this signaling pathway (T. Maehama and J. E. Dixon, J Biol Chem 1998, 273: 13375). The activity of PTEN reverses PI3K signaling by dephosphorylation of PIP3. PTEN activity can by modified by both genetic (deletions and mutations) and epigenetic processes (alterations in promoter methylation). The loss of PTEN function has a substantial impact in cell development a tumorigenesis. Decreased expression of PTEN has been described in many cancers, but is most prevalent in endometrial cancers, glioblastoma, prostate and breast cancers and melanoma (H. Tashiro et al., Cancer Res 1997, 57:3935; E. Chiariello, et al., Oncogene 1998, 16:541; J. Li et al., Science, 1997, 275:1943). Without wishing to be bound by a particular theory, modulation of PDK1 activity through pharmacological intervention may have elevated significance in tumors with genetic aberrations of PTEN.

The relationship between PDK and PTEN provides balance to cells during normal development and growth but has more malignant consequences in cancer. Several studies have described this relationship. In PTEN deficient drosophila, it was observed that flies engineered with a mutation in the PH domain of Akt, rescued the lethality of PTEN deficient flies (H. Stocker et al., Science, 2002, 295:2088). In PTEN+/− mice prone to developing tumors from many tissue origins, knocking down the levels of PDK1 by genetic alteration suppressed the development of tumors in these mice (J. R. Bayascas, et al., Curr Biol, 2005, 15:1839). This effect was observed over a wide range of tumor types and validates PDK1 as a potential therapeutic target in PTEN deficient tumors. In a related study, conditional PTEN−/− mice were crossed with Akt−/− mice another group found that the Akt deficient was sufficient to inhibit the development of several tumor types, the effect being most influential in endometrial carcinoma and prostate neoplasia (M. L. Chen et al., Genes Dev, 2006, 20:1569). This rescue was even detected in mice haplodeficeint with Akt. A similar phenomenon has also been demonstrated in neural tissue. A conditional deletion of PDK1 was observed to cause microcephaly in mice and that the combine deletion of PTEN and PDK1 was able to rescue this abnormality (N. Chalhoub, et al., Genes Dev, 2009, 23:1619). This further suggests the balance between the activities of PTEN and PDK1 in both normal physiology and disease. Without wishing to be bound by a particular theory, it is believed that reducing the activity of PDK through pharmacological intervention in diseases harboring PTEN deficiency can have an important therapeutic benefit.

In addition to targeting the proteins directly, the PDK1 pathway can regulate the sensitivity of breast cancer to tamoxifen and inhibition of PDK1 reverses the resistance of breast cancer to tamoxifen (E. Iorns, et al., Biochem J, 2009, 417:361). PTEN deficiency and its resulting molecular phenotype in human cancers may provide a molecular signature that could provide a biomarker that would be predictive of successful therapy with PDK1 inhibitors. Without wishing to be bound by a particular theory, it is believed that PDK1 will likely still demonstrate biochemical and clinical utility outside the PI3K/Akt pathway due to the regulation by PDK1 of the activity of kinases that are involved in similar hallmarks of cancer.

A great number of tumors have genetic abnormalities that result over-activation of the PI3K/Akt signaling pathway. Without wishing to be bound by a particular theory, it is believed that inhibition of PDK1 activity can resolve and rescue the excessive signaling that is a consequence of these mutations. As a whole, the many proteins that propagate signaling through PI3K pathway provide several attractive targets for cancer therapeutics (B. T. Hennessy, et al., Nat Rev Drug Discov, 2005, 4:988). This extensive family of signaling proteins regulates important cell processes that, when dysregulated, lead to typical tumorigenic phenotype features. Inhibition at any point along this signaling cascade is likely to provide clinical benefit to patients with pathologies that are driven by overactive signaling in this pathway. Some important proteins in this pathway have already been exploited as therapeutic targets including PI3K, mTORC1, and Akt (S. Brachmann, et al., Curr Opin Cell Biol, 2009, 21:194). Inhibition of the mTORC complex is another target in the PI3K pathway that has potential therapeutic value.

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of disorders of uncontrolled cellular proliferation. In one aspect, the disorder of uncontrolled cellular proliferation is associated with a dysfunction in the PI3K/Akt signaling pathway. In a further aspect, the disorder of uncontrolled cellular proliferation is associated with a protein kinase dysfunction. In a further aspect, the protein kinase dysfunction is disregulation of the PDK1.

Examples of disorders associated with a dysfunction in the PI3K/Akt pathway include cancers such as leukemias, lymphomas, and solid tumors. In one aspect, the cancer can be a cancer selected from cancers of the brain, genitourinary tract, gastrointestinal tract, colon, rectum, breast, kidney, lymphatic system, stomach, lung, pancreas, and skin. In a further aspect, the cancer is selected from. prostate cancer, glioblastoma multiforme, endometrial cancer, breast cancer, and colon cancer.

In one aspect, the compounds disclosed herein are useful treating a cancer associated with a loss of PTEN function. For example, the loss of PTEN function can result from a genetic mutation in the PTEN gene. In a further aspect, the genetic mutation in the PTEN gene is selected from K267fs*9, K267fs*9, K267fs*9, K6fs*4, K6fs*4, K6fs*4, N323fs*2, N323fs*2, N323fs*2, N323fs*21, N323fs*21, N323fs*21, P248fs*5, P248fs*5, P248fs*5, R130Q, R130Q, R130Q, R130fs*4, R130fs*4, R130fs*4, R130G, R130G, R130G, R130*, R130*, R130*, R173c, R173c, R173c, R173H, R173H, R173H, R233*, R233*, R233*, R335*, R335*, R335*, V317fs*3, V317fs*3, and V317fs*3.

In one aspect, the compounds disclosed herein are useful treating a cancer associated with PI3K activation. In a further aspect, the PI3K activation is associated with a genetic mutation in a gene. In an even further aspect, the genetic mutation is in a gene selected from PIK3CA, PIKR1, H-RAS, K-RAS, and N-RAS. In a still further aspect, the genetic mutation is a PIK3CA mutation selected from R38H, R88Q, N345K, C420R, P359R, E542K, E545K, Q546K, H701P, C901F, M1043I, H1047R/L, and H1047Y. In a yet further aspect, the genetic mutation is a PIK3R1 mutation selected from R574T and A634P. In an even further aspect, the genetic mutation is a H-RAS mutation selected from G12V/D, G13R/C/S, Q61H/H, G61L/R/P, and QQ61K. In a still further aspect, the genetic mutation is a K-RAS mutation selected from G12C, G12R, G12S, G12V, G12D, G12A, G12F, G13V/D, A59T, Q61E/K, Q61L/R/P, and Q61H. In a yet further aspect, the genetic mutation is a N-RAS mutation selected from G12V/A/D, G12C/R/S, G13V/A/D, G13C/R/S, A18T, Q61L/R/P, Q61H, and Q61E/K.

a. Treatment of a Disorder of Uncontrolled Cellular Proliferation

In one aspect, the invention relates to a method for the treatment of a disorder of uncontrolled cellular proliferation disorder in a mammal, the method comprising the step of administering to the mammal an effective amount of least one compound having a structure represented by a formula:

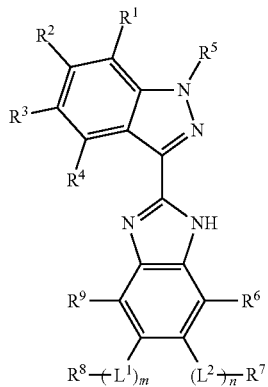

wherein $L^1$ is C=O or $(CH_2)_p$, wherein p is an integer from 1 to 3, wherein m is 0 or 1; wherein $L^2$ is C=O or $(CH_2)_q$, wherein q is an integer from 1 to 3, wherein n is 0 or 1; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino; wherein $R^{10}$ is selected from hydrogen and C1-C6 alkyl; wherein $R^1$ is selected from hydrogen, halogen, cyano, and C1-C6 alkyl; wherein $R^2$ is selected from hydrogen, halogen, cyano, and C1-C6 alkyl; wherein $R^3$ is selected from hydrogen, $Ar^1$, NHC=$OR^{11}$, and NHC=$ONHR^{11}$; wherein $R^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, C3-C6 heterocycloalkyl, and $Ar^1$; wherein $R^4$ is selected from hydrogen, $Ar^1$, $NHR^{11}$, and NHC=$ONR^{11}$, provided only one of $R^3$ and $R^4$ is not hydrogen; wherein $R^5$ is selected from hydrogen and C1-C6 alkyl; wherein $R^6$ is selected from hydrogen, halogen, and C1-C6 alkyl; wherein $R^7$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; wherein $R^8$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; and wherein $R^9$ is selected from hydrogen, halogen, and C1-C6 alkyl; or a pharmaceutically acceptable salt, hydrate, solvate, or polymorph thereof.

In a further aspect, the compound administered is a disclosed compound or a product of a disclosed method of making a compound. In a still further aspect, the effective amount is a therapeutically effective amount. In a yet still further aspect, the effective amount is a prophylactically effective amount.

In a further aspect, the compound is associated with inhibition of the PI3K/Akt pathway. In a still further aspect, the inhibition of PI3K/Akt pathway is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the compound is associated with inhibition of the phosphorylation of Akt. In a still further aspect, the inhibition of Akt phosphorylation is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the compound is associated with inhibition of a protein kinase. In a still further aspect, the protein kinase is selected from 3-phosphoinositide-dependent protein kinase 1, aurora kinase A, c-abl oncogene 1 kinase (T315I form), fms-related tyrosine kinase 3, fibroblast growth factor receptor 1, interleukin-1 receptor-associated kinase 4, Janus kinase 1, Janus kinase 2, Janus kinase 3, mitogen-activated protein kinase kinase kinase kinase 4 (MAP4K4), ret protooncogene, spleen tyrosine kinase, tyrosine-protein kinase Fyn, vascular endothelial growth factor receptor 2, and vascular endothelial growth factor receptor 3. In a yet further aspect, the protein kinase is 3-phosphoinositide-dependent protein kinase 1. In a still further aspect, the inhibition of the protein kinase is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the compound inhibits cell viability. In a still further aspect, inhibition of cell viability is determined in a cell line selected from AN3-CA, LNCaP, RL95-2, KG-1, MV4-11, BT-20, RKO, MCF7, BT549, U87-MG, PC3, and Kasumi cells. In a still further aspect, the inhibition of cell viability is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the mammal is a human. In a yet further aspect, the method further comprises the step of identifying a mammal in need of treatment of a disorder of uncontrolled cellular proliferation. In a still further aspect, the mammal has been diagnosed with a need for treatment of a disorder of uncontrolled cellular proliferation prior to the administering step.

In a further aspect, the disorder of uncontrolled cellular proliferation is associated with a protein kinase dysfunction. In a still further aspect, the disorder of uncontrolled cellular proliferation is a cancer. In a yet further aspect, the cancer is a leukemia. In an even further aspect, the cancer is a lymphoma. In a yet further aspect, the cancer is a solid tumor. In a still further aspect, the cancer is selected from cancers of the brain, genitourinary tract, gastrointestinal tract, colon, rectum, breast, kidney, lymphatic system, stomach, lung, pancreas, and skin. In an even further aspect, the cancer is selected from. prostate cancer, glioblastoma multiforme, endometrial cancer, breast cancer, and colon cancer.

In a further aspect, the cancer is associated with a loss of PTEN function. In a yet further aspect, the loss of PTEN function is due to a genetic mutation. In a still further aspect, the genetic mutation is in the PTEN gene. In an even further aspect, the genetic mutation is a PTEN mutation selected from K267fs*9, K267fs*9, K267fs*9, K6fs*4, K6fs*4, K6fs*4, N323fs*2, N323fs*2, N323fs*2, N323fs*21, N323fs*21, N323fs*21, P248fs*5, P248fs*5, P248fs*5, R130Q, R130Q, R130Q, R130fs*4, R130fs*4, R130fs*4, R130G, R130G, R130G, R130*, R130*, R130*, R173c, R173c, R173c, R173H, R173H, R173H, R233*, R233*, R233*, R335*, R335*, R335*, V317fs*3, V317fs*3, and V317fs*3.

In a further aspect, the cancer is associated with PI3K activation. In a yet further aspect, the genetic mutation is in a gene selected from PIK3CA, PIKR1, H-RAS, K-RAS, and N-RAS. In a still further aspect, the genetic mutation is a PIK3CA mutation selected from R38H, R88Q, N345K, C420R, P359R, E542K, E545K, Q546K, H701P, C901F, M1043I, H1047R/L, and H1047Y. In an even further aspect, the genetic mutation is a PIK3R1 mutation selected from R574T and A634P. In a still further aspect, the genetic mutation is a H-RAS mutation selected from G12V/D, G13R/C/S, Q61H/H, G61L/R/P, and QQ61K. In an even further aspect, the genetic mutation is a K-RAS mutation selected from G12C, G12R, G12S, G12V, G12D, G12A, G12F, G13V/D, A59T, Q61E/K, Q61L/R/P, and Q61H. In a still further aspect, the genetic mutation is a N-RAS mutation selected from G12V/A/D, G12C/R/S, G13V/A/D, G13C/R/S, A18T, Q61L/R/P, Q61H, and Q61E/K.

b. Decreasing Kinase Activity

In one aspect, the invention relates to a method for decreasing kinase activity in a mammal, the method comprising the step of administering to the mammal a therapeutically effective amount of at least one compound having a structure represented by a formula:

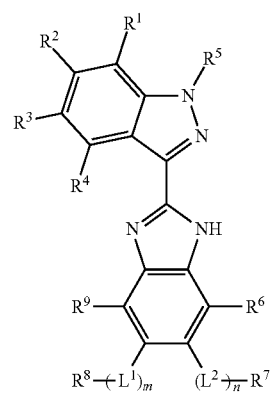

wherein $L^1$ is C=O or $(CH_2)_p$, wherein p is an integer from 1 to 3, wherein m is 0 or 1; wherein $L^2$ is C=O or $(CH_2)_q$, wherein q is an integer from 1 to 3, wherein n is 0 or 1; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino; wherein $R^{10}$ is selected from hydrogen and C1-C6 alkyl; wherein $R^1$ is selected from hydrogen, halogen, cyano, and C1-C6 alkyl; wherein $R^2$ is selected from hydrogen, halogen, cyano, and C1-C6 alkyl; wherein $R^3$ is selected from hydrogen, $Ar^1$, NHC=$OR^{11}$, and NHC=$ONHR^{11}$; wherein $R^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, C3-C6 heterocycloalkyl, and $Ar^1$; wherein $R^4$ is selected from hydrogen, $Ar^1$, $NHR^{11}$, and NHC=$ONR^{11}$, provided only one of $R^3$ and $R^4$ is not hydrogen; wherein $R^5$ is selected from hydrogen and C1-C6 alkyl; wherein $R^6$ is selected from hydrogen, halogen, and C1-C6 alkyl; wherein $R^7$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; wherein $R^8$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; and wherein $R^9$ is selected from hydrogen, halogen, and C1-C6 alkyl; or a pharmaceutically acceptable salt, hydrate, solvate, or polymorph thereof.

In a further aspect, the compound administered is a disclosed compound or a product of a disclosed method of making a compound. In a still further aspect, the effective amount is a therapeutically effective amount. In a yet still further aspect, the effective amount is a prophylactically effective amount.

In a further aspect, decreasing kinase activity is associated with inhibition of the PI3K/Akt pathway. In a still further aspect, the inhibition of PI3K/Akt pathway is with an $IC_{50}$ of less than about $1.0\times10^{-4}$ M, an $IC_{50}$ of less than about $1.0\times10^{-5}$ M, an $IC_{50}$ of less than about $1.0\times10^{-6}$ M, an $IC_{50}$ of less than about $1.0\times10^{-7}$ M, an $IC_{50}$ of less than about $1.0\times10^{-8}$ M, or an $IC_{50}$ of less than about $1.0\times10^{-9}$ M.

In a further aspect, decreasing kinase activity is associated with inhibition of the phosphorylation of Akt. In a still further aspect, the inhibition of Akt phosphorylation is with an $IC_{50}$ of less than about $1.0\times10^{-4}$ M, an $IC_{50}$ of less than about $1.0\times10^{-5}$ M, an $IC_{50}$ of less than about $1.0\times10^{-6}$ M, an $IC_{50}$ of less than about $1.0\times10^{-7}$ M, an $IC_{50}$ of less than about $1.0\times10^{-8}$ M, or an $IC_{50}$ of less than about $1.0\times10^{-9}$ M.

In a further aspect, the protein kinase is selected from 3-phosphoinositide-dependent protein kinase 1, aurora kinase A, c-abl oncogene 1 kinase (T315I form), fms-related tyrosine kinase 3, fibroblast growth factor receptor 1, interleukin-1 receptor-associated kinase 4, Janus kinase 1, Janus kinase 2, Janus kinase 3, mitogen-activated protein kinase kinase kinase 4 (MAP4K4), ret proto-oncogene, spleen tyrosine kinase, tyrosine-protein kinase Fyn, vascular endothelial growth factor receptor 2, and vascular endothelial growth factor receptor 3. In a yet further aspect, the protein kinase is 3-phosphoinositide-dependent protein kinase 1. In a still further aspect, the inhibition of the protein kinase is with an $IC_{50}$ of less than about $1.0\times10^{-4}$ M, an $IC_{50}$ of less than about $1.0\times10^{-5}$ M, an $IC_{50}$ of less than about $1.0\times10^{-6}$ M, an $IC_{50}$ of less than about $1.0\times10^{-7}$ M, an $IC_{50}$ of less than about $1.0\times10^{-8}$ M, or an $IC_{50}$ of less than about $1.0\times10^{-9}$ M.

In a further aspect, decreasing kinase activity inhibits cell viability. In a still further aspect, inhibition of cell viability is determined in a cell line selected from AN3-CA, LNCaP, RL95-2, KG-1, MV4-11, BT-20, RKO, MCF7, BT549, U87-MG, PC3, and Kasumi cells. In a still further aspect, the inhibition of cell viability is with an $IC_{50}$ of less than about $1.0\times10^{-4}$ M, an $IC_{50}$ of less than about $1.0\times10^{-5}$ M, an $IC_{50}$ of less than about $1.0\times10^{-6}$ M, an $IC_{50}$ of less than about $1.0\times10^{-7}$ M, an $IC_{50}$ of less than about $1.0\times10^{-8}$ M, or an $IC_{50}$ of less than about $1.0\times10^{-9}$ M.

In a further aspect, the mammal is a human. In a yet further aspect, the method further comprises the step of identifying a mammal in need of decreasing kinase activity. In a still further aspect, the mammal has been diagnosed with a need for decreasing kinase activity prior to the administering step.

In a further aspect, the need for decreasing kinase activity is associated with treatment of a disorder of uncontrolled cellular proliferation. In a still further aspect, the disorder of uncontrolled cellular proliferation is a cancer. In a yet further aspect, the cancer is a leukemia. In an even further aspect, the cancer is a lymphoma. In a yet further aspect, the cancer is a solid tumor. In a still further aspect, the cancer is selected from cancers of the brain, genitourinary tract, gastrointestinal tract, colon, rectum, breast, kidney, lymphatic system, stomach, lung, pancreas, and skin. In an even further aspect, the cancer is selected from. prostate cancer, glioblastoma multiforme, endometrial cancer, breast cancer, and colon cancer.

In a further aspect, the cancer is associated with a loss of PTEN function. In a yet further aspect, the loss of PTEN function is due to a genetic mutation. In a still further aspect, the genetic mutation is in the PTEN gene. In an even further aspect, the genetic mutation is a PTEN mutation selected from K267fs*9, K267fs*9, K267fs*9, K6fs*4, K6fs*4, K6fs*4, N323fs*2, N323fs*2, N323fs*2, N323fs*21, N323fs*21, N323fs*21, P248fs*5, P248fs*5, P248fs*5, R130Q, R130Q, R130Q, R130fs*4, R130fs*4, R130fs*4, R130G, R130G, R130G, R130*, R130*, R130*, R173c, R173c, R173c, R173H, R173H, R173H, R233*, R233*, R233*, R335*, R335*, R335*, V317fs*3, V317fs*3, and V317fs*3.

In a further aspect, the cancer is associated with PI3K activation. In a yet further aspect, the genetic mutation is in a gene selected from PIK3CA, PIKR1, H-RAS, K-RAS, and N-RAS. In a still further aspect, the genetic mutation is a PIK3CA mutation selected from R38H, R88Q, N345K, C420R, P359R, E542K, E545K, Q546K, H701P, C901F, M1043I, H1047R/L, and H1047Y. In an even further aspect, the genetic mutation is a PIK3R1 mutation selected from R574T and A634P. In a still further aspect, the genetic mutation is a H-RAS mutation selected from G12V/D, G13R/C/S, Q61H/H, G61L/R/P, and QQ61K. In an even further aspect, the genetic mutation is a K-RAS mutation selected from G12C, G12R, G12S, G12V, G12D, G12A, G12F, G13V/D, A59T, Q61E/K, Q61L/R/P, and Q61H. In a still further aspect, the genetic mutation is a N-RAS mutation selected from G12V/A/D, G12C/R/S, G13V/A/D, G13C/R/S, A18T, Q61L/R/P, Q61H, and Q61E/K.

C. Decreasing Kinase Activity in Cells

In one aspect, the invention relates to a method for decreasing kinase activity in at least one cell, the method comprising the step of contacting the at least one cell with an effective amount of least one compound having a structure represented by a formula:

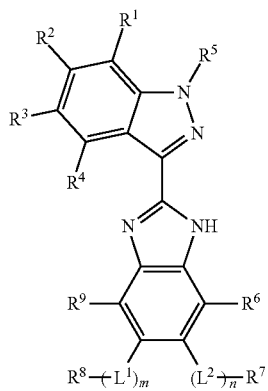

wherein $L^1$ is C=O or $(CH_2)_p$, wherein p is an integer from 1 to 3, wherein m is 0 or 1; wherein $L^2$ is C=O or $(CH_2)_q$, wherein q is an integer from 1 to 3, wherein n is 0 or 1; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino; wherein $R^{10}$ is selected from hydrogen and C1-C6 alkyl; wherein $R^1$ is selected from hydrogen, halogen, cyano, and C1-C6 alkyl; wherein $R^2$ is selected from hydrogen, halogen, cyano, and C1-C6 alkyl; wherein $R^3$ is selected from hydrogen, $Ar^1$, NHC=$OR^{11}$, and NHC=$ONHR^{11}$; wherein $R^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, C3-C6 heterocycloalkyl, and $Ar^1$; wherein $R^4$ is selected from hydrogen, $Ar^1$, $NHR^{11}$, and NHC=$ONR^{11}$, provided only one of $R^3$ and $R^4$ is not hydrogen; wherein $R^5$ is selected from hydrogen and C1-C6 alkyl; wherein $R^6$ is selected from hydrogen, halogen, and C1-C6 alkyl; wherein $R^7$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; wherein $R^8$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; and wherein $R^9$ is selected from hydrogen, halogen, and C1-C6 alkyl; or a pharmaceutically acceptable salt, hydrate, solvate, or polymorph thereof.

In a further aspect, the compound is a disclosed compound or a product of a disclosed method of making a compound. In a still further aspect, the effective amount is a therapeutically effective amount. In a yet still further aspect, the effective amount is a prophylactically effective amount.

In a further aspect, decreasing kinase activity is associated with inhibition of the PI3K/Akt pathway. In a still further aspect, the inhibition of PI3K/Akt pathway is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, decreasing kinase activity is associated with inhibition of the phosphorylation of Akt. In a still further aspect, the inhibition of Akt phosphorylation is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the protein kinase is selected from 3-phosphoinositide-dependent protein kinase 1, aurora kinase A, c-abl oncogene 1 kinase (T315I form), fms-related tyrosine kinase 3, fibroblast growth factor receptor 1, interleukin-1 receptor-associated kinase 4, Janus kinase 1, Janus kinase 2, Janus kinase 3, mitogen-activated protein kinase kinase kinase kinase 4 (MAP4K4), ret proto-oncogene, spleen tyrosine kinase, tyrosine-protein kinase Fyn, vascular endothelial growth factor receptor 2, and vascular endothelial growth factor receptor 3. In a yet further aspect, the protein kinase is 3-phosphoinositide-dependent protein kinase 1. In a still further aspect, the inhibition of the protein kinase is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, decreasing kinase activity inhibits cell viability. In a still further aspect, inhibition of cell viability is determined in a cell line selected from AN3-CA, LNCaP, RL95-2, KG-1, MV4-11, BT-20, RKO, MCF7, BT549, U87-MG, PC3, and Kasumi cells. In a still further aspect, the inhibition of cell viability is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the cell is mammalian. In a still further aspect, the cell is human. In a yet further aspect, contacting is via administration to a mammal.

In a further aspect, the method further comprises the step of identifying a mammal in need of decreasing kinase activity in a cell. In a still further aspect, the mammal has been diagnosed with a need for decreasing kinase activity prior to the administering step.

In a further aspect, the need for decreasing kinase activity in a cell is associated with a disorder of uncontrolled cellular. In a still further aspect, the disorder of uncontrolled cellular proliferation is a cancer. In a yet further aspect, the cancer is a leukemia. In an even further aspect, the cancer is a lymphoma. In a still further aspect, the cancer is a solid tumor. In a yet further aspect, the cancer is selected from cancers of the brain, genitourinary tract, gastrointestinal tract, colon, rectum, breast, kidney, lymphatic system, stomach, lung, pancreas, and skin. In an even further aspect, the cancer is selected from. prostate cancer, glioblastoma multiforme, endometrial cancer, breast cancer, and colon cancer.

In a further aspect, the cancer is associated with a loss of PTEN function. In a yet further aspect, the loss of PTEN function is due to a genetic mutation. In a still further aspect, the genetic mutation is in the PTEN gene. In an even further aspect, the genetic mutation is a PTEN mutation selected from K267fs*9, K267fs*9, K267fs*9, K6fs*4, K6fs*4, K6fs*4, N323fs*2, N323fs*2, N323fs*2, N323fs*21, N323fs*21, N323fs*21, P248fs*5, P248fs*5, P248fs*5, R130Q, R130Q, R130Q, R130fs*4, R130fs*4, R130fs*4, R130G, R130G, R130G, R130*, R130*, R130*, R173c, R173c, R173c, R173H, R173H, R173H, R233*, R233*, R233*, R335*, R335*, R335*, V317fs*3, V317fs*3, and V317fs*3.

In a further aspect, the cancer is associated with PI3K activation. In a yet further aspect, the genetic mutation is in a gene selected from PIK3CA, PIKR1, H-RAS, K-RAS, and N-RAS. In a still further aspect, the genetic mutation is a PIK3CA mutation selected from R38H, R88Q, N345K, C420R, P359R, E542K, E545K, Q546K, H701P, C901F, M1043I, H1047R/L, and H1047Y. In an even further aspect, the genetic mutation is a PIK3R1 mutation selected from R574T and A634P. In a still further aspect, the genetic mutation is a H-RAS mutation selected from G12V/D, G13R/C/S, Q61H/H, G61L/R/P, and QQ61K. In an even further aspect, the genetic mutation is a K-RAS mutation selected from G12C, G12R, G12S, G12V, G12D, G12A, G12F, G13V/D, A59T, Q61E/K, Q61L/R/P, and Q61H. In a still further aspect, the genetic mutation is a N-RAS mutation selected from G12V/A/D, G12C/R/S, G13V/A/D, G13C/R/S, A18T, Q61L/R/P, Q61H, and Q61E/K.

2. Manufacture of a Medicament

In one aspect, the invention relates to a method for the manufacture of a medicament for inhibition of the PI3K/Akt pathway in a mammal comprising combining a therapeutically effective amount of a disclosed compound or product of a disclosed method with a pharmaceutically acceptable carrier or diluent.

In a further aspect, the invention relates to a method for the manufacture of a medicament for inhibition of PDK1 in a mammal comprising combining a therapeutically effective amount of a disclosed compound or product of a disclosed method with a pharmaceutically acceptable carrier or diluent.

3. Use of Compounds

In one aspect, the invention relates to a use of a compound for decreasing kinase activity in a mammal, the compound having a structure represented by a formula:

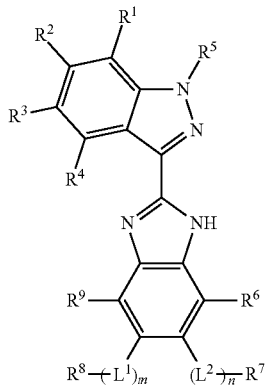

wherein $L^1$ is C=O or $(CH_2)_p$, wherein p is an integer from 1 to 3, wherein m is 0 or 1; wherein $L^2$ is C=O or $(CH_2)_q$, wherein q is an integer from 1 to 3, wherein n is 0 or 1; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino; wherein $R^{10}$ is selected from hydrogen and C1-C6 alkyl; wherein $R^1$ is selected from hydrogen, halogen, cyano, and C1-C6 alkyl; wherein $R^2$ is selected from hydrogen, halogen, cyano, and C1-C6 alkyl; wherein $R^3$ is selected from hydrogen, $Ar^1$, NHC=$OR^{11}$, and NHC=$ONHR^{11}$; wherein $R^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, C3-C6 heterocycloalkyl, and $Ar^1$; wherein $R^4$ is selected from hydrogen, $Ar^1$, $NHR^{11}$, and NHC=$ONR^{11}$, provided only one of $R^3$ and $R^4$ is not hydrogen; wherein $R^5$ is selected from hydrogen and C1-C6 alkyl; wherein $R^6$ is selected from hydrogen, halogen, and C1-C6 alkyl; wherein $R^7$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; wherein $R^8$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; and wherein $R^9$ is selected from hydrogen, halogen, and C1-C6 alkyl; or a pharmaceutically acceptable salt, hydrate, solvate, or polymorph thereof.

In a further aspect, the compound is a disclosed compound or a product of a disclosed method of making a compound.

In a further aspect, decreasing kinase activity is associated with inhibition of the PI3K/Akt pathway. In a still further aspect, the inhibition of PI3K/Akt pathway is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, decreasing kinase activity is associated with inhibition of the phosphorylation of Akt. In a still further aspect, the inhibition of Akt phosphorylation is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the protein kinase is selected from 3-phosphoinositide-dependent protein kinase 1, aurora kinase A, c-abl oncogene 1 kinase (T315I form), fms-related tyrosine kinase 3, fibroblast growth factor receptor 1, interleukin-1 receptor-associated kinase 4, Janus kinase 1, Janus kinase 2, Janus kinase 3, mitogen-activated protein kinase kinase kinase 4 (MAP4K4), ret proto-oncogene, spleen tyrosine kinase, tyrosine-protein kinase Fyn, vascular endothelial growth factor receptor 2, and vascular endothelial growth factor receptor 3. In a yet further aspect, the protein kinase is 3-phosphoinositide-dependent protein kinase 1. In a still further aspect, the inhibition of the protein kinase is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, decreasing kinase activity inhibits cell viability. In a still further aspect, inhibition of cell viability is determined in a cell line selected from AN3-CA, LNCaP, RL95-2, KG-1, MV4-11, BT-20, RKO, MCF7, BT549, U87-MG, PC3, and Kasumi cells. In a still further aspect, the inhibition of cell viability is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the mammal is a human.

In a further aspect, the need for decreasing kinase activity is associated with treatment of a disorder of uncontrolled cellular proliferation. In a still further aspect, the disorder of uncontrolled cellular proliferation is a cancer. In a yet further aspect, the cancer is a leukemia. In an even further aspect, the cancer is a lymphoma. In a yet further aspect, the cancer is a solid tumor. In a still further aspect, the cancer is selected from cancers of the brain, genitourinary tract, gastrointestinal tract, colon, rectum, breast, kidney, lymphatic system, stomach, lung, pancreas, and skin. In an even further aspect, the cancer is selected from. prostate cancer, glioblastoma multiforme, endometrial cancer, breast cancer, and colon cancer.

In a further aspect, the cancer is associated with a loss of PTEN function. In a yet further aspect, the loss of PTEN function is due to a genetic mutation. In a still further aspect, the genetic mutation is in the PTEN gene. In an even further aspect, the genetic mutation is a PTEN mutation selected from K267fs*9, K267fs*9, K267fs*9, K6fs*4, K6fs*4, K6fs*4, N323fs*2, N323fs*2, N323fs*2, N323fs*21, N323fs*21, N323fs*21, P248fs*5, P248fs*5, P248fs*5, R130Q, R130Q, R130Q, R130fs*4, R130fs*4, R130fs*4, R130G, R130G, R130G, R130*, R130*, R130*, R173c, R173c, R173c, R173H, R173H, R173H, R233*, R233*, R233*, R335*, R335*, R335*, V317fs*3, V317fs*3, and V317fs*3.

In a further aspect, the cancer is associated with PI3K activation. In a yet further aspect, the genetic mutation is in a gene selected from PIK3CA, PIKR1, H-RAS, K-RAS, and N-RAS. In a still further aspect, the genetic mutation is a PIK3CA mutation selected from R38H, R88Q, N345K, C420R, P359R, E542K, E545K, Q546K, H701P, C901F, M1043I, H1047R/L, and H1047Y. In an even further aspect, the genetic mutation is a PIK3R1 mutation selected from R574T and A634P. In a still further aspect, the genetic mutation is a H-RAS mutation selected from G12V/D, G13R/C/S, Q61H/H, G61L/R/P, and QQ61K. In an even further aspect, the genetic mutation is a K-RAS mutation selected from G12C, G12R, G12S, G12V, G12D, G12A, G12F, G13V/D, A59T, Q61E/K, Q61L/R/P, and Q61H. In a still further aspect, the genetic mutation is a N-RAS mutation selected from G12V/A/D, G12C/R/S, G13V/A/D, G13C/R/S, A18T, Q61L/R/P, Q61H, and Q61E/K.

4. Kits

In one aspect, the invention relates to a kit comprising at least one compound having a structure represented by a formula:

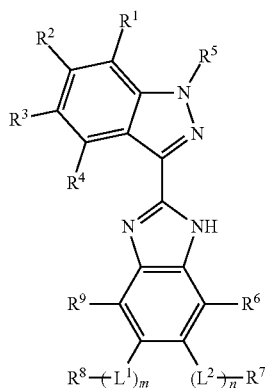

wherein $L^1$ is C=O or $(CH_2)_p$, wherein p is an integer from 1 to 3, wherein m is 0 or 1; wherein $L^2$ is C=O or $(CH_2)_q$, wherein q is an integer from 1 to 3, wherein n is 0 or 1; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{10}$, C1-C3 alkyl, C1-C3 alkylamine, and C1-C3 dialkylamino; wherein $R^{10}$ is selected from hydrogen and C1-C6 alkyl; wherein $R^1$ is selected from hydrogen, halogen, cyano, and C1-C6 alkyl; wherein $R^2$ is selected from hydrogen, halogen, cyano, and C1-C6 alkyl; wherein $R^3$ is selected from hydrogen, $Ar^1$, NHC=$OR^{11}$, and NHC=$ONHR^{11}$; wherein $R^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, C3-C6 heterocycloalkyl, and $Ar^1$; wherein $R^4$ is selected from hydrogen, $Ar^1$, $NHR^{11}$, and NHC=$ONR^{11}$, provided only one of $R^3$ and $R^4$ is not hydrogen; wherein $R^5$ is selected from hydrogen and C1-C6 alkyl; wherein $R^6$ is selected from hydrogen, halogen, and C1-C6 alkyl; wherein $R^7$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; wherein $R^8$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; and wherein $R^9$ is selected from hydrogen, halogen, and C1-C6 alkyl; or a pharmaceutically acceptable salt, hydrate, solvate, or polymorph thereof, and one or more of: (a) at least one agent known to increase kinase activity; (b) at least one agent known to decrease kinase activity; (c) at least one agent known to treat a disorder of uncontrolled cellular proliferation; or (d) instructions for treating a disorder associated with uncontrolled cellular proliferation.

In a further aspect, the compound is a disclosed compound or a product of a disclosed method of making a compound.

In a further aspect, the compound exhibits inhibition of the PI3K/Akt pathway. In a yet further aspect, the inhibition of the PI3K/Akt pathway is associated with inhibition of a protein kinase. In an even further aspect, inhibition of PI3K/Akt pathway is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the inhibition the PI3K/Akt pathway decreases the phosphorylation of Akt. In a still further aspect, the inhibition of Akt phosphorylation is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the compound exhibits inhibition of a protein kinase. In a still further aspect, the protein kinase is selected from 3-phosphoinositide-dependent protein kinase 1, aurora kinase A, c-abl oncogene 1 kinase (T315I form), fms-related tyrosine kinase 3, fibroblast growth factor receptor 1, interleukin-1 receptor-associated kinase 4, Janus kinase 1, Janus kinase 2, Janus kinase 3, mitogen-activated protein kinase kinase kinase kinase 4 (MAP4K4), ret proto-oncogene, spleen tyrosine kinase, tyrosine-protein kinase Fyn, vascular endothelial growth factor receptor 2, and vascular endothelial growth factor receptor 3. In a yet further aspect, the protein kinase is 3-phosphoinositide-dependent protein kinase 1. In a still further aspect, the inhibition of the protein kinase is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the compound inhibits cell viability. In a yet further aspect, inhibition of cell viability is determined in a cell line selected from AN3-CA, LNCaP, RL95-2, KG-1, MV4-11, BT-20, RKO, MCF7, BT549, U87-MG, PC3, and Kasumi cells. In a still further aspect, the inhibition of cell viability is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the mammal is a human.

In a further aspect, the disorder of uncontrolled cellular proliferation is associated with a kinase dysfunction. In a still further aspect, the disorder of uncontrolled cellular proliferation is a cancer. In a yet further aspect, the cancer is a leukemia. In an even further aspect, the cancer is a lymphoma. In a yet further aspect, the cancer is a solid tumor. In a still further aspect, the cancer is selected from cancers of the brain, genitourinary tract, gastrointestinal tract, colon, rectum, breast, kidney, lymphatic system, stomach, lung, pancreas, and skin. In an even further aspect, the cancer is selected from. prostate cancer, glioblastoma multiforme, endometrial cancer, breast cancer, and colon cancer.

In a further aspect, the cancer is associated with a loss of PTEN function. In a yet further aspect, the loss of PTEN function is due to a genetic mutation. In a still further aspect, the genetic mutation is in the PTEN gene. In an even further aspect, the genetic mutation is a PTEN mutation selected from K267fs*9, K267fs*9, K267fs*9, K6fs*4, K6fs*4, K6fs*4, N323fs*2, N323fs*2, N323fs*2, N323fs*21, N323fs*21, N323fs*21, P248fs*5, P248fs*5, P248fs*5, R130Q, R130Q, R130Q, R130fs*4, R130fs*4, R130fs*4, R130G, R130G, R130G, R130*, R130*, R130*, R173c, R173c, R173c, R173H, R173H, R173H, R233*, R233*, R233*, R335*, R335*, R335*, V317fs*3, V317fs*3, and V317fs*3.

In a further aspect, the cancer is associated with PI3K activation. In a yet further aspect, the genetic mutation is in a gene selected from PIK3CA, PIKR1, H-RAS, K-RAS, and N-RAS. In a still further aspect, the genetic mutation is a PIK3CA mutation selected from R38H, R88Q, N345K, C420R, P359R, E542K, E545K, Q546K, H701P, C901F, M1043I, H1047R/L, and H1047Y. In an even further aspect, the genetic mutation is a PIK3R1 mutation selected from R574T and A634P. In a still further aspect, the genetic mutation is a H-RAS mutation selected from G12V/D, G13R/C/S, Q61H/H, G61L/R/P, and QQ61K. In an even further aspect, the genetic mutation is a K-RAS mutation selected from G12C, G12R, G12S, G12V, G12D, G12A, G12F, G13V/D, A59T, Q61E/K, Q61L/R/P, and Q61H. In a still further aspect, the genetic mutation is a N-RAS mutation selected from G12V/A/D, G12C/R/S, G13V/A/D, G13C/R/S, A18T, Q61L/R/P, Q61H, and Q61E/K.

In a further aspect, the at least one compound or the at least one product and the at least one agent are co-formulated.

In a further aspect, the at least one compound or the at least one product and the at least one agent are co-packaged.

In a further aspect, the at least one agent is a hormone therapy agent. In a still further aspect, the hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt, hydrate, solvate, or polymorph thereof.

In a further aspect, the at least one agent is a chemotherapeutic agent. In a still further aspect, the chemotherapeutic agent is selected from one or more of the group consisting of an alkylating agent, an antimetabolite agent, an antineoplastic antibiotic agent, a mitotic inhibitor agent, a mTor inhibitor agent or other chemotherapeutic agent. In a yet further aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof. In an even further aspect, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof. In a still further aspect, the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof. In a yet further aspect, the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt, hydrate, solvate, or polymorph thereof. In an even further aspect, the mTor inhibitor agent is selected from one or more of the group consisting of everolimus, siroliumus, and temsirolimus, or a pharmaceutically acceptable salt, hydrate, solvate, or polymorph thereof.

5. Non-Medical Uses

Also provided are the uses of the disclosed compounds and products as pharmacological tools in the development and standardization of in vitro and in vivo test systems for the evaluation of the effects of inhibitors of PDK1 activity in laboratory animals such as cats, dogs, rabbits, monkeys, rats and mice, as part of the search for new therapeutic agents that inhibit PDK1.

In a further aspect, the invention relates to the use of a disclosed compound or a disclosed product as pharmacological tools in the development and standardization of in vitro and in vivo test systems for the evaluation of the effects of inhibitors of the PI3K/Akt pathway in laboratory animals such as cats, dogs, rabbits, monkeys, rats and mice, as part of the search for new therapeutic agents that inhibit the PI3/Akt pathway.

H. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. General Methods

All routine reagents and solvents were purchased from Sigma Aldrich and used as received. They were of reagent grade, purity ≥99%. Specialty chemicals and building blocks obtained from several suppliers were of the highest offered purity (always ≥95%).

NMR spectroscopy was performed on a Mercury 400 MHz operating at 400 MHz, equipped with a 5 mm broadband probe and using standard pulse sequences. Chemical shifts (δ) are reported in parts-per-million (ppm) relative to the residual solvent signals. Coupling constants (J-values) are expressed in Hz.

Mass spectrometry was performed on a Waters Quattro-II triple quadrupole mass spectrometer. All samples were analyzed by positive ESI-MS and the mass-to-charge ratio (m/z) of the protonated molecular ion is reported.

Microwave-assisted reactions were performed on a Biotage Initiator 2.5 at various powers.

Hydrogenation reactions were performed on a standard Parr hydrogenation apparatus.

Reactions were monitored by TLC on Baker flexible-backed plates coated with 200 μm of silica gel containing a fluorescent indicator. Preparative TLC was performed on 20 cm×20 cm Analtech Uniplates coated with a 1000 or 2000 μm silica gel layer containing a fluorescent (UV 254) indicator. Elution mixtures are reported as v:v. Spot visualization was achieved using UV light.

Flash chromatography was performed on a Teledyne Isco CombiFlash RF 200 using appropriately sized Redisep Rf Gold or Standard normal-phase silica or reversed-phase C-18 columns. Crude compounds were adsorbed on silica gel, 70-230 mesh 40 Å (for normal phase) or celite 503 (for reversed-phase) and loaded into solid cartridges. Elution mixtures are reported as v:v.

2. Molecular Modeling and Drug Docking

All computational studies were carried out using Molsoft ICM, Glide (Schrodinger, L.L.C), Gold and MOE docking programs for the fragment-based studies described above. The fragments were generated from a kinase inhibitor databases using simple iterative disconnection of fragment descriptors internally developed using Chemaxon (http://www.chemaxon.com). The fragmentation rules were applied to SDF file formats. Chemical fragments were classified as linkers defined as having more than one connecting atom to rings; rings and substituent are defined as group connected to single ring systems. In general, the fragments in these sets have MW<300, c log P of less than 3 and are relatively simple with few functional groups, making them chemically tractable and suitable for rapid optimization.

3. Preparation of 3-(1H-Benzo[d]imidazol-2-yl)-5-bromo-1H-indazole

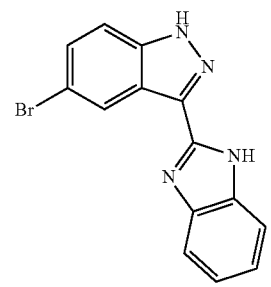 [SMILES: Brc1ccc2[nH]nc(-c3nc4ccccc4[nH]3)c2c1]

5-Bromo-1H-indazole-3-carbaldehyde (50 mg, 0.222 mmol) and o-phenylene diamine (24 mg, 0.222 mmol) were dissolved in dry THF (10 mL). One drop of 2N HCl was added. The solution was heated at a gentle reflux for 30 min and then 1N sodium bisulfite (1 mL) was added. After overnight at reflux, the solution was cooled to room temperature, and then diluted with ethyl acetate (30 mL). The mixture was washed with water and brine, dried over $Na_2SO_4$, and concentrated. Purification by flash chromatography (20% ethyl acetate/hexane) afforded the title compound as a pale yellow solid in a 50% yield. $^1$H NMR (400 MHz, $CDCl_3$): δ 8.73 (d, 1H, J=1.2 Hz), 7.80 (m, 1H), 7.48-7.45 (m, 2H), 7.37 (d, 1H, J=8.8 Hz), 7.23 (m, 2H); ESI-MS [M+H]⁺: 313.0.

4. Preparation of 5-bromo-1-(tetrahydro-2H-pyran-2-yl)-1H-indazole-3-carbaldehyde

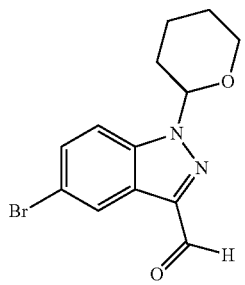 [SMILES: O=Cc1nn(C2CCCCO2)c2ccc(Br)cc12]

p-Toluenesulfonic acid (10 mg, 0.052 mmol) was added to a solution of 5-bromo-indazole-3-carbaldehyde (100 mg, 0.444 mmol) and 3,4-dihydro-2H-pyran (75 mg, 0.891 mmol) in a mixture of THF/$CH_2Cl_2$ (1:1, 6 mL). The reaction mixture was stirred for 12 h at room temperature after which the solvent was removed in vacuo. The residue was dissolved in $CH_2Cl_2$ (20 mL) and poured in water (20 mL). The organic layer was separated, and the aqueous layer was extracted with $CH_2Cl_2$ (20 mL). The combined organic layers were washed with water (40 mL) and brine (40 mL), dried over $Na_2SO_4$ and concentrated. Purification by flash chromatography ($CH_2Cl_2$) afforded 110 mg, (80% yield) of the title compound as a solid. ¹H NMR (400 MHz, $CDCl_3$): δ 10.21 (s, 1H), 8.47 (s, 1H), 7.56 (m, 2H), 5.80 (dd, 1H, J=3.2 and 9.2 Hz), 3.98 (m, 1H), 3.79-3.74 (m, 1H), 2.57-2.49 (m, 1H), 2.20-2.12 (m, 2H), 1.83-1.57 (m, 3H).

5. Preparation of 3-(1H-benzo[d]imidazol-2-yl)-5-bromo-1-(tetrahydro-2H-pyran-2-yl)-1H-indazole

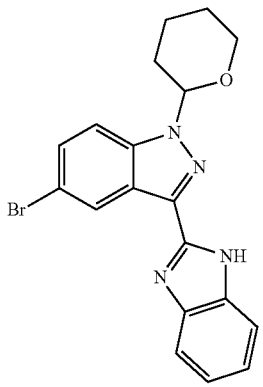 [SMILES: Brc1ccc2c(c1)c(-c1nc3ccccc3[nH]1)nn2C1CCCCO1]

5-Bromo-1-(tetrahydro-2H-pyran-2-yl)-1H-indazole-3-carbaldehyde (100 mg, 0.323 mmol) and o-phenylene diamine (38.5 mg, 0.356 mmol) were dissolved in dry THF (6 mL), and 2N HCl (2 drops) were added. The solution was heated at a gentle reflux for 30 min, and then 1N sodium bisulfite (2 mL) was added. After overnight at reflux, the solution was cooled to room temperature, and diluted with ethyl acetate (100 mL). The mixture was washed with water and brine, dried over $Na_2SO_4$, and concentrated. Purification by flash chromatography (20% ethyl acetate/hexane) afforded the title compound as a pale yellow solid in a 60% yield. ¹H NMR (400 MHz, $CDCl_3$): δ 9.86 (s, 1H), 8.79 (d, 1H, J=1.2 Hz), 7.83 (m, 1H), 7.50-7.41 (m, 3H), 7.25-7.22 (m, 2H), 5.69 (dd, 1H, J=2.8 and 8.8 Hz), 3.98 (m, 1H), 3.80 (m, 1H), 2.53 (m, 1H), 2.19 (m, 2H), 1.76 (m, 3H).

6. Preparation of 5-nitro-1-(tetrahydro-2H-pyran-2-yl)-1H-indazole-3-carbaldehyde

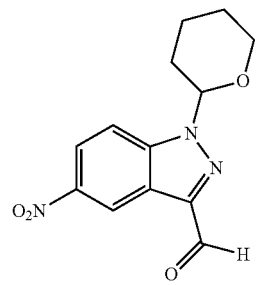 [SMILES: O=Cc1nn(C2CCCCO2)c2ccc([N+](=O)[O-])cc12]

p-Toluenesulfonic acid (30 mg, 0.158 mmol) was added to a solution of 5-nitro-indazole-3-carbaldehyde (300 mg, 1.569 mmol) and 3,4-dihydro-2H-pyran (265 mg, 3.150 mmol) in a mixture of THF/$CH_2Cl_2$ (1:1, 8 mL). The reaction mixture was stirred for 12 h at room temperature and then the solvent was removed in vacuo. The residue was taken in $CH_2Cl_2$ (50 mL) and poured in water (20 mL). The organic layer was separated, the aqueous layer was extracted with $CH_2Cl_2$ (50 mL), the combined organic layers were washed with water (40 mL) and brine (40 mL), dried over $Na_2SO_4$, and concentrated. Purification by flash chromatography ($CH_2Cl_2$) afforded title compound 215 mg (50% yield) as a solid. ¹H NMR (400 MHz, $CDCl_3$): δ 10.23 (s, 1H), 9.23 (d, 1H, J=2.0 Hz), 8.35 (dd, 1H, J=2.0 and 9.2 Hz), 7.80 (d, 1H, J=9.2 Hz), 5.89 (dd, 1H, J=2.8 and 8.8 Hz), 3.98 (m, 1H), 3.80 (m, 1H), 2.53 (m, 1H), 2.19 (m, 2H), 1.76 (m, 3H).

7. Preparation of 3-(1H-benzo[d]imidazol-2-yl)-5-nitro-1-(tetrahydro-2H-pyran-2-yl)-1H-indazole

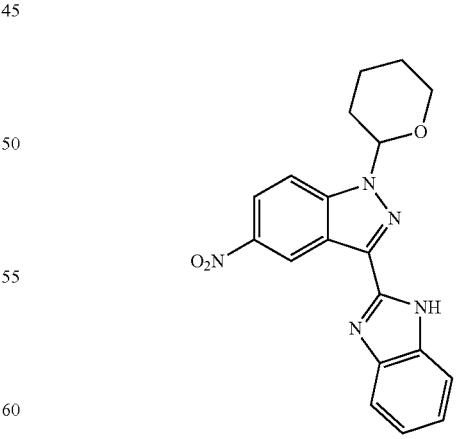

5-Nitro-1-(tetrahydro-2H-pyran-2-yl)-1H-indazole-3-carbaldehyde (100 mg, 0.363 mmol) and o-phenylene diamine (40 mg, 0.369 mmol) were dissolved in dry THF (8 mL), and 2N HCl (1 drop) was added. The solution was heated at a gentle reflux for 30 min and then 1N sodium bisulfite (1 mL)

was added. After overnight at reflux, the solution was cooled to room temperature, and diluted with ethyl acetate (40 mL). The mixture was washed with water and brine, dried over $Na_2SO_4$, and concentrated. Purification by flash chromatography (20% ethyl acetate/hexane) afforded the title compound as a pale yellow solid in a 50% yield. $^1$H NMR (400 MHz, $CDCl_3$): δ 9.82 (s, 1H), 9.60 (d, 1H, J=2.4 Hz), 8.30 (dd, 1H, J=2.0 & 9.2 Hz), 7.87 (m, 1H), 7.66 (d, 1H, J=9.2 Hz), 7.47 (m, 1H), 7.28 (m, 2H), 5.77 (dd, 1H, J=2.4 and 8.8 Hz), 4.00 (m, 1H), 3.76 (m, 1H), 2.53 (m, 1H), 2.13 (m, 2H), 1.77 (m, 3H).

8. Preparation of 3-(1H-benzo[d]imidazol-2-yl)-1-(tetrahydro-2H-pyran-2-yl)-1H-indazol-5-amine

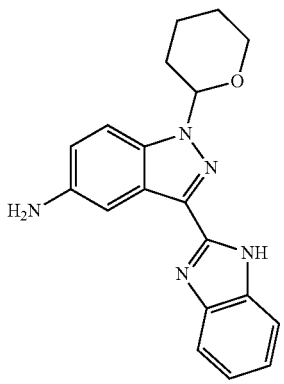 [SMILES: Nc1ccc2c(c1)c(-c1nc3ccccc3[nH]1)nn2C1CCCCO1]

3-(1H-Benzo[d]imidazol-2-yl)-5-nitro-1-(tetrahydro-2H-pyran-2-yl)-1H-indazole (50 mg, 0.137 mmol) was added to 10% Pd/C (10 mg) in ethanol (40 mL) and then pressurized with hydrogen (60 psi) for 6 h at room temperature. The reaction mixture was filtered through Celite, and the solvent was removed in vacuo. Purification by flash chromatography (5% $CH_3OH/CH_2Cl_2$) afforded the title compound in 60% yield. $^1$H NMR (400 MHz, $CD_3OD$): δ 7.69 (m, 2H), 7.55 (m, 2H), 7.26 (m, 2H), 7.05 (m, 1H), 5.84 (d, 1H, J=9.2 Hz), 4.00 (m, 1H), 3.82 (m, 1H), 2.65 (m, 1H), 2.14 (m, 2H), 1.78 (m, 3H).

9. Preparation of 3-(1H-benzo[d]imidazol-2-yl)-5-(3-(methylsulfonyl)phenyl)-1-(tetrahydro-2H-pyran-2-yl)-1H-indazole

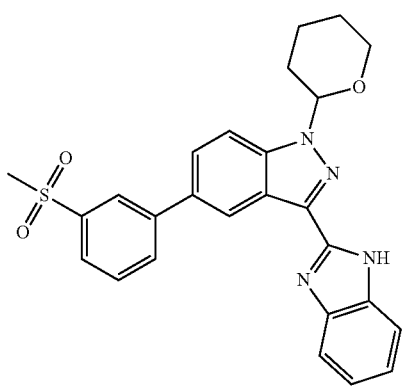 [SMILES: CS(=O)(=O)c1cccc(-c2ccc3c(c2)c(-c2nc4ccccc4[nH]2)nn3C2CCCCO2)c1]

3-(1H-Benzo[d]imidazol-2-yl)-5-bromo-1-(tetrahydro-2H-pyran-2-yl)-1H-indazole (30 mg, 0.0755 mmol), 3-(methylsulfonyl)phenyl boronic acid (15 mg, 0.075 mmol) and triphenylphosphine (2 mg, 0.007 mmol) were dissolved in a mixture of THF (6 mL), and 1M sodium carbonate (8 mg, 0.075 mmol) and palladium (II) acetate (2 mg, 0.009 mmol) were added. The solution was heated overnight at reflux. After cooling to room temperature, the solvent was removed in vacuo, the residue was dissolved in ethyl acetate (20 mL), and washed with water (10 mL). The organic layer was separated and the aqueous layer was extracted with ethyl acetate (20 mL). The combined organic layers were washed with brine (25 mL), dried over $Na_2SO_4$, and concentrated. Purification by flash chromatography (20% ethyl acetate/hexane) afforded the title compound (8 mg) as a white solid. $^1$H NMR (400 MHz, $CDCl_3$): δ 9.93 (s, 1H), 8.83 (s, 1H), 8.19 (s, 1H), 7.97 (d, 1H, J=8.0 Hz), 7.86 (m, 2H), 7.61 (t, 1H, J=7.6 Hz), 7.45 (m, 1H), 7.24 (m, 4H), 5.77 (dd, 1H, J=2.4 and 9.6 Hz), 4.04 (m, 1H), 3.75 (m, 1H), 3.07 (s, 3H), 2.59 (m, 1H), 2.12 (m, 2H), 1.76 (m, 3H); ESI-MS [M+H]$^+$: 473.3.

10. Preparation of 3-(1H-benzo[d]imidazol-2-yl)-5-(3-(methylsulfonyl)phenyl)-1H-indazole

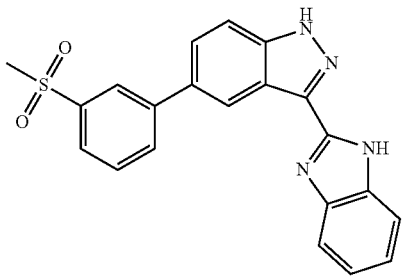 [SMILES: CS(=O)(=O)c1cccc(-c2ccc3[nH]nc(-c4nc5ccccc5[nH]4)c3c2)c1]

TFA (0.5 mL, 6.490 mmol) was added to a solution 3-(1H-benzo[d]imidazol-2-yl)-5-(3-(methylsulfonyl)phenyl)-1-(tetrahydro-2H-pyran-2-yl)-1H-indazole (7 mg, 0.015 mmol) in $CH_2Cl_2$ (4 mL). The reaction mixture was stirred at room temperature for 24 h, and then the solvent was removed in vacuo. Purification by flash chromatography (6% $CH_3OH/CH_2Cl_2$) afforded the title compound (4 mg) as an off-white solid. $^1$H NMR (400 MHz, $CD_3OD$): δ 8.84 (s, 1H), 8.39 (m, 1H), 7.17 (m, 1H), 7.95 (m, 1H), 7.85 (m, 2H), 7.78-7.73 (m, 3H), 7.28 (m, 2H); ESI-MS [M+H]$^+$: 389.3.

11. Preparation of 3-(1H-benzo[d]imidazol-2-yl)-1-(tetrahydro-2H-pyran-2-yl)-5-(3-(trifluoromethyl)phenyl)-1H-indazole

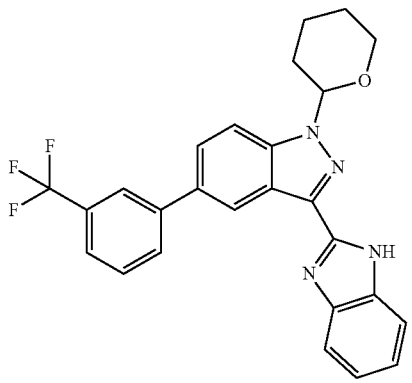 [SMILES: FC(F)(F)c1cccc(-c2ccc3c(c2)c(-c2nc4ccccc4[nH]2)nn3C2CCCCO2)c1]

1-(Tetrahydro-2H-pyran-2-yl)-5-(3-(trifluoromethyl)phenyl)-1H-indazole-3-carbaldehyde (15 mg, 0.040 mmol) and o-phenylene diamine (5 mg, 0.046 mmol) were dissolved in dry THF (5 mL) and 2N HCl (1 drop) was added. The solution was heated at a gentle reflux for 30 min and then 1N sodium bisulfite (1 mL) was added. After overnight at reflux, the solution was cooled to room temperature, and diluted with ethyl acetate (25 mL). The mixture was washed with water and brine, dried over $Na_2SO_4$, and concentrated. Purification by flash chromatography (20% ethyl acetate/hexane) afforded the title compound as a pale yellow solid in a 50% yield. $^1$H NMR (400 MHz, $CD_3OD$): δ 9.91 (s, 1H), 8.81 (s, 1H), 7.89-7.82 (m, 2H), 7.66 (m, 2H), 7.55-7.44 (m, 3H), 7.24 (m, 2H), 5.77 (dd, 1H, J=2.4 and 9.2 Hz), 4.02 (m, 1H), 3.75 (m, 1H), 2.59 (m, 1H), 2.12 (m, 2H), 1.75 (m, 3H); ESI-MS [M+H]$^+$: 463.3.

12. Preparation of 3-(1H-benzo[d]imidazol-2-yl)-5-(3-(trifluoromethyl)phenyl)-1H-indazole

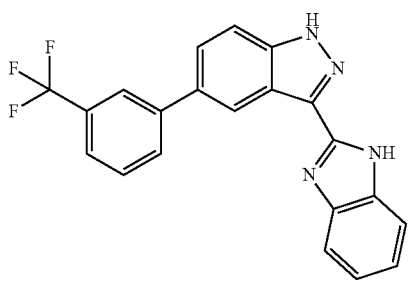 [SMILES: FC(F)(F)c1cccc(-c2ccc3[nH]nc(-c4nc5ccccc5[nH]4)c3c2)c1]

TFA (0.5 mL, 6.490 mmol) was added to a solution 3-(1H-benzo[d]imidazol-2-yl)-1-(tetrahydro-2H-pyran-2-yl)-5-(3-(trifluoromethyl)phenyl)-1H-indazole (8 mg, 0.017 mmol) in $CH_2Cl_2$ (4 mL). The reaction mixture was stirred at room temperature for 24 h, and then the solvent was removed in vacuo. Purification by flash chromatography (6% $CH_3OH$/$CH_2Cl_2$) afforded the title compound as an off-white solid in a 50% yield. ESI-MS [M+H]$^+$: 379.2.

13. Preparation of N-(3-(1H-benzo[d]imidazol-2-yl)-1-(tetrahydro-2H-pyran-2-yl)-1H-indazol-5-yl)-3-fluorobenzamide

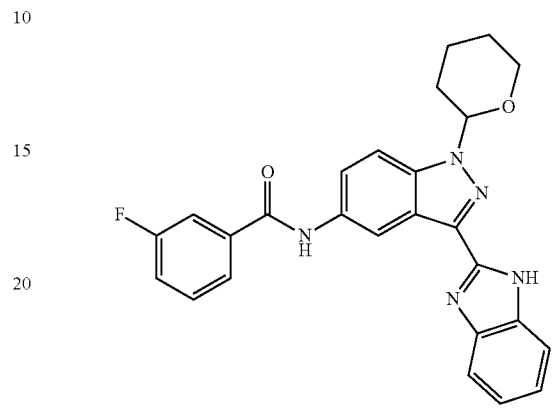

3-Fluorobenzoic acid (10 mg, 0.029 mmol), HOBt (6 mg, 0.044 mmol), EDC (9 mg, 0.045 mmol) and sodium bicarbonate (2.5 mg, 0.029 mmol) were added to a solution of 3-(1H-benzo[d]imidazol-2-yl)-1-(tetrahydro-2H-pyran-2-yl)-1H-indazol-5-amine (10 mg, 0.029 mmol) in DMF (6 mL). The reaction mixture was stirred at room temperature for 24 h, and then the solvent was removed in vacuo. Purification by flash chromatography (6% $CH_3OH$/$CH_2Cl_2$) afforded the title compound (8 mg) as a off white solid. $^1$H NMR (400 MHz, $CDCl_3$): δ 8.40 (d, 1H, J=1.6 Hz), 8.15-8.13 (m, 2H), 7.95 (s, 1H), 7.58 (m, 2H), 7.52 (d, 1H, J=9.6 Hz), 7.42-7.36 (m, 2H), 7.21 (m, 2H), 5.69 (dd, 1H, J=2.4 and 9.2 Hz), 3.99 (m, 1H), 3.72 (m, 1H), 2.55 (m, 1H), 2.06 (m, 2H), 1.67 (m, 3H).

14. Preparation of N-(3-(1H-benzo[d]imidazol-2-yl)-1H-indazol-5-yl)-3-fluorobenzamide

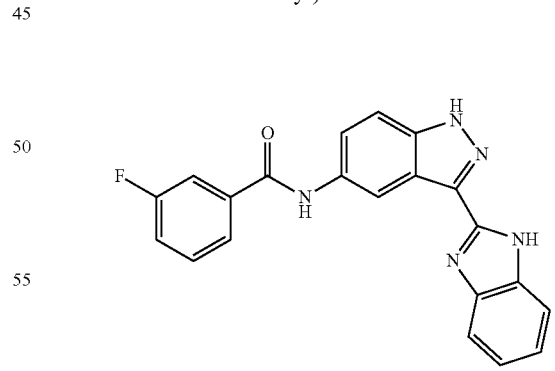

TFA (0.5 mL, 6.490 mmol) was added to a solution of N-(3-(1H-benzo[d]imidazol-2-yl)-1-(tetrahydro-2H-pyran-2-yl)-1H-indazol-5-yl)-3-fluorobenz amide (9 mg, 0.019 mmol) in $CH_2Cl_2$ (4 mL). The reaction mixture was stirred at room temperature for 24 h, and then the solvent was removed in vacuo. Purification by flash chromatography (6% $CH_3OH$/$CH_2Cl_2$) afforded the title compound as an off-white solid (4 mg). ¹H NMR (400 MHz, CD₃OD): δ 8.77 (bs, 1H), 7.85 (m, 3H), 7.76 (m, 3H), 7.58 (m, 3H), 7.39-7.35 (m, 1H); ESI-MS [M+H]⁺: 372.2.

15. Preparation of 2-(4-(3-(1H-benzo[d]imidazol-2-yl)-1-(tetrahydro-2H-pyran-2-yl)-1H-indazol-5-yl)phenyl)-2-methylpropanenitrile

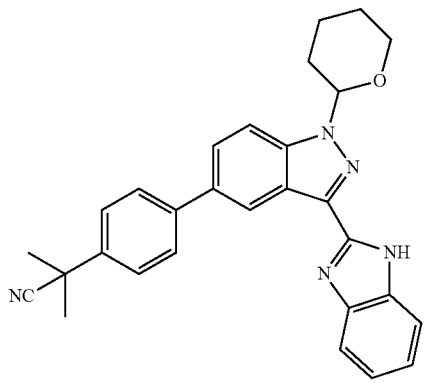 [SMILES: CC(C)(C#N)c1ccc(-c2ccc3c(c2)c(-c2nc4ccccc4[nH]2)nn3C2CCCCO2)cc1]

3-(1H-Benzo[d]imidazol-2-yl)-5-bromo-1-(tetrahydro-2H-pyran-2-yl)-1H-indazole (20 mg, 0.050 mmol), [4-(1cyano-1-methylethyl)phenyl]boronic acid (10 mg, 0.074053 mmol) and triphenylphosphine (2 mg, 0.007 mmol) were dissolved in a mixture of THF (6 mL) and 1M Na₂CO₃ (aq) (10 mg, 0.094 mmol). Palladium acetate (1 mg, 0.004 mmol) was added and the solution was heated overnight at reflux. After cooling to room temperature, and the solvent was removed in vacuo. The residue was dissolved in ethyl acetate (25 mL) and washed with water (20 mL). The organic layer was separated and the aqueous layer was extracted with ethyl acetate (25 mL). The combined organic layers were washed with brine (20 mL), dried over Na₂SO₄, and concentrated. Purification by flash chromatography (20% ethyl acetate/hexane) afforded the title compound (7 mg). ¹H NMR (400 MHz, CDCl₃): δ 8.79 (s, 1H), 7.80 (bs, 1H), 7.75 (m, 2H), 7.70 (m, 1H), 7.64 (m, 1H), 7.53-7.48 (m, 3H), 7.25-7.22 (m, 2H), 5.76 (d, 1H, J=8.4 Hz), 4.06 (m, 1H), 3.77 (m, 1H), 2.55 (m, 1H), 2.10 (m, 2H), 1.73 (m, 3H), 1.72 (s, 6H).

16. Preparation of 2-(4-(3-(1H-benzo[d]imidazol-2-yl)-1H-indazol-5-yl)phenyl)-2-methylpropanenitrile

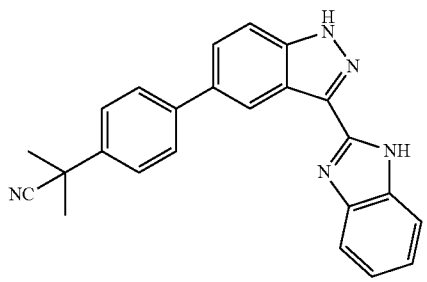 [SMILES: CC(C)(C#N)c1ccc(-c2ccc3[nH]nc(-c4nc5ccccc5[nH]4)c3c2)cc1]

TFA (0.25 mL, 3.245 mmol) was added to a solution of 2-(4-(3-(1H-benzo[d]imidazol-2-yl)-1-(tetrahydro-2H-pyran-2-yl)-1H-indazol-5-yl)phenyl)-2-methylpropanenitrile (7 mg, 0.015 mmol) in CH₂Cl₂ (4 mL). The reaction mixture was stirred at room temperature for 24 h, and then the solvent was removed in vacuo. Purification by flash chromatography (6% CH₃OH/CH₂Cl₂) afforded the title compound in a 55% yield. ¹H NMR (400 MHz, CD₃OD): δ 8.66 (bs, 1H), 7.87-7.80 (m, 6H), 7.66 (m, 2H), 7.56 (m, 2H), 1.78 (s, 6H); ESI-MS [M+H]⁺: 378.3.

17. Preparation of N-(3-(1H-benzo[d]imidazol-2-yl)-1-(tetrahydro-2H-pyran-2-yl)-1H-indazol-5-yl)-1,4-dimethylpiperidine-4-carboxamide

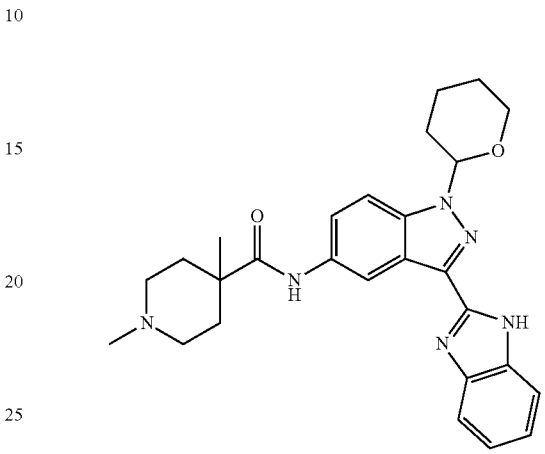

1,4-Dimethylpiperidine-4-carboxylic acid (3 mg, 0.019 mmol), HOBt (4 mg, 0.029 mmol), EDC (5.5 mg, 0.028 mmol) and sodium bicarbonate (1.6 mg, 0.019 mmol) were added to a solution of 3-(1H-benzo[d]imidazol-2-yl)-1-(tetrahydro-2H-pyran-2-yl)-1H-indazol-5-amine (6.4 mg, 0.019 mmol) in DMF (6 mL). The reaction mixture was stirred at room temperature for 24 h, and then the solvent was removed in vacuo. Purification by flash chromatography (6% CH₃OH/CH₂Cl₂) afforded the title compound (3.5 mg) as a solid. ¹H NMR (400 MHz, CD₃OD): δ 8.54 (s, 1H), 7.77 (m, 1H), 7.71 (m, 2H), 7.38 (m, 2H), 7.29 (m, 2H), 5.94 (d, 1H, J=8.0 Hz) 4.00 (m, 1H), 3.85 (m, 1H), 3.46 (m, 2H), 2.89 (s, 3H), 2.69 (m, 2H), 2.56 (m, 1H), 2.15 (m, 3H), 1.86 (m, 3H), 1.72 (m, 3H), 1.46 (s, 3H).

18. Preparation of N-(3-(1H-benzo[d]imidazol-2-yl)-1H-indazol-5-yl)-1,4-dimethylpiperidine-4-carboxamide

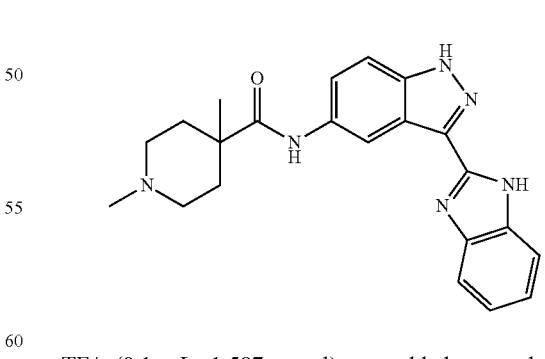

TFA (0.1 mL, 1.587 mmol) was added to a solution of N-(3-(1H-benzo[d]imidazol-2-yl)-1-(tetrahydro-2H-pyran-2-yl)-1H-indazol-5-yl)-1,4-dimethylpiperidine-4-carboxamide (5 mg, 0.010 mmol) in CH₂Cl₂ (4 mL). The reaction mixture was stirred at room temperature for 24 h, and then the solvent was removed in vacuo. Purification by flash chromatography (6% CH₃OH/CH₂Cl₂) afforded the title compound (2 mg) as a white solid. $^1$H NMR (400 MHz, CD$_3$OD): δ 8.49 (bs, 1H), 7.64 (m, 4H), 7.29 (m, 2H), 3.49 (m, 2H), 3.18 (m, 2H), 2.91 (s, 3H), 2.59 (m, 2H), 1.46 (m, 2H), 1.28 (s, 3H); ESI-MS [M+H]$^+$: 389.3.

19. Preparation of N-(3-(1H-benzo[d]imidazol-2-yl)-1-(tetrahydro-2H-pyran-2-yl)-1H-indazol-5-yl)-2,2-difluorocyclopropanecarboxamide

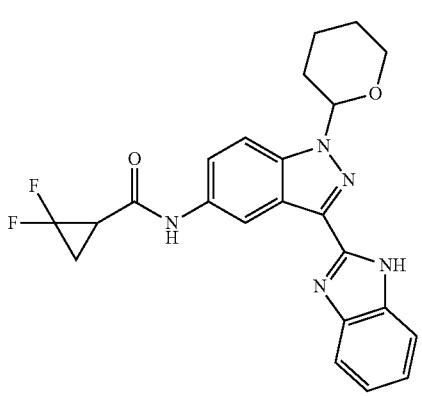 [SMILES: O=C(Nc1ccc2c(c1)c(-c1nc3ccccc3[nH]1)nn2C1CCCCO1)C1CC1(F)F]

2,2-Difluorocyclopropanecarboxylic acid (8 mg, 0.065 mmol), HOBt (12 mg, 0.089 mmol), EDC (17 mg, 0.089 mmol) and sodium bicarbonate (56 mg, 0.059 mmol) were added to a solution of 3-(1H-benzo[d]imidazol-2-yl)-1-(tetrahydro-2H-pyran-2-yl)-1H-indazol-5-amine (20 mg, 0.059 mmol) in DMF (6 mL). The reaction mixture was stirred at room temperature for 24 h, and then the solvent was removed in vacuo. Purification by flash chromatography (6% CH$_3$OH/CH$_2$Cl$_2$) afforded the title compound as a solid in a 50% yield. $^1$H NMR (400 MHz, CD$_3$OD): δ 8.51 (s, 1H), 7.77 (m, 1H), 7.67 (m, 3H), 7.27 (m, 2H), 5.86 (d, 1H, J=7.6 Hz), 4.00 (m, 1H), 3.81 (m, 1H), 2.74-2.61 (m, 2H), 2.13 (m, 3H), 1.84 (m, 2H), 1.69 (m, 2H).

20. Preparation of N-(3-(1H-benzo[d]imidazol-2-yl)-1H-indazol-5-yl)-2,2-difluorocyclopropanecarboxamide

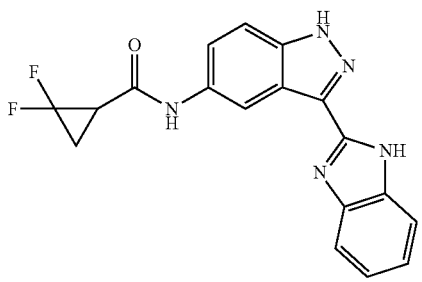 [SMILES: O=C(Nc1ccc2[nH]nc(-c3nc4ccccc4[nH]3)c2c1)C1CC1(F)F]

TFA (0.1 mL, 1.587 mmol) was added to a solution of N-(3-(1H-benzo[d]imidazol-2-yl)-1-(tetrahydro-2H-pyran-2-yl)-1H-indazol-5-yl)-2,2-difluorocyclopropanecarboxamide (10 mg, 0.023 mmol) in CH$_2$Cl$_2$ (4 mL). The reaction mixture was stirred at room temperature for 24 h, and then the solvent was removed in vacuo. Purification by flash chromatography (6% CH$_3$OH/CH$_2$Cl$_2$) afforded the title compound (6 mg). $^1$H NMR (400 MHz, CD$_3$OD): δ 8.69 (s, 1H), 7.82 (m, 2H), 7.70 (d, 1H, J=8.8 Hz), 7.56-7.50 (m, 3H), 2.82-2.73 (m, 1H), 2.21-2.12 (m, 1H), 1.94-1.85 (m, 1H); ESI-MS [M+H]$^+$: 354.2.

21. Preparation of 1-(3-(1H-benzo[d]imidazol-2-yl)-1-(tetrahydro-2H-pyran-2-yl)-1H-indazol-5-yl)-3-(2,4-difluorophenyl)urea

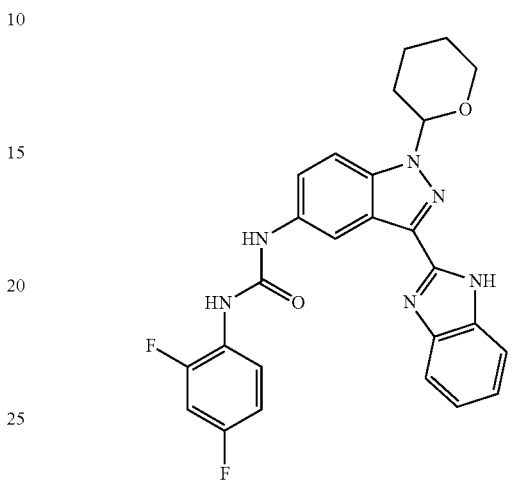

2,4-Difluorophenyl isocyanate (10 mg, 0.064 mmol) was added to a solution of 3-(1H-benzo[d]imidazol-2-yl)-1-(tetrahydro-2H-pyran-2-yl)-1H-indazol-5-amine (20 mg, 0.059 mmol) and pyridine (0.02 mL, 0.177 mmol) in CH$_2$Cl$_2$ (5 mL), and the mixture was stirred for 24 h. The reaction mixture was filtered through Celite, and the solvent was removed in vacuo. Purification by flash chromatography (2% CH$_3$OH/CH$_2$Cl$_2$) afforded the title compound (15 mg) as a solid. $^1$H NMR (400 MHz, CD$_3$OD): δ 8.39 (s, 1H), 8.04 (m, 1H), 7.86 (m, 1H), 7.72 (m, 3H), 7.27 (m, 2H), 7.00 (m, 1H), 6.92 (m, 1H), 5.92 (dd, 1H, J=3.2 and 9.2 Hz), 4.02 (m, 1H), 3.85 (m, 1H), 2.67 (m, 1H), 2.14 (m, 1H), 1.71 (m, 1H), 1.28 (m, 3H).

22. Preparation of 1-(3-(1H-benzo[d]imidazol-2-yl)-1H-indazol-5-yl)-3-(2,4-difluorophenyl)urea

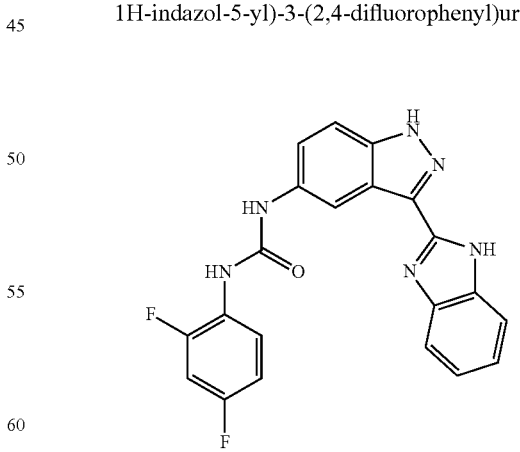

TFA (0.1 mL, 1.587 mmol) was added to a solution of 1-(3-(1H-benzo[d]imidazol-2-yl)-1-(tetrahydro-2H-pyran-2-yl)-1H-indazol-5-yl)-3-(2,4-difluorophenyl)urea (15 mg, 0.030 mmol) in CH$_2$Cl$_2$ (4 mL). The reaction mixture was stirred at room temperature for 24 h, and then the solvent was removed in vacuo. Purification by flash chromatography (6% CH₃OH/CH₂Cl₂) afforded the title compound in a 60% yield. ¹H NMR (400 MHz, CD₃OD): δ 8.38 (s, 1H), 8.05-7.99 (m, 1H), 764 (m, 3H), 7.56 (d, 1H, J=9.2 Hz), 7.26 (m, 2H), 7.01 (m, 1H), 6.92 (m, 1H); ESI-MS [M+H]⁺: 405.3.

23. Preparation of N-(3-(1H-benzo[d]imidazol-2-yl)-1-(tetrahydro-2H-pyran-2-yl)-1H-indazol-5-yl)-4,4-difluorocyclo hexane carboxamide

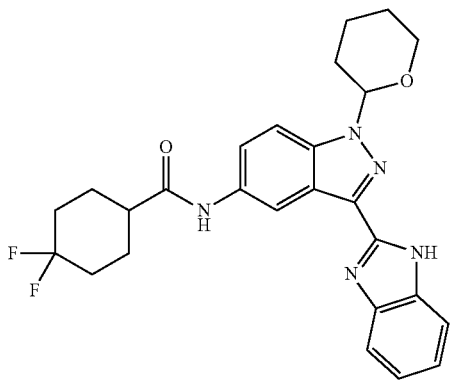 [SMILES: O=C(Nc1ccc2c(c1)c(-c1nc3ccccc3[nH]1)nn2C1CCCCO1)C1CCC(F)(F)CC1]

4,4-Difluorocyclohexanecarboxylic acid (8 mg, 0.048 mmol), HOBt (9 mg, 0.066 mmol), EDC (13 mg, 0.068 mmol) and sodium bicarbonate (4 mg, 0.047 mmol) was added to a solution of 3-(1H-benzo[d]imidazol-2-yl)-1-(tetrahydro-2H-pyran-2-yl)-1H-indazol-5-amine (15 mg, 0.045 mmol) in DMF (5 mL). The reaction mixture was stirred at room temperature for 24 h, and then the solvent was removed in vacuo. Purification by flash chromatography (6% CH₃OH/CH₂Cl₂) afforded the title compound (10 mg). ¹H NMR (400 MHz, CD₃OD): δ 8.51 (s, 1H), 7.74 (m, 2H), 7.66 (m, 2H), 7.28 (m, 2H), 5.92 (d, 1H, J=8.8 Hz), 4.01 (m, 1H), 3.84 (m, 1H), 2.66 (m, 1H), 2.54-2.44 (m, 2H), 2.17 (m, 3H), 2.01-1.70 (m, 9H).

24. Preparation of N-(3-(1H-benzo[d]imidazol-2-yl)-1H-indazol-5-yl)-4,4-difluorocyclohexanecarboxamide

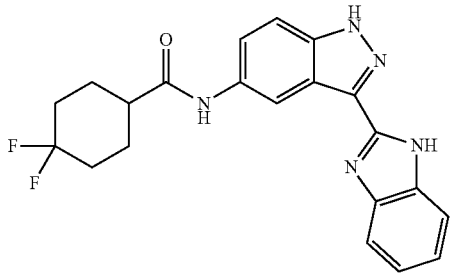 [SMILES: O=C(Nc1ccc2[nH]nc(-c3nc4ccccc4[nH]3)c2c1)C1CCC(F)(F)CC1]

TFA (0.5 mL, 6.490 mmol) was added to a solution of N-(3-(1H-benzo[d]imidazol-2-yl)-1-(tetrahydro-2H-pyran-2-yl)-1H-indazol-5-yl)-4,4-difluorocyclo hexane carboxamide (10 mg) in CH₂Cl₂ (4 mL). The reaction mixture was stirred at room temperature for 24 h, and then the solvent was removed in vacuo. Purification by flash chromatography (6% CH₃OH/CH₂Cl₂) afforded the title compound (6 mg) as an off-white solid. ¹H NMR (400 MHz, CD₃OD): δ 8.67 (s, 1H), 7.80 (m, 2H), 7.69 (d, 1H, J=9.2 Hz), 7.52 (m, 3H), 2.57 (m, 1H), 2.18 (m, 2H), 2.01 (m, 2H), 1.97-1.87 (m, 3H); ESI-MS [M+H]⁺: 396.3.

25. Preparation of 1-(3-(1H-benzo[d]imidazol-2-yl)-1H-indazol-5-yl)-3-cyclopentylurea

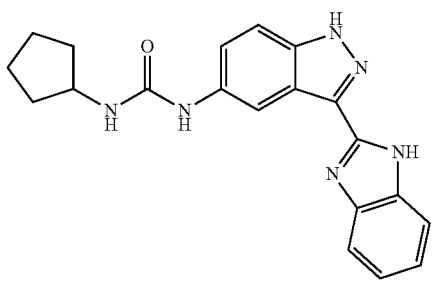 [SMILES: O=C(Nc1ccc2[nH]nc(-c3nc4ccccc4[nH]3)c2c1)NC1CCCC1]

TFA (0.3 mL, 4.03 mmol) was added to a solution of 1-(3-(1H-benzo[d]imidazol-2-yl)-1-(tetrahydro-2H-pyran-2-yl)-1H-indazol-5-yl)-3-cyclopentylurea (6 mg, 0.013 mmol) in CH₂Cl₂ (4 mL). The reaction mixture was stirred at room temperature for 24 h, and then the solvent was removed in vacuo. Purification by flash chromatography (6% CH₃OH/CH₂Cl₂) afforded the title compound (4 mg) as an off-white solid. ¹H NMR (400 MHz, CD₃OD): δ 8.36 (s, 1H), 7.81 (m, 2H), 7.60 (d, 1H, J=8.8 Hz), 7.46 (m, 3H), 4.11 (t, 1H, J=6.4 Hz), 2.00 (m, 2H), 1.75 (m, 2H), 1.65 (m, 2H), 1.51 (m, 2H); ESI-MS [M+H]⁺: 361.3.

26. Preparation of 1-(3-(1H-benzo[d]imidazol-2-yl)-1-(tetrahydro-2H-pyran-2-yl)-1H-indazol-5-yl)-3-cyclopropylurea

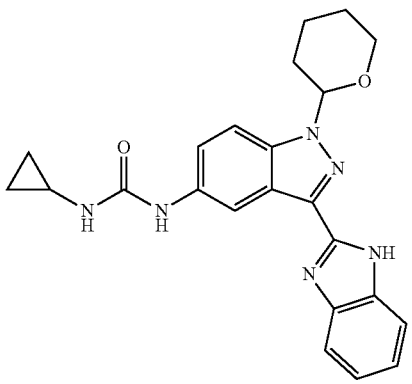 [SMILES: O=C(Nc1ccc2c(c1)c(-c1nc3ccccc3[nH]1)nn2C1CCCCO1)NC1CC1]

Cyclopropylisocyanate (4 g, 0.048 mmol) was added to a solution of 3-(1H-benzo[d]imidazol-2-yl)-1-(tetrahydro-2H-pyran-2-yl)-1H-indazol-5-amine (15 mg, 0.045 mmol) and pyridine (0.01 mL, 0.126 mmol) in CH₂Cl₂ (5 mL). The mixture was stirred for 24 h, and then the solvent was removed in vacuo. Purification by flash chromatography (2% CH₃OH/CH₂Cl₂) afforded the title compound (10 mg) as a solid. ¹H NMR (400 MHz, CDCl₃): δ 8.22 (s, 1H), 7.93 (d, 1H, J=8.8 Hz), 7.83 (m, 1H), 7.49 (d, 1H, J=8.8 Hz), 7.27-7.24 (m, 2H), 7.17 (s, 1H), 5.71 (dd, 1H, J=2.4 and 9.2 Hz), 4.04 (m, 1H), 3785 (m, 1H), 2.59 (m, 2H), 2.17-2.07 (m, 2H), 1.74 (m, 5H), 0.84 (q, 2H, J=5.2 Hz).

27. Preparation of 1-(3-(1H-benzo[d]imidazol-2-yl)-1H-indazol-5-yl)-3-cyclopropylurea

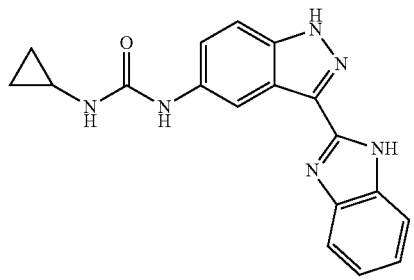 [SMILES: O=C(Nc1ccc2[nH]nc(-c3nc4ccccc4[nH]3)c2c1)NC1CC1]

TFA (0.5 mL, 7.20 mmol) was added to a solution of 1-(3-(1H-benzo[d]imidazol-2-yl)-1-(tetrahydro-2H-pyran-2-yl)-1H-indazol-5-yl)-3-cyclopropylurea (10 mg, 0.024 mmol) in CH$_2$Cl$_2$ (4 mL). The reaction mixture was stirred at room temperature for 24 h, and then the solvent was removed in vacuo. Purification by flash chromatography (6% CH$_3$OH/CH$_2$Cl$_2$) afforded the title compound (6 mg) as an off-white solid. $^1$H NMR (400 MHz, CD$_3$OD): δ 8.53 (s, 1H), 7.69-7.67 (m, 2H), 7.59 (d, 1H, J=8.8 Hz), 7.27 (m, 3H), 3.91 (t, 2H, J=5.6 Hz), 3.62 (m, 1H), 2.64 (t, 2H, J=6.0 Hz); ESI-MS [M+H]$^+$: 333.1.

28. Preparation of N-(3-(1H-benzo[d]imidazol-2-yl)-1-(tetrahydro-2H-pyran-2-yl)-1H-indazol-5-yl)-1-(pyridin-4-yl)piperidine-4-carboxamide

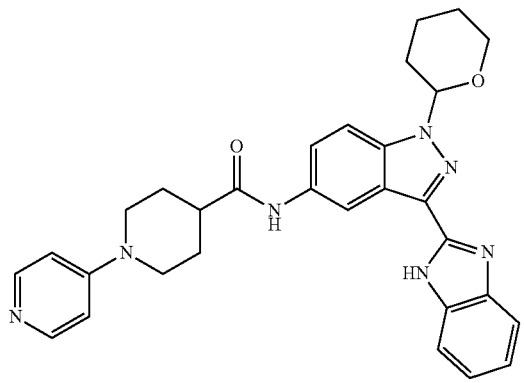 [SMILES: O=C(Nc1ccc2c(c1)c(-c1nc3ccccc3[nH]1)nn2C1CCCCO1)C1CCN(c2ccncc2)CC1]

1-(Pyridin-4-yl)piperidine-4-carboxylic acid (14 mg, 0.068 mmol), HOBt (12 mg, 0.088 mmol), EDC (17 mg, 0.088 mmol) and sodium bicarbonate (5 mg, 0.059 mmol) were added to a solution of 3-(1H-benzo[d]imidazol-2-yl)-1-(tetrahydro-2H-pyran-2-yl)-1H-indazol-5-amine (20 mg, 0.059 mmol) in DMF (5 mL). The reaction mixture was stirred at room temperature for 24 h, and then the solvent was removed in vacuum. Purification by flash chromatography (6% CH$_3$OH/CH$_2$Cl$_2$) afforded the title compound (12 mg).

29. Preparation of N-(3-(1H-benzo[d]imidazol-2-yl)-1H-indazol-5-yl)-1-(pyridin-4-yl)piperidine-4-carboxamide

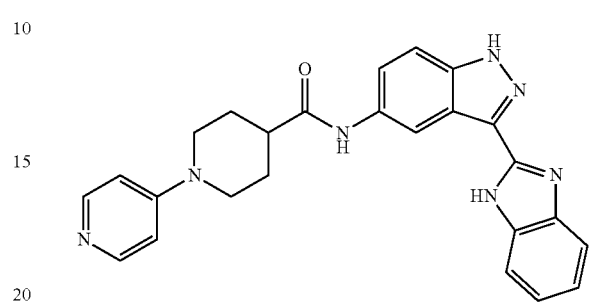

TFA (0.5 mL, 6.90 mmol) was added to a solution of N-(3-(1H-benzo[d]imidazol-2-yl)-1-(tetrahydro-2H-pyran-2-yl)-1H-indazol-5-yl)-1-(pyridin-4-yl)piperidine-4-carboxamide (12 mg, 0.023 mmol) in CH$_2$Cl$_2$ (4 mL). The reaction mixture was stirred at room temperature for 24 h, and then the solvent was removed in vacuo. Purification by flash chromatography (6% CH$_3$OH/CH$_2$Cl$_2$) afforded the title compound (7 mg) as an off-white solid. $^1$H NMR (400 MHz, CD$_3$OD): δ 8.50 (s, 1H), 8.10 (m, 2H), 7.73 (d, 1H, J=8.8 Hz), 7.65 (m, 2H), 7.57 (d, 1H, J=9.2 Hz), 7.27 (m, 2H), 6.94 (m, 2H), 4.17 (m, 2H), 3.11 (m, 2H), 2.77 (m, 1H), 2.03 (m, 2H), 1.89 (m, 2H); ESI-MS [M+2H/2]$^+$: 219.61.

30. Preparation of (3,4-dinitrophenyl)(morpholino)methanone

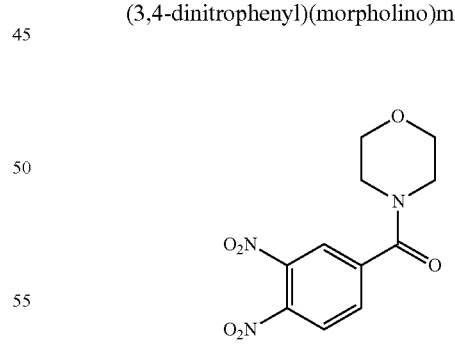

A solution of 3,4-dinitrobenzoic acid (200 mg, 0.943 mmol) and DMF (2 drops) in THF (7 mL) was treated with thionyl chloride (0.14 mL, 224 mmol) and then heated at reflux for 2.5 h. The mixture was cooled to 0° C. and triethylamine (286 mg, 1.883 mmol) was added over 25 min while keeping the internal temperature at 0° C. Morpholine (164 mg, 1.883 mmol) was added. The mixture was stirred overnight and allowed to warm to ambient temperature. Purification by flash chromatography afforded the title compound (150 mg). ¹H NMR (400 MHz, CD₃OD): δ 8.36 (s, 1H), 8.10 (d, 1H, J=8.8 Hz), 7.28 (d, 1H, J=9.2 Hz), 3.79 (m, 4H), 3.16 (m, 4H).

31. Preparation of 4-(3,4-dinitrobenzyl)morpholine

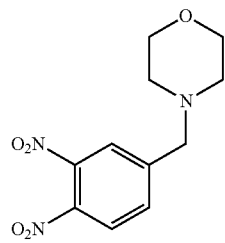 [SMILES: O=[N+]([O-])c1ccc(CN2CCOCC2)cc1[N+](=O)[O-]]

Sodium borohydride (40 mg, 1.06 mmol) was placed in a nitrogen flushed flask and suspended in THF (7 mL). After the mixture was cooled to 0° C., boron trifluoride etherate (0.13 mL, 1.06 mmol) was added by syringe and followed by the addition of (3,4-dinitrophenyl)(morpholino)methanone (150 mg, 0.53 mmol) in a single portion. The suspension was stirred at room temperature for 3 h. Methanol (5 mL) was added to the reaction mixture at 0° C., and the mixture was heated at reflux for 1 h. The mixture was concentrated in vacuo and the resulting residue was partitioned between ethyl acetate (50 mL) and saturated NaHCO₃ (50 mL). The organic phase was separated, washed with water (30 mL) and brine (30 mL), and dried with Na₂SO₄. Purification by flash chromatography (3% CH₃OH/CH₂Cl₂) afforded the title compound (120 mg) as a solid. ¹H NMR (400 MHz, CD₃OD): δ 8.03 (m, 2H), 7.85 (m, 1H), 3.71 (m, 6H), 2.49 (m, 4H).

32. Preparation of 4-(morpholinomethyl)benzene-1,2-diamine

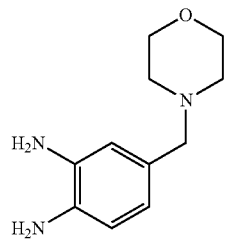

4-(3,4-Dinitrobenzyl)morpholine (200 mg, 0.748 mmol) and 10% Pd/C (10 mg) were suspended in ethanol (10 mL) under nitrogen. The reaction mixture's atmosphere was exchanged for hydrogen and hydrogenation continued at ambient temperature and pressure for 24 h. The vessel was purged with nitrogen, and then the mixture was filtered through Celite with an ethanol (10 mL) rinsing. The solvent was removed in vacuo and purification by flash chromatography (5% CH₃OH/CH₂Cl₂) afforded the title compound in a 65% yield. ¹H NMR: (400 MHz, DMSO-d₆): δ 6.46 (s, 1H), 6.40 (d, 1H, J=7.6 Hz), 6.27 (d, 1H, J=7.2 Hz), 4.37 (s, 2H), 4.32 (s, 2H), 3.52 (m, 4H), 3.18 (m, 4H), 2.26 (m, 4H).

33. Preparation of 4-((2-(5-nitro-1-(tetrahydro-2H-pyran-2-yl)-1H-indazol-3-yl)-1H-benzo[d]imidazol-6-yl)methyl)morpholine

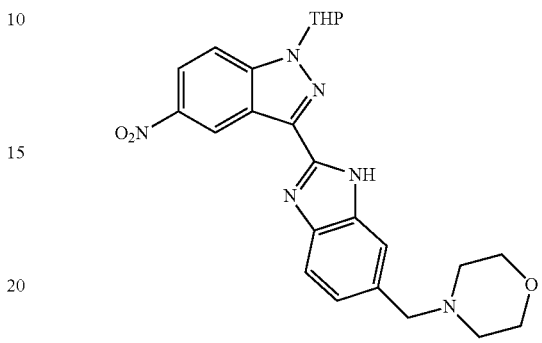

5-Nitro-1-(tetrahydro-2H-pyran-2-yl)-1H-indazole-3-carbaldehyde (85 mg, 0.309 mmol) and 4-(morpholinomethyl)benzene-1,2-diamine (64 mg, 0.309 mmol) were dissolved in dry THF (8 mL) and 2N HCl (1 drop) was added. The solution was heated at a gentle reflux for 30 min and then 1N sodium bisulfite (1 mL) was added. After overnight at reflux, the solution was cooled to room temperature, and diluted with ethyl acetate (40 mL). The mixture was washed with water and brine, dried over Na₂SO₄, and concentrated. Purification by flash chromatography (20% ethyl acetate/hexane) afforded the title compound as a pale yellow solid in a 50% yield. ¹H NMR: (400 MHz, CD₃OD): δ 9.42 (d, 1H, J=2.0 Hz), 8.32 (dd, 1H, J=2.0 and 8.8 Hz), 7.92-7.87 (m, 1H), 7.67 (m, 2H), 7.32 (d, 1H, J=8.4 Hz), 5.97 (dd, 1H, J=2.8 and 8.8 Hz), 3.99 (m, 1H), 3.88-3.82 (m, 1H), 3.72 (m, 6H), 2.57 (m, 5H), 2.19 (m, 2H), 1.88 (m, 1H), 1.73 (m, 2H).

34. Preparation of 3-(6-(morpholinomethyl)-1H-benzo[d]imidazol-2-yl)-1-(tetrahydro-2H-pyran-2-yl)-1H-indazol-5-amine

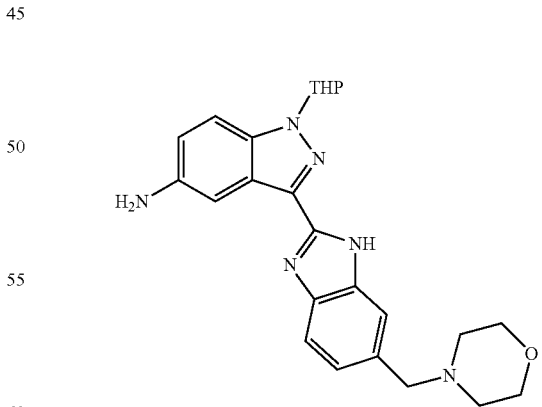

4-((2-(5-Nitro-1-(tetrahydro-2H-pyran-2-yl)-1H-indazol-3-yl)-1H-benzo[d]imidazol-6-yl)methyl)morpholine (20 mg, 0.043 mmol) was added to the 10% Pd/C (5 mg) in ethanol (10 mL) and then hydrogen gas (60 psi) was applied for 6 h at room temperature. The reaction mixture was filtered through Celite, and the solvent was removed in vacuo. Purification by flash chromatography (5% CH₃OH/CH₂Cl₂) afforded the title compound (15 mg) as a white solid.

35. Preparation of 2,2-difluoro-N-(3-(5-(morpholinomethyl)-1H-benzo[d]imidazol-2-yl)-1-(tetrahydro-2H-pyran-2-yl)-1H-indazol-5-yl)cyclopropanecarboxamide

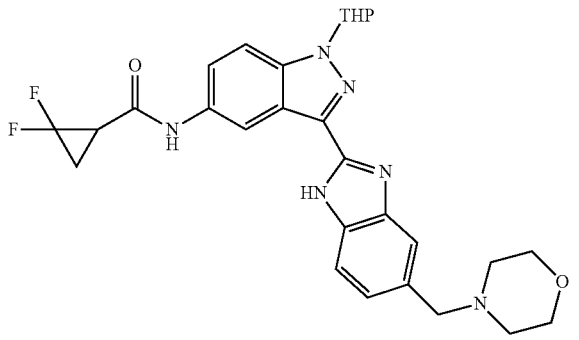

2,2-Difluorocyclopropane carboxylic acid (3 mg, 0.024 mmol), HOBt (5 mg, 0.037 mmol), EDC (6.6 mg, 0.035 mmol) and sodium bicarbonate (2 mg, 0.024 mmol) were added to a solution of 3-(6-(morpholinomethyl)-1H-benzo[d]imidazol-2-yl)-1-(tetrahydro-2H-pyran-2-yl)-1H-indazol-5-amine (10 mg, 0.023 mmol) in DMF (5 mL). The reaction mixture was stirred at room temperature for 24 h, and then the solvent was removed in vacuo. Purification by flash chromatography (6% CH₃OH/CH₂Cl₂) yielded the title compound (10 mg) as a solid. ¹H NMR: (400 MHz, CD₃OD): δ 8.62 (s, 1H), 7.75-7.66 (m, 4H), 7.34 (d, 1H, J=8.0 Hz), 5.94 (dd, 1H, J=2.8 and 9.6 Hz), 4.01 (m, 3H), 3.85 (m, 1H), 3.77 (m, 4H), 2.81 (m, 4H), 2.68 (m, 1H), 2.18-2.10 (m, 3H), 1.91-1.83 (m, 3H), 1.71 (m, 2H); ESI-MS [M+H]⁺: 537.2.

36. Preparation of 2,2-difluoro-N-(3-(5-(morpholinomethyl)-1H-benzo[d]imidazol-2-yl)-1H-indazol-5-yl)cyclopropane carboxamide

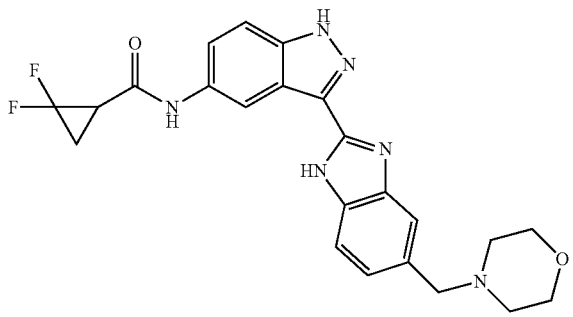

TFA (0.15 mL, 1.86 mmol) was added to solution of 2,2-difluoro-N-(3-(6-(morpholinomethyl)-1H-benzo[d]imidazol-2-yl)-1-(tetrahydro-2H-pyran-2-yl)-1H-indazol-5-yl)cyclopropane carboxamide (10 mg, 0.018 mmol) in CH₂Cl₂ (5 mL). The reaction mixture was stirred overnight at room temperature, and then the solvent was removed by vacuum. Purification by flash column chromatography (5% CH₃OH/CH₂Cl₂) afforded the title compound (4 mg) as a solid. ¹H NMR: (400 MHz, CD₃OD): δ 8.49 (d, 1H, J=1.6 Hz), 7.69 (dd, 1H, J=1.6 and 8.8 Hz), 7.63-7.58 (m, 3H), 7.28 (m, 1H), 3.71 (m, 4H), 3.67 (m, 2H), 2.79-2.70 (m, 1H), 2.52 (m, 4H), 2.36-2.32 (m, 1H), 2.15-2.06 (m, 1H); ESI-MS [M+H]⁺: 453.2.

37. Preparation of 5-morpholino-2-nitroaniline

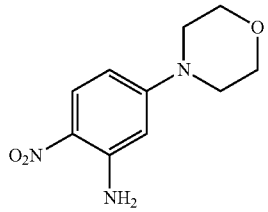 [SMILES: Nc1cc(N2CCOCC2)ccc1[N+](=O)[O-]]

A solution of 5-chloro-2-nitroaniline (100 mg, 0.58 mmol) in NMP (4.5 mL) was treated with morpholine (75 mg, 0.86 mmol) in the presence of triethylamine (0.2 mL, 1.44 mmol). The reaction mixture was heated via microwave irradiation to 100° C. for 1 h and upon cooling, the solvent was removed by vacuum. Purification by flash column chromatography afforded the title compound in a 77% yield. ¹H NMR: (400 MHz, DMSO-d₆): δ 7.82 (d, 1H, J=9.6 Hz), 7.29 (bs, 2H), 6.39 (dd, 1H, J=2.8 and 9.6 Hz), 6.22 (d, 1H, J=2.4 Hz), 3.70 (m, 4H), 3.27 (m, 4H).

38. Preparation of 4-morpholinobenzene-1,2-diamine

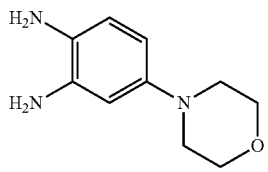 [SMILES: Nc1ccc(N2CCOCC2)cc1N]

5-Morpholino-2-nitroaniline (200 mg, 0.896 mmol) was added to the 10% Pd/C (25 mg) in ethanol (25 mL) and then hydrogen gas (60 psi) was applied for overnight at room temperature. The reaction mixture was filtered through Celite, and the solvent was removed in vacuum. Purification by flash chromatography (5% CH₃OH/CH₂Cl₂) afforded the title compound (150 mg). ¹H NMR: (400 MHz, DMSO-d₆): δ 6.38 (d, 1H, J=8.0 Hz), 6.18 (d, 1H, J=2.4 Hz), 5.99 (dd, 1H, J=2.4 and 8.4 Hz), 4.35 (bs, 2H), 3.97 (bs, 2H), 3.66 (m, 4H), 2.81 (m, 4H).

39. Preparation of 4-(2-(5-nitro-1-(tetrahydro-2H-pyran-2-yl)-1H-indazol-3-yl)-1H-benzo[d]imidazol-5-yl)morpholine

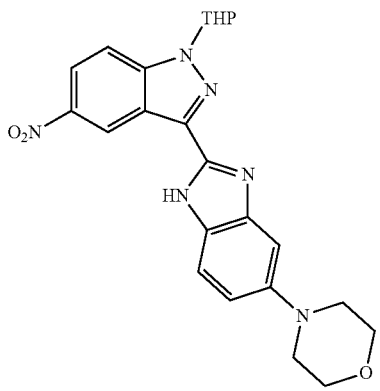

5-Nitro-1-(tetrahydro-2H-pyran-2-yl)-1H-indazole-3-carbaldehyde (214 mg, 0.777 mmol) and 4-morpholinobenzene-1,2-diamine (150 mg, 0.777 mmol) were dissolved in dry THF (10 mL), and 2N HCl (1 drop) was added. The solution was heated at a gentle reflux for 30 min and then 1N sodium bisulfite (1 mL) was added. After overnight at reflux, the solution was cooled to room temperature, and diluted with ethyl acetate (40 mL). The mixture was washed with water and brine, dried over $Na_2SO_4$, and concentrated. Purification by flash chromatography (20% ethyl acetate/hexane) afforded the title compound as a pale yellow solid in a 50% yield. $^1$H NMR: (400 MHz, DMSO-$d_6$): δ 9.49 (d, 1H, J=2.0 Hz), 8.41 (dd, 1H, J=2.0 and 9.2 Hz), 8.00 (d, 1H, J=9.2 Hz), 7.71 (m, 1H), 7.12 (m, 2H), 6.05 (dd, 1H, J=2.4 and 9.2 Hz), 4.75 (dd, 1H, J=2.4 and 6.8 Hz), 4.05 (m, 1H), 3.89 (m, 4H), 3.63 (m, 1H), 3.54-3.47 (m, 1H), 3.22 (m, 4H), 2.21 (m, 2H), 1.87 (m, 1H), 1.73 (m, 1H).

40. Preparation of 3-(5-morpholino-1H-benzo[d]imidazol-2-yl)-1-(tetrahydro-2H-pyran-2-yl)-1H-indazol-5-amine

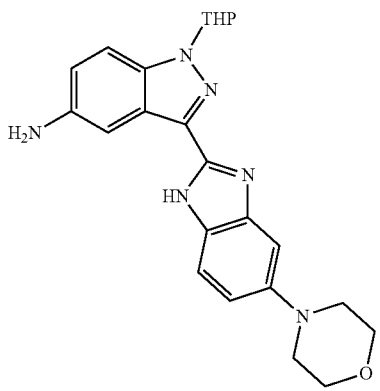

4-(2-(5-Nitro-1-(tetrahydro-2H-pyran-2-yl)-1H-indazol-3-yl)-1H-benzo[d]imidazol-6-yl)morpholine (50 mg, 0.111 mmol) was added to the 10% Pd/C (10 mg) in ethanol (20 mL) and then hydrogen gas (60 psi) was applied for overnight at room temperature. Upon The reaction mixture was filtered through Celite, and the solvent was removed in vacuum. Purification by flash chromatography (5% $CH_3OH/CH_2Cl_2$) afforded the title compound (25 mg) as a solid. $^1$H NMR: (400 MHz, $CD_3OD$): δ 7.66 (d, 1H, J=2.4 Hz), 7.56-7.51 (m, 2H), 7.15 (m, 1H), 7.06-7.01 (m, 2H), 5.81 (dd, 1H, J=2.4 and 9.6 Hz), 4.01 (m, 1H), 3.87 (m, 4H), 3.81 (m, 1H), 3.65 (t, 1H, J=6.8 Hz), 3.16 (m, 4H), 2.67-2.58 (m, 1H), 2.16 (m, 1H), 2.08 (m, 1H), 1.84 (m, 1H), 1.69 (m, 1H).

41. Preparation of 2,2-difluoro-N-(3-(5-morpholino-1H-benzo[d]imidazol-2-yl)-1-(tetrahydro-2H-pyran-2-yl)-1H-indazol-5-yl)cyclopropanecarboxamide

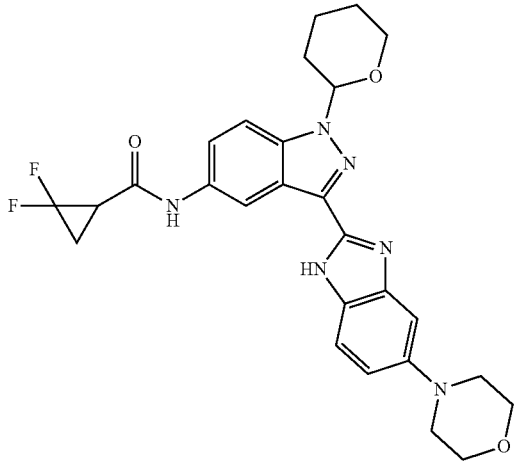 [SMILES: O=C(Nc1ccc2c(c1)c(-c1nc3cc(N4CCOCC4)ccc3[nH]1)nn2C1CCCCO1)C1CC1(F)F]

2,2-Difluorocyclopropanecarboxylic acid (6.42 mg, 0.053 mmol), 1H-benzo[d][1,2,3]triazol-1-ol (9.69 mg, 0.072 mmol), EDC (13.74 mg, 0.072 mmol) and sodium bicarbonate (4.01 mg, 0.048 mmol) was added to a solution of 3-(5-morpholino-1H-benzo[d]imidazol-2-yl)-1-(tetrahydro-2H-pyran-2-yl)-1H-indazol-5-amine (20 mg, 0.048 mmol) in DMF (6 mL). The reaction mixture was stirred at room temperature for 24 h, and then the solvent was removed in vacuo. Upon purification by flash chromatography (6% $CH_3OH/CH_2Cl_2$) afforded the title compound (15 mg). $^1$H NMR: (400 MHz, $CD_3OD$): δ 8.51 (s, 1H), 7.76-7.72 (m, 1H), 7.68 (m, 1H), 7.58 (m, 1H), 7.05 (m, 2H), 5.86 (dd, 1H, J=2.4 and 9.6 Hz), 3.99 (m, 1H), 3.86 (m, 4H), 3.81 (m, 1H), 3.16 (m, 4H), 2.77-2.69 (m, 1H), 2.61 (m, 1H), 2.18-2.08 (m, 3H), 1.89-1.80 (m, 2H), 1.74-1.68 (m, 2H); ESI-MS [M+H]$^+$: 523.2.

42. Preparation of 2,2-difluoro-N-(3-(5-morpholino-1H-benzo[d]imidazol-2-yl)-1H-indazol-5-yl)cyclopropanecarboxamide

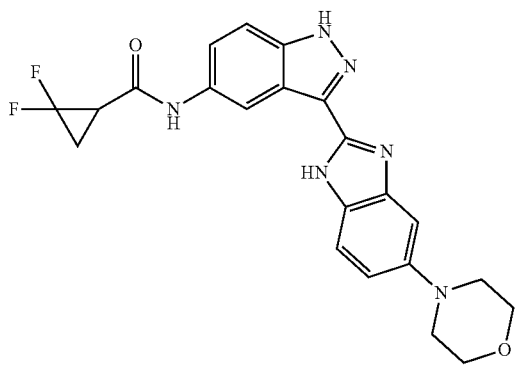 [SMILES: O=C(Nc1ccc2[nH]nc(-c3nc4cc(N5CCOCC5)ccc4[nH]3)c2c1)C1CC1(F)F]

TFA (2.212 μL, 0.029 mmol) was added to solution of 2,2-difluoro-N-(3-(5-morpholino-1H-benzo[d]imidazol-2-yl)-1-(tetrahydro-2H-pyran-2-yl)-1H-indazol-5-yl)cyclopropane carboxamide (15 mg, 0.029 mmol) in CH$_2$Cl$_2$ (5 mL). The reaction mixture was stirred overnight at room temperature, and then the solvent was removed in vacuo. Purification by flash column chromatography (5% CH$_3$OH/CH$_2$Cl$_2$) afforded the title compound (10 mg) as a yellow solid. $^1$H NMR: (400 MHz, CD$_3$OD): δ 8.69 (d, 1H, J=1.2 Hz), 7.71 (d, 1H, J=9.2 Hz), 7.68 (d, 1H, J=8.8 Hz), 7.48 (dd, 1H, J=1.6 and 9.2 Hz), 7.35 (dd, 1H, J=1.6 and 9.6 Hz), 7.19 (m, 1H), 3.88 (m, 4H), 3.26 (m, 4H), 2.82-2.74 (m, 1H), 2.19-2.12 (m, 1H), 1.93-1.87 (m, 1H); ESI-MS: [M+H]$^+$: 439.1.

43. Preparation of 4,4-difluoro-N-(3-(5-morpholino-1H-benzo[d]imidazol-2-yl)-1-(tetrahydro-2H-pyran-2-yl)-1H-indazol-5-yl)cyclohexanecarboxamide

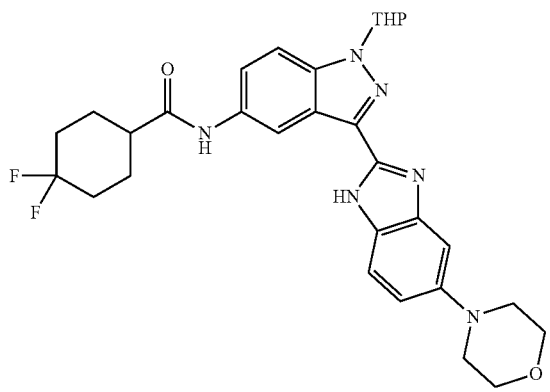

4,4-Difluorocyclohexanecarboxylic acid (3.92 mg, 0.024 mmol), HOBt (4.84 mg, 0.036 mmol), EDC (6.87 mg, 0.036 mmol) and sodium bicarbonate (2.007 mg, 0.024 mmol) was added to a solution of 3-(6-morpholino-1H-benzo[d]imidazol-2-yl)-1-(tetrahydro-2H-pyran-2-yl)-1H-indazol-5-amine (10 mg, 0.024 mmol) in DMF (5 mL). The reaction mixture was stirred at room temperature for 24 h after and then the solvent was removed in vacuo. Purification by flash column chromatography (6% CH$_3$OH/CH$_2$Cl$_2$) afforded the title compound (6 mg) as a solid. $^1$H NMR: (400 MHz, CD$_3$OD): δ 8.49 (s, 1H), 7.76-7.70 (m, 2H), 7.57 (d, 1H, J=8.8 Hz), 7.17 (m, 1H), 7.07 (dd, 1H, J=2.0 & 8.8 Hz), 5.90 (dd, 1H, J=2.0 and 9.6 Hz), 4.01 (m, 1H), 3.86 (m, 4H), 3.81 (m, 1H), 3.17 (m, 4H), 2.65 (m, 1H), 2.53 (m, 1H), 2.43 (m, 1H), 2.18-2.10 (m, 2H), 1.99 (m, 3H), 1.92-1.82 (m, 4H), 1.75 (m, 3H); ESI-MS [M+H]$^+$: 565.17.

44. Preparation of 4,4-difluoro-N-(3-(5-morpholino-1H-benzo[d]imidazol-2-yl)-1H-indazol-5-yl)cyclohexanecarboxamide

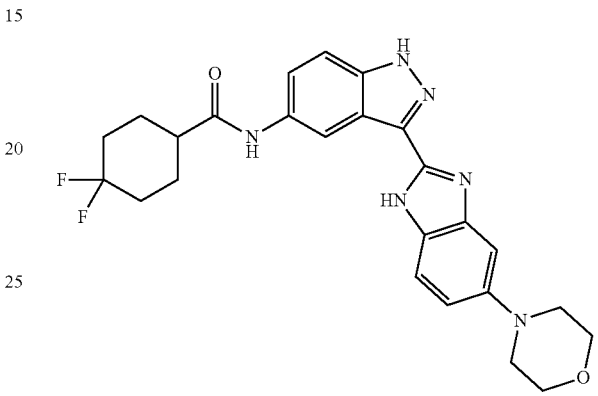

TFA (0.082 mL, 1.063 mmol) was added to a solution of 4,4-difluoro-N-(3-(5-morpholino-1H-benzo[d]imidazol-2-yl)-1-(tetrahydro-2H-pyran-2-yl)-1H-indazol-5-yl)cyclohexanecarboxamide (6 mg, 10.63 μmol) in CH$_2$Cl$_2$ (5 mL). The reaction mixture was stirred overnight at room temperature, and the solvent was removed in vacuo. Purification by flash column chromatography (5% CH$_3$OH/CH$_2$Cl$_2$) afforded the title compound (4 mg) as a solid. $^1$H NMR: (400 MHz, CD$_3$OD): δ 8.46 (s, 1H), 7.69 (m, 1H), 7.57 (m 2H), 7.18 (d, 1H, J=1.6 Hz), 7.07 (dd, 1H, J=2.0 and 8.8 Hz), 3.88 (m, 4H), 3.18 (m, 4H), 2.55 (m, 1H), 2.17 (m, 2H), 2.01 (m, 2H), 1.96-1.83 (m, 4H); ESI-MS [M+H]$^+$: 481.28.

45. Preparation of N-(3-(1H-benzo[d]imidazol-2-yl)-1-(tetrahydro-2H-pyran-2-yl)-1H-indazol-5-yl)cyclopropanecarboxamide

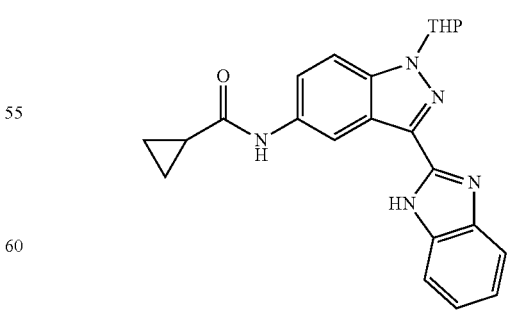

Cyclopropanecarboxylic acid (6.46 mg, 0.075 mmol), HOBT (15.20 mg, 0.112 mmol), EDC (21.56 mg, 0.112 mmol) and sodium bicarbonate (6.30 mg, 0.075 mmol) was added to a solution of 3-(1H-benzo[d]imidazol-2-yl)-1-(tetrahydro-2H-pyran-2-yl)-1H-indazol-5-amine (25 mg, 0.075 mmol) in DMF (5 mL). The reaction mixture was stirred at room temperature for 24 h, and then the solvent was removed in vacuo. Purification by flash column chromatography (6% CH₃OH/CH₂Cl₂) afforded the title compound (20 mg) as a solid. ¹H NMR: (400 MHz, CD₃OD): δ 8.50 (d, 1H, J=1.6 Hz), 7.96 (s, 1H), 7.75 (dd, 1H, J=2.0 and 8.8 Hz), 7.65 (m, 2H), 7.26 (m, 2H), 5.86 (dd, 1H, J=2.0 and 9.2 Hz), 3.97 (m, 1H), 3.81 (m, 1H), 2.63 (m, 1H), 2.14 (m, 2H), 1.82 (m, 2H), 1.68 (m, 2H), 0.99 (m, 2H), 0.87 (m, 2H); ESI-MS [M+H]⁺: 402.22.

46. Preparation of N-(3-(1H-benzo[d]imidazol-2-yl)-1H-indazol-5-yl)cyclopropane carboxamide

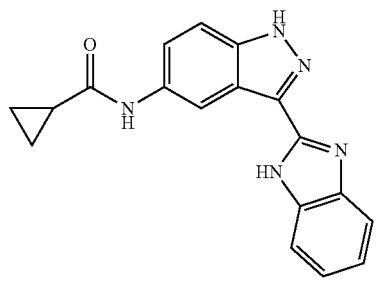 [SMILES: O=C(Nc1ccc2[nH]nc(-c3nc4ccccc4[nH]3)c2c1)C1CC1]

TFA (568 mg, 4.98 mmol) was added to solution of N-(3-(1H-benzo[d]imidazol-2-yl)-1-(tetrahydro-2H-pyran-2-yl)-1H-indazol-5-yl)cyclopropanecarboxamide (20 mg, 0.050 mmol) in CH₂Cl₂ (5 mL). The reaction mixture was stirred overnight at room temperature, and then the solvent was removed in vacuo. Purification by flash column chromatography (5% CH₃OH/CH₂Cl₂) afforded the title compound (10 mg) as a pale yellow solid. ¹H NMR: (400 MHz, CD₃OD): δ 8.63 (s, 1H), 7.80 (m, 2H), 7.68 (d, 1H, J=9.2 Hz), 7.57 (m 2H), 7.49 (d, 1H, J=8.8 Hz), 1.85 (m, 1H), 1.03 (m, 2H), 0.92 (m, 2H); ESI-MS [M+H]⁺: 318.06.

47. Preparation of N-(3-(5-morpholino-1H-benzo[d]imidazol-2-yl)-1-(tetrahydro-2H-pyran-2-yl)-1H-indazol-5-yl)cyclopropanecarboxamide

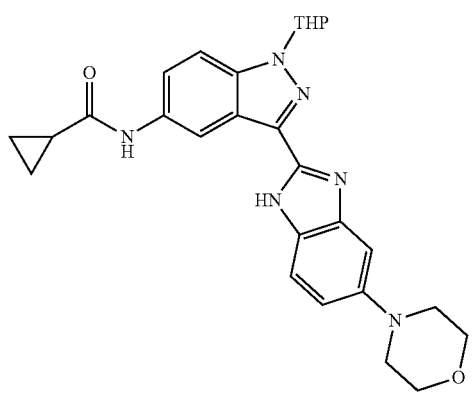

3-(5-Morpholino-1H-benzo[d]imidazol-2-yl)-1-(tetrahydro-2H-pyran-2-yl)-1H-indazol-5-amine (30 mg, 0.072 mmol), 1H-benzo[d][1,2,3]triazol-1-ol (14.53 mg, 0.108 mmol), EDC (20.61 mg, 0.108 mmol) and sodium bicarbonate (6.02 mg, 0.072 mmol) was added to a solution of cyclopropanecarboxylic acid (6.17 mg, 0.072 mmol) in DMF (6 mL). The reaction mixture was stirred at room temperature for 24 h, and then the solvent was removed in vacuo. Purification by flash column chromatography (6% CH₃OH/CH₂Cl₂) afforded the title compound (20 mg) as a solid. ¹H NMR: (400 MHz, CD₃OD): δ 8.47 (d, 1H, J=1.6 Hz), 7.75 (dd, 1H, J=2.0 and 9.2 Hz), 7.67 (d, 1H, J=8.8 Hz), 7.55 (d, 1H, J=8.4 Hz), 7.14 (m, 1H), 7.05 (dd, 1H, J=2.0 and 8.4 Hz), 5.86 (dd, 1H, J=2.4 and 9.6 Hz), 3.98 (m, 1H), 3.87 (m 4H), 3.81 (m, 1H), 3.16 (m, 4H), 2.64 (m, 1H), 2.14 (m, 2H), 1.81 (m, 2H), 1.71 (m, 2H), 0.99 (m, 2H), 0.88 (m, 2H); ESI-MS [M+H]⁺:487.22.

48. Preparation of N-(3-(5-morpholino-1H-benzo[d]imidazol-2-yl)-1H-indazol-5-yl)cyclopropanecarboxamide

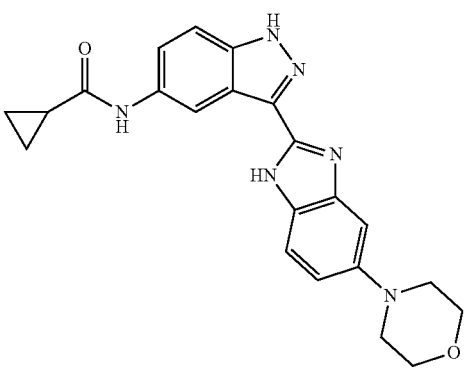 [SMILES: O=C(Nc1ccc2[nH]nc(-c3nc4cc(N5CCOCC5)ccc4[nH]3)c2c1)C1CC1]

TFA (0.238 mL, 3.08 mmol) was added to solution of N-(3-(5-morpholino-1H-benzo[d]imidazol-2-yl)-1-(tetrahydro-2H-pyran-2-yl)-1H-indazol-5-yl)cyclopropanecarboxamide (15 mg, 0.031 mmol) in CH₂Cl₂ (5 mL). The reaction mixture was stirred overnight at room temperature, and then the solvent was removed in vacuum. Purification by flash column chromatography (5% CH₃OH/CH₂Cl₂) afforded the title compound (10 mg) as a solid. ¹H NMR: (400 MHz, CD₃OD): δ 8.59 (d, 1H, J=1.2 Hz), 7.66 (m, 2H), 7.47 (dd, 1H, J=1.6 and 9.2 Hz), 7.31 (dd, 1H, J=2.0 and 9.2 Hz), 7.16 (s, 1H), 3.87 (m, 4H), 3.23 (m, 4H), 1.85 (m, 1H), 1.03 (m, 2H), 0.93 (m, 2H); ESI-MS [M+H]⁺: 403.19.

49. Preparation of 5-(2-methylmorpholino)-2-nitroaniline

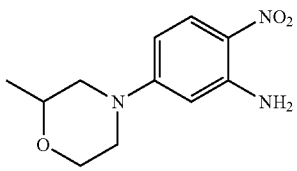 [SMILES: CC1CN(c2ccc([N+](=O)[O-])c(N)c2)CCO1]

5-Chloro-2-nitroaniline (200 mg, 1.159 mmol) was added to a solution of 2-methylmorpholine (176 mg, 1.738 mmol) in NMP (5 mL) in the presence of triethylamine (0.404 mL, 2.90 mmol). The reaction mixture was heated via microwave irradiation to 100° C. for 1 h. and upon cooling, the solvent was removed by vacuum. Purification by flash column chromatography (5% CH₃OH/CH₂Cl₂) afforded the title compound as a solid in a 70% yield. ¹H NMR: (400 MHz, DMSO-d₆): δ 7.79 (d, 1H, J=9.6 Hz), 7.25 (bs, 2H), 6.39 (dd, 1H, J=2.8 and 9.6 Hz), 6.20 (d, 1H, J=2.8 Hz), 3.88 (dd, 1H, J=2.8 and 12.0 Hz), 3.69 (d, 1H, J=12.8 Hz), 3.56 (m, 2H), 2.82 (m, 1H), 2.15 (t, 1H, J=7.6 Hz), 1.88 (m, 1H), 1.12 (d, 3H, J=6.0 Hz).

50. Preparation of 4-(2-methylmorpholino)benzene-1,2-diamine

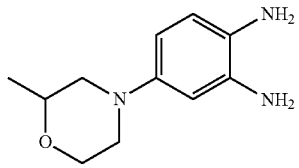

5-(2-Methylmorpholino)-2-nitroaniline (200 mg, 0.843 mmol) was added to the 10% Pd/C (25 mg) in ethanol (25 mL) and then hydrogen gas (60 psi) was applied for overnight at room temperature. The reaction mixture was filtered through Celite, and the solvent was removed in vacuo. Purification by flash chromatography (5% CH₃OH/CH₂Cl₂) afforded the title compound (150 mg). ¹H NMR: (400 MHz, DMSO-d₆): δ 6.38 (d, 1H, J=8.0 Hz), 6.18 (d, 1H, J=2.4 Hz), 5.99 (dd, 1H, J=2.8 and 8.0 Hz), 4.34 (bs, 2H), 3.96 (bs, 2H), 3.82 (m, 1H), 3.57 (m, 2H), 3.19 (d, 1H, J=11.2 Hz), 3.11 (d, 1H, J=11.2 Hz), 2.44 (m, 1H), 2.13 (t, 1H, J=11.2 Hz), 1.08 (d, 3H, J=6.4 Hz).

51. Preparation of 2-methyl-4-(2-(5-nitro-1-(tetrahydro-2H-pyran-2-yl)-1H-indazol-3-yl)-1H-benzo[d]imidazol-5-yl)morpholine

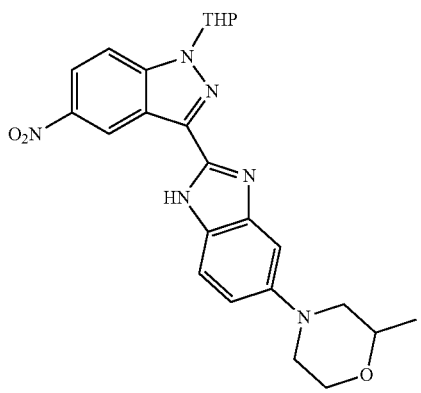

5-Nitro-1-(tetrahydro-2H-pyran-2-yl)-1H-indazole-3-carbaldehyde (150 mg, 0.545 mmol) and 4-(2-methylmorpholino)benzene-1,2-diamine (113 mg, 0.545 mmol) were dissolved in THF (10 mL) and 2N HCl (1 drop) was added. The solution was heated at a gentle reflux for 30 min. Then, 1N sodium bisulfite (104 mg, 1 mmol; 2 mL of a 1N solution) was added and heated at reflux (70° C.) overnight. The solution was cooled to room temperature, and diluted with ethyl acetate (40 mL). The mixture was washed with water and brine, dried over Na₂SO₄, and concentrated. Purification by flash chromatography (5% CH₃OH/CH₂Cl₂) afforded the title compound (140 mg). ¹H NMR: (400 MHz, CDCl₃): δ 9.56 (d, 1H, J=1.6 Hz), 8.28 (m, 1H), 7.74 (d, 1H, J=8.8 Hz), 7.64 (m, 1H), 7.36 (m, 1H), 7.03-6.96 (m, 1H), 5.75 (dd, 1H, J=2.8 and 6.4 Hz), 3.99 (m, 2H), 3.79 (m, 3H), 3.38 (m, 2H), 2.84 (m, 1H), 2.51 (m, 2H), 2.11 (m, 2H), 1.86 (m, 1H), 1.74 (m, 2H), 1.22 (d, 3H, J=6.4 Hz).

52. Preparation of 3-(5-(2-methylmorpholino)-1H-benzo[d]imidazol-2-yl)-1-(tetrahydro-2H-pyran-2-yl)-1H-indazol-5-amine

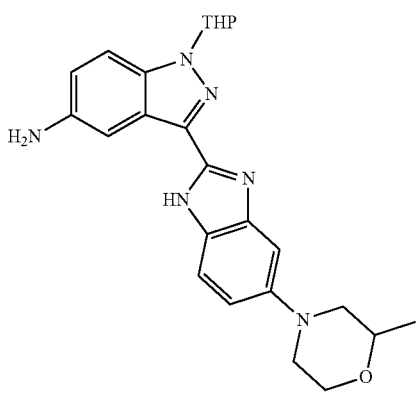

2-Methyl-4-(2-(5-nitro-1-(tetrahydro-2H-pyran-2-yl)-1H-indazol-3-yl)-1H-benzo[d]imida-zol-5-yl)morpholine (60 mg, 0.130 mmol) was added to 10% Pd/C (10 mg) in ethanol (25 mL) and then hydrogen gas (60 psi) was applied for 8 h at room temperature. The reaction mixture was filtered through Celite, and the solvent was removed in vacuo. Purification by flash chromatography (5% CH₃OH/CH₂Cl₂) afforded the title compound (40 mg). ¹H NMR: (400 MHz, CD₃OD): δ 7.66 (d, 1H, J=2.0 Hz), 7.52 (m, 2H), 7.13 (s, 1H), 7.04-7.00 (m, 2H), 5.79 (dd, 1H, J=2.4 and 9.2 Hz), 3.97 (m, 2H), 3.79 (m, 3H), 3.49 (m, 1H), 3.41 (m, 1H), 2.76 (m, 1H), 2.62 (m, 1H), 2.44 (m, 1H), 2.13 (m, 1H), 2.05 (m, 1H), 1.80 (m, 1H), 1.68 (m, 2H), 1.22 (d, 3H, J=6.4 Hz); ESI-MS [M+H]⁺: 433.2.

53. Preparation of 2,2-difluoro-N-(3-(5-(2-methylmorpholino)-1H-benzo[d]imidazol-2-yl)-1-(tetrahydro-2H-pyran-2-yl)-1H-indazol-5-yl)cyclopropanecarboxamide

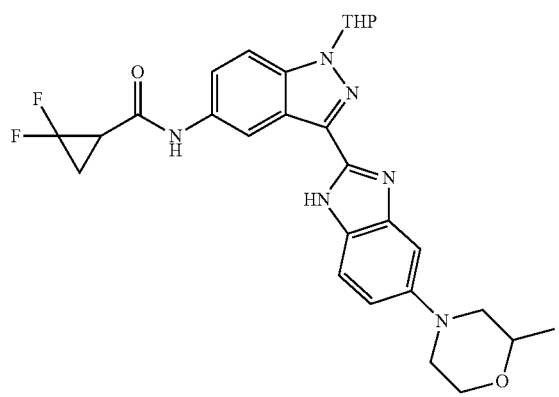

3-(5-(2-Methylmorpholino)-1H-benzo[d]imidazol-2-yl)-1-(tetrahydro-2H-pyran-2-yl)-1H-indazol-5-amine (20 mg, 0.046 mmol), 1H-benzo[d][1,2,3]triazol-1-ol (9.37 mg, 0.069 mmol), EDC (13.30 mg, 0.069 mmol) and sodium bicarbonate (3.88 mg, 0.046 mmol) was added to a solution of 2,2-difluorocyclopropanecarboxylic acid (5.64 mg, 0.046 mmol) in DMF (6 mL). The reaction mixture was stirred at room temperature for 24 h and then the solvent was removed in vacuo. Purification by flash chromatography (6% $CH_3OH$/$CH_2Cl_2$) afforded the title compound (16 mg) as a solid. $^1$H NMR: (400 MHz, $CD_3OD$): δ 8.51 (s, 1H), 7.75-7.65 (m, 2H), 7.56 (m, 1H), 7.04 (m, 2H), 5.84 (dd, 1H, J=2.4 and 9.6 Hz), 3.98 (m, 2H), 3.80 (m, 3H), 3.51 (m, 1H), 3.43 (m, 1H), 2.77 (m, 2H), 2.60 (m, 1H), 2.11 (m, 3H), 1.85 (m, 2H), 1.70 (m, 2H), 1.23 (d, 3H, J=6.0 Hz); ESI-MS [M+H]$^+$: 537.1.

54. Preparation of 2,2-difluoro-N-(3-(5-(2-methyl-morpholino)-1H-benzo[d]imidazol-2-yl)-1H-indazol-5-yl)cyclopropanecarboxamide

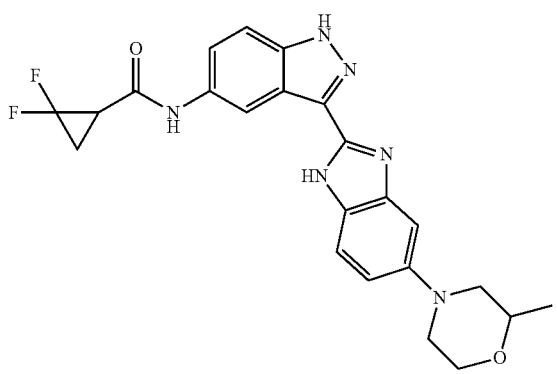 [SMILES: CC1CN(c2ccc3[nH]c(-c4n[nH]c5ccc(NC(=O)C6CC6(F)F)cc45)nc3c2)CCO1]

TFA (0.215 mL, 2.80 mmol) was added to solution of 2,2-difluoro-N-(3-(5-(2-methylmorpholino)-1H-benzo[d]imidazol-2-yl)-1-(tetrahydro-2H-pyran-2-yl)-1H-indazol-5-yl)cyclopropanecarboxamide (15 mg, 0.028 mmol) in $CH_2Cl_2$ (5 mL). The reaction mixture was stirred overnight at room temperature, and then the solvent was removed in vacuo. Purification by flash chromatography (5% $CH_3OH$/$CH_2Cl_2$) afforded the title compound (9 mg) as a solid. $^1$H NMR: (400 MHz, $CD_3OD$): δ 8.44 (d, 1H, J=0.8 Hz), 7.64 (dd, 1H, J=1.6 and 8.8 Hz), 7.58-7.54 (m, 2H), 7.17 (d, 1H, J=1.6 Hz), 7.04 (dd, 1H, J=2.0 and 8.8 Hz), 3.99 (m, 1H), 3.82 (m, 2H), 3.52 (m, 1H), 3.44 (m, 1H), 2.84-2.70 (m, 2H), 2.47 (m, 1H), 2.12 (m, 1H), 1.85 (m, 1H), 1.24 (d, 3H, J=6.0 Hz); ESI-MS [M+H]$^+$: 453.1.

55. Preparation of 5-(4-methylpiperidin-1-yl)-2-nitroaniline

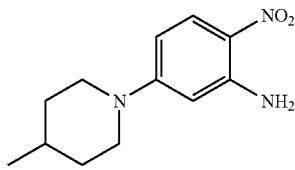 [SMILES: CC1CCN(c2ccc([N+](=O)[O-])c(N)c2)CC1]

4-Methylpiperidine (172 mg, 1.738 mmol) was added to a solution of 5-chloro-2-nitroaniline (200 mg, 1.159 mmol) in NMP (5 mL) in the presence of triethylamine (0.404 mL, 2.90 mmol). The reaction mixture was heated via microwave irradiation to 100° C. for 1 h, and. Upon cooling, the solvent was removed by vacuum. Purification by flash column chromatography (5% $CH_3OH$/$CH_2Cl_2$) afforded the title compound (300 mg) as a solid. $^1$H NMR: (400 MHz, $CDCl_3$): δ 7.98 (d, 1H, J=10.0 Hz), 6.26 (dd, 1H, J=2.8 and 10.0 Hz), 6.13 (bs, 2H), 5.92 (d, 1H, J=2.0 Hz), 3.85 (m, 2H), 2.89 (m, 2H), 1.72 (m, 2H), 1.62 (m, 1H), 1.23 (m, 2H), 0.96 (d, 3H, J=6.8 Hz).

56. Preparation of 4-(4-methylpiperidin-1-yl)benzene-1,2-diamine

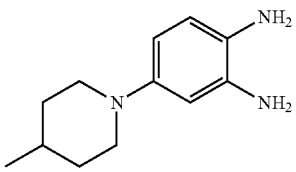

5-(4-Methylpiperidin-1-yl)-2-nitroaniline (200 mg, 0.850 mmol) was added to 10% Pd/C (10 mg) in ethanol (25 mL) and then hydrogen gas (60 psi) was applied for 24 h at room temperature. Upon TLC-based completion of the reaction, the reaction mixture was filtered through Celite, and the solvent was removed in vacuo. Purification by flash chromatography (5% $CH_3OH$/$CH_2Cl_2$) afforded the title compound (150 mg) as a brown solid. $^1$H NMR: (400 MHz, DMSO-$d_6$): δ 6.35 (d, 1H, J=8.4 Hz), 6.19 (d, 1H, J=2.4 Hz), 5.99 (m, 1H), 4.29 (bs, 2H), 3.92 (bs, 2H), 3.26 (m, 2H), 2.39 (m, 2H), 1.61 (m, 2H), 1.36 (m, 1H), 1.20 (m, 2H), 0.89 (d, 3H, J=6.8 Hz); ESI-MS [M+H]$^+$: 206.1.

57. Preparation of 3-(5-(4-methylpiperidin-1-yl)-1H-benzo[d]imidazol-2-yl)-1-(tetrahydro-2H-pyran-2-yl)-1H-indazol-5-amine

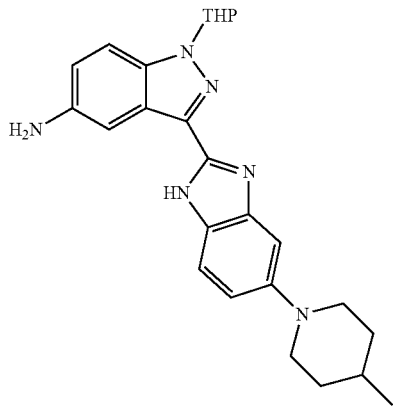

3-(5-(4-Methylpiperidin-1-yl)-1H-benzo[d]imidazol-2-yl)-5-nitro-1-(tetrahydro-2H-pyran-2-yl)-1H-indazole (100 mg, 0.217 mmol) was added to 10% Pd/C (2.302 mg, 0.022 mmol) in ethanol (25 mL) and then hydrogen gas (60 psi) was applied for 8 h at room temperature. The reaction mixture was filtered through Celite, and the solvent was removed in vacuo. Purification by flash chromatography (5% $CH_3OH$/$CH_2Cl_2$) afforded the title compound (75 mg) as a solid. $^1$H NMR: (400 MHz, $CD_3OD$): δ 7.66 (d, 1H, J=2.0 Hz), 7.51 (m, 2H), 7.17 (bs, 1H), 7.05-7.00 (m, 2H), 5.78 (dd, 1H, J=2.4 & 9.2 Hz), 3.98 (m, 1H), 3.78 (m, 1H), 3.56 (m, 2H), 2.67 (m, 3H), 2.14-2.03 (m, 2H), 1.76 (m, 3H), 1.65 (m, 2H), 1.40 (m, 3H), 0.98 (d, 3H, J=6.0 Hz); ESI-MS [M+H]$^+$: 431.3.

58. Preparation of 2,2-difluoro-N-(3-(5-(4-methylpiperidin-1-yl)-1H-benzo[d]imidazol-2-yl)-1-(tetrahydro-2H-pyran-2-yl)-1H-indazol-5-yl)cyclopropanecarboxamide

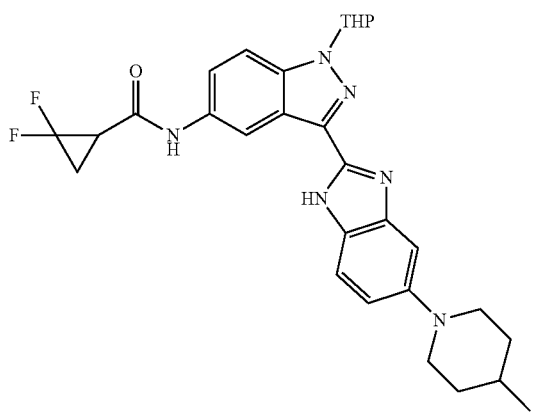

3-(5-(4-Methylpiperidin-1-yl)-1H-benzo[d]imidazol-2-yl)-1-(tetrahydro-2H-pyran-2-yl)-1H-indazol-5-amine (50 mg, 0.116 mmol), 1H-benzo[d][1,2,3]triazol-1-ol (HOBt) (23.54 mg, 0.174 mmol), EDC (33.4 mg, 0.174 mmol) and sodium bicarbonate (9.76 mg, 0.116 mmol) was added to a solution of 2,2-difluorocyclopropanecarboxylic acid (14.18 mg, 0.116 mmol) in DMF (6 mL). The reaction mixture was stirred at room temperature for 24 h, and the solvent was removed in vacuo. Purification by flash chromatography (6% $CH_3OH/CH_2Cl_2$) afforded the title compound (35 mg). $^1H$ NMR: (400 MHz, $CD_3OD$): δ 8.49 (s, 1H), 7.75 (m, 1H), 7.66 (d, 1H, J=8.8 Hz), 7.54 (bs, 1H), 7.06 (m, 2H), 5.84 (dd, 1H, J=2.8 and 9.2 Hz), 3.96 (m, 1H), 3.80 (m, 1H), 3.58 (m, 2H), 2.69 (m, 4H), 2.11 (m, 3H), 1.82 (m, 4H), 1.70 (m, 2H), 1.49 (m, 1H), 1.41 (m, 2H), 0.99 (d, 3H, J=6.0 Hz); ESI-MS $[M+H]^+$: 535.2.

59. Preparation of 2,2-difluoro-N-(3-(5-(4-methylpiperidin-1-yl)-1H-benzo[d]imidazol-2-yl)-1H-indazol-5-yl)cyclopropane-carboxamide

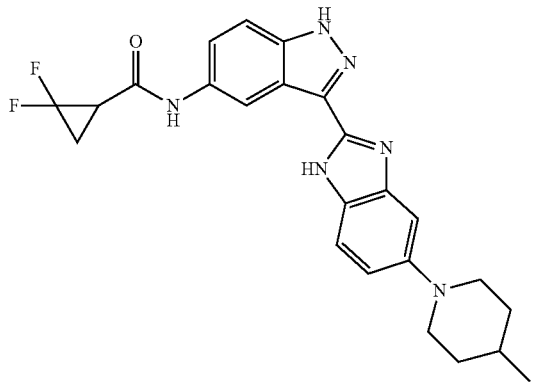 [SMILES: CC1CCN(c2ccc3[nH]c(-c4n[nH]c5ccc(NC(=O)C6CC6(F)F)cc45)nc3c2)CC1]

TFA (0.432 mL, 5.61 mmol) was added to solution of 2,2-difluoro-N-(3-(5-(4-methylpiperidin-1-yl)-1H-benzo[d]imidazol-2-yl)-1-(tetrahydro-2H-pyran-2-yl)-1H-indazol-5-yl)cyclopropanecarboxamide (30 mg, 0.056 mmol) in $CH_2Cl_2$ (5 mL). The reaction mixture was stirred overnight at room temperature, and then the solvent was removed in vacuo. Purification by flash chromatography (5% $CH_3OH/CH_2Cl_2$) afforded the title compound (20 mg) as an off-white solid. $^1H$ NMR: (400 MHz, $CD_3OD$): δ 8.48 (d, 1H, J=1.2 Hz), 7.43 (dd, 1H, J=1.2 and 8.8 Hz), 7.55 (m, 2H), 7.20 (d, 1H, J=2.0 Hz), 7.06 (dd, 1H, J=2.0 and 9.2 Hz), 3.59 (m, 2H), 2.73 (m, 3H), 2.13 (m, 1H), 1.89-1.77 (m, 3H), 1.53-1.37 (m, 3H), 1.00 (d, 3H, J=6.0 Hz); ESI-MS $[M+H]^+$: 451.2.

60. Preparation of 2,2-difluoro-N-(3-(6-morpholino-1H-benzo[d]imidazol-2-yl)-1H-indazol-4-yl)cyclopropanecarboxamide

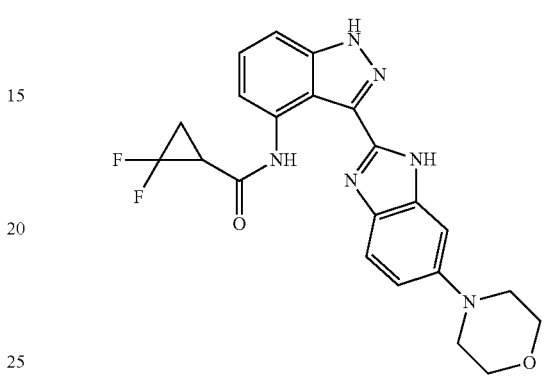

TFA (327 mg, 2.87 mmol) was added to solution of 2,2-difluoro-N-(3-(5-morpholino-1H-benzo[d]imidazol-2-yl)-1-(tetrahydro-2H-pyran-2-yl)-1H-indazol-4-yl)cyclopropane carboxamide (15 mg, 0.029 mmol) in $CH_2Cl_2$ (5 mL). The reaction mixture was stirred overnight at room temperature, and then the solvent was removed in vacuo. Purification by flash chromatography (5% $CH_3OH/CH_2Cl_2$) afforded the title compound (8 mg) as a solid. $^1H$ NMR: (400 MHz, $CD_3OD$): δ 8.18 (d, 1H, J=8.0 Hz), 7.49 (d, 1H, J=8.8 Hz), 7.35 (m, 1H), 7.25 (d, 1H, J=8.0 Hz), 7.18 (s, 1H), 7.09 (d, 1H, J=7.6 Hz), 3.89 (m, 4H), 3.22 (m, 4H), 3.08-3.01 (m, 1H), 2.21-2.15 (m, 1H), 1.96 (m, 1H); ESI-MS $[M+H]^+$: 439.1.

61. Preparation of 2,2-difluoro-N-(3-(6-morpholino-1H-benzo[d]imidazol-2-yl)-1H-indazol-6-yl)cyclopropanecarboxamide

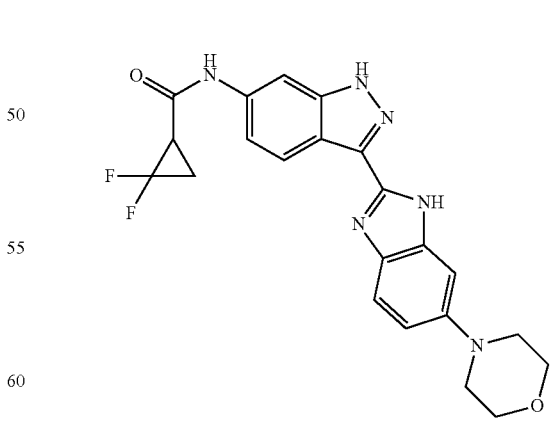

TFA (546 mg, 4.78 mmol) was added to solution of 2,2-difluoro-N-(3-(5-morpholino-1H-benzo[d]imidazol-2-yl)-1-(tetrahydro-2H-pyran-2-yl)-1H-indazol-6-yl)cyclopropanecarboxamide (25 mg, 0.048 mmol) in $CH_2Cl_2$ (5 mL). The reaction mixture was stirred overnight at room temperature, and then the solvent was removed in vacuo. Purification by flash chromatography (5% $CH_3OH/CH_2Cl_2$) afforded the title compound (11 mg) as a solid. $^1H$ NMR: (400 MHz, $CD_3OD$): δ 8.28 (d, 1H, J=1.2 Hz), 8.19 (d, 1H, J=8.8 Hz), 7.61 (d, 1H, J=9.2 Hz), 7.33 (dd, 1H, J=1.6 and 8.8 Hz), 7.25 (dd, 1H, J=2.0 and 8.8 Hz), 7.13 (s, 1H), 3.86 (m, 4H), 3.21 (m, 4H), 2.78-2.70 (m, 1H), 2.14 (m, 1H), 1.90-1.84 (m, 1H); ESI-MS $[M+H]^+$: 439.1.

62. Cell Culture

All cell lines were cultured in RPMI-1640 media supplemented with 10% fetal bovine serum ("FBS") and 1% penicillin/streptomycin (100 IU/ml pencillin and 100 μg/ml streptomycin) at 37° C. and 5% $CO_2$. The cell lines used in these studies included AN3-CA (ATCC# HTB-111), RL95-2 (ATCC# CRL-1671), and HEC-1-A (ATCC# HTB-112).

63. Western Blotting

Cells were washed with PBS and whole cell lysates were prepared by incubating cells in MP-40 Lysis buffer (Invitrogen Corporation, Carlsbad, Calif.) supplemented with Protease Inhibitor Cocktail (Roche Applied Science, a division of Roche Diagnostics Corporation, Indianapolis, Ind.) and Phosphatase Inhibitor Cocktail (Roche) on ice for 30 minutes. After centrifuging the lysates at 12,000 rpm for 10 minutes at 4° C., the supernatant was collected. Protein concentration was determined using BCA Assay. The same amounts of protein were run on NuPAGE 4-12% Bis-Tris Gel, and then transferred onto a PVDF membrane. After blocking with Odyssey Blocking Buffer for 1 hour at room temperature, the membrane was incubated with primary antibodies (Cell Signaling Technology, Inc., Danvers, Massachussetts) overnight at 4° C. followed by 40 minute incubation with IRDye secondary antibody. The membrane was scanned using Odyssey Infrared Imaging System. For In-Cell Western blotting, AN3-CA cells were treated with the drugs at a concentration of 1000, 300, 100, 30, 10 or 3 nM or with vehicle for 2 hours at 37° C. The cells were processed according to PhosphoPlus In-Cell Duet Protocol (Cell Signaling). The plate was scanned immediately using Odyssey Infrared Imaging System.

64. shRNA Knockdown Experiments

The lentiviral particles with PTEN shRNA or scrambled siRNA (ssi RNA) were purchased from Thermo Scientific. The cells were seeded in a 24-well plate and incubated overnight in RPMI full media. The media was removed and the cells were transfected with either siRNA or ssiRNA particles in serum/antibiotic free RPMI media. Six hours post-transduction, 1 ml of full media (serum plus penicillin/streptomycin) was added and the cells were incubated overnight. At 48 hours post-transduction fresh media with puromycin was added. The media was replaced with fresh puromycin containing media every 2 days. qPCR and western blot analysis was used to evaluate the level of PTEN knockdown.

65. PDK1 ATP Depletion Kinase Assay

The primary assay for compound inhibitory activity was the ATP depletion assay described herein. Test compounds were diluted to desired concentrations in kinase reaction buffer and briefly incubated with human recombinant PDK1 kinase which is histidine-tagged (Invitrogen Corporation, Carlsbad, Calif.). The reaction was subsequently initiated by the addition of ATP and PDKtide substrate (Millipore Corporation, Billerica, Massachussetts). PDKtide is a synthetic PDK peptide substrate with the sequence: KTFCG TPEYL APEVR REPRI LSEEE QEMFR DFDYI ADWC. Final concentrations for the assay were (10 μl total volume): 1% DMSO, 6.7 ng/ml PDK1, 4 μM ATP, and 70 μM PDKtide substrate. After an incubation of 60 minutes at room temperature, 10 μl of the Kinase-Glo reagent (Promega Corporation, Madison, Wis.) was added to each well and incubated for an additional 10 minutes. Luminescence was measured on an EnVision microplate reader (PerkinElmer). The amount of luminescence from each reaction is inversely correlated with PDK1 kinase activity. Percent inhibition and $IC_{50}$ values can be calculated by comparing enzyme activity in drug-treated wells to the appropriate controls, e.g. vehicle control.

66. PDK1 Binding Assay

Activity of compounds was routinely assessed using a secondary assay as described herein. The secondary assay was a time resolved-FRET LanthaScreen Kinase Binding Assay (Invitrogen Corporation, Carlsbad, Calif.). This assay evaluates the ability of the test compound to compete with a fluorescently-labeled tracer molecule to bind in the ATP pocket of a kinase. The assay signal is generated when a Europium-conjugated anti-His tag antibody (Invitrogen) bound to the His-tagged kinase produces a TR-FRET signal with the tracer molecule bound in the ATP pocket of the kinase. In this reaction, 5 μl of test compound was incubated with 5 μl of a kinase/antibody mixture, followed by the addition of 5 μl of Kinase Tracer 236 (Invitrogen). Final concentrations for the assay were (15 μl total volume): 1% DMSO, 5 nM PDK1, 2 nM Eu-Anti-His Antibody, and 6 nM Kinase Tracer 236. After 60 minutes of incubation at room temperature, the TR-FRET signal was measured on an EnVision microplate reader.

67. PDK1 Fluorometric Activity Assay

PDK1 biochemical activity was measured by a fluorometric assay performed by Life Technologies (Grand Island, N.Y.). The assay conditions for PDK1 are as follows. The 2×PDK1/Ser/Thr-07 mixture is prepared in 50 mM Tris pH 8.5, 0.01% BRIJ-35, 10 mM MgCl2, 1 mM EGTA, 0.02% NaN3. The final 10 μL Kinase Reaction consists of 7.36-38.7 ng PDK1 and 2 μM Ser/Thr 07. After the 1 hour kinase reaction incubation, 5 μL of a 1:32768 dilution of Development Reagent A is added.

68. Cell Viability Assay

AN3-CA (PTEN-deficient), RL95-2 (PTEN-deficient), and HEC-1A (PTEN-wild type) cells were plated in 45 μl of RPMI-1640 media supplemented with 10% FBS and 1% Pen/Strep at a density of 1000 cells per well in white 384-well plates. Cells were allowed to attach by incubation overnight at 37° C. and 5% $CO_2$. Test compounds were diluted to 10× concentrations in RPMI-1640 media (containing 3% DMSO) and 5 μl 1 of these dilutions were added in triplicate to the appropriate wells containing the cells. The plates containing the drug-treated cells and appropriate controls were incubated for 96 hours. At the end of the incubation, 40 μl of ATP-lite (PerkinElmer, Inc., Waltham, Massachussetts) reagent were added to each well and luminescence signal was measured on an EnVision microplate reader.

Alternatively, AN3-CA, RL95-2, HEC-1A endometrial cancer cell lines were plated at a density of 2000 cells per well in a 96 well culture plate in 45 μl of cell culture media and incubated overnight. The following day, test compounds were added to the cells in 5 μl of serum-free media to generate final concentrations of 10, 3, 1, 0.3, 0.1, 0.03, 0.01, or 0.003 μM.

Vehicle treated controls were also included and each condition was applied in quadruplicate. Following 96 hours of incubation, 35 μL of ATP-lite (PerkinElmer) reagent was added each well and allowed to react for 10 minutes. Plate was read on a Envision 2104 MultiLabel reader (PerkinElmer).

69. AKT (T308) Phosphorylation Assay

AN3-CA cells were plated in 900 μl of RPMI-1640 media supplemented with 10% FBS and 1% Pen/Strep at a density of $8 \times 10^5$ cells per well in 6-well plates. Cells were allowed to attach by incubation overnight at 37° C. and 5% $CO_2$. Test compounds were diluted to 10× concentrations in RPMI-1640 media (containing 3% DMSO) and 100 μl of these dilutions were added to the appropriate wells containing the cells. The plates containing the drug-treated cells and appropriate controls were incubated for 24 hours. At the end of incubation, phosphorylated AKT was evaluated in treated and control samples using a Meso Scale Discovery (Gaithersburg, Md.) assay kit (human Phospho-Akt (Thr308) kit) and by following the manufacturer's instructions included with the kit. Total AKT (phosphorylated and unphosphorylated) was also evaluated in the samples using a separate kit (Meso Scale Discovery). The percentage of AKT phosphorylated at the Thr308 position (also indicated as T308 herein) was determined by normalizing the phospho-AKT signal to the total AKT signal and then showing the percent phosphorylation in the treated samples relative to the controls.

70. $IC_{50}$ Calculation $IC_{50}$ values are determined using GraphPad Prism 5 software. The data were entered as an X-Y plot into the software as percent inhibition for each concentration of the drug. The concentration values of the drug were log transformed and the nonlinear regression was carried out using the "sigmoidal dose-response (variable slope)" option within the GraphPad software to model the data and calculate $IC_{50}$ values. The $IC_{50}$ values reported are the concentration of drug at which 50% inhibition was reached.

Figure 5:
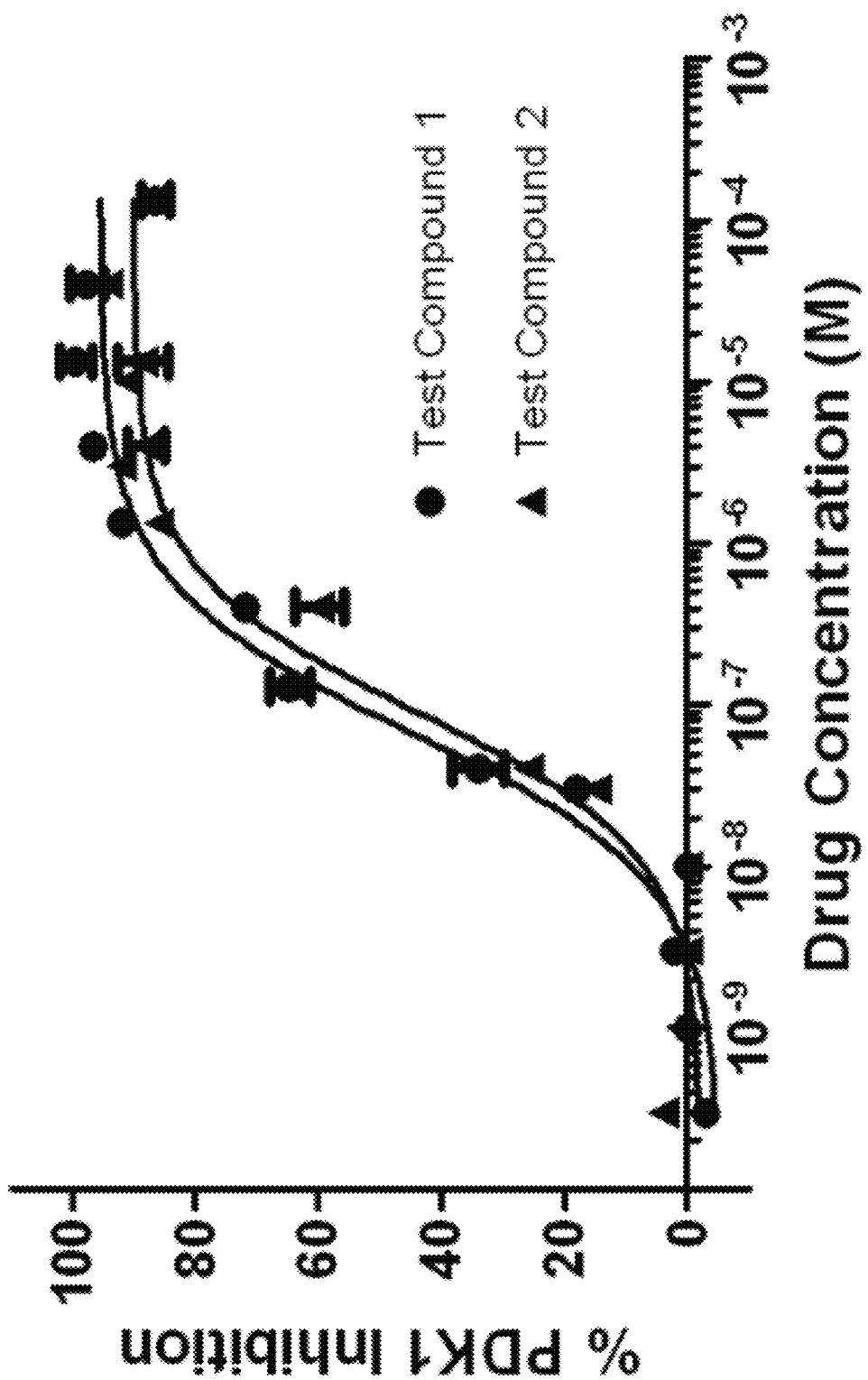
FIG. 5 shows representative data of inhibition activity in a PDK1 kinase binding assay by two representative disclosed compounds, Test Compound 1 (2,2-difluoro-N-(3-(5-morpholino-1H-benzo[d]imidazol-2-yl)-1H-indazol-5-yl)cyclopropanecarboxamide) and Test Compound 2 (2,2-difluoro-N-(3-(5-(2-methylmorpholino)-1H-benzo[d]imidazol-2-yl)-1H-indazol-5-yl)cyclopropanecarboxamide).

71. Inhibition of Kinase Activity: Determination of $IC_{50}$ for Representative Compounds Typical examples of $IC_{50}$ determinations in the PDK1 time resolved-FRET LanthaScreen Kinase Binding Assay are shown in FIG. 5. The compounds tested were: 2,2-difluoro-N-(3-(5-morpholino-1H-benzo[d]imidazol-2-yl)-1H-indazol-5-yl)cyclopropanecarboxamide and 2,2-difluoro-N-(3-(5-(2-methylmorpholino)-1H-benzo[d]imidazol-2-yl)-1H-indazol-5-yl)cyclopropanecarboxamide (labeled as "Test Compound 1" and "Test Compound 2", respectively, in the figure). In the data shown, the compounds were tested in triplicate as described above. $IC_{50}$ values generated from this assay were 80 nM and 94 nM for Test Compound 1 and 2, respectively. Similar activities from these compounds were observed in luminescence-based activity assays.

72. Compound Activity in Cell Viability Assay

The ability of compounds to inhibit the viability of cultured cells was determined using the cell viability assay described above. Activity data for representative compounds is shown below in Table V for the compounds tested using the indicated cell lines (AN3-CA, RL95-2, and HEC-1A). The cell lines have different mutational backgrounds: AN3-CA (PTEN and PIK3R1 mutations), RL-95-2 (PTEN mutation), and HEC-1A (no mutation in neither). $IC_{50}$ values were determined as described above.

Figure 6:
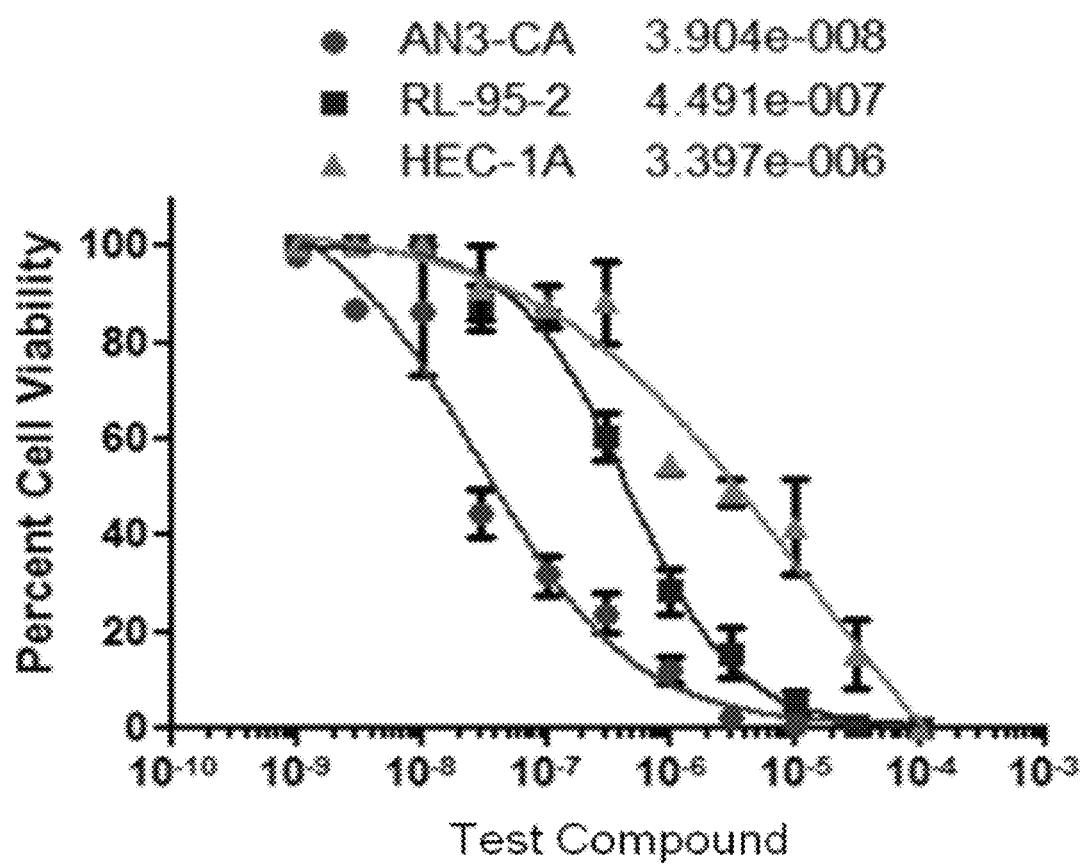
FIG. 6 shows representative data for inhibition of cell viability in selected cell-lines using a representative disclosed compound, 2,2-difluoro-N-(3-(5-morpholino-1H-benzo[d]imidazol-2-yl)-1H-indazol-5-yl)cyclopropanecarboxamide.

A typical example of $IC_{50}$ determination in the cell viability assay is shown in FIG. 6 for a representative test compound, 2,2-difluoro-N-(3-(5-morpholino-1H-benzo[d]imidazol-2-yl)-1H-indazol-5-yl)cyclopropanecarboxamide. The data in FIG. 6 show that the Test Compound demonstrated preferential activity in cells with PTEN loss-of-function mutations and particularly in cells that also have activating mutations in PI3K. That is, the Test Compound was most potent against AN3-CA (PTEN and PIK3R1 mutations), moderately potent against RL-95-2 (PTEN mutation), and relatively inactive against HEC-1A (no mutation in either PTEN or PIK3R1 gene). Without wishing to be bound by a particular theory, it is believed therapeutic effect of PDK1 inhibition is enhanced in cells with additional defects in the PI3K/Akt pathway, including mutations resulting in PTEN loss of function and/or PI3K activating mutations.

TABLE V

| No. | Structure | Cell Viability * $IC_{50}$ (μM) | | |
|---|---|---|---|---|
| | | AN3-CA | RL95-2 | HEC-1A |
| 1 | 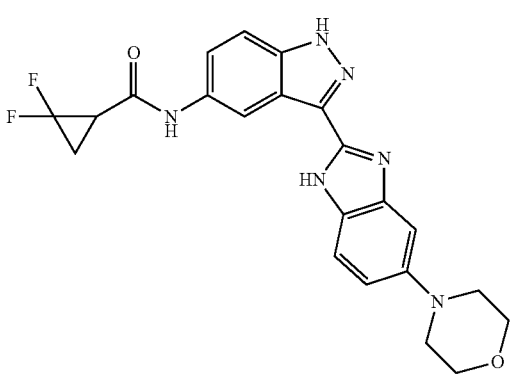 [SMILES: O=C(Nc1ccc2[nH]nc(-c3nc4cc(N5CCOCC5)ccc4[nH]3)c2c1)C1CC1(F)F] | 0.027 | 0.479 | 3.78 |

TABLE V-continued
| No. | Structure | Cell Viability * IC$_{50}$ (μM) | | |
| --- | --- | --- | --- | --- |
| | | AN3-CA | RL95-2 | HEC-1A |
| 2 | 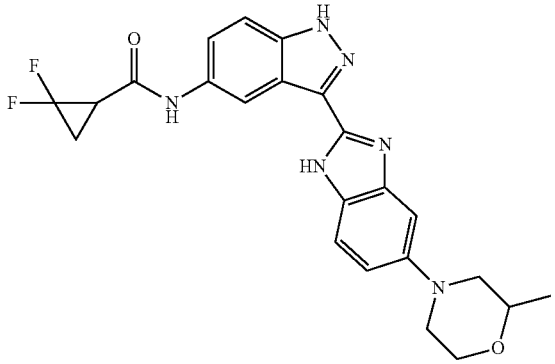 [SMILES: CC1CN(c2ccc3[nH]c(-c4n[nH]c5ccc(NC(=O)C6CC6(F)F)cc45)nc3c2)CCO1] | <0.03 | 0.760 | 5.09 |
| 3 | 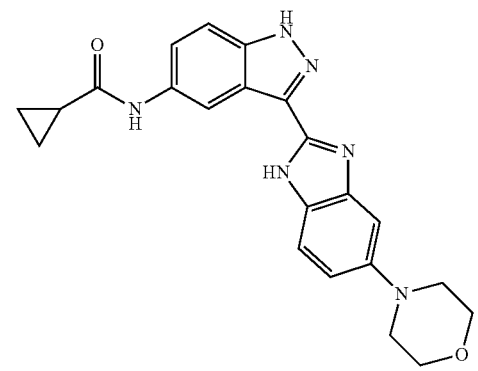 [SMILES: O=C(Nc1ccc2[nH]nc(-c3nc4cc(N5CCOCC5)ccc4[nH]3)c2c1)C1CC1] | Not Tested | Not Tested | Not Tested |
| 4 | 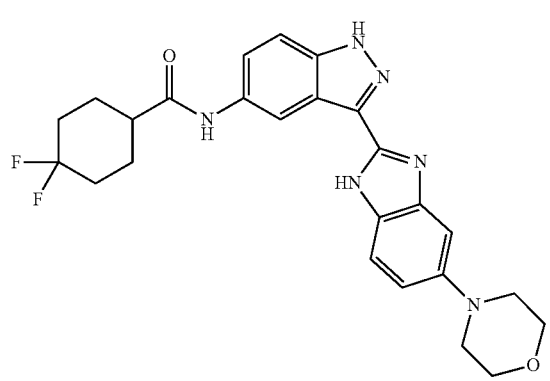 [SMILES: O=C(Nc1ccc2[nH]nc(-c3nc4cc(N5CCOCC5)ccc4[nH]3)c2c1)C1CCC(F)(F)CC1] | Not Tested | Not Tested | Not Tested |
| 5 | 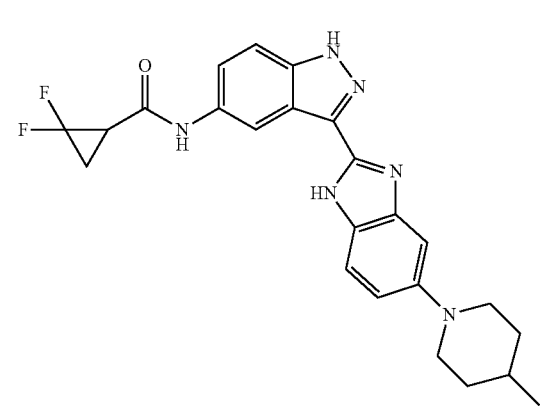 [SMILES: CC1CCN(c2ccc3[nH]c(-c4n[nH]c5ccc(NC(=O)C6CC6(F)F)cc45)nc3c2)CC1] | Not Tested | Not Tested | Not Tested |

TABLE V-continued

| No. | Structure | Cell Viability * IC₅₀ (µM) | | |
|---|---|---|---|---|
| | | AN3-CA | RL95-2 | HEC-1A |
| 6 | 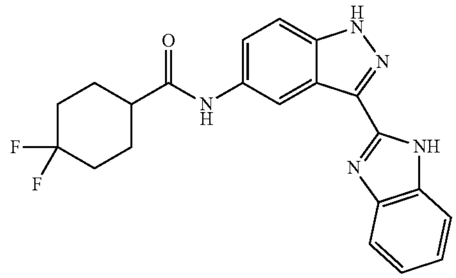 [SMILES: O=C(Nc1ccc2[nH]nc(-c3nc4ccccc4[nH]3)c2c1)C1CCC(F)(F)CC1] | 2.07 | 2.30 | 9.65 |
| 7 | 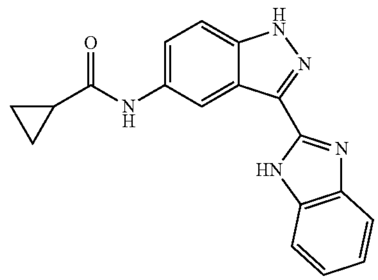 [SMILES: O=C(Nc1ccc2[nH]nc(-c3nc4ccccc4[nH]3)c2c1)C1CC1] | Not Tested | Not Tested | Not Tested |
| 8 | 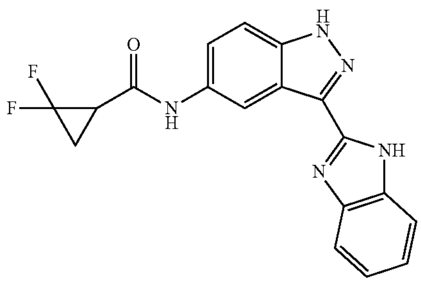 [SMILES: O=C(Nc1ccc2[nH]nc(-c3nc4ccccc4[nH]3)c2c1)C1CC1(F)F] | 0.330 | 6.97 | 14.8 |
| 9 | 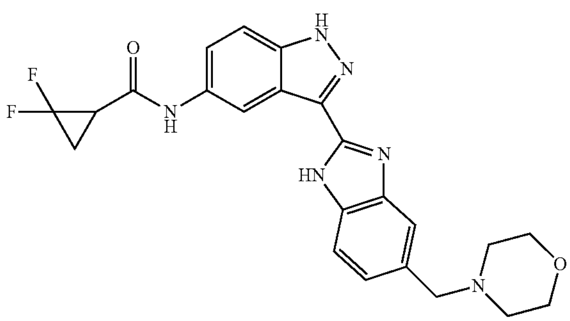 [SMILES: O=C(Nc1ccc2[nH]nc(-c3nc4cc(CN5CCOCC5)ccc4[nH]3)c2c1)C1CC1(F)F] | 0.443 | 3.22 | 18.4 |
| 10 | 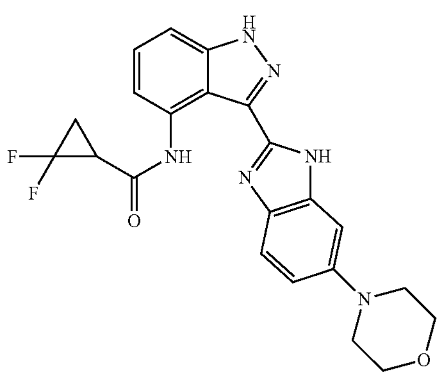 [SMILES: O=C(Nc1cccc2[nH]nc(-c3nc4ccc(N5CCOCC5)cc4[nH]3)c12)C1CC1(F)F] | Not Tested | Not Tested | Not Tested |

TABLE V-continued

| | | Cell Viability * IC$_{50}$ (μM) | | |
|---|---|---|---|---|
| No. | Structure | AN3-CA | RL95-2 | HEC-1A |
| 11 | | 12.1 | 11.5 | 29.5 |
| 12 | | 18.0 | 17.0 | 12.7 |
| 13 | | 23.8 | 15.3 | 50.7 |
| 14 | | 10.1 | 35.1 | 20.1 |
| 15 | | Not Tested | Not Tested | Not Tested |

TABLE V-continued

| No. | Structure | Cell Viability * IC$_{50}$ (μM) | | |
| --- | --- | --- | --- | --- |
| | | AN3-CA | RL95-2 | HEC-1A |
| 16 | 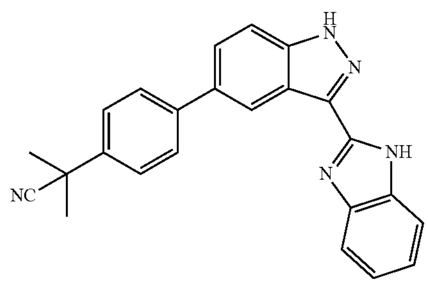 [SMILES: CC(C)(C#N)c1ccc(-c2ccc3[nH]nc(-c4nc5ccccc5[nH]4)c3c2)cc1] | 79.3 | 15.1 | 28.7 |
| 17 | 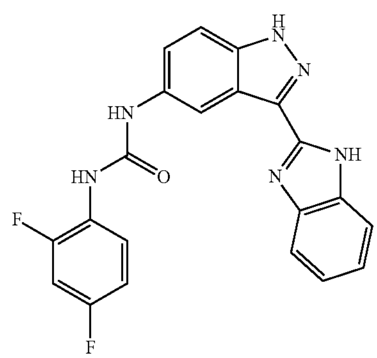 [SMILES: O=C(Nc1ccc2[nH]nc(-c3nc4ccccc4[nH]3)c2c1)Nc1ccc(F)cc1F] | Not Tested | Not Tested | Not Tested |
| 18 | 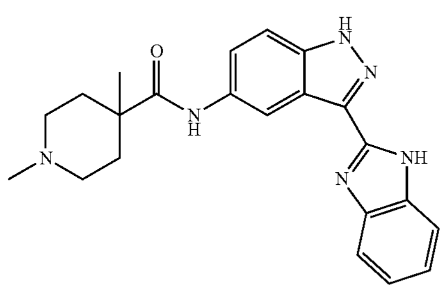 [SMILES: CN1CCC(C)(C(=O)Nc2ccc3[nH]nc(-c4nc5ccccc5[nH]4)c3c2)CC1] | 15.4 | 6.24 | 56.3 |
| 19 | 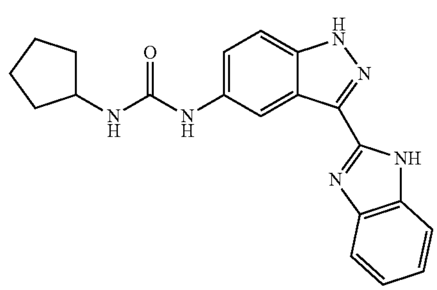 [SMILES: O=C(Nc1ccc2[nH]nc(-c3nc4ccccc4[nH]3)c2c1)NC1CCCC1] | Not Tested | Not Tested | Not Tested |
| 20 | 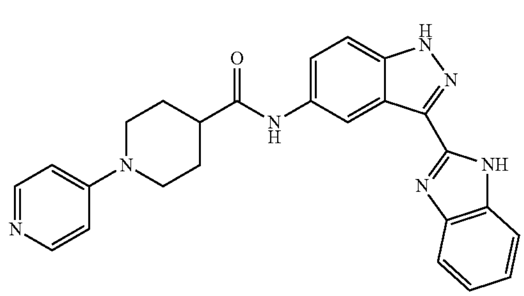 [SMILES: O=C(Nc1ccc2[nH]nc(-c3nc4ccccc4[nH]3)c2c1)C1CCN(c2ccncc2)CC1] | Not Tested | Not Tested | Not Tested |

TABLE V-continued

| No. | Structure | Cell Viability * IC$_{50}$ (µM) | | |
| --- | --- | --- | --- | --- |
| | | AN3-CA | RL95-2 | HEC-1A |
| 21 | [structure] | Not Tested | Not Tested | Not Tested |

73. Effect of Mutational Context on Sensitivity to Inhibition by 2,2-difluoro-N-(3-(5-morpholino-1H-benzo[d]imidazol-2-yl)-1H-indazol-5-yl)cyclopropanecarboxamide PDK1 inhibition has been proposed and demonstrated in several model systems to be synthetically lethal with PTEN loss-of-function mutations. With this in mind, the activity of a representative test compound, 2,2-difluoro-N-(3-(5-morpholino-1H-benzo[d]imidazol-2-yl)-1H-indazol-5-yl)cyclopropanecarboxamide, was determined in a small panel of cancer cell lines that harbored PTEN mutations and/or PI3K activating mutations using the cell viability assay described above. The data are shown below in Table VI. The data show that two of the most sensitive cell lines to treatment with this compound where the endometrial cancer lines AN3-CA and RL95-2, which both have PTEN loss-of-function mutations (Table VI).

Further analysis of these data in view of additional mutations contained in the cell lines in the panel suggested that the two most sensitive lines not only had mutations in PTEN (a negative regulator of the PI3K/AKT pathway), but they each had activating mutations in the pathway as well. For example, AN3-CA cells have an additional mutation in PIK3R1, a regulatory subunit of PI3K and RL95-2 cells have a mutation in HRAS, which signals downstream to the PI3K/AKT pathway. Although not wishing to be bound to any particular theory, it is believed that this that sensitivity to this test compound required PTEN loss-of-function and further activation of the PI3K/AKT pathway through direct mutation or due to mutation in an ancillary pathway that leads to AKT activation. Furthermore, without wishing to be bound by a particular theory, the disclosed compounds can have preferential activity in cancer cells that have PTEN mutations, and can have even greater activity in target cells with both a PTEN mutation and a PI3K.

In order to determine if there were additional cell lines that were profoundly sensitive to this compound, a further 82 cell lines were screened which represented more than 20 different tumor types of origin. The IC$_{50}$ for the test compound was determined using an 8-point concentration serial dilution ranging from 10 µM down to 3 nM. Data this screen showed that 68 of the cell lines had an IC$_{50}$ greater than 1 µM, 9 cell lines had an IC$_{50}$ in the hundreds of nano-molar range, and 5 cell lines had an IC$_{50}$ less than 100 nM. In addition to the original AN3-CA and RL95-2 cell lines, the KG-1, MV4-11 and Kasumi cell lines were all found to be very sensitive to the test compound. Without wishing to bound by a particular theory, these three additional cell lines are all acute myeloid leukemic lines that have different activating mutations in oncogenes that have been associated with elevated PI3K activity. MV4-11 has the FLT3 internal tandem duplication (ITD) and Kasumi-1 has amplified and mutated c-kit as well as the AML-ETO gene fusion. KG-1 is an AML line that harbors del(5q) and shows constitutive PI3K/AKT activity and sensitivity to m-TOR inhibitors. All three lines have wild-type PTEN but have shown to express very low levels of PTEN protein, which makes them functionally deficient for PTEN.

TABLE VI

| Cell Line | Mutation | IC$_{50}$ (µM) |
| --- | --- | --- |
| AN3-CA | PTEN, PIK3R1 | 0.048 |
| RL95-2 | PTEN, HRAS | 0.654 |
| SK-OV-3 | PIK3CA | 1.89 |
| NCCIT | PTEN | 2.11 |
| HCT-116 | KRAS, PIK3CA | 2.52 |
| AGS | KRAS, PIK3CA | 2.77 |
| BT549 | PTEN | 3.16 |
| RKO | PIK3CA | 3.24 |
| Hec-1A | KRAS, PIK3CA | 3.76 |
| 786-O | PTEN | 6.01 |
| HCT-15 | KRAS, PIK3CA | 6.99 |
| U87-MG | PTEN | 7.22 |
| PC-3 | PTEN | 7.56 |
| MCF-7 | PIK3CA | 8.79 |
| H1975 | PIK3CA | 9.86 |
| HT-29 | PIK3CA, BRAF | 10.6 |
| T47D | PIK3CA | 12.8 |
| BT-20 | PIK3CA | 13.1 |
| LNCap | PTEN | 24.8 |

In separate experiments carried out in the endometrial cancer cell lines, AN3-CA, RL-95-A, and HEC-1A, the IC$_{50}$ values were determined for two test compounds (data in Table VII below). It should be noted that in Table VII, Test Compound 1 is 2,2-difluoro-N-(3-(5-morpholino-1H-benzo[d] imidazol-2-yl)-1H-indazol-5-yl)cyclopropanecarboxamide; and Test Compound 2 is 2,2-difluoro-N-(3-(5-(2-methylmorpholino)-1H-benzo[d]imidazol-2-yl)-1H-indazol-5-yl)cyclopropanecarboxamide. As discussed above, these cell-lines have a particular mutational profile for the PI3K/AKT pathway. In addition, HEC-1A cells have a mutation in PIK3CA (catalytic subunit of PI3K). Test Compound 1 showed potent activity against AN3-CA cells with an IC$_{50}$ of 27 nM, moderate activity against RL-95-A (479 nM) and very little activity against the HEC-1A cell line (3.78 µM). Similar results were obtained with Test Compound 2 in these assays as shown in Table VII.

TABLE VII

| Compound | Cell Line (IC$_{50}$, µM) | | |
|---|---|---|---|
| | AN3-CA | RL95-2 | HEC-1A |
| Test Compound 1 | 0.027 | 0.479 | 3.78 |
| Test Compound 2 | 0.023 | 0.760 | — |

74. Knockdown of PTEN Expression with shRNA

Figure 9:
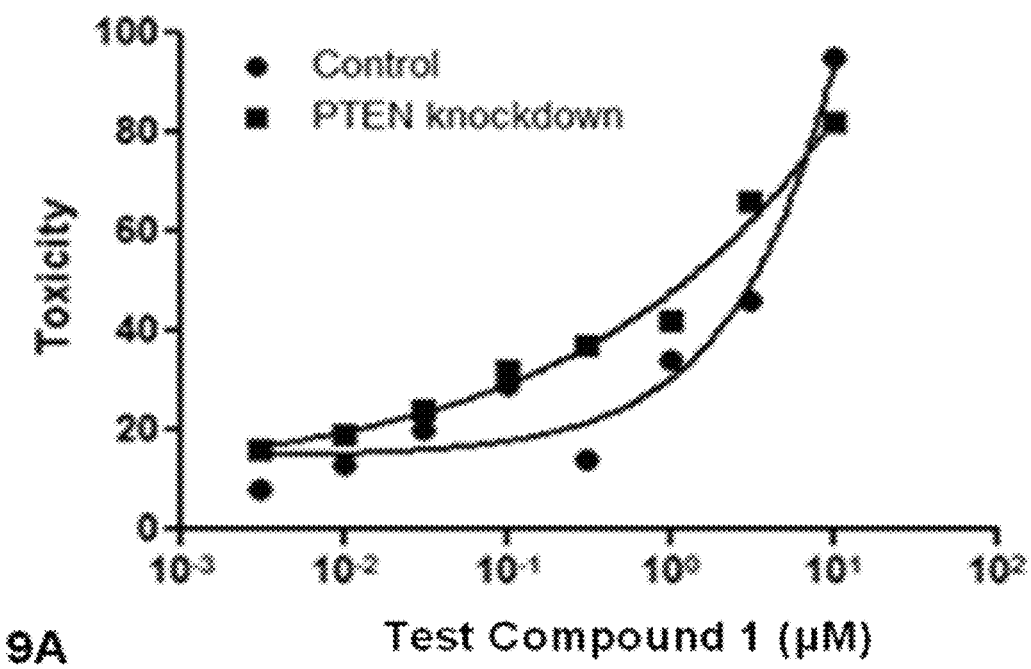
FIG. 9 shows representative toxicity data in AN3CA cells transfected with PTEN siRNA or ssiRNA control for two representative disclosed compounds: (Panel A): Test Compound 1 (2,2-difluoro-N-(3-(5-morpholino-1H-benzo[d]imidazol-2-yl)-1H-indazol-5-yl)cyclopropanecarboxamide); and (Panel B) Test Compound 2 (2,2-difluoro-N-(3-(5-(2-methylmorpholino)-1H-benzo[d]imidazol-2-yl)-1H-indazol-5-yl)cyclopropanecarboxamide).
Figure 9:
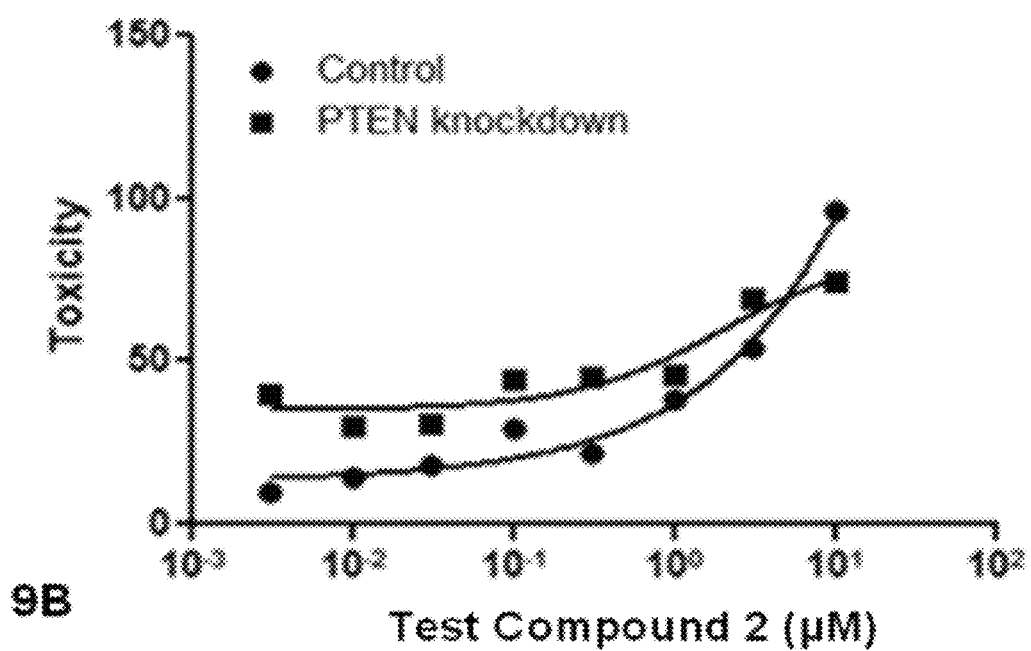

To examine the role of PTEN loss of function and PI3K activation in mediating sensitivity to the disclosed compounds, shRNA was used to decrease the expression of PTEN in the HS578T cell line which has mutated PIK3R1 and wild type PTEN. Data are shown in FIG. 9A for Test Compound 1 (2,2-difluoro-N-(3-(5-morpholino-1H-benzo[d]imidazol-2-yl)-1H-indazol-5-yl)cyclopropanecarboxamide) and FIG. 9B for Test Compound 2 (2,2-difluoro-N-(3-(5-(2-methylmorpholino)-1H-benzo[d]imidazol-2-yl)-1H-indazol-5-yl)cyclopropanecarboxamide). In the figures, cell viability is shown as "Toxicity" and the cell viability assay was carried out as described above. The data show that cells in which expression of PTEN had decreased by shRNA treatment were more sensitize to exposure to the test compounds. For example, Test Compound 1 had an IC$_{50}$ for cell viability that 3.1 µM in control treated cells, but an IC$_{50}$ 1.2 µM in cells treated with the PTEN knockdown shRNA. Similarly, Test Compound 2 had an IC$_{50}$ of 2.2 µM in control cells, but only 0.80 µM in cells with the PTEN knockdown.

Figure 7:
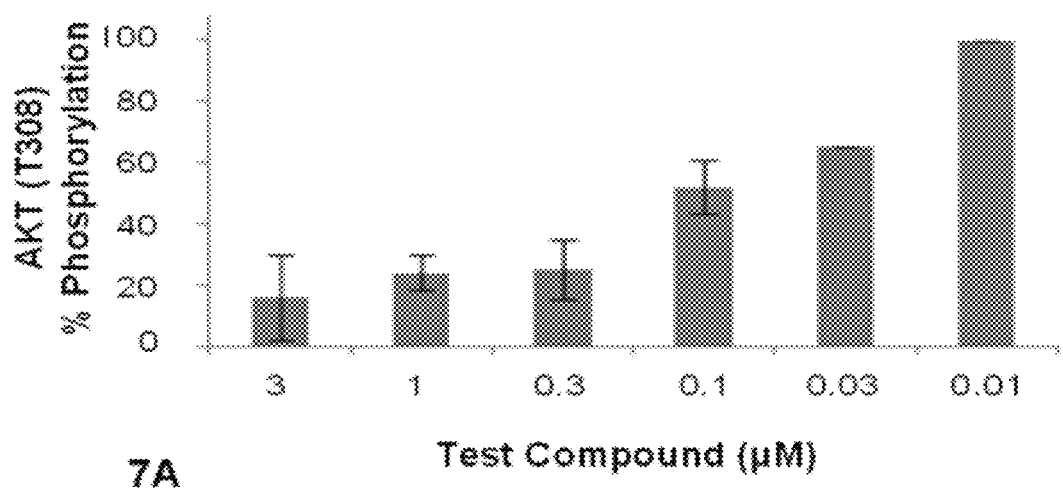
FIG. 7 shows representative data for inhibition of AKT phosphorylation (Thr308) by a representative disclosed compound, 2,2-difluoro-N-(3-(5-morpholino-1H-benzo[d]imidazol-2-yl)-1H-indazol-5-yl)cyclopropanecarboxamide. Panels A and B show data from two separate experiments.
Figure 7:
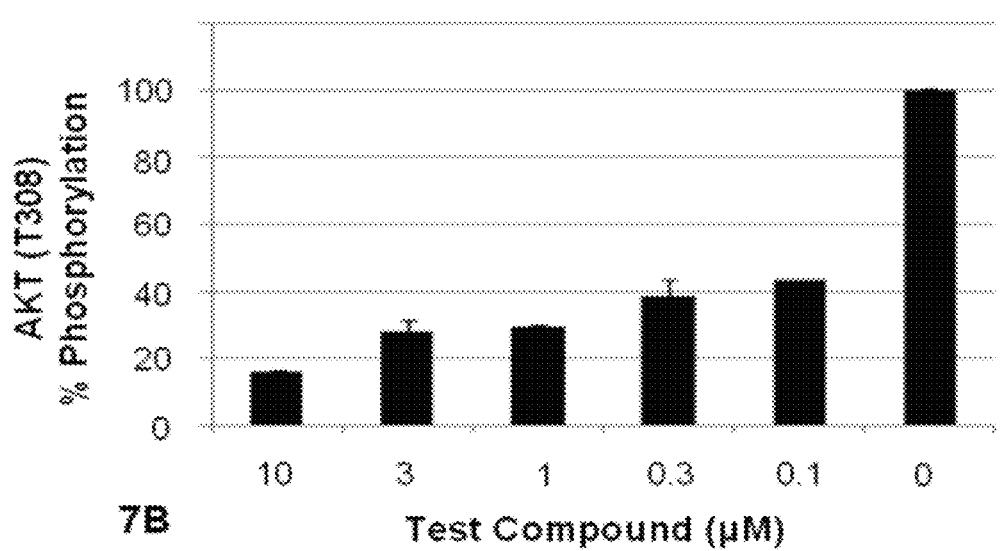

75. Inhibition of AKT (T308) Phosphorylation Assay by 2,2-difluoro-N-(3-(5-morpholino-1H-benzo[d]imidazol-2-yl)-1H-indazol-5-yl)cyclopropanecarboxamide To further explore the activity of a representative compound, 2,2-difluoro-N-(3-(5-morpholino-1H-benzo[d]imidazol-2-yl)-1H-indazol-5-yl)cyclopropanecarboxamide, in inhibiting PDK1 in a cell line system, the effect of this test compound on AKT phosphorylation (at the Thr308 position) was determined. Briefly, AN3-CA cells were treated with the compound for 24 hours and lysates from these treatments were analyzed for phospho-AKT (Thr308) using the Meso Scale Discovery technology platform as described above. Data from one experiment are shown in FIG. 7A. Data from a separate experiment are shown in FIG. 7B.

Drug concentrations of the test compound as low as 100 nM exhibited efficacy at knocking down pAKT levels to below 50% of control, correlating strongly with the low nM activity in the cell viability assays. For example, it can be seen that the test compound effectively knocked down phospho-AKT levels in a dose-dependent manner with an IC$_{50}$ of 51 nM in FIG. 7A. This value is very similar to the IC$_{50}$ value generated in the cell viability assay (48 nM).

Furthermore, test compound and a second compound, 2,2-difluoro-N-(3-(5-(2-methylmorpholino)-1H-benzo[d]imidazol-2-yl)-1H-indazol-5-yl)cyclopropanecarboxamide, were evaluated using an in-cell western approach to assess the phosphorylation levels of the ribosomal protein s6, which is downstream of mTOR, in AN3-CA cells (data not shown). Briefly, ribosomal protein S6 was detected using differentially labeled antibodies specific for either total S6 protein or the phosphorylated form of the protein. In-cell detection with visual overlay of the signals for each antibody, e.g. total ribosomal protein s6 (red) and phospho-ribosomal protein s6 (green), allowed simultaneous detection and quantitation. Quantitation of signal intensity allowed determination of IC$_{50}$ values for the test compounds. The data showed that both compounds efficiently lowered phosphorylation of the ribosomal protein s6 with IC$_{50}$ values of 75.6 nM and 76.7 nM, respectively.

While not wishing to be bound by a particular theory, it is believed that the mechanism responsible for decreasing cell viability in AN3-CA cells involves decreasing phospho-AKT through PDK1 inhibition.

Figure 8:
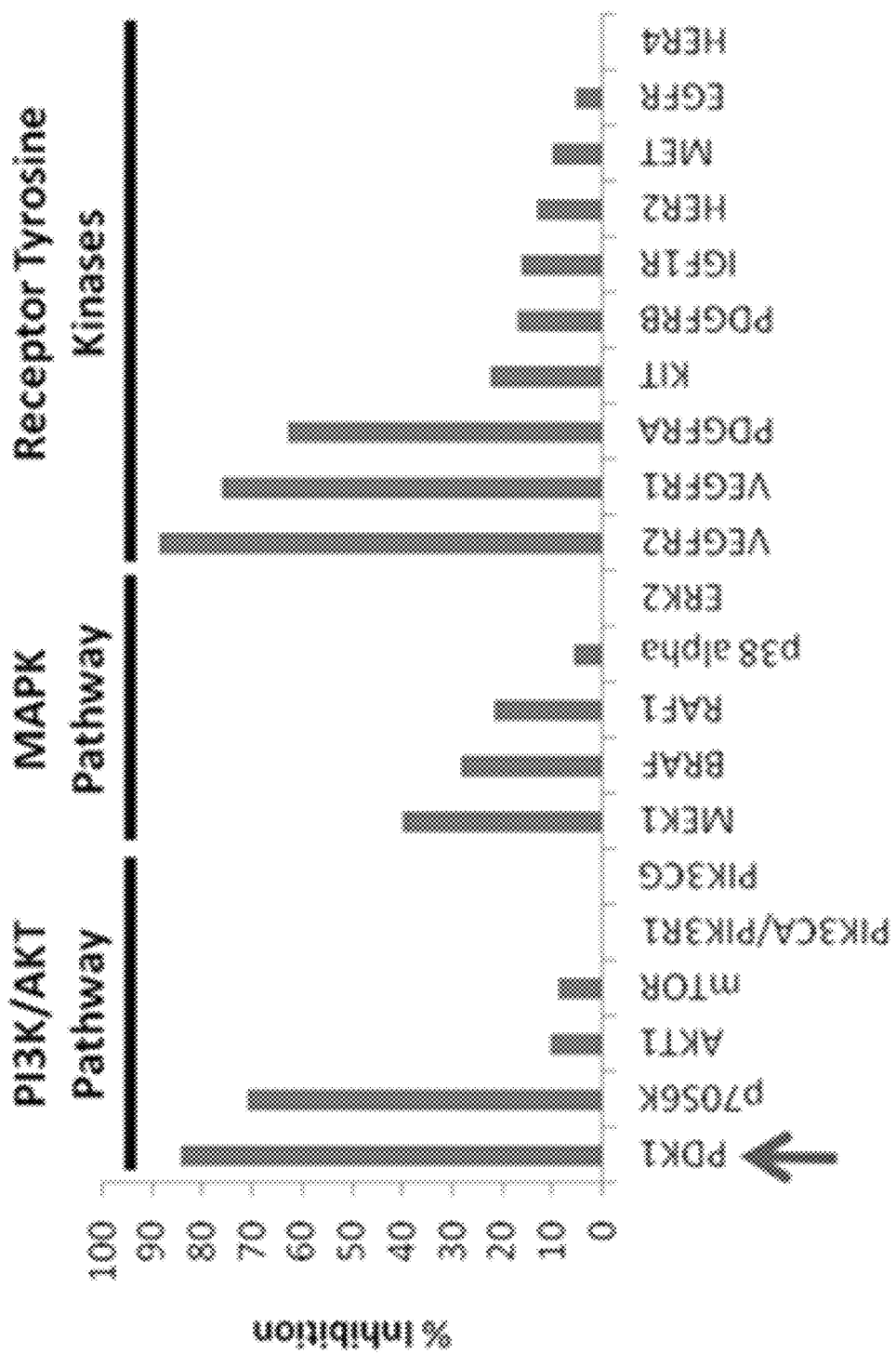
FIG. 8 shows representative data for inhibition of a panel of kinases by a representative disclosed compound, 2,2-difluoro-N-(3-(5-morpholino-1H-benzo[d]imidazol-2-yl)-1H-indazol-5-yl)cyclopropanecarboxamide.

76. Kinase Inhibition Specificity of 2,2-difluoro-N-(3-(5-morpholino-1H-benzo[d]imidazol-2-yl)-1H-indazol-5-yl)cyclopropanecarboxamide The specificity of kinase inhibition was assessed with a representative compound, 2,2-difluoro-N-(3-(5-morpholino-1H-benzo[d]imidazol-2-yl)-1H-indazol-5-yl)cyclopropanecarboxamide, by determining the activity of this test compound against a panel of protein kinases. The panel comprised 78 distinct protein kinases, and data are shown for a subset of 20 kineases (see FIG. 8). Kinase profiling was performed against a focus panel of kinases relevant to PDK1 signaling and other known oncogenic kinases. The activity profiling as performed at 500 nM and percent inhibition at that concentration was determined for each kinase shown.

The kinase specificity was measured using fluorometric assays performed by Life Technologies (Grand Island, N.Y.). Assay conditions vary for each kinase and are available from Life Technologies, Grand Island, NY. For example, the assay conditions for PDK1 are as follows. The 2×PDK1/Ser/Thr-07 mixture is prepared in 50 mM Tris pH 8.5, 0.01% BRIJ-35, 10 mM MgCl2, 1 mM EGTA, 0.02% NaN3. The final 10 µL Kinase Reaction consists of 7.36-38.7 ng PDK1 and 2 µM Ser/Thr 07. After the 1 hour kinase reaction incubation, 5 µL of a 1:32768 dilution of Development Reagent A is added.

The subset of kinases represent a panel kinases in the PI3K/AKT and the MAPK signaling pathways and also included several cancer relevant receptor tyrosine kinases (RTK). The results from this screen confirmed good activity against PDK1 and also showed that the test compound did not have potent activity against other kinases in the PI3K/AKT signaling pathway, except against p70S6K, a kinase downstream of AKT. In addition to potent activity against the PI3K/AKT signaling pathway kinases PDK1 and p70S6K, the test compound did show relatively potent activity against three receptor tyrosine kinases, namely VEGFR2, VEGFR1, and PDGFRA.

77. Pharmacokinetics of 2,2-difluoro-N-(3-(5-morpholino-1H-benzo[d]imidazol-2-yl)-1H-indazol-5-yl)cyclopropanecarboxamide and 2,2-difluoro-N-(3-(5-(2-methylmorpholino)-1H-benzo[d]imidazol-2-yl)-1H-indazol-5-yl)cyclopropanecarboxamide Pharmacokinetic parameters were determined by dosing mice by oral ("po") and intravenous ("iv") administration of two representative disclosed compounds. The compounds were as follows: 1) 2,2-difluoro-N-(3-(5-morpholino-1H-benzo[d]imidazol-2-yl)-1H-indazol-5-yl)cyclopropanecarboxamide; and 2) 2,2-difluoro-N-(3-(5-(2-methylmorpholino)-1H-benzo[d]imidazol-2-yl)-1H-indazol-5-yl)cyclopropanecarboxamide.

Figure 11:
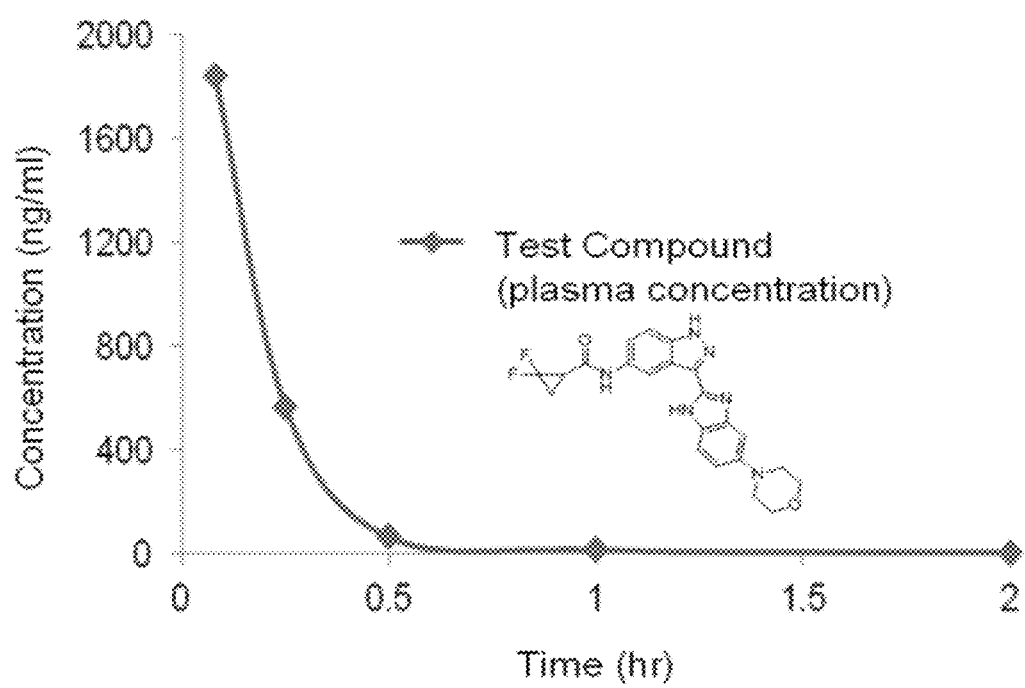
FIG. 11 shows representative pharmacokinetic data for intravenous administration (5.0 mg/kg) of a representative disclosed compound, 2,2-difluoro-N-(3-(5-morpholino-1H-benzo[d]imidazol-2-yl)-1H-indazol-5-yl)cyclopropanecarboxamide, to mice (n=3 for each time point).

Data for iv administration of 5.0 mg/kg of 2,2-difluoro-N-(3-(5-morpholino-1H-benzo[d]imidazol-2-yl)-1H-indazol-5-yl)cyclopropanecarboxamide are shown in FIG. 11 (n=3 for each time point; 27 mice total for nine time point study). The vehicle was 1% DMSO, 10% ethanol, 35% PEG 400, and the balance H$_2$O. Blood was collected (about 50 µl per individual animal) into heparin-containing collection tubes, and cells were removed by centrifugation. The concentration of compound was determined at the indicated time points for each sample using mass spectrometry. Standard PK parameters were calculated for iv administration from data in FIG. 11 for 2,2-difluoro-N-(3-(5-morpholino-1H-benzo[d]imidazol-2-yl)-1H-indazol-5-yl)cyclopropanecarboxamide is shown in Table VIII. PK parameters were calculated using WinNonLin (Pharsight Products, Saint Louis, Mo.). Oral administration of the compound was also carried out, but was below the limit of detection after 0.08 hr. The level detected at 0.08 hr was 9 ng/ml±5.0 ng/ml.

Figure 12:
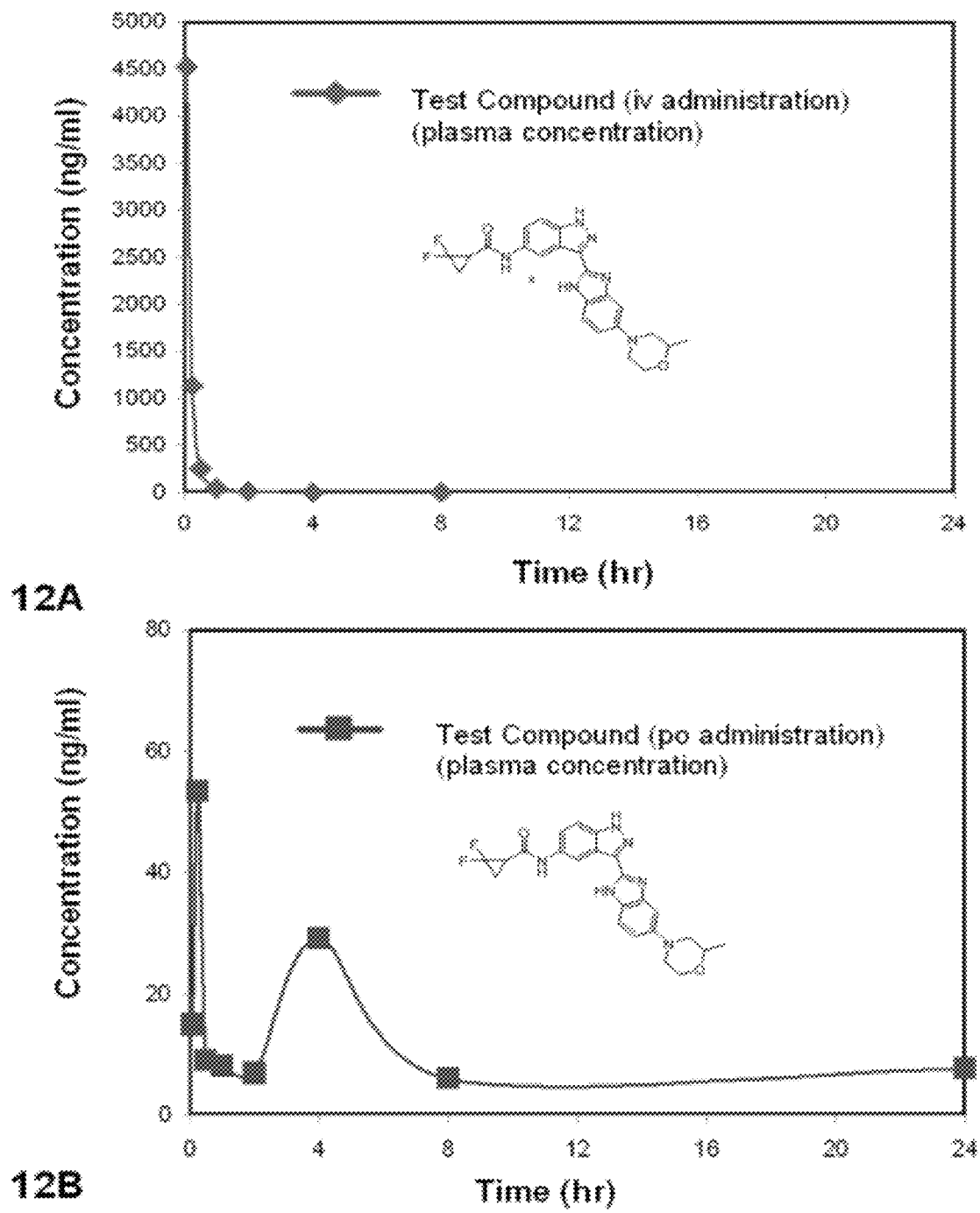
FIG. 12 shows representative pharmacokinetic data for (Panel A) intravenous administration (5.0 mg/kg) and (Panel B) oral administration (30 mg/kg) of a representative disclosed compound, 2,2-difluoro-N-(3-(5-(2-methylmorpholino)-1H-benzo[d]imidazol-2-yl)-1H-indazol-5-yl)cyclopropanecarboxamide, to mice (n=3 for each time point).

Data for iv and po administration of 2,2-difluoro-N-(3-(5-(2-methylmorpholino)-1H-benzo[d]imidazol-2-yl)-1H-indazol-5-yl)cyclopropanecarboxamide are shown in FIG. 12 (Panel A shows data obtained from iv administration of 5.0 mg/kg; Panel B shows data from po administration at 30 mg/kg). Vehicle, sample collection and analysis is as described above. PK parameters were calculated as described above and are shown in Table IX.

TABLE VIII

| PK Parameter | Route of Administration[#] | |
| --- | --- | --- |
| | iv | po |
| C$_{max}$ (ng/mL) | 1843 | 9 |
| T$_{max}$ (hr) | 0.08 | 0.25 |
| AUC$_{0-t}$ (hr * ng/mL) | 516 | n.a. |
| Vss (L/kg) | 1.6 | n.a. |
| CL (mL/min/kg) | 161 | n.a. |
| T$_{1/2}$ (hr) | 0.4 | n.a. |
| % F | n.a. | n.a. |

[#]"n.a." indicates that the parameter is not available or was not calculated.

TABLE IX

| PK Parameter | Route of Administration[#] | |
| --- | --- | --- |
| | iv | po |
| C$_{max}$ (ng/mL) | 4527 | 53 |
| T$_{max}$ (hr) | 0.08 | 0.25 |
| AUC$_{0-t}$ (hr * ng/mL) | 1281 | 244 |
| Vss (L/kg) | 0.63 | n.a. |
| CL (mL/min/kg) | 65 | n.a. |
| T$_{1/2}$ (hr) | 0.4 | n.a. |
| % F | n.a. | 19 |

[#]"n.a." indicates that the parameter is not available or was not calculated.

Figure 10:
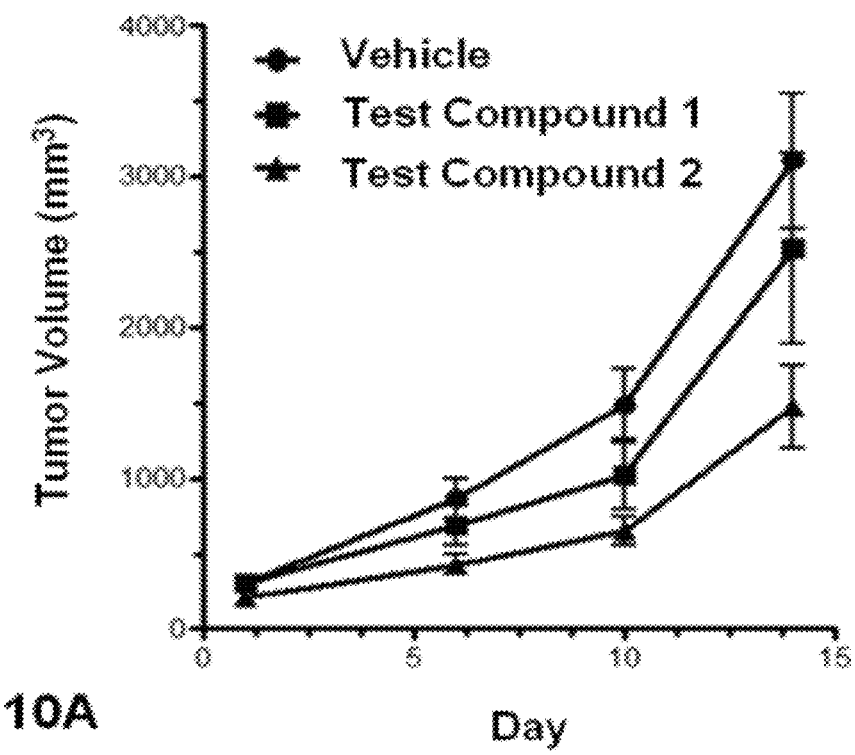
FIG. 10 shows representative in vivo data for the efficacy of two representative disclosed compounds, Test Compound 1 (2,2-difluoro-N-(3-(5-morpholino-1H-benzo[d]imidazol-2-yl)-1H-indazol-5-yl)cyclopropanecarboxamide) and Test Compound 2 (2,2-difluoro-N-(3-(5-(2-methylmorpholino)-1H-benzo[d]imidazol-2-yl)-1H-indazol-5-yl)cyclopropanecarboxamide), in a tumor xenograft model. The panels are as follows: (Panel A) effect of test compounds on tumor volume; (Panel B) effect of test compounds on body weight; and (Panel C) effect of test compounds on phosphorylation of the S6 ribosomal protein.
Figure 10:
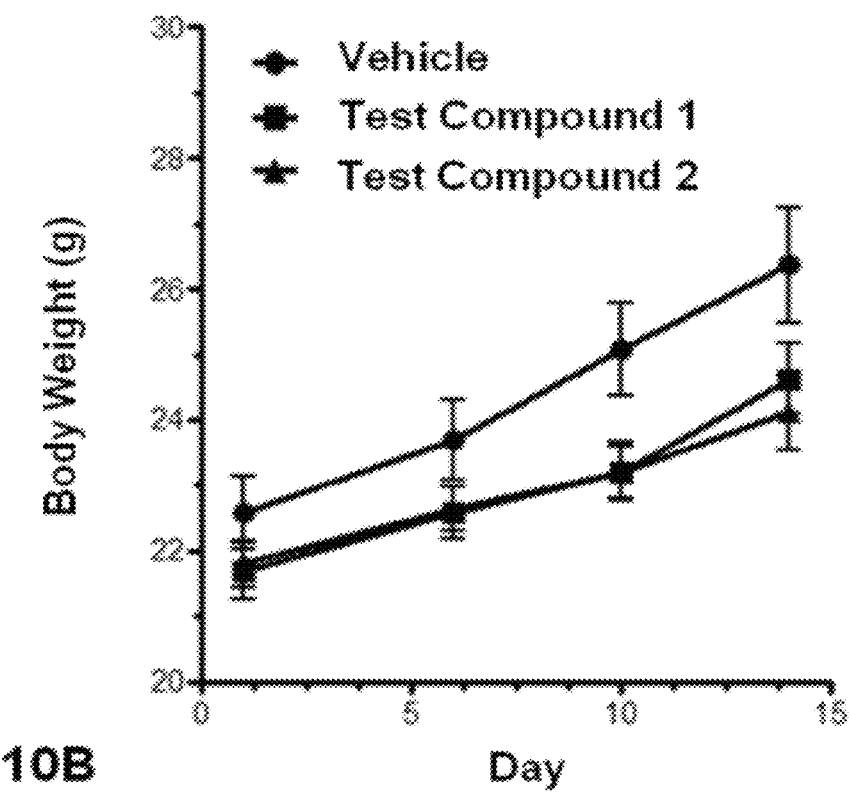
Figure 10:
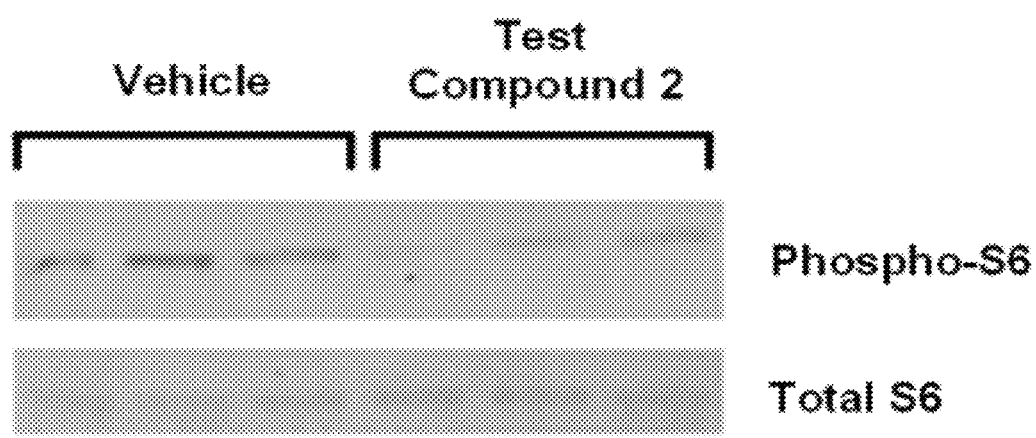

78. Vivo Anti-Tumor Effects of 2,2-difluoro-N-(3-(5-morpholino-1H-benzo[d]imidazol-2-yl)-1H-indazol-5-yl)cyclopropanecarboxamide The in vivo effects of compounds were determined in a mouse subcutaneous xenograft tumor model wherein AN3-CA cells were implanted subcutaneously into the hind flank of athymic nude mice. Briefly, seven-week-old mice were injected with 2×10^6 AN3-CA cells on the right hind flank. After tumors reached 250 mm$^3$, the mice were randomized into test compound, 2,2-difluoro-N-(3-(5-morpholino-1H-benzo[d]imidazol-2-yl)-1H-indazol-5-yl)cyclopropanecarboxamide, or vehicle treated group (10 animals each group). The vehicle for these studies was 20% DMSO, 20% cremophor, and 60% water. The test compound was administered on daily schedule (Monday through Friday) for two weeks at a concentration of 50 mg/kg by intraperitoneal ("IP") injection. The mice were sacrificed and the tumors were excised for western blot analysis. Tumor volume was determined using the formula L×W2×0.5, where L is the longest length, and W is the shortest length. Tumor volume and body weight was measured twice a week. Data for 2,2-difluoro-N-(3-(5-morpholino-1H-benzo[d]imidazol-2-yl)-1H-indazol-5-yl)cyclopropanecarboxamide are shown in FIGS. 10A and 10B for the effect of the compound on tumor volume and body weight, respectively. The data show that the test compound had a modest effect on tumor burden compared to the vehicle control. However, the test compound did not appear to cause any body weight loss over the course of the study. Taken together, these data suggest that the test compound has in vivo efficacy at a dose level that has minimal toxicity.

79. Vivo Anti-Tumor Effects of 2,2-difluoro-N-(3-(5-(2-methylmorpholino)-1H-benzo[d]imidazol-2-yl)-1H-indazol-5-yl)cyclopropanecarboxamide The study was carried out as described above for 2,2-difluoro-N-(3-(5-morpholino-1H-benzo[d]imidazol-2-yl)-1H-indazol-5-yl)cyclopropanecarboxamide, except that the test compound used was 2,2-difluoro-N-(3-(5-(2-methylmorpholino)-1H-benzo[d]imidazol-2-yl)-1H-indazol-5-yl)cyclopropanecarboxamide. Data are shown in FIGS. 10A and 10B for the effect of the compound on tumor volume and body weight, respectively. The data show that the test compound had a profound and significant effect on tumor burden compared to the vehicle control. However, the test compound did not appear to cause any body weight loss over the course of the study. Taken together, these data suggest that the test compound has in vivo efficacy at a dose level that has minimal toxicity.

In addition the effect of the compound on the relative phosphorylation of the ribosomal S6 protein is shown in FIG. 10C. Following the study, the tumors from the vehicle and test compound groups were removed from the animals and analyzed for phosho-S6 levels by western blot (FIG. 10C). Western blot analysis was carried out as described above. Treatment with the test compound appears to correlate with down-regulation of phospho-S6 levels compared to the vehicle group with no changes observed in total S6 protein levels. Without wishing to be bound by a particular theory, these data suggest that the test compound targeted the PDK1 and p70S6K pathway, and that the observed anti-tumor activity correlated with this pharmacodynamic effect.

80. Prospective In Vivo Anti-Tumor Effects

The following example of the in vivo effect of the disclosed compounds are prophetic. Generally agents which inhibit the PI3K/Akt pathway, including PDK1 inhibitors, display efficacy in preclinical models of cancer. In vivo effects of the compounds described in the preceding examples are expected to be shown in various animal models of cancer known to the skilled person, such as tumor xenograft models. These models are typically conducted in rodent, most often in mouse, but may be conducted in other animal species as is convenient to the study goals. Compounds, products, and compositions disclosed herein are expected to show in vivo effects in various animal models of cancer known to the skilled person, such as mouse tumor xenograft models.

In vivo effects of compounds can be assessed with in a mouse tumor xenograft study, one possible study protocol is described herein. Briefly, cells (2-5×10$^6$ cells in 100 μL cell culture media) are implanted subcutaneously in the right hind flank of a mouse. For test compounds of the present invention, a typical cell-line used for the tumor xenograft study would be AN3-CA cells (ATCC# HTB-111). Other suitable cell-lines for these studies are RL95-2 (ATCC# CRL-1671) or HEC-1-A (ATCC# HTB-112). The cells are cultured prior to harvesting for this protocol as described herein.

Following implantation, the tumors are allowed to grow to 100 mm$^3$ before the animals are randomized into treatment groups (vehicle, positive control and various dose levels of the test compound). Day 1 of study corresponds to the day that the animals receive their first dose. The efficacy of a test compound can be determined in studies of various length dependent upon the goals of the study. Typical study periods are for 14, 21 and 28-days. The dosing frequency (e.g. whether animals are dosed with test compound daily, every other day, every third day or other frequencies) is determined for each study depending upon the toxicity and potency of the test compound. A typical study design would involve dosing daily (M-F) with the test compound with recovery on the weekend. Throughout the study, tumor volumes and body weights are measured twice a week. At the end of the study the animals are euthanized and the tumors harvested and frozen for further analysis.

For example, compounds having a structure represented by a formula:

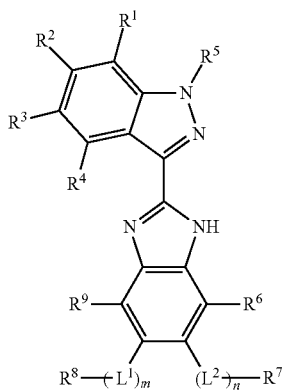

wherein L$^1$ is C=O or (CH$_2$)$_p$, wherein p is an integer from 1 to 3, wherein m is 0 or 1; wherein L$^2$ is C=O or (CH$_2$)$_q$, wherein q is an integer from 1 to 3, wherein n is 0 or 1; wherein R$^1$ is selected from hydrogen, halogen, cyano, and C1-C6 alkyl; wherein R$^2$ is selected from hydrogen, halogen, cyano, and C1-C6 alkyl; wherein R$^3$ is selected from hydrogen, Ar$^1$, NHC=OR$^{11}$, and NHC=ONHR$^{11}$; wherein Ar$^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, SO$_2$R$^{10}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, SO$_2$R$^{10}$, C1-C3 alkyl, C1-C3 alkylamine, and C1-C3 dialkylamino; wherein R$^{10}$ is selected from hydrogen and C1-C6 alkyl; wherein R$^{11}$ is selected from optionally substituted C1-C3 haloalkyl, C1-C3 polyhaloalkyl, C3-C6 cycloalkyl C3-C6 halocycloalkyl, C3-C6 polyhalocycloalkyl, C3-C6 heterocycloalkyl, and Ar$^1$; wherein R$^4$ is selected from hydrogen, Ar$^1$, NHR$^{11}$, and NHC=ONR$^{11}$, provided only one of R$^3$ and R$^4$ is not hydrogen; wherein R$^5$ is selected from hydrogen and C1-C6 alkyl; wherein R$^6$ is selected from hydrogen, halogen, and C1-C6 alkyl; wherein R$^7$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl) piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; wherein R$^8$ is selected from hydrogen, halogen, cyano, C1-C6 alkyl, and C3-C6 heterocycloalkyl; wherein the C3-C6 heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; unsubstituted, monosubstituted and disubstituted 1-(C1-C6 alkylsulfonyl)piperazinyl; wherein the substituents, when present, are independently selected from halogen, cyano, C3-C6 cycloalkyl, C1-C6 alkyl, C1-C6 alkoxy, C1-C6 haloalkyl, C1-C6 polyhaloalkyl, and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl; and wherein R$^9$ is selected from hydrogen, halogen, and C1-C6 alkyl; or a pharmaceutically acceptable salt, hydrate, solvate, or polymorph thereof, wherein; or a pharmaceutically acceptable salt, hydrate, solvate, or polymorph thereof, are expected to show such in vivo effects.

Moreover, compounds prepared using the disclosed synthetic methods are also expected to show such in vivo effects.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A compound of structure(I):

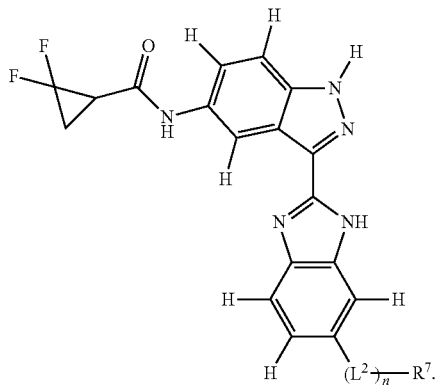

(I)

or a pharmaceutically acceptable salt thereof, wherein:
$L^2$ is —(C=O)— or —$(CH_2)_q$—,
$R^7$ is selected from hydrogen, halogen, cyano, $C_1$-$C_6$ alkyl and $C_3$-$C_6$ heterocycloalkyl;
q is an integer from 1 to 3; and
n is 0 or 1,
wherein the $C_3$-$C_6$ heterocycloalkyl is selected from unsubstituted, monosubstituted, and geminally disubstituted morpholinyl; unsubstituted, monosubstituted and disubstituted piperidinyl; unsubstituted, monosubstituted and disubstituted aziridinyl; unsubstituted, monosubstituted and disubstituted piperazinyl; unsubstituted, monosubstituted and disubstituted hexahydropyrimidinyl; unsubstituted, monosubstituted and disubstituted hexahydropyridazinyl; unsubstituted, monosubstituted and disubstituted pyrrolidinyl; unsubstituted, monosubstituted and disubstituted oxazolidinyl; unsubstituted, monosubstituted and disubstituted imidazolidinyl; unsubstituted, monosubstituted and disubstituted pyrazolidinyl; unsubstituted, monosubstituted and disubstituted 1,3-oxazinanyl; unsubstituted, monosubstituted and disubstituted thiomorpholinyl 1,1-dioxide; and unsubstituted, monosubstituted and disubstituted 1-($C_1$-$C_6$ alkylsulfonyl)piperazinyl;
wherein the substituents, when present, are independently selected from halogen, cyano, $C_3$-$C_6$ cycloalkyl, $C_1$-$C_6$ alkyl, $C_1$-$C_6$ alkoxy, $C_1$-$C_6$ haloalkyl, $C_1$-$C_6$ polyhaloalkyl and an optionally substituted heterocycle selected from aziridinyl, piperazinyl, morpholinyl, pyrollidinyl, oxazolidinyl, imidazolidinyl, pyrazolidinyl, thiomorpholinyl 1,1-dioxide; and 1-(alkylsulfonyl)piperazinyl.
2. The compound of claim 1, wherein n is 0.
3. The compound of claim 1, wherein $R^7$ is hydrogen.
4. The compound of claim 1, wherein $R^7$ is unsubstituted morpholinyl.

5. The compound of claim 1, wherein $R^7$ is monosubstituted morpholinyl, wherein the substituent group is selected from halogen, cyano, methyl, ethyl, methoxy, ethoxy, —$CH_2Cl$, —$CHCl_2$, —$CCl_3$, —$CH_2F$, —$CHF_2$, and —$CF_3$.

6. A method for the stabilizing, relieving the symptoms of or causing the regression of of leukemia, prostate cancer or colon cancer in a mammal, the method comprising the step of administering to the mammal an effective amount of least one compound of claim 1, or a pharmaceutically acceptable table salt thereof.

7. The method of claim 6, wherein the effective amount is a therapeutically effective amount.

8. The method of claim 6, further comprising the step of identifying a mammal in need of stabilizing, relieving the symptoms of or causing the regression of of leukemia, prostate cancer or colon cancer.

9. The method of claim 6, wherein the mammal has been diagnosed with a need for stabilizing, relieving the symptoms of or causing the regression of of leukemia, prostate cancer or colon cancer prior to the administering step.

10. A kit comprising at least one compound of claim 1, or a pharmaceutically acceptable salt thereof,
and one or more of:
(a) at least one agent known to increase kinase activity;
(b) at least one agent known to decrease kinase activity;
(c) at least one agent known to stabilize, relieve the symptoms of or cause the regression of leukemia, prostate cancer or colon cancer; or
(d) instructions for stabilizing, relieving the symptoms of or causing the regression of leukemia, prostate cancer or colon cancer.

11. The kit of claim 10 wherein the compound and the at least one agent are co-packaged.

12. The kit of claim 10 wherein the compound and the at least one agent are packaged for co-administration.

13. The compound of claim 1, wherein n is 1.

14. The compound of claim 1, wherein $L^2$ is —$(CH_2)$—.

15. The compound of claim 1, wherein $R^7$ is unsubstituted, monosubstituted or disubstituted piperidinyl.

16. The compound of claim 1, wherein the compound is selected from:

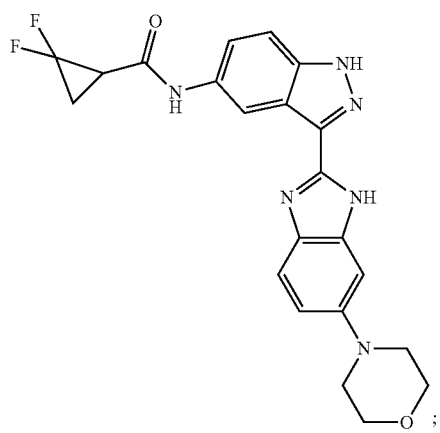

-continued
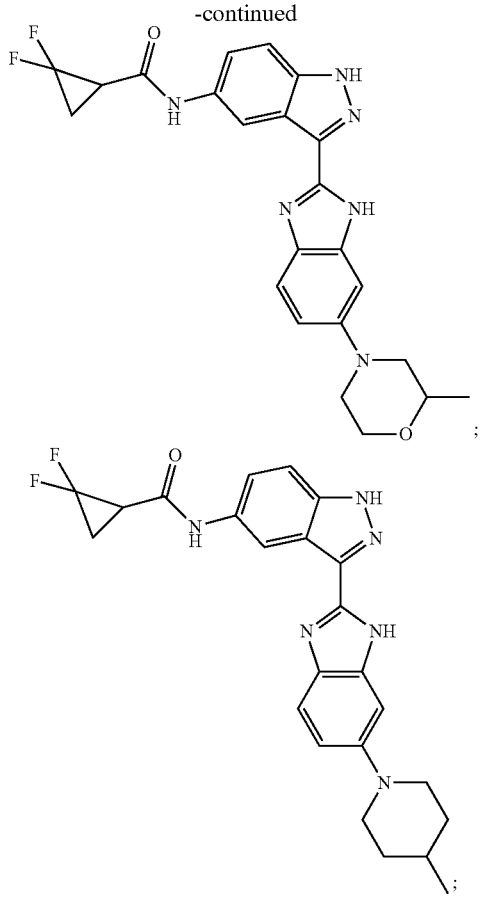
-continued
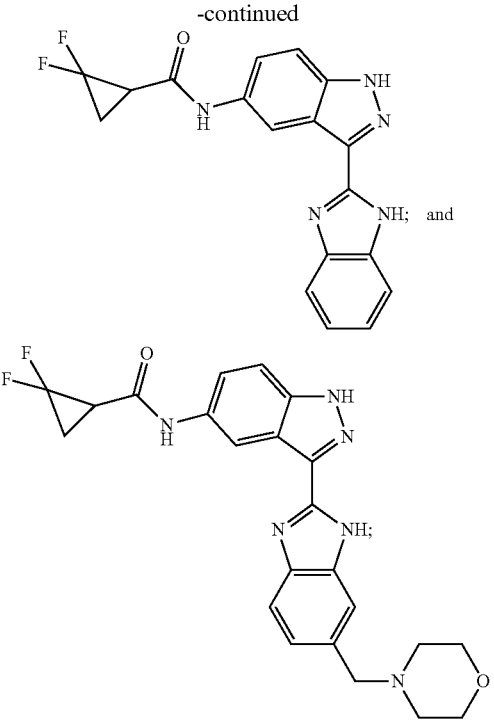
or a pharmaceutically acceptable salt thereof.
17. A composition comprising the compound of claim 1, or a pharmaceutically acceptable salt thereof, and pharmaceutically acceptable carrier.
* * * * *

UNITED STATES PATENT AND TRADEMARK OFFICE
CERTIFICATE OF CORRECTION

PATENT NO. : 8,569,511 B2  
APPLICATION NO. : 13/436905  
DATED : October 29, 2013  
INVENTOR(S) : David J. Bearss et al.

It is certified that error appears in the above-identified patent and that said Letters Patent is hereby corrected as shown below:

In the claims

Column 212, Line 7:
"or causing the regression of of leukemia, prostate cancer or" should read, --or causing the regression of leukemia, prostate cancer or--.

Column 212, Line 10:
"compound of claim 1, or a pharmaceutically acceptable table" should read, --compound of claim 1, or a pharmaceutically acceptable--.

Column 212, Line 15:
"symptoms of or causing the regression of of leukemia," should read, --symptoms of or causing the regression of leukemia,--.

Column 212, Line 21:
"of or causing the regression of of leukemia, prostate cancer or" should read, --symptoms of or causing the regression of leukemia, prostate cancer or--.

Signed and Sealed this  
Twenty-ninth Day of December, 2015

Michelle K. Lee  
*Director of the United States Patent and Trademark Office*